United States Patent
Di Biase et al.

(10) Patent No.: US 9,896,424 B2
(45) Date of Patent: *Feb. 20, 2018

(54) METHODS OF MAKING SULFURIZED DERIVATIVES

(71) Applicant: Elevance Renewable Sciences, Inc., Woodridge, IL (US)

(72) Inventors: Stephen A. Di Biase, River Forest, IL (US); Syed Q. A. Rizvi, Painesville, OH (US); Georgeta Hategan, Plainfield, IL (US)

(73) Assignee: Elevance Renewable Sciences, Inc., Woodridge, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/241,799

(22) Filed: Aug. 19, 2016

(65) Prior Publication Data

US 2016/0355492 A1 Dec. 8, 2016

Related U.S. Application Data

(63) Continuation of application No. 13/428,268, filed on Mar. 23, 2012, now Pat. No. 9,738,618, which is a
(Continued)

(51) Int. Cl.
*C10M 135/06* (2006.01)
*C07D 307/60* (2006.01)
(Continued)

(52) U.S. Cl.
CPC ............ *C07D 307/60* (2013.01); *C08F 20/14* (2013.01); *C08F 20/68* (2013.01); *C08F 120/04* (2013.01); *C08F 120/10* (2013.01); *C08F 122/105* (2013.01); *C08F 210/14* (2013.01); *C10L 1/1883* (2013.01); *C10L 1/1905* (2013.01); *C10L 1/224* (2013.01); *C10M 107/32* (2013.01); *C10M 129/68* (2013.01); *C10M 129/72* (2013.01); *C10M 133/16* (2013.01); *C10M 135/04* (2013.01); *C10M 135/06* (2013.01); *C10M 145/08* (2013.01); *C10M 149/02* (2013.01); *C10M 159/20* (2013.01); *C11C 3/00* (2013.01); *C11C 3/003* (2013.01); *C11D 3/3746* (2013.01); *C10M 2201/02* (2013.01); *C10M 2201/062* (2013.01); *C10M 2203/1006* (2013.01); *C10M 2203/1025* (2013.01); *C10M 2205/028* (2013.01);
(Continued)

(58) Field of Classification Search
CPC .................. C10M 129/68; C10M 169/95; C10M 135/06; C10M 2219/024
See application file for complete search history.

(56) References Cited

U.S. PATENT DOCUMENTS 2,188,887 A 1/1940 Clocker
2,964,545 A 12/1960 Harrison
(Continued)

*Primary Examiner* — Taiwo Oladapo
(74) *Attorney, Agent, or Firm* — Kilpatrick Townsend & Stockton LLP

(57) ABSTRACT

This disclosure relates to sulfurized derivatives made from functionalized monomers. The disclosure relates to lubricants, functional fluids, fuels, dispersants, detergents and functional compositions (e.g., cleaning solutions, food compositions, etc.)

19 Claims, 2 Drawing Sheets

Related U.S. Application Data continuation-in-part of application No. 13/281,108, filed on Oct. 25, 2011, now Pat. No. 8,846,587.

(60) Provisional application No. 61/510,159, filed on Jul. 21, 2011, provisional application No. 61/467,273, filed on Mar. 24, 2011, provisional application No. 61/467,275, filed on Mar. 24, 2011, provisional application No. 61/467,276, filed on Mar. 24, 2011, provisional application No. 61/467,279, filed on Mar. 24, 2011, provisional application No. 61/467,292, filed on Mar. 24, 2011.

(51) Int. Cl.
*C10M 129/68* (2006.01)
*C08F 20/14* (2006.01)
*C08F 20/68* (2006.01)
*C08F 210/14* (2006.01)
*C10L 1/188* (2006.01)
*C10L 1/19* (2006.01)
*C10L 1/224* (2006.01)
*C10M 129/72* (2006.01)
*C10M 133/16* (2006.01)
*C10M 145/08* (2006.01)
*C10M 149/02* (2006.01)
*C10M 159/20* (2006.01)
*C11C 3/00* (2006.01)
*C08F 120/04* (2006.01)
*C08F 120/10* (2006.01)
*C08F 122/10* (2006.01)
*C11D 3/37* (2006.01)
*C10M 107/32* (2006.01)
*C10M 135/04* (2006.01)

(52) U.S. Cl.
CPC ............ *C10M 2205/0285* (2013.01); *C10M 2207/123* (2013.01); *C10M 2207/282* (2013.01); *C10M 2209/04* (2013.01); *C10M 2209/1023* (2013.01); *C10M 2215/08* (2013.01); *C10M 2215/28* (2013.01); *C10M 2217/06* (2013.01); *C10M 2219/022* (2013.01); *C10M 2219/024* (2013.01); *C10M 2219/044* (2013.01); *C10M 2219/046* (2013.01); *C10N 2210/01* (2013.01); *C10N 2210/02* (2013.01); *C10N 2210/03* (2013.01); *C10N 2210/04* (2013.01); *C10N 2210/05* (2013.01); *C10N 2220/021* (2013.01); *C10N 2220/022* (2013.01); *C10N 2230/06* (2013.01); *C10N 2230/08* (2013.01); *C10N 2230/70* (2013.01); *C10N 2240/10* (2013.01); *C10N 2250/10* (2013.01); *C10N 2260/06* (2013.01); *C10N 2260/09* (2013.01); *C10N 2270/02* (2013.01)

(56) References Cited

U.S. PATENT DOCUMENTS

| | | |
|---|---|---|
| 3,293,201 A | 12/1966 | Shahade et al. |
| 3,776,866 A | 12/1973 | Nakayama |
| 4,376,068 A | 3/1983 | Mookherjee et al. |
| 4,390,444 A | 6/1983 | Mookherjee et al. |
| 4,446,125 A | 5/1984 | Mookherjee et al. |
| 4,505,934 A | 3/1985 | Gut et al. |
| 4,518,757 A | 5/1985 | Schulz et al. |
| 4,545,939 A | 10/1985 | Sekiguchi et al. |
| 4,605,507 A * | 8/1986 | Windgassen ......... C10M 125/06 508/152 |
| 5,275,747 A | 1/1994 | Gutierrez et al. |
| 5,425,789 A | 6/1995 | Lewtas et al. |
| 5,484,542 A | 1/1996 | Cahoon et al. |
| 5,730,029 A | 3/1998 | Stoldt et al. |
| 5,773,391 A | 6/1998 | Lawate et al. |
| 5,814,110 A | 9/1998 | Bartz et al. |
| 6,224,642 B1 | 5/2001 | Daly et al. |
| 6,458,175 B1 | 10/2002 | Lehmann et al. |
| 6,503,285 B1 | 1/2003 | Murphy |
| 6,645,261 B2 | 11/2003 | Murphy et al. |
| 6,727,357 B2 | 4/2004 | Polovsky et al. |
| 6,770,104 B2 | 8/2004 | Murphy |
| 6,773,469 B2 | 8/2004 | Murphy |
| 6,797,020 B2 | 9/2004 | Murphy |
| 7,022,637 B2 | 4/2006 | Song et al. |
| 7,053,159 B2 | 5/2006 | Inoue et al. |
| 7,067,587 B2 | 6/2006 | Kaneko et al. |
| 7,128,766 B2 | 10/2006 | Murphy et al. |
| 7,192,457 B2 | 3/2007 | Murphy et al. |
| 7,217,301 B2 | 5/2007 | Murphy et al. |
| 7,247,742 B2 | 7/2007 | McMahon et al. |
| 7,309,817 B2 | 12/2007 | Green et al. |
| 7,314,904 B2 | 1/2008 | Nadolsky et al. |
| 7,393,907 B2 | 7/2008 | Imuta et al. |
| 7,399,323 B2 | 7/2008 | Renninger et al. |
| 7,462,205 B2 | 12/2008 | Murphy |
| 7,465,835 B2 | 12/2008 | Zones et al. |
| 7,473,284 B2 | 1/2009 | Krull |
| 7,476,264 B2 | 1/2009 | Krull |
| 7,494,961 B2 | 2/2009 | Small et al. |
| 7,531,082 B2 | 5/2009 | Mukherjee et al. |
| 7,592,295 B1 | 9/2009 | Fisher et al. |
| 7,637,968 B2 | 12/2009 | Murphy |
| 7,655,739 B1 | 2/2010 | McPhee et al. |
| 7,659,097 B2 | 2/2010 | Renninger et al. |
| 7,691,792 B1 | 4/2010 | Fisher et al. |
| 7,759,444 B1 | 7/2010 | McPhee |
| 7,812,185 B2 | 10/2010 | Burdett et al. |
| 7,833,294 B2 | 11/2010 | Murphy et al. |
| 7,846,222 B2 | 12/2010 | Renninger et al. |
| 7,854,774 B2 | 12/2010 | Renninger et al. |
| 7,868,114 B1 | 1/2011 | McPhee |
| 7,868,115 B1 | 1/2011 | McPhee |
| 8,846,587 B2 * | 9/2014 | DiBiase ................ C08F 20/14 508/178 |
| 9,012,385 B2 * | 4/2015 | Di Biase ............... C08F 220/68 508/463 |
| 2003/0136046 A1 | 7/2003 | Jackson et al. |
| 2005/0154221 A1 | 7/2005 | Lysenko et al. |
| 2007/0039237 A1 | 2/2007 | Murphy et al. |
| 2007/0197731 A1 | 8/2007 | Kando |
| 2007/0227400 A1 | 10/2007 | Zullo et al. |
| 2007/0270621 A1 | 11/2007 | Millis et al. |
| 2007/0282000 A1 | 12/2007 | Murphy et al. |
| 2008/0027194 A1 | 1/2008 | Schrodi |
| 2008/0044026 A1 | 2/2008 | Zullo et al. |
| 2008/0064891 A1 | 3/2008 | Lee |
| 2008/0119377 A1 | 5/2008 | Delvin et al. |
| 2008/0141580 A1 | 6/2008 | Tack |
| 2008/0194443 A1 | 8/2008 | Stohr et al. |
| 2009/0005610 A1 | 1/2009 | Hassan et al. |
| 2009/0048459 A1 | 2/2009 | Tupy et al. |
| 2009/0065736 A1 | 3/2009 | Johnson et al. |
| 2009/0119977 A1 | 5/2009 | Murphy |
| 2009/0126602 A1 | 5/2009 | Murphy et al. |
| 2009/0137014 A1 | 5/2009 | Tsuruta et al. |
| 2009/0217568 A1 | 9/2009 | Murphy et al. |
| 2009/0220443 A1 | 9/2009 | Braksmayer et al. |
| 2009/0259065 A1 | 10/2009 | Abraham et al. |
| 2009/0264672 A1 | 10/2009 | Abraham et al. |
| 2010/0024281 A1 | 2/2010 | Lemke et al. |
| 2010/0047499 A1 | 2/2010 | Braksmayer et al. |
| 2010/0056714 A1 | 3/2010 | McPhee |
| 2010/0056743 A1 | 3/2010 | McPhee |
| 2010/0094034 A1 | 4/2010 | Kaido et al. |
| 2010/0112672 A1 | 5/2010 | Keasling et al. |
| 2010/0120643 A1 * | 5/2010 | Brown ................ C10M 105/38 508/496 |
| 2010/0132250 A1 | 6/2010 | Uptain et al. |
| 2010/0145086 A1 | 6/2010 | Schrodi et al. |
| 2010/0160506 A1 | 6/2010 | Wu et al. |

(56) References Cited

U.S. PATENT DOCUMENTS

| | | |
|---|---|---|
| 2010/0190671 A1 | 7/2010 | Stoehr et al. |
| 2010/0191008 A1 | 7/2010 | Olson |
| 2010/0267971 A1 | 10/2010 | Ohler et al. |
| 2011/0015436 A1 | 1/2011 | Aoki et al. |
| 2011/0287989 A1 | 11/2011 | Filippini |
| 2012/0245063 A1 | 9/2012 | DiBiase et al. |
| 2012/0264662 A1 | 10/2012 | DiBiase et al. |
| 2012/0264664 A1 | 10/2012 | DiBiase et al. |
| 2012/0277133 A1 | 11/2012 | DiBiase et al. |
| 2012/0283156 A1 | 11/2012 | DiBiase et al. |

* cited by examiner

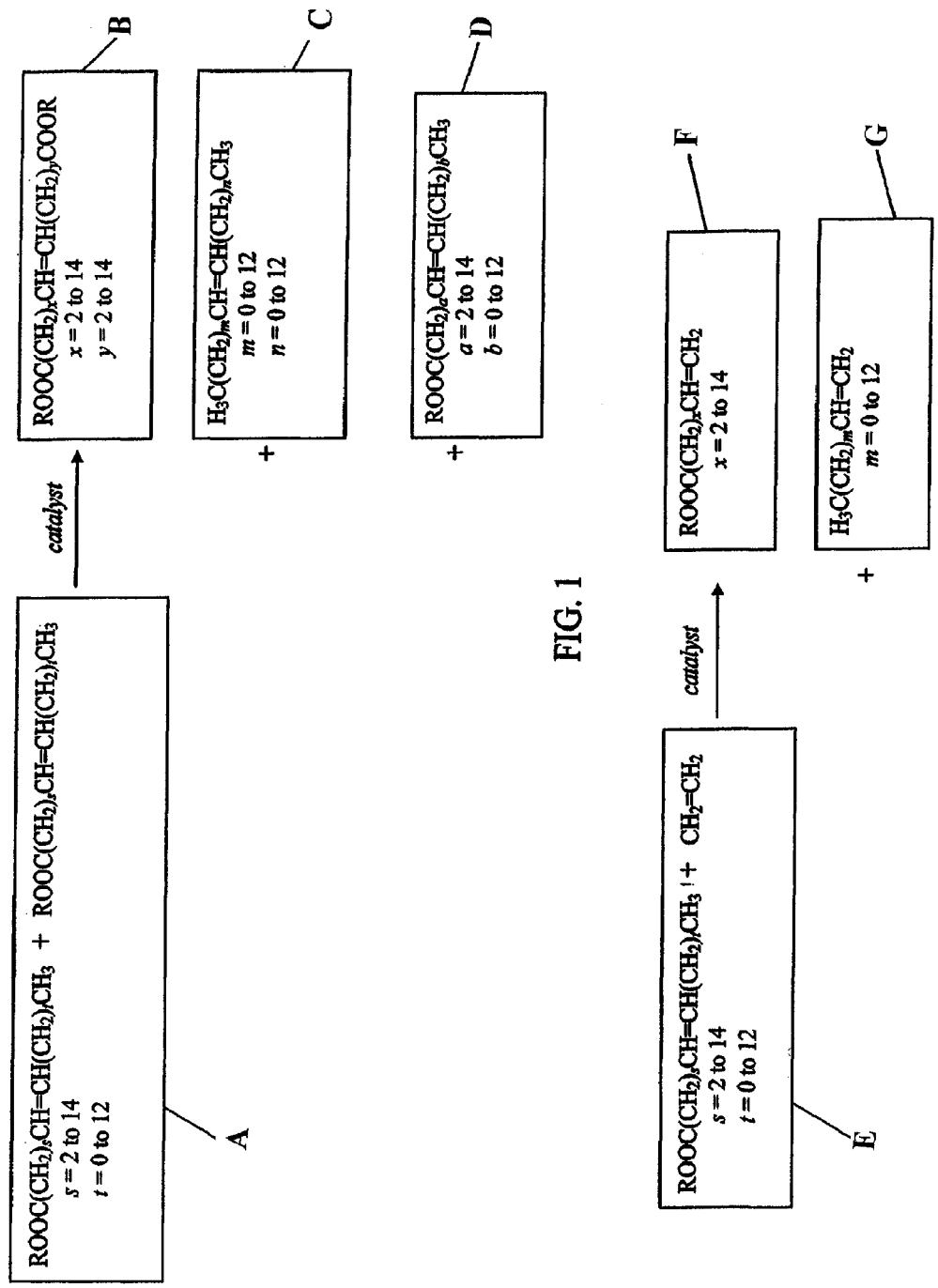

METHODS OF MAKING SULFURIZED DERIVATIVES

The present application is a continuation of U.S. patent application Ser. No. 13/428,268, filed Mar. 23, 2012, which is continuation-in-part of U.S. patent application Ser. No. 13/281,108, filed Oct. 25, 2011, and now issued as U.S. Pat. No. 8,846,587, which claims the benefit of priority of U.S. Provisional Application No. 61/510,159, filed Jul. 21, 2011; 61/467,273, filed Mar. 24, 2011; 61/467,275 filed Mar. 24, 2011; 61/467,276 filed Mar. 24, 2011; 61/467,279 filed Mar. 24, 2011; and 61/467,292 filed Mar. 24, 2011. Each of the foregoing applications is hereby incorporated by reference as though fully set forth herein in its entirety.

TECHNICAL FIELD

This invention relates to sulfurized derivatives, and to lubricants, functional fluids, fuels, functional additives for such lubricants, functional fluids and fuels including dispersants, detergents, and the like, polymeric resins or plastics, adhesives, coatings, pharmaceuticals, cosmetics, personal care products, industrial cleaners, institutional cleaners, foods, beverages, oil field chemicals, agricultural chemicals, and the like.

BACKGROUND

Monomers are often mono-functional in nature. This limits potential uses for derivatives.

SUMMARY

The sulfurized derivatives of the present invention may be derived from a functionalized monomer.

Certain derivatives disclosed herein may undergo high degrees of polymerization, resulting in polymers of unique molecular weight distributions and structural shapes, some of which may have use as specialty polymers to be employed in new applications. The term "polymer" is used herein to refer to polymers, including homopolymers and copolymers, as well as oligomers and co-oligomers.

The functionalized monomer used in making the sulfurized derivatives may be derived from a natural product, for example, a natural oil, a metathesized natural oil, carbohydrate, and the like. The functionalized monomer may be derived from one or more estolides. The natural oils, metathesized natural oils, carbohydrates, and estolides employed herein may provide the advantage of comprising or being derived from renewable sources (e.g., vegetable oils, animal fats or oils, and the like) and may be obtained using environmentally friendly production techniques with less energy than conventional processes for making lubricants, functional fluids, fuels, functional additives for such lubricants, functional fluids and fuels, including dispersants and detergents, polymeric resins, adhesives, coatings, pharmaceuticals, cosmetics, personal care products, industrial cleaners, institutional cleaners, foods, beverages, oil field chemicals, agricultural chemicals, and the like, derived from petroleum. This technology may be referred to as "green" technology.

Synthetic lubricants are commonly used in passenger car motor oils, heavy-duty diesel engine oils, marine and railroad engine lubricants, automatic transmission fluids, hydraulic fluids, gear oils, and industrial lubricants, such as metalworking fluids and lubricating greases. The purpose of these oils is to provide improved friction and wear control, rapid dissipation of heat, and the dissolution of and/or facilitating the removal of service-related contaminants. Achieving a proper balance between various performance characteristics is an important consideration in selecting a synthetic lubricant for a particular application. For example, polyolefin based lubricants typically exhibit good low-temperature properties, high viscosity index, and excellent thermal stability, but poor solvency. As a result, these lubricants tend to be inadequate without the presence of additional polar base stock-containing components. Conversely, polar base stock-containing lubricants, such as those based on synthetic esters and vegetable oils, typically exhibit good solvency and high surface affinity. However, these lubricants tend to be inadequate with respect to resistance to wear. The problem, therefore, is to provide a synthetic lubricant that exhibits both good solvency and good resistance to wear reduction characteristics. This invention provides a solution to this problem.

Ashless dispersants are additives used in lubricants, functional fluids and fuels to prevent oxidation-derived deposits from impairing function. Lubricants, functional fluids and fuels that employ these additives include passenger car motor oils, heavy-duty diesel engine oils, marine and railroad engine lubricants, automatic transmission fluids, gear oils, and the like, with the largest use typically being in automotive and industrial engine oils. The amount of dispersant used in a lubricant or functional fluid depends upon the specific application but, typically, constitutes from about 0.1 percent to about 30 percent by weight of the lubricant or functional fluid. In fuels, the amount of dispersant is typically less than in lubricants or functional fluids. The problem is to provide a dispersant having improved tendencies for suspending the by-products of combustion (e.g., soot) and lubricant or functional fluid degradation (e.g., resin, varnish, lacquer and carbon deposits) in order to keep equipment surfaces and passageways clean. This invention provides a solution to this problem.

Detergents (e.g., metal-containing detergents that form ash upon combustion) are used as additives in lubricants and functional fluids to prevent oxidation-derived deposits from separating on surfaces and impairing function. Lubricants and functional fluids that typically employ these additives include passenger car motor oils, heavy-duty diesel engine oils, marine and railroad engine lubricants, and to a lesser degree automatic transmission fluids, gear oils, and the like, with the largest use typically being in automotive and industrial engine oils. The amount of detergent used in a lubricant or functional fluid depends upon the specific application but, typically, constitutes from about 0.1 percent to about 35 percent by weight of the lubricant or functional fluid. The problem is to provide detergents having improved tendencies for neutralizing acidic combustion and fuel oxidation-derived deposit precursors, and for suspending these by-products and their resultant salts in oil, thereby controlling corrosion and reducing the formation of surface deposits. This invention provides a solution to this problem.

The functionalized monomer or polymer disclosed herein may be reacted with one or more sulfurizing agents to form a sulfurized derivative. The sulfurized derivative may be referred to as a polyfunctionalized monomer or polymer.

The functionalized monomer may be derived from a natural product. The natural product may comprise a natural oil such as vegetable oil, algae oil, fungus oil, animal oil or fat, tall oil, or a mixture of two or more thereof. The natural product may comprise one or more carbohydrates. The carbohydrates may comprise one or more monosaccharides, disaccharides, oligosaccharides and/or polysaccharides, including sucrose, lactose, glucose, fructose, and the like. The natural product may comprise one or more of grass, green plants, starches, crops, grains, lignocellulosic feeds, wood, forest harvesting residues, barks, sawdust, pulping liquors, fibers, agricultural wastes, crop residues, industrial organic wastes, and the like.

The functionalized monomer may comprise a natural product or natural oil derived unsaturated fatty acid, unsaturated fatty ester, polyunsaturated fatty acid, polyunsaturated fatty ester, or a mixture of two or more thereof. The functionalized monomer may comprise a natural product or natural oil derived unsaturated monoglyceride, unsaturated diglyceride, unsaturated triglyceride, or a mixture of two or more thereof.

The functionalized monomer may be derived from a natural oil, the natural oil comprising vegetable oil, algae oil, fungus oil, animal oil or fat, tall oil, sucrose, lactose, glucose, fructose, or a mixture of two or more thereof.

The functionalized monomer may be derived from a natural oil, the natural oil comprising refined, bleached and/or deodorized natural oil. The refined, bleached and/or deodorized natural oil may comprise refined, bleached and/or deodorized soybean oil.

The functionalized monomer may comprise an estolide. The functionalized monomer may be derived from an estolide.

The functionalized monomer may be derived from a metathesized natural oil or natural oil derived unsaturated carboxylic acid and/or ester, the metathesized natural oil or natural oil derived unsaturated carboxylic acid and/or ester comprising the product of a self-metathesis process or a cross-metathesis process. The metathesized natural oil or natural oil derived unsaturated carboxylic acid and/or ester may be made by reacting one or more natural oils and/or natural oil derived unsaturated carboxylic acids and/or esters in the presence of a metathesis catalyst to form the metathesized natural oil or natural oil derived unsaturated carboxylic acid and/or ester. The metathesized natural oil may be made by reacting (a) one or more natural oils and/or natural oil derived unsaturated carboxylic acids and/or esters with (b) another olefinic compound in the presence of a metathesis catalyst. The metathesized natural oil may be made by reacting a natural oil and/or natural oil derived unsaturated carboxylic acid and/or ester in the presence of a metathesis catalyst to form a first metathesized natural oil; and then reacting the first metathesized natural oil in a self-metathesis reaction to form another metathesized natural oil, or reacting the first metathesized natural oil in a cross-metathesis reaction with a natural oil and/or natural oil derived unsaturated carboxylic acid and/or ester to form another metathesized natural oil. The metathesized natural oil may be formed in the presence of a metathesis catalyst, the metathesis catalyst comprising a metal carbene catalyst based upon ruthenium, molybdenum, osmium, chromium, rhenium, and/or tungsten. The natural oil or natural oil derived unsaturated carboxylic acid and/or ester may be partially hydrogenated prior to the reaction in the presence of the metathesis catalyst. The metathesized natural oil or natural oil derived unsaturated carboxylic acid and/or ester may comprise from 1 to about 100, or from 2 to about 50, or from 2 to about 30, or from 2 to about 10 metathesis repeating groups.

BRIEF DESCRIPTION OF THE DRAWINGS

FIG. 1 illustrates an exemplary self-metathesis reaction scheme.

FIG. 2 illustrates an exemplary cross-metathesis reaction scheme.

DETAILED DESCRIPTION

Figure 3:
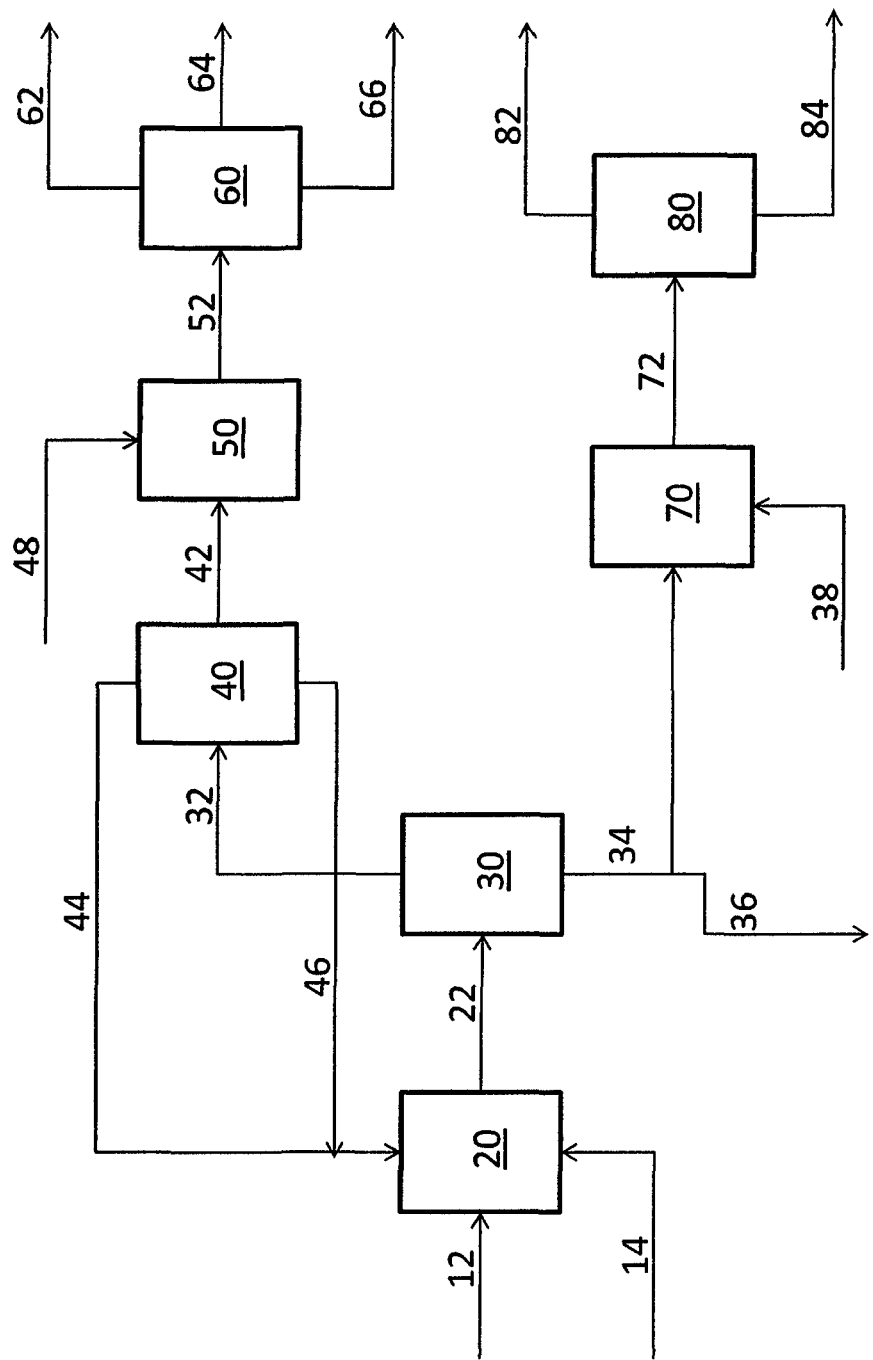
FIG. 3 is a flow sheet showing a metathesis process for metathesizing natural oil, and then treating the resulting metathesized natural oil.

All ranges and ratio limits disclosed in the specification and claims may be combined in any manner. It is to be understood that unless specifically stated otherwise, references to "a," "an," and/or "the" may include one or more than one, and that reference to an item in the singular may also include the item in the plural.

The term "functional group" is used herein to refer to a group of atoms in a molecule that is responsible for a characteristic chemical reaction of that molecule. The functional group may comprise a carboxylic acid group or derivative thereof, a hydroxyl group, an amino group, a carbonyl group, a cyano group, or a mixture of two or more thereof. The functional group may also comprise a carbon-carbon double bond.

The term "functionalized monomer" refers to a monomer comprising a hydrocarbyl group and one or more functional groups attached to the hydrocarbyl group, the hydrocarbyl group containing one or more (e.g., 1 to about 4, or 1 to about 3, or 1 to about 2, or 1) carbon-carbon double bonds, at least about 5 carbon atoms, or from about 5 to about 30 carbon atoms, or from about 6 to about 30 carbon atoms, or from about 8 to about 30 carbon atoms, or from about to about 30 carbon atoms, or from about 12 to about 30 carbon atoms, or from about 14 to about 30 carbon atoms, or from about 16 to about 30 carbon atoms, or from about 5 to about 18 carbon atoms, or from about 12 to about 18 carbon atoms, or about 18 carbon atoms, or from about 8 to about 12 carbon atoms, or about 10 carbon atoms. The functional group may comprise a carboxylic acid group or derivative thereof, a hydroxyl group, an amino group, a carbonyl group, a cyano group, or a mixture of two or more thereof. The functionalized monomer may contain from 1 to about 4 functional groups, or from 1 to about 3, or 1 to about 2, or 1 functional group. Examples of such functionalized monomers may include alkene substituted carboxylic acids, alkene substituted carboxylic esters (e.g., unsaturated fatty acids and fatty esters), alkene-substituted carboxylic acid anhydrides, alkene substituted alcohols, alkene substituted amines, alkene substituted aldehydes, alkene substituted amides, alkene substituted imides, mixtures of two or more thereof, and the like. The functionalized monomer may comprise an ester derived from the transesterification of an alkene substituted carboxylic ester with an alcohol. The functionalized monomer may be referred to as being difunctional or polyfunctional since it has at least one carbon-carbon double bond and at least one functional group.

The terms "hydrocarbyl" or "hydrocarbyl group," when referring to groups attached to the remainder of a molecule, refer to one or more groups having a purely hydrocarbon or predominantly hydrocarbon character. These groups may include: (1) purely hydrocarbon groups (i.e., aliphatic, alicyclic, aromatic, aliphatic- and alicyclic-substituted aromatic, aromatic-substituted aliphatic and alicyclic groups, as well as cyclic groups wherein the ring is completed through another portion of the molecule (that is, any two indicated substituents may together form an alicyclic group)); (2) substituted hydrocarbon groups (i.e, groups containing non-hydrocarbon substituents such as hydroxy, amino, nitro, cyano, alkoxy, acyl, halo, etc.); and (3) hetero groups (i.e., groups which contain atoms, such as N, O or S, in a chain or ring otherwise composed of carbon atoms). In general, no more than about three substituents or hetero atoms, or no more than one, may be present for each 10 carbon atoms in the hydrocarbyl group. The hydrocarbyl group may contain one, two, three or four carbon-carbon double bonds.

The term "carboxylic acid group or derivative thereof" refers to a carboxylic acid group (e.g., —COOH), or a group that may be derived from a carboxylic acid group, including a carboxylic acid anhydride group, a carboxylic ester group (e.g., —COOR), amide group (e.g., —CONR$_2$), imide group (e.g., —CONRCO—), carbonyl or keto group (e.g., —COR), aldehyde or formyl group (e.g., —CHO), or a mixture of two or more thereof. The methods used to form these derivatives may include one or more of addition, neutralization, overbasing, saponification, transesterification, esterification, amidification, hydrogenation, isomerization, oxidation, alkylation, acylation, sulfurization, sulfonation, rearrangement, reduction, fermentation, pyrolysis, hydrolysis, liquefaction, anerobic digestion, hydrothermal processing, gasification, or a combination of two or more thereof. In the foregoing formulas, R may be hydrogen or a hydrocarbyl group. When the carboxylic acid derivative group is bivalent, such as with anhydrides or imides, two hydrocarbyl groups may be attached, at least one of hydrocarbyl groups containing from about 5 to about 30 carbon atoms, or from about 6 to about 30 carbon atoms, or from about 8 to about 30 carbon atoms, or from about 10 to about 30 carbon atoms, or from about 12 to about 30 carbon atoms, or from about 14 to about 30 carbon atoms, or from about 16 to about 30 carbon atoms, or from about 5 to about 18 carbon atoms, or from about 12 to about 18 carbon atoms, or about 18 carbon atoms.

The term "unsaturated carboxylic acid or derivative thereof" refers to an unsaturated carboxylic acid, or an unsaturated carboxylic acid anhydride, ester, amide, imide, aldehyde, ketone, or a mixture of two or more thereof, that may be derived from the unsaturated carboxylic acid.

The term "unsaturated fatty acid or derivative thereof" refers to an unsaturated fatty acid, or an unsaturated fatty anhydride, ester, amide, imide, aldehyde, ketone, or a mixture of two or more thereof, that may be derived from the unsaturated fatty acid.

The term "olefin" is used herein to refer to a compound containing one or more carbon-carbon double bonds. The olefin may be a monoene (e.g., ethene), diene (e.g., butadiene), triene (e.g., octatriene), tetraene (e.g., fanesene), or a mixture of two or more thereof. The olefin may be a conjugated diene (e.g., 1,3-butadiene).

The term "olefin comonomer" refers to an olefin of from 2 to about 30 carbon atoms, or from 2 to about 24 carbon atoms, or from about 4 to about 24 carbon atoms, or from about 6 to about 24 carbon atoms. The olefin may comprise an alpha olefin, an internal olefin, or a mixture thereof. The internal olefin may be symmetric or asymmetric. The olefin may be linear or branched. The olefin may comprise a monoene, diene, triene, tetraene, or a mixture of two or more thereof. The monoenes may comprise one or more of ethene, 1-propene, 1-butene, 2-butene, isobutene, 1-pentene, 2-pentene, 3-pentene, cyclopentene, 1-hexene, 2-hexene, 3-hexene, cyclohexene, 1-heptene, 2-heptene, 3-heptene, 1-octene, 2-octene, 3-octene, 1-nonene, 2-nonene, 3-nonene, 4-nonene, 1-decene, 1-undecene, 1-dodecene, 1-tridecene, 1-tetradecene, 1-pentadecene, 1-hexadecene, 1-octadecene, 1-eicosene, 2-methyl-1-butene, 2-methyl-2-butene, 3-methyl-1-butene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, 2,2-dimethyl-3-pentene, styrene, vinyl cyclohexane, or a mixture of two or more thereof. The dienes, trienes and tetraenes may comprise butadiene, isoprene, hexadiene, decadiene, octatriene, ocimene, farnesene, tetraeicosene, or a mixture of two or more thereof. The dienes may include conjugated dienes, examples of which may include 1,3-butadiene, 1,3-pentadiene, mixtures thereof, and the like.

The term "normally liquid fuel" is used herein to refer to a fuel that is liquid at atmospheric pressure and at the temperature at which it is likely to be stored or used. These may include gasoline and middle distillate fuels. The normally liquid fuels are distinguished from solid fuels such as coal and gaseous fuels such as natural gas.

The term "natural product" is used herein to refer to products of nature, including natural oil, carbohydrates, and the like.

The term "natural oil" refers to oils or fats derived from plants or animals. The term "natural oil" includes natural oil derivatives, unless otherwise indicated, and such natural oil derivatives may include one or more natural oil derived unsaturated carboxylic acids or derivatives thereof. The natural oils may include vegetable oils, algae oils, fungus oils, animal oils or fats, tall oils, derivatives of these oils, combinations of two or more of these oils, and the like. The natural oils may include, for example, canola oil, rapeseed oil, coconut oil, corn oil, cottonseed oil, olive oil, palm oil, peanut oil, safflower oil, sesame oil, soybean oil, sunflower seed oil, linseed oil, palm kernel oil, tung oil, jatropha oil, mustard oil, camellina oil, pennycress oil, castor oil, coriander oil, almond oil, wheat germ oil, bone oil, lard, tallow, poultry fat, yellow grease, fish oil, mixtures of two or more thereof, and the like. The natural oil (e.g., soybean oil) may be refined, bleached and/or deodorized.

The terms "natural product derived unsaturated carboxylic acids and/or derivatives thereof" and "natural oil derived unsaturated carboxylic acid and/or derivatives thereof" refer to unsaturated carboxylic acids or derivatives thereof derived from natural products or natural oil, respectively. The methods used to form these derivatives may include one or more of addition, neutralization, overbasing, saponification, transesterification, esterification, amidification, partial hydrogenation, isomerization, oxidation, alkylation, acylation, sulfurization, sulfonation, rearrangement, reduction, fermentation, pyrolysis, hydrolysis, liquefaction, anaerobic digestion, hydrothermal processing, gasification, or a combination of two or more thereof. Examples of natural oil derived unsaturated carboxylic acids or derivatives thereof may include gums, phospholipids, soapstock, acidulated soapstock, distillate or distillate sludge, unsaturated fatty acids, unsaturated fatty acid esters, as well as hydroxy substituted variations thereof. The unsaturated carboxylic acid or derivative thereof, may comprise an alkene chain in the carboxylic acid or derivative portion of the molecule of at least about 5 carbon atoms, or from about 5 to about 30 carbon atoms, or from about 6 to about 30 carbons, or from about 8 to about 30 carbon atoms, or from about 10 to about 30 carbon atoms, or from about 12 to about 30 carbon atoms, or from about 14 to about 30 carbons, or from about 16 to about 30 carbon atoms, or from about 5 to about 18 carbon atoms, or from about 6 to about 24 carbon atoms, or from about 6 to about 18 carbon atoms, or from about 8 to about 24 carbon atoms, or from about 8 to about 18 carbon atoms, or from about 10 to about 24 carbon atoms, or from about 10 to about 18 carbon atoms, or from about 12 to about 24 carbon atoms, or from about 12 to about 18 carbon atoms, or from about 16 to about 20 carbon atoms, or from about 12 to about 18 carbon atoms, or from about 15 to about 18 carbon atoms, or about 18 carbon atoms, or from about 8 to about 12 carbon atoms, or about 10 carbon atoms, with one or more carboxylic acid and/or ester groups, and at least one carbon-carbon double bond in the alkene chain. The unsaturated carboxylic acid or derivative thereof may contain an alkene chain with 1 to about 4, or 1 to about 3, or 1 or 2, or 1 carbon-carbon double bond in the alkene chain. The natural product derived or natural oil derived unsaturated carboxylic acid or derivative thereof may comprise an unsaturated fatty acid alkyl (e.g., methyl) ester derived from a glyceride (e.g., a triglyceride) of the natural product or natural oil.

The natural oil may comprise a refined, bleached and/or deodorized natural oil, for example, a refined, bleached, and/or deodorized soybean oil (i.e., RBD soybean oil). Soybean oil may comprises about 95% by weight or greater (e.g., 99% weight or greater) triglycerides of fatty acids. The fatty acids in the soybean oil may include saturated fatty acids, including palmitic acid (hexadecanoic acid) and stearic acid (octadecanoic acid), and unsaturated fatty acids, including oleic acid (9-octadecenoic acid), linoleic acid (9, 12-octadecadienoic acid), and linolenic acid (9,12,15-octadecatrienoic acid).

The term "carbohydrate" is used herein to refer to a class of compounds with the empirical formula $C_m(H_2O)_n$ that comprise carbon, hydrogen and oxygen atoms, with a hydrogen:oxygen ratio of 2:1. An example is deoxyribose which has the empirical formula $C_5H_{10}O_4$. The carbohydrates include the saccharides. The saccharides may include: monosaccharides, disaccharides, oligosaccharides, and polysaccharides. The monosaccharides and disaccharides may be referred to as sugars. The sugars, which may be in the form of crystalline carbohydrates, may include sucrose, lactose, glucose, fructose, fruit sugar, and the like. These may be obtained from sugar cane, sugar beet, corn syrup, and the like.

The term "estolide" refers to natural and synthetic compounds derived from fats and oils, e.g., renewable vegetable and animal based oils. The estolide structure may be identified by a secondary ester linkage of one fatty acyl molecule to the alkyl backbone of another fatty acid fragment. Estolides may be free acids or esters, or they may be found within a triglyceride structure. The later form of estolide may occur naturally in the genus *lesquerella* where the species *lesquerella auriculata* may produce up to about 96% of its seed oil as estolides. Triglyceride estolides may be synthesized from castor and *lesquerella* oils. Estolides may be synthesized from unsaturated fatty acids. The estolides may include natural and synthetic glyceride estolides, and estolides derived from fatty acids, including hydroxy fatty acids, unsaturated fatty acids and epoxy fatty acids. These are discussed in Isabell, "Chemistry and Physical Properties of Estolides," Grasas Y Acertes, 62 (1), Enero-Marzo, 8-20, 2011, ISSN: 0017-3495, DOI: 10.3989/gya 010810, which is incorporated herein by reference.

The unsaturated carboxylic (e.g., fatty) acid or derivative thereof may be functionalized at one or more double bonds in the alkene chain by reacting it with an enophilic reagent. The enophilic reagent may comprise an enophilic acid reagent, an oxidizing agent, an aromatic compound, a sulfurizing agent, a hydroxylating agent, a halogenating agent, or a mixture of two or more thereof.

The term "another olefinic compound" is used herein to refer to a natural oil, a natural oil derived unsaturated carboxylic acid or derivative thereof, or one of the above-described olefin comonomers.

The term "metathesis reaction" refers to a catalytic reaction which involves the interchange of alkylidene units among compounds containing one or more carbon-carbon double bonds (e.g., olefinic compounds) via the formation and cleavage of the carbon-carbon double bonds. Metathesis may occur between two like molecules (often referred to as self-metathesis) and/or between two different molecules (often referred to as cross-metathesis).

The term "metathesis catalyst" refers to any catalyst or catalyst system that catalyzes a metathesis reaction.

The terms "metathesize" and "metathesizing" refer to the reacting of one or more reactant compounds (e.g., a natural oil or natural oil derived unsaturated carboxylic acid or derivative thereof) in the presence of a metathesis catalyst to form a metathesized product (e.g., metathesized natural oil) comprising one or more metathesis monomers, oligomers and/or polymers. Metathesizing may refer to self-metathesis or cross-metathesis. For example, metathesizing may refer to reacting two triglycerides present in a natural oil (self-metathesis) in the presence of a metathesis catalyst, wherein each triglyceride has an unsaturated carbon-carbon double bond, thereby forming a monomer, oligomer and/or polymer containing bonded groups derived from the triglycerides. The number of metathesis bonded groups in the metathesized monomers, oligomers and/or polymers may range from 1 to about 100, or from 2 to about 50, or from 2 to about 30, or from 2 to about 10. These may include metathesis monomers, metathesis dimers, metathesis trimers, metathesis tetramers, metathesis pentamers, as well as high order metathesis oligomers (e.g., metathesis hexamers, heptamers, octamers, nonamers, decamers, and the like).

The term "metathesized natural oil" refers to the product formed from the metathesis reaction of a natural oil (or a natural oil derived unsaturated carboxylic acid or derivative thereof) in the presence of a metathesis catalyst to form one or more functionalized olefins and/or olefins comprising one or more metathesis monomers, oligomers and/or polymers derived from the natural oil. The number of metathesis bonded groups in the metathesized natural oil monomers, oligomers and/or polymers may range from 1 to about 100, or from 2 to about 50, or from 2 to about 30, or from 2 to about 10. These may include one or more metathesis monomers, metathesis dimers, metathesis trimers, metathesis tetramers, metathesis pentamers, and higher order metathesis oligomers or polymers (e.g., metathesis hexamers, heptamers, octamers, nonamers, decamers, and the like). The metathesized natural oil may be partially hydrogenated, forming a "partially hydrogenated metathesized natural oil." The partial hydrogenation step may be conducted prior to or subsequent to the metathesis reaction. The metathesized natural oil may be epoxidized. The metathesized natural oil may be formed from the metathesis reaction of a natural oil comprising more than one natural oil (e.g., a mixture of soybean oil and palm oil). The metathesized natural oil may be formed from the metathesis reaction of a natural oil comprising a mixture of one or more natural oils and one or more natural oil derivatives. The metathesized natural oil may be in the form of a liquid or a solid. The solid may comprise a wax.

The term "metathesized natural oil derived unsaturated carboxylic acid" refers to an unsaturated carboxylic acid or a derivative thereof derived from a metathesized natural oil.

The term "metathesized natural oil derivative" refers to the product made by the reaction of a metathesized natural oil with a nitrogen-containing reagent, an oxygen-containing reagent, and/or an enophilic reagent. The enophilic reagent may comprise an enophilic acid reagent, oxidizing agent, sulfurizing agent, aromatic compound, hydroxylating agent, halogenating agent, or a mixture of two or more thereof. The metathesized natural oil derivative may be in the form of a liquid or a solid, and may be oil soluble and/or fuel soluble. The solid may comprise a wax.

The term "metathesis monomer" refers to a single entity that is the product of a metathesis reaction which comprises a molecule of a compound with one or more carbon-carbon double bonds which has undergone an alkylidene unit interchange via one or more of the carbon-carbon double bonds either within the same molecule (intramolecular metathesis) and/or with a molecule of another compound containing one or more carbon-carbon double bonds such as an olefin (intermolecular metathesis).

The term "metathesis dimer" refers to the product of a metathesis reaction wherein two reactant compounds, which can be the same or different and each with one or more carbon-carbon double bonds, are bonded together via one or more of the carbon-carbon double bonds in each of the reactant compounds as a result of the metathesis reaction.

The term "metathesis trimer" refers to the product of one or more metathesis reactions wherein three molecules of two or more reactant compounds, which can be the same or different and each with one or more carbon-carbon double bonds, are bonded together via one or more of the carbon-carbon double bonds in each of the reactant compounds as a result of the one or more metathesis reactions, the trimer containing three bonded groups derived from the reactant compounds.

The term "metathesis tetramer" refers to the product of one or more metathesis reactions wherein four molecules of two or more reactant compounds, which can be the same or different and each with one or more carbon-carbon double bonds, are bonded together via one or more of the carbon-carbon double bonds in each of the reactant compounds as a result of the one or more metathesis reactions, the tetramer containing four bonded groups derived from the reactant compounds.

The term "metathesis pentamer" refers to the product of one or more metathesis reactions wherein five molecules of two or more reactant compounds, which can be the same or different and each with one or more carbon-carbon double bonds, are bonded together via one or more of the carbon-carbon double bonds in each of the reactant compounds as a result of the one or more metathesis reactions, the pentamer containing five bonded groups derived from the reactant compounds.

The term "metathesis hexamer" refers to the product of one or more metathesis reactions wherein six molecules of two or more reactant compounds, which can be the same or different and each with one or more carbon-carbon double bonds, are bonded together via one or more of the carbon-carbon double bonds in each of the reactant compounds as a result of the one or more metathesis reactions, the hexamer containing six bonded groups derived from the reactant compounds.

The term "metathesis heptamer" refers to the product of one or more metathesis reactions wherein seven molecules of two or more reactant compounds, which can be the same or different and each with one or more carbon-carbon double bonds, are bonded together via one or more of the carbon-carbon double bonds in each of the reactant compounds as a result of the one or more metathesis reactions, the heptamer containing seven bonded groups derived from the reactant compounds.

The term "metathesis octamer" refers to the product of one or more metathesis reactions wherein eight molecules of two or more reactant compounds, which can be the same or different and each with one or more carbon-carbon double bonds, are bonded together via one or more of the carbon-carbon double bonds in each of the reactant compounds as a result of the one or more metathesis reactions, the octamer containing eight bonded groups derived from the reactant compounds.

The term "metathesis nonamer" refers to the product of one or more metathesis reactions wherein nine molecules of two or more reactant compounds, which can be the same or different and each with one or more carbon-carbon double bonds, are bonded together via one or more of the carbon-carbon double bonds in each of the reactant compounds as a result of the one or more metathesis reactions, the nonamer containing nine bonded groups derived from the reactant compounds.

The term "metathesis decamer" refers to the product of one or more metathesis reactions wherein ten molecules of two or more reactant compounds, which can be the same or different and each with one or more carbon-carbon double bonds, are bonded together via one or more of the carbon-carbon double bonds in each of the reactant compounds as a result of the one or more metathesis reactions, the decamer containing ten bonded groups derived from the reactant compounds.

The term "metathesis oligomer" refers to the product of one or more metathesis reactions wherein two or more molecules (e.g., 2 to about 10, or 2 to about 4) of two or more reactant compounds, which can be the same or different and each with one or more carbon-carbon double bonds, are bonded together via one or more of the carbon-carbon double bonds in each of the reactant compounds as a result of the one or more metathesis reactions, the oligomer containing a few (e.g., 2 to about 10, or 2 to about 4) bonded groups derived from the reactant compounds.

The term "metathesis polymer" refers to the product of one or more metathesis reactions wherein many molecules of two or more reactant compounds, which can be the same or different and each with one or more carbon-carbon double bonds, are bonded together via one or more of the carbon-carbon double bonds in each of the reactant compounds as a result of the one or more metathesis reactions, the polymer containing more than one (e.g., 2 to about 100, or 2 to about 50, or 2 to about 10, or 2 to about 4) bonded groups derived from the reactant compounds.

The term "oil soluble" is used herein to refer to a material which is soluble in mineral oil to the extent of at least about 10 grams of the material per liter of mineral oil at a temperature of 20° C., or at least about 1% by weight.

The term "fuel soluble" is used herein to refer to a material which is soluble in a normally liquid fuel (e.g., gasoline and/or middle distillate) to the extent of at least about 100 mg of the material per liter of the normally liquid fuel at a temperature of 20° C.

The Functionalized Monomer

The functionalized monomer may comprise an unsaturated hydrocarbyl group with one or more attached functional groups. The hydrocarbyl group may be an alkene group. The hydrocarbyl group may contain at least about 5 carbon atoms, or from about 5 to about 30 carbon atoms, or from about 5 to about 18 carbon atoms, or from about 6 to about 30 carbons, or from about 8 to about 30 carbon atoms, or from about 10 to about 30 carbon atoms, or from about 12 to about 30 carbon atoms, or from about 14 to about 30 carbons, or from about 16 to about 30 carbon atoms, or from about 8 to about 24 carbon atoms, or from about 10 to about 24 carbon atoms, or from about 12 to about 24 carbon atoms, or from about 8 to about 20 carbon atoms, or from about 10 to about 20 carbon atoms, or from about 12 to about 20 carbon atoms, or from about 12 to about 18 carbon atoms, or from about 14 to about 18 carbon atoms, or from about 15 to about 18 carbon atoms, or from about 16 to about 18 carbon atoms, or about 18 carbon atoms, or from about 8 to about 12 carbon atoms, or about 10 carbon atoms. The hydrocarbyl group may be monounsaturated or polyunsaturated with from 1 to about 4 carbon-carbon double bonds, or from 1 to about 3 carbon-carbon double bonds, or from 1 to about 2 carbon-carbon double bonds, or 1 carbon-carbon double bond. The hydrocarbyl group may contain a carbon-carbon double bond in the terminal position of the hydrocarbyl group (e.g., 1-pentenyl, 1-heptenyl, 1-decenyl, 1-dodecnyl, 1-octadecenyl, and the like), and/or one or more internal carbon-carbon double bonds. The hydrocarbyl group may be linear or branched and may optionally include one or more functional groups in addition to the carboxylic acid group or derivative thereof. For example, the hydrocarbyl group may include one or more hydroxyl groups.

The functional group may comprise a carboxylic acid group or derivative thereof, a hydroxyl group, an amino group, a carbonyl group, a cyano group, or a mixture of two or more thereof. The functional group may be attached to a terminal carbon atom on the hydrocarbyl group and/or on an internal carbon atom. The functionalized monomer may contain from 1 to about 4 functional groups, or from 1 to about 3 functional groups, or 1 to about 2 functional groups, or 1 functional group.

The functionalized monomer may have one or more additional functional groups attached to the hydrocarbyl group. These may be provided by reacting the functionalized monomer with an enophilic reagent which may react on the hydrocarbyl group, or may be reactive towards one or more of the carbon-carbon double bonds in the hydrocarbyl group, and/or the functional group. The enophilic reagent may be an enophilic acid, anhydride and/or ester reagent, an oxidizing agent, an aromatic compound, a sulfurizing agent, a hydroxylating agent, a halogenating agent, or a mixture of two or more thereof. These functionalized monomers may be referred to as enophilic reagent modified functionalized monomers or polyfunctionalized monomers.

The functionalized monomer, or polymer derived from the functionalized monomer, may comprise an ester salt and/or a carboxylic salt. The salt portion of the compound may be derived from ammonia, an amine, a polyamine, an aminoalcohol, amine terminated poly(oxyalkylene), and/or a metal. Any of ammonia, or the amines, polyamines, aminoalcohols and/or amine terminated poly (oxyalkylenes) discussed below may be used. The metal may be an alkali metal (e.g., a Group IA metal such as Li, Na, K, Rb, and Cs); alkaline earth metal (e.g., Group IIA metals such as Be, Mg, Ca, Sr, and Ba); Group IIIA metal (e.g., B, Al, Ga, In, and Tl); Group IVA metal (e.g., Sn and Pb), Group VA metal (e.g., Sb and Bi), transition metal (e.g., Sc, Ti, V, Cr, Mn, Fe, Co, Ni, Cu, Zn, Zr, Mo, Ru, Rh, Pd, Ag and Cd), lanthanide or actinides, or a mixture of two or more thereof. The metal may comprise an alkali metal, alkaline earth metal, titanium, zirconium, molybdenum, iron, copper, aluminum, zinc, or a mixture of two or more thereof.

The functionalized monomer may be derived from one or more natural products, including natural oil, metathesized natural oil, carbohydrates, and the like. The functional monomer may be derived from or comprise an estolide. The functionalized monomer may be derived from or comprise a metathesized polyol ester, for example, a metathesized monoglyceride, metathesized diglyceride, metathesized triglyceride, a mixture of two or more thereof, and the like. An advantage of employing a metathesized natural oil is that the structure of the functionalized monomer may be tailored as a result of the metathesis process. For example, it may be advantageous to employ a functionalized monomer with a carbon-carbon double bond in the terminal position of the structural backbone of the compound. This may be possible to achieve with the metathesis process. Also, with metathesis, olefins may be separated from the carboxylic acids or derivatives thereof.

The natural oil may comprise one or more oils or fats derived from plants and/or animals. The natural oils may include vegetable oils, algae oils, fungus oils, animal oils or fats, tall oils, derivatives of these oils, combinations of two or more of these oils, and the like. The natural oils may include canola oil, rapeseed oil, coconut oil, corn oil, cottonseed oil, olive oil, palm oil, peanut oil, safflower oil, sesame oil, soybean oil, sunflower seed oil, linseed oil, palm kernel oil, tung oil, jatropha oil, mustard oil, camellina oil, pennycress oil, castor oil, tall oil, coriander oil, almond oil, wheat germ oil, bone oil, lard, tallow, poultry fat, yellow grease, fish oil, bone oil, mixtures of two or more thereof, and the like. The natural oil may be refined, bleached and/or deodorized.

The natural oil may comprise soybean oil. Soybean oil may comprise unsaturated glycerides, for example, in many embodiments about 95% weight or greater (e.g., 99% weight or greater) triglycerides. Major fatty acids making up soybean oil may include saturated fatty acids, palmitic acid (hexadecanoic acid) and stearic acid (octadecanoic acid), and unsaturated fatty acids, oleic acid (9-octadecenoic acid), linoleic acid (9, 12-octadecadienoic acid), and linolenic acid (9,12,15-octadecatrienoic acid). Soybean oil may be a highly unsaturated vegetable oil with many of the triglyceride molecules having at least two unsaturated fatty acids.

The functionalized monomer may comprise an unsaturated carboxylic acid or derivative thereof (e.g., anhydride, ester, aminde or imide), or an unsaturated alcohol, amine, aldehyde, ketone, nitrile, or a mixture of two or more thereof. The unsaturated monomer may comprise a hydrocarbyl group (e.g., an alkene chain) of at least about 5 carbon atoms, or from about 5 to about 30 carbon atoms, or from about 5 to about 18 carbon atoms, or from about 6 to about 30 carbons, or from about 8 to about 30 carbon atoms, or from about 10 to about 30 carbon atoms, or from about 12 to about 30 carbon atoms, or from about 14 to about 30 carbons, or from about 16 to about 30 carbon atoms, or from about 8 to about 24 carbon atoms, or from about 10 to about 24 carbon atoms, or from about 12 to about 24 carbon atoms, or from about 8 to about 20 carbon atoms, or from about to about 20 carbon atoms, or from about 12 to about 20 carbon atoms, or from about 12 to about 18 carbon atoms, or from about 14 to about 18 carbon atoms, or from about 15 to about 18 carbon atoms, or from about 16 to about 18 carbon atoms, or about 18 carbon atoms, or from about 8 to about 12 carbon atoms, or about 10 carbon atoms, with one or more functional groups, and at least one carbon-carbon double bond in the hydrocarbyl group or alkene chain. The unsaturated carboxylic acid or derivative thereof may be a mono-unsaturated or polyunsaturated carboxylic acid or derivative thereof with, for example, an alkene chain containing from 1 to about 4 carbon-carbon double bonds. The functionalized monomer may comprise or be derived from an unsaturated polyol ester, for example, an unsaturated monoglyceride, an unsaturated diglyceride, an unsaturated triglyceride, or a mixture of two or more thereof.

The functionalized monomer may comprise an olefin chain with 1, 2, 3 or 4 carbon-carbon double bonds in the chain. The olefin chain may be derived from pentene, hexene, heptene, octene, nonene, decene, undecene, dodecene, tridecene, tetradecene, pentadecene, hexadecene, heptadecene, octadecene, or a mixture of two or more thereof. The olefin chain may be derived from octadiene, nonadiene, decadiene, undecadiene, dodecadiene, tridecadiene, tetradecadiene, pentadecadiene, tetradecatriene, pentadecatriene, hexadecatriene, heptadecatriene, octadecatriene, tetradecatetraene, pentadecatetraene, hexadecatetraene, heptadecatetraene, octadecatetraene, or a mixture of two or more thereof. The olefin chain may be derived from nonene, decene, dodecene, octadecene, or a mixture of two or more thereof, each of which may be alpha olefins.

The functionalized monomer may comprise an unsaturated fatty acid or unsaturated fatty ester. The unsaturated fatty ester may be an "unsaturated monoester" and/or an "unsaturated polyol ester". The unsaturated monoesters may comprise one or more unsaturated fatty acids that are esterified with one or more monofunctional alcohols. These alcohols may contain from 1 to about 20 carbon atoms, or from 1 to about 12 carbon atoms, or from 1 to about 8 carbon atoms, or from 1 to about 4 carbon atoms, and may include methanol, ethanol, propanol, butanol, mixtures of two or more thereof, and the like. The unsaturated polyol esters may comprise at least one unsaturated fatty acid that is esterified by the hydroxyl group of one or more polyols. The polyol may contain from 2 to about 10 carbon atoms, and from 2 to about 6 hydroxyl groups. Examples may include ethylene glycol, glycerol, trimethylolpropane, 1,2-propanediol, 1,3-propanediol, 1,2-butanediol, 1,3-butanediol, 2,3-butanediol, 2-ethyl-1,3-propanediol, 2-ethyl-2-butyl-1,3-propanediol, neopentyl glycol, 2,2,4-trimethyl-1,3-pentanediol, pentaerythritol, sorbitol, mixtures of two or more thereof, and the like.

The unsaturated fatty esters may be transesterified with one or more alcohols and/or polyols. For example, the unsaturated fatty ester may comprise methyl 8-nonenoate, methyl 9-decenoate, methyl 10-undecenoate, methyl 9-dodecenoate, methyl 9-octadecenoate, or a mixture of two or more thereof, which may be transesterified with one or more of the following alcohols and/or a polyols. The alcohols may contain 2 to about 20 carbon atoms, or from 2 to about 12 carbon atoms, or from 2 to about 8 carbon atoms, or from 2 to about 4 carbon atoms, and may include ethanol, propanol, butanol, mixtures of two or more thereof, and the like. The polyols may contain from 2 to about 10 carbon atoms, and from 2 to about 6 hydroxyl groups. Examples may include ethylene glycol, glycerol, trimethylolpropane, 1,2-propanediol, 1,3-propanediol, 1,2-butanediol, 1,3-butanediol, 2,3-butanediol, 2-ethyl-1,3-propanediol, 2-ethyl-2-butyl-1,3-propanediol, neopentyl glycol, 2,2,4-trimethyl-1,3-pentanediol, pentaerythritol, sorbitol, mixtures of two or more thereof, and the like.

The unsaturated fatty acid and/or ester may have a straight alkene chain and may be represented by the formula:

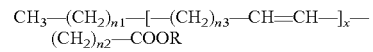

where:
R is hydrogen (fatty acid), or an aliphatic or aromatic group (fatty ester);
$n_1$ is an integer equal to or greater than 0 (typically 0 to about 15; more typically 0, 3, or 6);
$n_2$ is an integer equal to or greater than 0 (typically 1 to about 11; more typically 3, 4, 7, 9, or 11);
$n_3$ is an integer equal to or greater than 0 (typically 0 to about 6; more typically 1); and
x is an integer equal to or greater than 1 (typically 1 to about 6, more typically 1 to about 3).

The unsaturated fatty acids and esters may include those provided in the following table.

| Unsaturated Fatty Acids/Esters | | |
|---|---|---|
| General Formula | Examples of fatty acids | Examples of fatty esters |
| Diunsaturated $CH_3-(CH_2)_{n1}-[-(CH_2)_{n3}-CH=CH-]_x-(CH_2)_{n2}-COOR$ Where x is 2, and n1, n2, n3, and R are as described above. | Linoleic acid (x = 2, n1 = 3; n2 = 7; n3 = 1; and R is H.) | Methyl Linoleate (x = 2, n1 = 3; n2 = 7; n3 = 1; and R is CH3.) |
| Triunsaturated $CH_3-(CH_2)_{n1}-[-(CH_2)_{n3}-CH=CH-]_x-(CH_2)_{n2}-COOR$ Where x is 3, and n1, n2, n3, and R are as described above. | Linolenic acid (x = 3, n1 = 0; n2 = 7; n3 = 1; and R is H.) | Methyl Linolenate (x = 3, n1 = 0; n2 = 7; n3 = 1; and R is CH3.) |

Unsaturated monoesters may be alkyl esters (e.g., methyl esters) or aryl esters and may be derived from unsaturated fatty acids or unsaturated glycerides by transesterifying with a monohydric alcohol. The monohydric alcohol may be any monohydric alcohol that is capable of reacting with an unsaturated free fatty acid or unsaturated glyceride to form the corresponding unsaturated monoester. The monohydric alcohol may be a $C_1$ to $C_{20}$ monohydric alcohol, or a $C_1$ to $C_{12}$ monohydric alcohol, or a $C_1$ to $C_8$ monohydric alcohol, or a $C_1$ to $C_4$ monohydric alcohol. The carbon atoms of the monohydric alcohol may be arranged in a straight chain or in a branched chain structure, and may be substituted with one or more substituents. Representative examples of monohydric alcohols include methanol, ethanol, propanol (e.g., isopropanol), butanol, mixtures of two or more thereof, and the like.

The functionalized monomer may comprise a tranesterified unsaturated triglyceride. Transesterification of an unsaturated triglyceride may be represented as follows.

1 Polyunsaturated Triglyceride+3 Alcohol→1 Glycerol+1-3 Polyunsaturated Monoester Depending upon the make-up of the polyunsaturated triglyceride, the above reaction may yield one, two, or three moles of polyunsaturated monoester. Transesterification may be conducted in the presence of a catalyst, for example, alkali catalysts, acid catalysts, or enzymes. Representative alkali transesterification catalysts may include NaOH, KOH, sodium and potassium alkoxides (e.g., sodium methoxide), sodium ethoxide, sodium propoxide, sodium butoxide. Representative acid catalysts may include sulfuric acid, phosphoric acid, hydrochloric acid, and sulfonic acids. Organic or inorganic heterogeneous catalysts may also be used for transesterification. Organic heterogeneous catalysts may include sulfonic and fluorosulfonic acid-containing resins. Inorganic heterogeneous catalysts may include alkaline earth metals or their salts such as CaO, MgO, calcium acetate, barium acetate, natural clays, zeolites, Sn, Ge or Pb, which may be supported on various support materials such as ZnO, MgO, $TiO_2$, activated carbon or graphite, inorganic oxides such as alumina, silica-alumina, boria, and the like. The catalysts may comprise one or more of P, Ti, Zr, Cr, Zn, Mg, Ca, Fe, or an oxide thereof. The triglyceride may be transesterified with methanol ($CH_3OH$) in order to form free fatty acid methyl esters.

The unsaturated fatty esters may comprise unsaturated polyol esters. The unsaturated polyol ester compounds may have at least one unsaturated fatty acid that is esterified by the hydroxyl group of a polyol. The other hydroxyl groups of the polyol may be unreacted, may be esterified with a saturated fatty acid, or may be esterified with a monounsaturated fatty acid. Examples of polyols include glycerol and 1, 3 propanediol, as well as those mentioned above. The unsaturated polyol esters may have the general formula:

$$R(O-Y)_m(OH)_n(O-X)_b$$

where
R is an organic group having a valency of (n+m+b);
m is an integer from 0 to (n+m+b−1), typically 0 to 2;
b is an integer from 1 to (n+m+b), typically 1 to 3;
n is an integer from 0 to (n+m+b−1), typically 0 to 2;
(n+m+b) is an integer that is 2 or greater;
X is —(O)C—$(CH_2)_{n2}$—[—CH=CH—$(CH_2)_{n3}$—]$_x$—$(CH_2)_{n1}$—$CH_3$;
Y is —(O)C—R';
R' is a straight or branched chain alkyl or alkenyl group;
n1 is an integer equal to or greater than 0 (typically 0 to 15; more typically 0, 3, or 6);
n2 is an integer equal to or greater than 0 (typically 2 to 11; more typically 3, 4, 7, 9, or 11);
n3 is an integer equal to or greater than 0 (typically 0 to 6; more typically 1); and
x is an integer equal to or greater than 2 (typically 2 to 6, more typically 2 to 3).

The unsaturated polyol esters may be unsaturated glycerides. The term "unsaturated glyceride" refers to a polyol ester having at least one (e.g., 1 to 3) unsaturated fatty acid that is esterified with a molecule of glycerol. The fatty acid groups may be linear or branched and may include pendant hydroxyl groups. The unsaturated glycerides may be represented by the general formula:

$CH_2A$-CH B—$CH_2C$ where —A; —B; and —C are selected from
—OH;
—O(O)C—$(CH_2)_{n2}$—[—CH=CH—$(CH_2)_{n3}$—]$_x$—$(CH_2)_{n1}$—$CH_3$; and
—O(O)C—R';
with the proviso that at least one of —A, —B, or —C is
—O(O)C—$(CH_2)_{n2}$—[—CH=CH—$(CH_2)_{n3}$—]$_x$—$(CH_2)_{n1}$—$CH_3$.

In the above formula:
R' is a straight or branched chain alkyl or alkenyl group;
n1 is an integer equal to or greater than 0 (typically 0 to 15; more typically 0, 3, or 6);
n2 is an integer equal to or greater than 0 (typically 2 to 11; more typically 3, 4, 7, 9, or 11);
n3 is an integer equal to or greater than 0 (typically 0 to 6; more typically 1); and
x is an integer equal to or greater than 2 (typically 2 to 6, more typically 2 to 3).

Unsaturated glycerides having two —OH groups (e.g., —A and —B are —OH) may be referred to as unsaturated monoglycerides. Unsaturated glycerides having one —OH group may be referred to as unsaturated diglycerides. Unsaturated glycerides having no —OH groups may be referred to as unsaturated triglycerides.

The unsaturated glyceride may include monounsaturated fatty acids, polyunsaturated fatty acids, and saturated fatty acids that are esterified with the glycerol molecule. The main chain of the individual fatty acids may have the same or different chain lengths. Accordingly, the unsaturated glyceride may contain up to three different fatty acids so long as at least one fatty acid is an unsaturated fatty acid.

The functionalized monomer may comprise a Δ9 polyunsaturated fatty acid, a Δ9 polyunsaturated fatty ester (e.g., monoesters or polyol esters), or a mixture thereof. Δ9 polyunsaturated fatty acids and/or esters may have at least two carbon-carbon double bonds with one carbon-carbon double bond being located between the 9$^{th}$ and 10$^{th}$ carbon atoms (i.e., between $C_9$ and $C_{10}$) in the alkene chain of the polyunsaturated fatty acid and/or ester. In determining this position, the alkene chain is numbered starting with the carbon atom of the carbonyl group of the unsaturated fatty acid and/or ester. Included within the definition of Δ9 polyunsaturated fatty acids and/or esters are Δ9, Δ12 polyunsaturated fatty acids and/or esters, and Δ9, Δ12, Δ15 polyunsaturated fatty acids and/or esters.

The Δ9 polyunsaturated acid or ester may have a straight alkene chain and may be represented by the structure:

$CH_3$—$(CH_2)_{n1}$—[—$(CH_2)_{n3}$—CH=CH—]$_x$—$(CH_2)_7$—COOR where
R is hydrogen (fatty acid), or an aliphatic group (fatty monoester);
n1 is an integer equal to or greater than 0 (typically 0 to 6; or 0, 3 or 6);
n3 is an integer equal to or greater than 0 (typically 1); and
x is an integer equal to or greater than 2 (typically 2 to 6, more typically 2 to 3).

The Δ9 polyunsaturated fatty acid and/or ester may have a total of about 12, 15 or 18 carbons in the alkene chain. Examples may include $CH_3$—$(CH_2)_4$—CH=CH—$CH_2$—CH=CH—$(CH_2)_7$—COOR;

$CH_3$—$CH_2$—CH=CH—$CH_2$—CH=CH—$CH_2$—CH=CH—$(CH_2)_7$—COOR.

$CH_2=CH-CH_2-CH=CH-(CH_2)_7-COOR$; and $CH_2=CH-CH_2-CH=CH-CH_2-CH=CH-(CH_2)_7-COOR$, where R is hydrogen (fatty acid), or an aliphatic group (fatty monoester);

Δ9 unsaturated fatty esters may be monoesters or polyol esters. The Δ9 unsaturated polyol ester may have the general structure $CH_2A\text{-}CHB-CH_2C$ where —A; —B; and —C are independently selected from
—OH;
—O(O)C—R'; and
—O(O)C—$(CH_2)_7$—[—CH=CH—$CH_2$—]$_{x-}$—$(CH_2)_{n1}CH_3$ with the proviso that at least one of —A, —B, or —C is
—O(O)C—$(CH_2)_7$—[—CH=CH—$CH_2$—]$_{x-}$—$(CH_2)_{n1}$ $CH_3$ In the above formula:
R' is a straight or branched chain alkyl or alkenyl group;
n1 is independently an integer equal to or greater than 0 (typically 0 to 6); and
x is an integer greater than or equal to 2 (typically 2 to 6, more typically 2 to 3).

Δ9, Δ12 di-unsaturated esters and Δ9, Δ12, Δ15 tri-unsaturated esters may be used.

The functionalized monomer may comprise one or more $C_{18}$ fatty acids, for example, linoleic acid (i.e., 9, 12-octadecadienoic acid) and linolenic acid (i.e., 9, 12, 15-octadecatrienoic acid). The functionalized monomer may comprise one or more $C_{18}$ fatty esters, for example, methyl linoleate and methyl linolenate. The functionalized monomer may comprise an unsaturated glyceride comprising Δ9 fatty acids, for example, C18:Δ9 fatty acids.

Δ9, Δ12 and Δ15 functionalized monomers may be derived from vegetable oils such as soybean oil, rapeseed oil, corn oil, sesame oil, cottonseed oil, sunflower seed oil, canola oil, safflower oil, palm oil, palm kernel oil, linseed oil, castor oil, olive oil, peanut oil, coriander oil, almond oil, wheat germ oil, and the like. Since these vegetable oils yield predominately the glyceride form of the Δ9, Δ12 and Δ15 unsaturated fatty esters, the oils may be processed (e.g., by transesterification) to yield an unsaturated free fatty ester and/or unsaturated fatty acid. Δ9, Δ12 and Δ15 unsaturated fatty acids and/or esters, and salts may also be also be derived from tall oil, fish oil, lard, algal oil, poultry fat, yellow grease, and tallow. A summary of some useful functionalized monomers is provided in the following table.

| Functionalized Monomer | Description | Classification | Bond Locations |
|---|---|---|---|
| Linoleic acid | C18 diunsaturated fatty acid (C18:2) | Δ9 | Δ9, 12 |
| Linolenic acid | C18 triunsaturated fatty acid (C18:3) | Δ9 | Δ9, 12, 15 |
| Alkyl linoleate | C18 diunsaturated fatty ester (C18:2) | Δ9 | Δ9, 12 |
| Alkyl linolenate | C18 triunsaturated fatty ester (C18:3) | Δ9 | Δ9, 12, 15 |
| Unsaturated glyceride | Unsaturated glycerides of C18:1, C18:2, and C18:3 fatty acids | Δ9 | Δ9<br>Δ9, 12<br>Δ9, 12, 15 |

The functionalized monomer may comprise an unsaturated carboxylic acid and/or ester used with an alkene chain of from about 10 to about 30 carbon atoms, or from about 10 to about 24 carbon atoms, or about 18 carbon atoms, and a carbon-carbon double bond between the $C_9$ and $C_{10}$ carbon atoms in the alkene chain.

The functionalized monomer may comprise an unsaturated fatty acid and/or the unsaturated fatty ester with an alkene chain of from 8 to about 30 carbon atoms, or from about 8 to about 18 carbon atoms, or about 18 carbon atoms, and a carbon-carbon double bond between the $C_6$ and $C_7$ carbon atoms in the alkene chain.

The functionalized monomer may comprise an unsaturated fatty acid and/or unsaturated fatty ester with an alkene chain of about 14 to about 30 carbon atoms, or from about 14 to about 18 carbon atoms, or about 18 carbon atoms, and a carbon-carbon double bond between the $C_{12}$ and $C_{13}$ carbon atoms in the alkene chain.

The functionalized monomer may comprise an unsaturated fatty acid and/or unsaturated fatty ester with an alkene chain of from about 16 to about 30 carbon atoms, or from about 16 to about 18 carbon atoms, or about 18 carbon atoms, and a carbon-carbon double bond between the $C_{15}$ and $C_{16}$ carbon atoms in the alkene chain.

The functionalized monomer may comprise an unsaturated fatty acid and/or unsaturated fatty ester with an alkene chain of from 14 to about 30 carbon atoms, or from about 14 to about 18 carbon atoms, or about 18 carbon atoms, and carbon-carbon double bonds between the $C_9$ and $C_{10}$ carbon atoms and between the $C_{12}$ and $C_{13}$ carbon atoms in the alkene chain.

The functionalized monomer may comprise an unsaturated fatty acid and/or unsaturated fatty ester with an alkene chain of from 16 to about 30 carbon atoms, or from about 16 to about 18 carbon atoms, or about 18 carbon atoms, with carbon-carbon double bonds between the $C_9$ and $C_{10}$ carbon atoms, between the $C_{12}$ and $C_{13}$ carbon atoms, and between Cis and $C_{16}$ carbon atoms in the alkene chain.

The functionalized monomer may comprise an unsaturated fatty acid and/or unsaturated fatty ester with an alkene chain from 16 to about 30 carbon atoms, or from about 16 to about 18 carbon atoms, or about 18 carbon atoms, and carbon-carbon double bonds between the $C_6$ and C7 carbon atoms, between the $C_9$ and $C_{10}$ carbon atoms, between the $C_{12}$ and $C_{13}$ carbon atoms, and between the $C_{15}$ and $C_{16}$ carbon atoms in the alkene chain.

The functionalized monomer may comprise 8-nonenoic acid, a functionalized derivative of 8-nonenoic acid, or a combination thereof. The functionalized derivative of 8-nonenoic acid may comprise an ester. The ester may comprise 8-nonenoic acid methyl ester, 8-nonenoic acid ethyl ester, 8-nonenoic acid n-propyl ester, 8-nonenoic acid iso-propyl ester, 8-nonenoic acid n-butyl ester, 8-nonenoic acid sec-butyl ester, 8-nonenoic acid tert-butyl ester, 8-nonenoic acid neopentyl ester, 8-nonenoic acid pentaerythritol ester, or a mixture of two or more thereof.

The functionalized monomer may comprise 9-decenoic acid, a functionalized derivative of 9-decenoic acid, or a combination thereof. The functionalized derivative of 9-decenoic acid may comprise an ester. The ester may comprise 9-decenoic acid methyl ester, 9-decenoic acid ethyl ester, 9-decenoic acid n-propyl ester, 9-decenoic acid iso-propyl ester, 9-decenoic acid n-butyl ester, 9-decenoic acid sec-butyl ester, 9-decenoic acid tert-butyl ester, 9-decenoic acid neopentyl ester, 9-decenoic acid pentaerythritol ester, or a mixture of two or more thereof. The functionalized monomer may comprise methyl 9-decenoate.

The functionalized monomer may comprise 10-undecenoic acid, a functionalized derivative of 10-undecenoic acid, and a combination thereof. The functionalized derivative of 10-undecenoic acid may comprise an ester. The ester may comprise 10-undecenoic acid methyl ester, 10-undecenoic acid ethyl ester, 10-undecenoic acid n-propyl ester, 10-undecenoic acid iso-propyl ester, 10-undecenoic acid n-butyl ester, 10-undecenoic acid sec-butyl ester, 10-undecenoic acid tert-butyl ester, 10-undecenoic acid neopentyl ester, 10-undecenoic acid pentaerythritol ester, or a mixture of two or more thereof.

The functionalized monomer may comprise 9-dodecenoic acid, a functionalized derivative of 9-dodecenoic acid, or a combination thereof. The functionalized derivative of 9-dodecenoic acid may comprise an ester. The ester may comprise 9-dodecenoic acid methyl ester, 9-dodecenoic acid ethyl ester, 9-dodecenoic acid n-propyl ester, 9-dodecenoic acid iso-propyl ester, 9-dodecenoic acid n-butyl ester, 9-dodecenoic acid sec-butyl ester, 9-dodecenoic acid tert-butyl ester, 9-dodecenoic acid neopentyl ester, 9-dodecenoic acid pentaerythritol ester, or a mixture of two or more thereof.

The functionalized monomer may comprise 9-octadecenedioic acid, a functionalized derivative of 9-octadecenedioic acid, or a combination thereof. The functionalized derivative of 9-octadecenedioic acid may comprise a mono- or a di-ester. The ester may comprise 9-octadecenedioic acid mono- or di-methyl ester, 9-octadecenedioic acid mono- or di-ethyl ester, 9-octadecenedioic acid mono- or di-n-propyl ester, 9-octadecenedioic acid mono- or di-iso-propyl ester, 9-octadecenedioic acid mono- or di-n-butyl ester, 9-octadecenedioic acid mono- or di-sec-butyl ester, 9-octadecenedioic acid mono- or di-tert-butyl ester, 9-octadecenedioic acid mono- or di-neopentyl ester, 9-octadecenedioic acid mono- or di-pentaerythritol ester, or a mixture of two or more thereof.

The Metathesis Process

The functionalized monomer may comprise a metathesized natural oil derived unsaturated carboxylic acid and/or ester. The metathesized natural oil derived unsaturated carboxylic acid and/or ester may be produced using a self-metathesis process, a cross-metathesis process, or a combination thereof. The self-metathesis process may comprise reacting a natural oil or natural oil derived unsaturated carboxylic acid and/or ester in the presence of a metathesis catalyst to form a metathesized natural oil from which the metathesized natural oil derived unsaturated carboxylic acid and/or ester may be derived.

The cross-metathesis process may comprise reacting a natural oil or natural oil derivative with another olefinic compound in the presence of a metathesis catalyst to form the metathesized natural oil. The another olefinic compound may be a natural oil, a natural oil derivative or a short chain olefin. The short chain olefin may comprise an alpha olefin, an internal olefin, or a mixture thereof. The internal olefin may be symmetric or asymmetric. The olefin may comprise one or more of ethene, propene, 2-butene, 3-hexene, 4-octene, 2-pentene, 2-hexene, 2-heptene, 3-heptene, 2-octene, 3-octene, 2-nonene, 3-nonene, 4-nonene, ethylene, 1-propene, 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-octadecene, 1-eicosene, or a mixture of two or more thereof.

Multiple, sequential metathesis reaction steps may be employed. For example, the metathesized natural oil or metathesized natural oil derived unsaturated carboxylic acid and/or ester may be made by reacting a natural oil or natural oil derived unsaturated carboxylic acid and/or ester in the presence of a metathesis catalyst to form a first metathesized natural oil or first metathesized natural oil derived unsaturated carboxylic acid and/or ester. The first metathesized natural oil or first metathesized natural oil derived unsaturated carboxylic acid and/or ester may then be reacted in a self-metathesis reaction to form another metathesized natural oil or metathesized natural oil derived unsaturated carboxylic acid and/or ester. Alternatively, the first metathesized natural oil or metathesized natural oil derived unsaturated carboxylic acid and/or ester may be reacted in a cross-metathesis reaction with a natural oil and/or natural oil derived unsaturated carboxylic acid and/or ester to form another metathesized natural oil or metathesized natural oil derived unsaturated carboxylic acid and/or ester. These procedures may be used to form metathesis dimers, trimers as well as higher order metathesis oligomers and polymers. These procedures can be repeated as many times as desired (for example, from 2 to about 50 times, or from 2 to about 30 times, or from 2 to about 10 times, or from 2 to about 5 times, or from 2 to about 4 times, or 2 or 3 times) to provide the desired metathesis oligomer or polymer which may comprise, for example, from 2 to about 100 bonded groups, or from 2 to about 50, or from 2 to about 30, or from 2 to about 10, or from 2 to about 8, or from 2 to about 6 bonded groups, or from 2 to about 4 bonded groups, or from 2 to about 3 bonded groups.

The metathesized natural oil or metathesized natural oil derived unsaturated carboxylic acid and/or ester produced by the metathesis reaction process may comprise a mixture of carboxylic acids and/or esters, and olefins, comprising one or more metathesis monomers, oligomers and/or polymers derived from the unsaturates in the natural oil. The number of bonded groups in the metathesized natural oil monomers, oligomers or polymers may range from 1 to about 100, or from 2 to about 50, or from 2 to about 30, or from 2 to about 10.

These may include metathesis monomers, metathesis dimers, metathesis trimers, metathesis tetramers, metathesis pentamers, and higher order metathesis oligomers or polymers (e.g., metathesis hexamers, heptamers, octamers, nonamers, decamers, and the like). These may be useful as the functionalized polymers or copolymers of the invention.

The metathesis starting materials or reactants may be subjected to a metathesis reaction to produce the desired metathesized product. Metathesis is a catalytic reaction that involves the interchange of alkylidene units among compounds containing one or more double bonds (i.e., olefinic compounds) via the formation and cleavage of the carbon-carbon double bonds. Metathesis can occur between two of the same molecules (often referred to as self-metathesis) and/or it can occur between two different molecules (often referred to as cross-metathesis).

Self-metathesis may be represented generally as shown in Equation I.

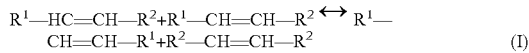

where $R^1$ and $R^2$ are organic groups.

Cross-metathesis may be represented generally as shown in Equation II.

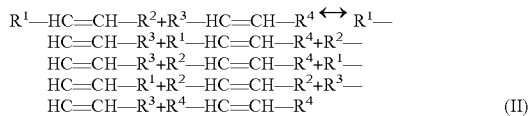

where $R^1$, $R^2$, $R^3$, and $R^4$ are organic groups.

When an unsaturated polyol ester comprises molecules having more than one carbon-carbon double bond, self-metathesis may result in oligomerization or polymerization of the unsaturates in the starting material. For example, reaction sequence (III) depicts metathesis oligomerization of a representative species (e.g., an unsaturated polyol ester) having more than one carbon-carbon double bond. In reaction sequence (III), the self-metathesis reaction results in the formation of metathesis dimers, metathesis trimers, and metathesis tetramers. Although not shown, higher order oligomers such as metathesis pentamers, hexamers, heptamers, octamers, nonamers, decamers, and mixtures of two or more thereof, may also be formed. The number of metathesis repeating units or groups in the metathesized oil may range from 1 to about 100, or from 2 to about 50, or from 2 to about 30, or from 2 to about 10, or from 2 to about 4. The molecular weight of the metathesis dimer may be greater than the molecular weight of the unsaturated polyol ester from which the dimer is formed. Each of the bonded polyol ester molecules may be referred to as a "repeating unit or group." Typically, a metathesis trimer may be formed by the cross-metathesis of a metathesis dimer with an unsaturated polyol ester. Typically, a metathesis tetramer may be formed by the cross-metathesis of a metathesis trimer with an unsaturated polyol ester or formed by the cross-metathesis of two metathesis dimers.

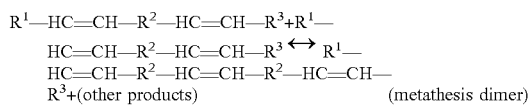
(metathesis dimer)

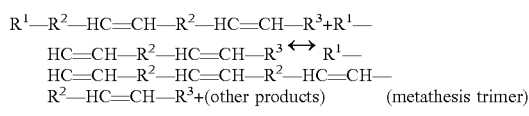
(metathesis trimer)

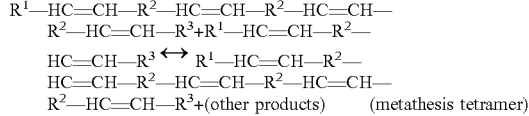
(metathesis tetramer)

where $R^1$, $R^2$, and $R^3$ are organic groups.

III

An unhydrogenated or partially hydrogenated polyol ester may be subjected to metathesis (self or cross). An exemplary self-metathesis reaction scheme is shown in FIG. 1. The reaction scheme shown in FIG. 1 highlights the reaction of the major fatty acid group component of the hydrogenation product composition (i.e., triacylglycerides having a monounsaturated fatty acid group). As shown in FIG. 1, a triglyceride having a monounsaturated fatty acid group is self-metathesized in the presence of a metathesis catalyst to form a metathesis product composition. Within FIG. 1, the R group designates a diglyceride. In FIG. 1, the reactant composition A comprises triglyceride having a monounsaturated fatty acid group. The resulting metathesized product composition includes, as major components, monounsaturated diacid esters in triglyceride form B, internal olefins C and monounsaturated fatty acid esters in triglyceride form D. Any one or more of the starting material A and each of the products shown, B, C and D, may be present as the cis or trans isomer. Unreacted starting material may also be present (not shown). As illustrated, the metathesized products, B, C and D may have overlapping chain lengths.

A concern when performing metathesis of natural oils in their triglyceride or other form may be the generation light co-products. Naturally occurring methylene interrupted cis, cis configuration may form cyclic compounds that may be present as volatile organic compounds (VOCs). Depending upon the identity and amount of the VOC, it may represent a yield loss and/or a hazardous emission. It may thus be desirable to reduce the formation of VOCs during the metathesis reaction. As the concentration of polyunsaturates is reduced, this in turn reduces the likelihood of generating such metathesis products as cyclohexadienes (e.g., 1,3-cyclohexadiene, 1,4-cyclohexadiene, and the like), which themselves can be VOCs and/or be converted to other VOCs, such as benzene. Thus, in some aspects, the metathesis process may reduce the generation of VOCs and/or control the identity of any yield loss that can result from the metathesis reaction.

In some aspects, then, the invention can provide methods wherein the occurrence of methylene interrupted cis-cis diene structures may be reduced in the metathesis reaction mixture. These structures may be converted to other structures by geometric isomerization, positional isomerization, and/or hydrogenation. In turn, these methods may reduce volatile co-product formation, e.g., in the form of cyclohexadiene.

An exemplary cross-metathesis reaction scheme is illustrated in FIG. 2. As shown in FIG. 2, a triglyceride having a monounsaturated fatty acid group is cross-metathesized with a short chain olefin (ethylene shown in figure), in the presence of a metathesis catalyst to form a metathesis product composition. The short chain olefins may include, for example, ethylene, propylene, 1-butene, 2-butene, isobutene, 1-pentene, 2-pentene, isopentene, 2-hexene, 3-hexene, and the like.

As shown in FIG. 2, the reactant composition E includes triglyceride having a monounsaturated fatty acid group and ethylene. The resulting metathesized product composition includes, as major components, monounsaturated fatty acid esters in triglyceride form having terminal double bonds F, as well as olefins with terminal double bonds G. Unreacted starting material can also be present, as well as products from some amount of self-metathesis (not shown in figure). The starting material and each of the products shown, E and F, may be present as the cis or trans isomer (except when ethylene is used in which case the product is a terminal olefin). As illustrated, the metathesized products, E and F, may have overlapping chain lengths. The chain lengths of the terminal monounsaturated fatty acid esters may be in the range from about 5 to about 17 carbons. In some aspects, the majority (e.g., 50% or more) of the terminal monounsaturated fatty acids may have chain lengths in the range of from about 9 to about 13 carbon atoms.

The metathesis process can be conducted under any conditions adequate to produce the desired metathesis products. For example, stoichiometry, atmosphere, solvent, temperature and pressure can be selected to produce a desired product and to minimize undesirable byproducts. The metathesis process may be conducted under an inert atmosphere. Similarly, if the olefin reagent is supplied as a gas, an inert gaseous diluent can be used. The inert atmosphere or inert gaseous diluent typically is an inert gas, meaning that the gas does not interact with the metathesis catalyst to substantially impede catalysis. For example, particular inert gases are selected from the group consisting of helium, neon, argon, nitrogen and combinations thereof.

Similarly, if a solvent is used, the solvent chosen may be selected to be substantially inert with respect to the metathesis catalyst. For example, substantially inert solvents include, without limitation, aromatic hydrocarbons, such as benzene, toluene, xylenes, etc.; halogenated aromatic hydrocarbons, such as chlorobenzene and dichlorobenzene; aliphatic solvents, including pentane, hexane, heptane, cyclohexane, etc.; and chlorinated alkanes, such as dichloromethane, chloroform, dichloroethane, etc.

In certain embodiments, a ligand may be added to the metathesis reaction mixture. In many embodiments using a ligand, the ligand is selected to be a molecule that stabilizes the catalyst, and may thus provide an increased turnover number for the catalyst. In some cases the ligand can alter reaction selectivity and product distribution. Examples of ligands that can be used include Lewis base ligands, such as, without limitation, trialkylphosphines, for example tricyclohexylphosphine and tributyl phosphine; triarylphosphines, such as triphenylphosphine; diarylalkylphosphines, such as, diphenylcyclohexylphosphine; pyridines, such as 2,6-dimethylpyridine, 2,4,6-trimethylpyridine; as well as other Lewis basic ligands, such as phosphine oxides and phosphinites. Additives may also be present during metathesis that increase catalyst lifetime.

Any useful amount of the selected metathesis catalyst can be used in the process. For example, the molar ratio of the unsaturated polyol ester to catalyst may range from about 5:1 to about 10,000,000:1, or from about 50:1 to 500,000:1.

The metathesis reaction temperature may be a rate-controlling variable where the temperature is selected to provide a desired product at an acceptable rate. The metathesis temperature may be greater than −40° C., may be greater than about −20° C., and is typically greater than about 0° C. or greater than about 20° C. Typically, the metathesis reaction temperature is less than about 150° C., typically less than about 120° C. An exemplary temperature range for the metathesis reaction may range from about 20° C. to about 120° C.

The metathesis reaction can be run under any desired pressure. Typically, it will be desirable to maintain a total pressure that is high enough to keep the cross-metathesis reagent in solution. Therefore, as the molecular weight of the cross-metathesis reagent increases, the lower pressure range typically decreases since the boiling point of the cross-metathesis reagent increases. The total pressure may be selected to be greater than about 10 kPa, in some embodiments greater than about 30 kPa, or greater than about 100 kPa. Typically, the reaction pressure is no more than about 7000 kPa, in some embodiments no more than about 3000 kPa. An exemplary pressure range for the metathesis reaction is from about 100 kPa to about 3000 kPa. In some embodiments, it may be desirable to conduct self-metathesis under vacuum conditions, for example, at low as about 0.1 kPa.

The metathesis reaction may be used to convert triglycerides having relatively long-chain fatty acid esters (e.g., $C_{16}$-$C_{22}$) to a product mixture comprising: linear alpha-olefins (e.g., $C_6$-$C_{12}$ alpha-olefins), for example, 1-octene, 1-decene, 1-dodecene, and the like; internal olefins (e.g., $C_{16}$-$C_{22}$ internal olefins), for example, 9-octadecene; di-olefins, for example, 1,4-octadiene, 1,4-decadiene, 1,4-dodecadiene, and the like; and reduced chain length triglycerides (e.g., $C_8$-$C_{14}$). The reaction may be a cross-metathesis reaction wherein the triglyceride and an olefin (e.g., ethylene, propylene, butene, etc.) are reacted in the presence of a metathesis catalyst to produce the desired product mix. The product mix may be referred to as a metathesized triglyceride.

A process for metathesizing a natural and treating the resulting metathesized natural oil is illustrated in FIG. 3. In this process, the metathesized natural oil is separated into olefins, and carboxylic acids and/or esters which may then undergo subsequent treatment. Referring to FIG. 3, natural oil reactant 12 may be reacted with itself, or optionally with another olefinic compound 14, in metathesis reactor 20 in the presence of a metathesis catalyst. The natural oil reactant 12 may undergo a self-metathesis reaction, or it may undergo a cross-metathesis reaction with the another olefinic compound 14. The natural oil reactant 12 may undergo both self- and cross-metathesis reactions in separate metathesis reactors. Multiple parallel or sequential metathesis reactions may be conducted. The self-metathesis and/or cross-metathesis reactions may be used to form a metathesized natural oil product 22. The metathesized natural oil product 22 may comprise one or more olefins 32 (e.g., 1-decene) and one or more carboxylic acids and/or esters (e.g., methyl 9-decenoate). The metathesized natural oil product 22 may undergo a separation process in separation unit 30 to form olefin stream 32, and carboxylic acid and/or ester stream 34. Separation unit 30 may comprise a distillation unit.

The olefins from 32 and/or olefins from downstream of 32 (e.g., 42, etc.) may be used as a source of olefin comonomers in forming the functionalized copolymer of the present invention. The carboxylic acids and/or esters from 34 and/or from downstream of 34 (e.g., 72, etc.) may be used as a source of the functionalized monomers of the present invention.

The use of branched short chained olefins in the metathesis reaction may provide for the formation of a metathesized natural oil product with branched olefins. These may be subsequently hydrogenated to form iso-paraffins. The branched short chain olefins may be useful for providing desired performance properties for middle distillate fuels such as jet fuels, kerosene, diesel fuel, and the like.

It may be possible to use a mixture of various linear or branched short chain olefins in the metathesis reaction to achieve a desired product distribution. For example, a mixture of butenes (e.g., 1-butene, 2-butene, and, optionally, isobutene) may be employed as the another olefinic compound. This may allow for the use of a low cost, commercially available feedstock instead of a purified source of one particular butene. These low cost butene feedstocks may be diluted with n-butane and/or isobutane.

Recycled streams from downstream separation units may be combined with the reactant 12 and, optionally, the another olefinic compound 14, in the metathesis reactor 20. For example, a low molecular weight (e.g., $C_2$-$C_6$) olefin stream 44 and bottoms (e.g., $C_{15}$+) olefin stream 46 from separation unit 40 may be recycled to the metathesis reactor 20.

The metathesized natural oil product 22 may flow through a flash vessel or flash drum (not shown in FIG. 3) operated under temperature and pressure conditions that may be used to target $C_2$ or $C_2$-$C_3$ olefin compounds as light ends. These compounds may be flashed off and removed. The light ends may be sent to another separation unit (now shown in FIG. 3), where the $C_2$ or $C_2$-$C_3$ olefin compounds may be further separated from higher molecular weight or heavier compounds that may have flashed off with the $C_2$ or $C_2$-$C_3$ olefin compounds. The heavier compounds may comprise, for example, $C_3$-$C_5$ olefin compounds. After separation, the $C_2$ or $C_2$-$C_3$ olefins may be used as the olefin comonomer of the present invention. Alternatively, these olefins may be used for other applications or as a fuel source. The bottoms stream from the flash vessel or flash drum may contain mostly $C_3$-$C_5$ olefin compounds which may be used as the olefin comonomer of the present invention, returned as a recycle stream to the metathesis reactor 20, or separated from the process and used for other applications or as a fuel source. The metathesized natural oil product 22 that does not flash in the flash vessel or flash drum may be advanced downstream to separation unit 30.

The metathesized natural oil product 22 may be treated in an adsorbent bed to facilitate the separation of the metathesized natural oil product 22 from the metathesis catalyst prior to entering the flash vessel or drum and/or prior to entering separation unit 30. The adsorbent may comprise a clay bed. The clay bed may adsorb the metathesis catalyst. After a filtration step, the metathesized natural oil product 22 may be sent to the flash vessel or flash drum and/or to the separation unit 30. Alternatively, the adsorbent may comprise a water soluble phosphine reagent such as trishydroxymethyl phosphine (THMP). The catalyst may be separated using the water soluble phosphine via liquid-liquid extraction. Alternatively, the metathesized natural oil product 22 may be reacted with a reagent to deactivate or to extract the catalyst.

In the separation unit 30, the metathesized natural oil product 22 may be separated into two or more product streams, these product streams comprising olefin stream 32, and carboxylic acid and/or ester stream 34. In an embodiment, a byproduct stream comprising desired olefins, and/or acids and/or esters may be removed in a side-stream from the separation unit 30. The separated olefins 32 may comprise hydrocarbons with carbon numbers up to, for example, about 24, or higher. The carboxylic acids and/or esters 34 may comprise one or more triglycerides. The olefins 32 may be separated or distilled overhead for processing into olefin compositions, while the carboxylic acids and/or esters 34 may be drawn into a bottoms stream. Based on the quality of the separation, it is possible for some lighter acids and/or esters to be carried into the olefin stream 32, and it is also possible for some heavier olefins to be carried into the acid and/or ester stream 34.

The olefins 32 may be collected and sold for any number of known uses and/or used as a source of the olefin comonomers in accordance with the present invention. The olefins 32 may be further processed in an olefin separation unit 40 and/or in separation unit 60.

The carboxylic acids and/or esters 34 may comprise one or more unsaturated carboxylic acids, and/or one or more unsaturated carboxylic esters. These may include glycerides and free fatty acids. The acids and/or esters 34 may be separated or distilled for further processing into various products and/or used as a source of functionalized monomers in accordance with the present invention. In an embodiment, further processing may target, for example, $C_5$-$C_{18}$ fatty acids and/or $C_5$-$C_{18}$ fatty acid esters. These may include fatty acid methyl esters, such as 9-decenoic acid (9DA) esters, 10-undecenoic acid (10UDA) esters, 9-dodecenoic acid (9DDA) esters and/or 9-octadecenoic (9ODA) esters; 9DA, 10UDA, 9DDA and/or 9ODA; and/or diesters of transesterified products; or mixtures of two or more thereof. Further processing may target, for example, the production of diacids, anhydrides, diesters, amides, imides, and the like. These may be used as the functionalized monomers in accordance with the present invention.

The olefins 32 may be further separated or distilled in the olefin separation unit 40. Light end olefins, which may comprise, for example, $C_2$-$C_9$ olefins, or $C_3$-$C_8$ olefins, may be distilled into an overhead stream 44. Heavier olefins (e.g., $C_{16}$+ olefins) in olefin bottoms stream 46 may be combined with the light end olefin stream 44 to assist in targeting a specific monomer composition. The light end olefins 44 may be recycled to the metathesis reactor 20 and/or purged from the system for further processing. The light end olefins 44 may be partially purged from the system and partially recycled to the metathesis reactor 20. The olefin bottoms stream 46 may be purged and/or recycled to the metathesis reactor 20 for further processing. The light end olefins 44 and/or olefin bottoms stream 46 may be used as the olefin comonomers of the present invention. A center-cut olefin stream 42 may be separated in the olefin distillation unit 40 and subjected to further processing. The center-cut olefins 42 may be used to target a selected olefin distribution for a specific end use. For example, the center cut stream 42 may comprise a $C_6$-$C_{24}$ olefin distribution which may be used as the olefin comonomers in accordance with the present invention. A $C_5$-$C_{15}$ olefin distribution may be targeted for further processing as a naphtha-type jet fuel. A $C_8$-$C_{16}$ distribution may be targeted for further processing into a kerosene-type jet fuel. A $C_8$-$C_{25}$ distribution may be targeted for further processing into a diesel fuel.

The olefins 32, 42, 44 and/or 46 may be oligomerized or polymerized to form poly-alpha-olefins (PAOs) and/or poly-internal-olefins (PIOs). The oligomerization or polymerization reaction may be conducted downstream of the separation unit 30 or downstream of the separation unit 40. Byproducts from the oligomerization or polymerization reactions may be recycled back to the metathesis reactor 20 for further processing.

The carboxylic acids and/or esters 34 from the separation unit 30 may be withdrawn as product stream 36 and processed further or sold for their own value. These acids and/or esters may be used as the functionalized monomers in accordance with the present invention. Based upon the quality of separation between olefins 32 and acids and/or esters 34, the acid and/or esters 34 may contain some heavier olefin components carried over with the functionalized olefins. The acids and/or esters 34 may be polymerized, copolymerized or functionalized in accordance with the invention. The acids and/or esters 34 may be further processed in a biorefinery or another chemical or fuel processing unit, thereby producing various products such as biofuels (e.g., biodiesel) or specialty chemicals. The acids and/or esters 34 may be partially withdrawn from the system and sold, with the remainder further processed in the biorefinery or chemical or fuel processing unit.

The carboxylic acid and/or ester stream 34 may be advanced to transesterification unit 70. In the transesterification unit 70, the esters may be transesterified with one or more alcohols 38 in the presence of a transesterification catalyst. The alcohol may comprise methanol, ethanol, propanol, butanol, pentanol, hexanol, heptanol, octanol, decanol, dodecanol, tetradecanol, hexadecanol, octadecanol, isopropanol, isobutanol, sec-butanol, tert-butanol, isopentanol, amyl alcohol, tert-pentanol, cyclopentanol, cyclohexanol, allyl alcohol, crotyl alcohol, methylvinyl carbinol, benzyl alcohol, alpha-phenylethyl alcohol, beta-phenylethyl alcohol, diphenylcarbinol, triphenylcarbinol, cinnamyl alcohol, or a mixture of two or more thereof. The transesterification reaction may be conducted at any suitable temperature, for example, in the range from about 60 to about 70° C., and at a suitable pressure, for example, atmospheric pressure. The transesterification catalyst may comprise a homogeneous sodium methoxide catalyst. Varying amounts of catalyst may be used in the reaction. The transesterification catalyst may be used at a concentration of about 0.5 to about 1% by weight based on the weight of the esters.

The transesterification reaction may be used to produce transesterified products 72, which may include saturated and/or unsaturated fatty acid methyl esters (FAME), glycerin, methanol, and/or free fatty acids. The transesterified products 72, or a fraction thereof, may be used as a middle distillate fuel such as biodiesel. The transesterified products 72 may comprise 9-decenoic acid (9DA) esters, 10-undecenoic acid (10UDA) esters, 9-dodecenoic acid (9DDA) esters, and/or 9-octadecenoic acid (9ODDA) esters. Examples of the 9DA esters, 10UDA esters, 9DDA esters, and 9ODDA esters may include methyl 9-decenoate ("9-DAME"), methyl 10-undecenoate ("10-UDAME"), methyl 9-dodecenoate ("9-DDAME"), methyl 9-octadecenoate ("9-ODDAME"), respectively. The esters may include ethyl-, n-propyl-, isopropyl-, n-butyl-, sec-butyl-, tert-butyl- and/or pentaerythritol esters of 9DA, 10UDA, 9DDA and/or 9ODDA, mixtures of two or more thereof, and the like. In the transesterification reaction, a 9DA moiety of a metathesized glyceride may be removed from the glycerol backbone to form a 9DA ester.

In an embodiment, glycerol may be used in the transesterification reaction with a glyceride stream. This reaction may be used to produce monoglycerides and/or diglycerides.

The transesterified products 72 from the transesterification unit 70 may be advanced to a liquid-liquid separation unit, wherein the transesterified products 72 (e.g., fatty acid esters, free fatty acids, and/or alcohols) may be separated from glycerin. In an embodiment, the glycerin byproduct stream may be further processed in a secondary separation unit, wherein the glycerin may be removed and any remaining alcohols may be recycled back to the transesterification unit 70 for further processing.

In an embodiment, the transesterified products 72 may be further processed in a water-washing unit. In this unit, the transesterified products may undergo a liquid-liquid extraction when washed with water. Excess alcohol, water, and glycerin may be removed from the transesterified products 72. In another embodiment, the water-washing step may be followed by a drying unit in which excess water may be removed from the desired mixture of esters which may be used as specialty chemicals. These specialty chemicals may include, for example, esters of 9DA, 10UDA, 9DDA and/or 9ODDA.

The transesterified products 72 from the transesterification unit 70 or specialty chemicals from the water-washing unit or drying unit may be advanced to ester distillation column 80 for further separation of various individual or groups of compounds. This separation may be used to provide for the separation of 9DA esters, 10UDA esters, 9DDA esters and/or 9ODDA esters. In an embodiment, 9DA ester 82 may be distilled or individually separated from the remaining mixture 84 of transesterified products or specialty chemicals. The 9DA ester 82 may be the lightest component in the transesterified product or specialty chemical stream, and may come out at the top of the ester distillation column 80. In an embodiment, the remaining mixture 84, or heavier components, of the transesterified products or specialty chemicals may be separated at the bottom end of the distillation column 80. This bottoms stream 84 may be used as a middle distillate fuel such as biodiesel.

The 9DA esters, 10UDA esters, 9DDA esters and/or 9ODDA esters may be further processed after the distillation step in the ester distillation column 80 and/or used as a source of the functionalized monomer in accordance with the present invention. In an embodiment, the 9DA ester, 10UDA ester, 9DDA ester and/or 9ODDA may undergo a hydrolysis reaction with water to form 9DA, 10UDA, 9DDA and/or 9ODDA.

In an embodiment, the fatty acid esters from the transesterified products 72 may be reacted with each other to form other specialty chemicals such as dimers.

Hydrogenation

The natural oil and/or natural oil derived unsaturated carboxylic acid and/or ester may be partially hydrogenated prior to undergoing a chemical reaction (e.g., a metathesis reaction). Also, the functionalized monomer and/or functionalized polymer derived from the functionalized monomer may be partially or fully hydrogenated to accommodate end use requirements.

Multiple unsaturated bonds within a polyunsaturated reactant provide multiple reaction sites. Multiple reaction sites may exponentially increase the chemical identity of the reaction products, which in turn may increase the complexity of the product composition. Multiple reaction sites within the reactants may also increase catalyst demand for the reaction. These factors may increase the overall complexity and inefficiency of the reaction process.

More efficient reaction processes that can reduce catalyst demand and reduce complexity of the reaction product compositions may be provided by partially hydrogenating polyunsaturated reactants in the starting material prior to conducting the reaction process. The partially hydrogenated reactant may then be subjected to the desired reaction process (e.g., a metathesis reaction process) to provide a desired product.

The fatty esters may be hydrolyzed to yield linear fatty acids having terminal carbon-carbon double bonds. In some embodiments, the linear fatty acids with terminal carbon-carbon double bonds are monounsaturated. In some embodiments, the terminal linear fatty acids have a chain length in the range of 3 to n carbon atoms (where n is the chain length of the partially hydrogenated composition which has a double bond at the 2 to (n−1) position after partial hydrogenation). In other embodiments, the terminal fatty acids have a chain length in the range of 5 to (n−1) carbon atoms (where n is the chain length of the partially hydrogenated composition which has a double bond at the 4 to (n−2) position after partial hydrogenation). In exemplary embodiments, the terminal fatty acids have a chain length in the range of about 5 to about 17 carbon atoms. In other aspects, the reaction (e.g., metathesis reaction) products are monounsaturated diesters having a chain length in the range of about 4 to (2n−2) carbon atoms (where n is the chain length of the partially hydrogenated composition, which has a double bond at the 2 to (n−1) position after partial hydrogenation). In other embodiments, the monounsaturated diesters have a chain length in the range of about 8 to (2n−4) carbon atoms (where n is the chain length of the partially hydrogenated composition which has a double bond at the 4 to (n−2) position after partial hydrogenation). In exemplary embodiments, the monounsaturated diesters may have a chain length in the range of about 8 to about 32 carbon atoms.

The polyunsaturated starting materials may be partially hydrogenated under conditions to optimize the starting composition for the chemical reactions. Partial hydrogenation may be used to reduce the number of double bonds that are available to participate in the reaction.

Partial hydrogenation can also alter the fatty acid composition of the polyunsaturated fatty acid starting materials or reactants. Positional and/or geometrical isomerization can occur during hydrogenation, thus changing the location and/or orientation of the double bonds. These reactions may occur concurrently. In the geometrical isomers, the cis bonds originally present in naturally occurring soybean oil may be converted in part to the trans form.

Partial hydrogenation can be conducted according to any known method for hydrogenating double bond-containing compounds such as vegetable oils. Catalysts for hydrogenation are known and can be homogeneous or heterogeneous (e.g., present in a different phase, typically the solid phase, than the substrate). A useful hydrogenation catalyst is nickel. Other useful hydrogenation catalysts include copper, palladium, platinum, molybdenum, iron, ruthenium, osmium, rhodium, iridium, zinc or cobalt. Combinations of catalysts can also be used. Bimetallic catalysts can be used, for example, palladium-copper, palladium-lead, nickel-chromite.

The metal catalysts can be utilized with promoters that may or may not be other metals. Illustrative metal catalysts with promoter include, for example, nickel with sulfur or copper as promoter; copper with chromium or zinc as promoter; zinc with chromium as promoter; or palladium on carbon with silver or bismuth as promoter.

The polyunsaturated starting composition may be partially hydrogenated in the presence of a nickel catalyst that has been chemically reduced with hydrogen to an active state. Commercial examples of supported nickel hydrogenation catalysts may include those available under the trade designations "NYSOFACT," "NYSOSEL," and "NI 5248 D" (from Engelhard Corporation, Iselin, N.J.). Additional supported nickel hydrogenation catalysts may include those commercially available under the trade designations "PRICAT 9910," "PRICAT 9920," "PRICAT 9908" and "PRICAT 9936" (from Johnson Matthey Catalysts, Ward Hill, Mass.).

The metal catalysts can be in the form of fine dispersions in a hydrogenation reaction (slurry phase environment). For example, in some embodiments, the particles of supported nickel catalyst may be dispersed in a protective medium comprising hardened triacylglyceride, edible oil, or tallow. In an exemplary embodiment, the supported nickel catalyst may be dispersed in the protective medium at a level of about 22 wt % nickel.

The catalysts may be impregnated on solid supports. Some useful supports include carbon, silica, alumina, magnesia, titania, and zirconia, for example. Illustrative support embodiments include, for example, palladium, platinum, rhodium or ruthenium on carbon or alumina support; nickel on magnesia, alumina or zirconia support; palladium on barium sulfate ($BaSO_4$) support; or copper on silica support.

The catalysts may be supported nickel or sponge nickel type catalysts. The hydrogenation catalyst may comprise nickel that has been chemically reduced with hydrogen to an active state (i.e., reduced nickel) provided on a support. The support may comprise porous silica (e.g., kieselguhr, infusorial, diatomaceous, or siliceous earth) or alumina. The catalysts may be characterized by a high nickel surface area per gram of nickel.

The supported nickel catalysts may be of the type reported in U.S. Pat. No. 3,351,566. These catalysts comprise solid nickel-silica having a stabilized high nickel surface area of 45 to 60 sq. meters per gram and a total surface area of 225 to 300 sq. meters per gram. The catalysts are prepared by precipitating the nickel and silicate ions from solution such as nickel hydrosilicate onto porous silica particles in such proportions that the activated catalyst contains 25 wt % to 50 wt % nickel and a total silica content of 30 wt % to 90 wt %. The particles are activated by calcining in air at 600° F. to 900° F. (315.5° C. to 482.2° C.), then reducing with hydrogen.

Useful catalysts having a high nickel content may include those described in EP 0 168 091. A soluble aluminum compound may be added to the slurry of the precipitated nickel compound while the precipitate is maturing. After reduction of the resultant catalyst precursor, the reduced catalyst typically has a nickel surface area on the order of 90 to 150 sq. meters per gram of total nickel. The catalysts may have a nickel/aluminum atomic ratio in the range of 2 to 10 and have a total nickel content of more than about 66% by weight.

Useful high activity nickel/alumina/silica catalysts may include those described in EP 0 167 201. The reduced catalysts may have a high nickel surface area per gram of total nickel in the catalyst.

Useful nickel/silica hydrogenation catalysts may include those described in U.S. Pat. No. 6,846,772. The catalysts may be produced by heating a slurry of particulate silica (e.g., kieselguhr) in an aqueous nickel amine carbonate solution for a total period of at least 200 minutes at a pH above 7.5, followed by filtration, washing, drying, and optionally calcination. The nickel/silica hydrogenation catalysts are reported to have improved filtration properties. U.S. Pat. No. 4,490,480 reports high surface area nickel/alumina hydrogenation catalysts having a total nickel content of 5% to 40% by weight.

The amount of hydrogenation catalysts may be selected in view of a number of factors including, for example, the type of hydrogenation catalyst(s) used, the degree of unsaturation in the material to be hydrogenated, the desired rate of hydrogenation, the desired degree of hydrogenation (for example, as measured by the IV, see below), the purity of the reagent and the $H_2$ gas pressure. The hydrogenation catalyst may be used in an amount of about 10 wt % or less, for example about 5 wt % or less, about 1 wt % or less, or about 0.5 wt % or less.

Hydrogenation may be carried out in a batch, continuous or semi-continuous process. In a representative batch process, a vacuum is pulled on the headspace of a stirred reaction vessel and the reaction vessel is charged with the material to be hydrogenated (for example, RBD soybean oil). The material is then heated to a desired temperature, typically in the range of about 50° C. to about 350° C., or about 100° C. to about 300° C., or about 150° C. to about 250° C. The desired temperature can vary, for example, with hydrogen gas pressure. Typically, a higher gas pressure will require a lower temperature. In a separate container, the hydrogenation catalyst is weighed into a mixing vessel and is slurried in a small amount of the material to be hydrogenated (for example, RBD soybean oil). When the material to be hydrogenated reaches the desired temperature (typically a temperature below a target hydrogenation temperature), the slurry of hydrogenation catalyst may be added to the reaction vessel. Hydrogen may then be pumped into the reaction vessel to achieve a desired pressure of $H_2$ gas. Typically, the $H_2$ gas pressure ranges from about 15 psig (103.4 kilopascals) to about 3000 psig (20684.3 kilopascals), for example, about psig (103.4 kilopascals) to about 90 psig (620.5 kilopascals). As the gas pressure increases, more specialized high-pressure processing equipment can be required. Under these conditions the hydrogenation reaction may begin and the temperature may be allowed to increase to the desired hydrogenation temperature (for example, about 120° C. to about 200° C.), where it may be maintained by cooling the reaction mass, for example, with cooling coils. When the desired degree of hydrogenation has been reached, the reaction mass may be cooled to the desired filtration temperature.

The polyunsaturated starting materials or reactants may be subjected to electrocatalytic hydrogenation to achieve a partially hydrogenated product. Various electrocatalytic hydrogenation processes can be utilized. For example, low temperature electrocatalytic hydrogenation that uses an electrically conducting catalyst such as Raney Nickel or Platinum black as a cathode are described in Yusem and Pintauro, *J. Appl. Electrochem.* 1997, 27, 1157-71. Another system that utilizes a solid polymer electrolyte reactor composed of a ruthenium oxide ($RuO_2$) powder anode and a platinum-black (Pt-black) or palladium-black (Pd-black) powder cathode that are hot-pressed as thin films onto a Nafion cation exchange membrane is described in An et al. *J. Am. Oil Chem. Soc.* 1998, 75, 917-25. A further system that involves electrochemical hydrogenation using a hydrogen transfer agent of formic acid and a nickel catalyst is described in Mondal and Lalvani, *J. Am. Oil Chem. Soc.* 2003, 80, 1135-41.

Hydrogenation may be performed under supercritical fluid state, as described in U.S. Pat. Nos. 5,962,711 and 6,265,596.

Hydrogenation may be conducted in a manner to promote selectivity toward monounsaturated fatty acid groups, i.e., fatty acid groups containing a single carbon-carbon double bond. Selectivity is understood here as the tendency of the hydrogenation process to hydrogenate polyunsaturated fatty acid groups over monounsaturated fatty acid groups. This form of selectivity is often called preferential selectivity, or selective hydrogenation.

The level of selectivity of hydrogenation may be influenced by the nature of the catalyst, the reaction conditions, and the presence of impurities. Generally speaking, catalysts having a high selectivity for one fat or oil reactant may also have a high selectivity in other fat or oil reactants. As used herein, "selective hydrogenation" refers to hydrogenation conditions (e.g., selection of catalyst, reaction conditions such as temperature, rate of heating and/or cooling, catalyst concentration, hydrogen availability, and the like) that are chosen to promote hydrogenation of polyunsaturated compounds to monounsaturated compounds. Using soybean oil as an example, the selectivity of the hydrogenation process may be determined by examining the content of the various $C_{18}$ fatty acids and their ratios. Hydrogenation on a macro scale may be regarded as a stepwise process:

$$C18:3 \xrightarrow{k_3} C18:2 \xrightarrow{k_2} C18:1 \xrightarrow{k_1} C18:0$$

The following selectivity ratios (SR) may be defined: $SRI=k_2/k_3$; $SRII=k_3/k_2$; $SRIII=k_2/k_1$. Characteristics of the starting oil and the hydrogenated product may be utilized to determine the selectivity ratio (SR) for each acid. This may be done with the assistance of gas-liquid chromatography. For example, polyol esters may be saponified to yield free fatty acids (FFA) by reacting with NaOH/MeOH. The FFAs may then be methylated into fatty acid methyl esters (FAMEs) using $BF_3$/MeOH as the acid catalyst and MeOH as the derivatization reagent. The resulting FAMEs may then be separated using a gas-liquid chromatograph and are detected with a flame ionization detector (GC/FID). An internal standard may be used to determine the weight percent of the fatty esters. The rate constants may be calculated by either the use of a computer or graph.

In addition to the selectivity ratios, the following individual reaction rate constants may be described within the hydrogenation reaction: $k_3$ (C18:3 to C18:2), $k_2$ (C18:2 to C18:1), and $k_1$ (C18:1 to C18:0). In some aspects, hydrogenation under conditions sufficient to provide a selectivity or preference for $k_2$ and/or $k_3$ (i.e., $k_2$ and/or $k_3$ are greater than $k_1$) may be used. In these aspects, hydrogenation may be conducted to reduce levels of polyunsaturated compounds within the starting material or reactants, while minimizing the generation of saturated compounds.

In one illustrative embodiment, selective hydrogenation can promote hydrogenation of polyunsaturated fatty acid groups toward monounsaturated fatty acid groups (having one carbon-carbon double bond), for example, tri- or diunsaturated fatty acid groups to monounsaturated groups. In some embodiments, the invention involves selective hydrogenation of a polyunsaturated polyol ester (such as soybean oil) to a hydrogenation product having a minimum of about 65% monounsaturated fatty acid groups, or a minimum of about 75% monounsaturated fatty acid groups, or a minimum of about 85% monounsaturated fatty acid groups. The target minimum percentage of monounsaturated fatty acid groups may depend upon the starting composition (i.e., the polyunsaturated polyol ester), since each polyol ester may have different starting levels of saturates, monounsaturates and polyunsaturates. It is also understood that high oleic oils may have about 80% or more oleic acid. In such cases, very little hydrogenation may be required to reduce polyunsaturates.

In one illustrative embodiment, selective hydrogenation can promote hydrogenation of polyunsaturated fatty acid groups in soybean oil toward C18:1, for example, C18:2 to C18:1, and/or C18:3 to C18:2. Selective hydrogenation of a polyunsaturated composition (e.g., a polyol ester such as soybean oil) to a hydrogenation product may have reduced polyunsaturated fatty acid group content, while minimizing complete hydrogenation to saturated fatty acid groups (C18:0).

Selective hydrogenation may be accomplished by controlling reaction conditions (such as temperature, rate of heating and/or cooling, hydrogen availability, and catalyst concentration), and/or by selection of catalyst. For some hydrogenation catalysts, increased temperature or catalyst concentration may result in an increased selectivity for hydrogenating C18:2 over C18:1. In some aspects, when a nickel-supported catalyst is utilized, pressure and/or temperature may be modified to provide selectivity. Illustrative lower pressures may include pressures of 50 psi (344.7 kilopascals) or less. Lower pressures can be combined, in some embodiments, with increased temperature to promote selectivity. Illustrative conditions in accordance with these embodiments include temperatures in the range of 180° C. to 220° C., pressure of about 5 psi (34.47 kilopascals), with nickel catalyst present in an amount of about 0.5 wt %. See, for example, Allen et al. "*Isomerization During Hydrogenation. Ill. Linoleic Acid,*" *JAOC* August 1956.

In some aspects, selectivity may be enhanced by diminishing the availability of hydrogen. For example, reduced reaction pressure and/or agitation rate can diminish hydrogen supply for the reaction.

Selective hydrogenation may be accomplished by selection of the catalyst. One illustrative catalyst that can enhance selectivity is palladium. Palladium reaction conditions for sunflower seed oil may include low temperatures (e.g., 40° C.) in ethanol solvent, with catalyst present in an amount of about 1 wt %. Palladium may be provided on a variety of different supports known for hydrogenation processes. See, for example, Bendaoud Nohaira et al., *Palladium supported catalysts for the selective hydrogenation of sunflower oil,"* J. of Molecular Catalysts A: Chemical 229 (2005) 117-126, Nov. 20, 2004.

Optionally, additives such as lead or copper may be included to increase selectivity. When catalysts containing palladium, nickel or cobalt are used, additives such as amines can be used.

Useful selective hydrogenation conditions are described, for example, in U.S. Pat. Nos. 5,962,711 and 6,265,596. Hydrogenation may be performed by mixing the substrate (polyunsaturated polyol ester), hydrogen gas and solvent, and bringing the whole mixture into a super-critical or near-critical state. This substantially homogeneous super-critical or near-critical solution is led over the catalyst, whereby the reaction products formed (i.e., the hydrogenated substrates) will also be a part of the substantially homogeneous super-critical or near-critical solution.

Reaction conditions for supercritical hydrogenation may occur over a wide experimental range, and this range can be described as follows: temperature (in the range of about 0° C. to about 250° C., or about 20° C. to about 200° C.); pressure (in the range of about 1000 to about 35,000 kilopascals, or about 2000 to about 20,000 kilopascals); reaction time (up to about 10 minutes, or in the range of about 1 second to about 1 minute); and solvent concentration (in the range of about 30 wt % to about 99.9 wt %, or about 40 wt % to about 99 wt %). Useful solvents include, for example, ethane, propane, butane, $CO_2$, dimethyl ether, "freons," $N_2O$, $N_2$, $NH_3$, or mixtures of these. The catalyst may be selected according to the reaction to be carried out; any useful catalyst for hydrogenation can be selected. Concentration of hydrogen gas ($H_2$) can be up to 3 wt %, or in the range of about 0.001 wt % to about 1 wt %. Concentration of substrate (polyunsaturated polyol ester) in the reaction mixture can be in the range of about 0.1 wt % to about 70 wt %, or about 1 wt % to about 60 wt %. A continuous reactor can be used to conduct the hydrogenation reaction, such as described in U.S. Pat. Nos. 5,962,711 and 6,265,596.

The content of the starting material may influence the selectivity. Various substances that are naturally occurring in fats and oils may influence the selectivity of hydrogenation. For example, sulfur is known to be an irreversible surface poison for nickel catalysts. Other compounds that may inhibit catalyst activity include phosphatides, nitrogen and halogen derivatives. As a result, a refining step to remove substances that may have a net negative impact on the hydrogenation process may be used. This, in turn, may increase selectivity.

Products of the partial hydrogenation reaction may include one or more identifiable properties and/or compounds. Products formed from polyunsaturated compositions may include characteristic monounsaturated fatty acid groups in an acid profile and may contain minor amounts of polyunsaturated fatty acid groups. In some aspects, the acid profile comprises polyunsaturated fatty acid groups in an amount of about 1 wt % or less. In some aspects, the starting material may be soybean oil, and the acid profile of the hydrogenation product may comprise a majority of monounsaturated fatty acid groups having a carbon-carbon double bond in the $C_4$ to $C_{16}$ position on the fatty acid or ester. More generally speaking, the carbon-carbon double bond may be located on the fatty acid or ester in the $C_2$ to $C(n-1)$ position, where n is the chain length of the fatty acid or ester. The carbon-carbon double bond may be located on the fatty acid or ester in the $C_4$ to $C(n-2)$, where n is the chain length of the fatty acid or ester. Typically, n may range from about 4 to about 30, or from about 4 to about 22.

When the starting material is derived from soybean oil, the acid profile of the partial hydrogenation product composition may comprise saturated fatty acid groups in an amount that is slightly higher than the starting concentration of saturated fatty acid groups in the starting material (i.e., unhydrogenated polyunsaturated polyol ester). The acid profile of the partial hydrogenation product composition may comprise saturated fatty acid groups in an amount of about 0.5 wt % to about 10 wt % higher than the concentration of saturated fatty acid groups in the starting material (polyunsaturated polyol ester starting material). The acid profile of the partial hydrogenation product composition may comprise saturated fatty acid groups in an amount of about 0.5 wt % to about 6 wt % higher than the concentration of saturated fatty acid groups in the starting material. It is understood that partial hydrogenation may result in generation of some additional saturated fatty acid groups. The generation of such additional saturated fatty acid groups may be controlled through selectivity.

As one example of a partial hydrogenation product composition, when the starting material comprises soybean oil, a partial hydrogenation product composition may include saturated fatty acid groups in an amount of about 30 wt % or less, or about 25 wt % or less, or about 20 wt % or less. The acid profile may comprise saturated fatty acid groups in an amount in the range of about 15 wt % to about 20 wt %. For soybean oil, illustrative saturated fatty acid groups may include stearic and palmitic acids. The relative amount and identity of the saturated fatty acids within the partial hydrogenated product composition may vary, depending upon such factors as the starting material (polyunsaturated polyol ester), reaction conditions (including catalyst, temperature, pressure, and other factors impacting selectivity of hydrogenation), and positional isomerization. A representative example of a hydrogenation product from selective hydrogenation of soybean oil (SBO) is shown in the table below.

| Percentages of Octadecenoates from Partially Hydrogenated Soybean Oil | |
|---|---|
| Relative Percent | Proposed C18:1 Compounds |
| 0.09 | C18:1,4t |
| 0.23 | C18:1,5t |
| 6.01 | C18:1,6-8t |
| 5.88 | C18:1,9t |
| 9.75 | C18:1,10t |
| 8.64 | C18:1,11t |
| 4.89 | C18:1,12t |
| 6.62 | C18:1,13t + 14t (C18:1,6-8c) |
| 14.00 | C18:1,9c (Oleic) (C18:1,14-16t) |
| 3.64 | C18:1,10c (C18:1,15t) |
| 3.00 | C18:1,11c |
| 4.47 | C18:1,12c |

-continued

Percentages of Octadecenoates from Partially Hydrogenated Soybean Oil

| Relative Percent | Proposed C18:1 Compounds |
|---|---|
| 1.02 | C18:1,13c |
| 1.16 | C18:1,14c (C18:1,16t) |

Within the above table, isomers are indicated as trans ("t") or cis ("c"), with the position of the double bond immediately preceding the isomer designation. Thus, "4t" is a trans isomer with the double bond at the C4 position within the carbon chain. Species in parenthesis denote minor products that may be present with similar elution times.

The acid profile of the partial hydrogenation product composition from soybean oil may comprise at least about 65 wt % monounsaturated fatty acid groups. The acid profile of the partial hydrogenation product composition may comprise at least about 70 wt %, or at least about 75 wt %, or at least about 80 wt %, or at least about 85 wt % monounsaturated fatty acid groups. The monounsaturated fatty acid groups may include the carbon-carbon double bond at any position from $C_2$ to $C_{16}$. Using soybean oil as an example, the monounsaturated fatty acid groups of the fatty acid profile may include the following:

octadec-2-enoic acid (—OOCCH=CH(CH$_2$)$_{14}$CH$_3$),
octadec-3-enoic acid (—OOC(CH$_2$)CH=CH(CH$_2$)$_{13}$CH$_3$),
octadec-4-enoic acid (—OOC(CH$_2$)$_2$CH=CH(CH$_2$)$_{12}$CH$_3$),
octadec-5-enoic acid (—OOC(CH$_2$)$_3$CH=CH(CH$_2$)$_{11}$CH$_3$),
octadec-6-enoic acid (—OOC(CH$_2$)$_4$CH=CH(CH$_2$)$_{10}$CH$_3$),
octadec-7-enoic acid (—OOC(CH$_2$)$_5$CH=CH(CH$_2$)$_9$CH$_3$),
octadec-8-enoic acid (—OOC(CH$_2$)$_6$CH=CH(CH$_2$)$_8$CH$_3$),
octadec-9-enoic acid (—OOC(CH$_2$)$_7$CH=CH(CH$_2$)$_7$CH$_3$),
octadec-10-enoic acid (—OOC(CH$_2$)$_8$CH=CH(CH$_2$)$_6$CH$_3$),
octadec-11-enoic acid (—OOC(CH$_2$)$_9$CH=CH(CH$_2$)$_5$CH$_3$),
octadec-12-enoic acid (—OOC(CH$_2$)$_{10}$CH=CH(CH$_2$)$_4$CH$_3$),
octadec-13-enoic acid (—OOC(CH$_2$)$_{11}$CH=CH(CH$_2$)$_3$CH$_3$),
octadec-14-enoic acid (—OOC(CH$_2$)$_{12}$H=CH(CH$_2$)$_2$CH$_3$),
octadec-15-enoic acid (—OOC(CH$_2$)$_{13}$CH=CH(CH$_2$)$_1$CH$_3$),
octadec-16-enoic acid (—OOC(CH$_2$)$_{14}$CH=CHCH$_3$), and For each monounsaturated fatty acid, the fatty acid can be the cis or trans isomer.

An objective of selective hydrogenation may be the reduction in the amount of polyunsaturated fatty acid groups of the polyunsaturated composition (e.g., polyunsaturated polyol ester). The hydrogenation product composition may have a polyunsaturated fatty acid group content of about 10 wt % or less, based upon total fatty acid content in the composition. Particularly with respect to the hydrogenation product that is to be subjected to self-metathesis, hydrogenation may be performed to drive down the concentration of polyunsaturated fatty acid groups even lower than about 5 wt %, for example to concentrations of about 1 wt % or less, or about 0.75 wt % or less, or about 0.5 wt % or less.

The hydrogenation product composition thus may comprise a reduced polyunsaturate content relative to the polyunsaturated starting material. The hydrogenation product composition may comprise polyunsaturated fatty acid groups in an amount of about 1 wt % or less; saturated fatty acid groups in an amount in the range of about 30 wt % or less, or about 25 wt % or less, or about 20 wt % or less; and monounsaturated fatty acid groups comprising the balance of the mixture, for example, about 65 wt % or more, or about 70 wt % or more, or about 75 wt % or more, or about 80 wt % or more, or about 85 wt % or more. This product composition is understood to be illustrative for soybean oil, and it is understood that the relative amounts of each level of saturated, monounsaturated and polyunsaturated components may vary depending upon such factors as the starting material (e.g., polyunsaturated polyol ester), the hydrogenation catalyst selected, the hydrogenation reaction conditions, and the like factors described herein.

It may be desirable to maximize the concentration of monounsaturated fatty acid groups in the hydrogenation product composition. In many embodiments, the monounsaturated fatty acid groups may comprise monounsaturated fatty acid groups having the carbon-carbon double bond in the $C_4$ to $C_{16}$ position within the carbon chain.

The hydrogenation product composition thus may comprise a partially hydrogenated polyol ester. As mentioned previously, in addition to effecting a reduction of unsaturation of the polyol ester, partial hydrogenation can also cause geometric and positional isomers to be formed. A goal of selective hydrogenation may be reduction in the amount of polyunsaturation in the polyol esters.

The hydrogenation product composition may also be characterized as having an iodine number within a desired range. The iodine number is a measure of the degree of unsaturation of a compound. When used in reference to an unsaturated material, such as an unsaturated polyol ester, the iodine number is a measure of the unsaturation, or the number of carbon-carbon double bonds, of that compound or mixture.

Generally speaking, the iodine number may range from about 8 to about 180 in naturally-occurring seed oils, and from about 90 to about 210 in naturally-occurring marine oils. Illustrative iodine numbers for some natural oils are the following:

| Oil | Iodine Number |
|---|---|
| soy | 125-138 |
| canola | 110-115 |
| palm | 45-56 |
| rapeseed | 97-110 |
| sunflower seed | 122-139 |
| fish | 115-210 |

At complete hydrogenation of oils or fats, all double bonds would be hydrogenated and the iodine number would therefore be zero or near zero. For partially hydrogenated triglycerides the iodine number may be about 90 or lower, or about 85 or lower, or about 80 or lower, or about 75 or lower. The iodine number target may depend upon such factors as the initial iodine number, the content of the monounsaturates in the starting material, the selectivity of the hydrogenation catalyst, the economic optimum level of unsaturation, and the like. An optimum partial hydrogenation would leave only the saturates that were initially present in the polyunsaturated polyol ester starting material and react all of the polyunsaturates. For example, a triolein oil would have an iodine number of about 86. Soybean oil starts with an iodine number of around 130 with a saturates content of about 15%. An optimum partial hydrogenation product may have an iodine number of about 73 and would maintain the 15% level of saturates. Canola oil has an initial iodine number of about 113 and 7% saturates; an optimum partial hydrogenation product may have an iodine number of about 80, while maintaining the 7% saturate level. The balance between additional saturate production and allowable polyunsaturate content may depend upon such factors as product quality parameters, yield costs, catalyst costs, and the like. If catalyst costs dominate, then some saturate production may be tolerable. If yield is critical, then some remaining polyunsaturates may be tolerable. If the formation of cyclic byproducts is unacceptable, then it may be acceptable to drive polyunsaturate levels to near zero.

The iodine number may represent a hydrogenation product composition wherein a certain percentage of double bonds have reacted, on a molar basis, based upon the starting iodine number of the polyunsaturated composition. For example, soybean oil with an iodine number of about 130 may be used as the starting material for the metathesis reaction process.

After partial hydrogenation, the hydrogenation catalyst may be removed from the partial hydrogenated product using known techniques, for example, by filtration. The hydrogenation catalyst may be removed using a plate and frame filter such as those commercially available from Sparkle Filters, Inc., Conroe, Tex. The filtration may be performed with the assistance of pressure or a vacuum. In order to improve filtering performance, a filter aid can optionally be used. A filter aid can be added to the hydrogenated product directly or it can be applied to the filter. Representative examples of filtering aids include diatomaceous earth, silica, alumina and carbon. Typically, the filtering aid is used in an amount of about 10 wt % or less, for example, about 5 wt % or less, or about 1 wt % or less. Other filtering techniques and filtering aids can also be employed to remove the used hydrogenation catalyst. In other embodiments, the hydrogenation catalyst is removed by using centrifugation followed by decantation of the product.

Partial hydrogenation of a polyunsaturated composition may impart one or more desirable properties to the partially hydrogenated composition and, consequently, to chemical (e.g., metathesis) processes performed on the partially hydrogenated composition. For example, partial hydrogenation may be used to decrease the amount of polyunsaturated fatty acid groups in the composition, thereby reducing unneeded sites of reaction for a catalyst. This, in turn, may reduce catalyst demand. Another benefit may be seen in the final product composition. Because less polyunsaturated fatty acid groups are present in the reaction mixture prior to the reaction, a more predictable product composition may be provided. For example, the carbon chain length and double bond position of products may be predicted, based upon fatty acid composition and catalyst utilized. This, in turn, may reduce the purification requirements for the product composition.

The Metathesis Catalyst

The metathesis reaction may be conducted in the presence of a catalytically effective amount of a metathesis catalyst. The term "metathesis catalyst" includes any catalyst or catalyst system which catalyzes the metathesis reaction.

The metathesis catalyst may be used, alone or in combination with one or more additional catalysts. Exemplary metathesis catalysts may include metal carbene catalysts based upon transition metals, for example, ruthenium, molybdenum, osmium, chromium, rhenium, and/or tungsten. The metathesis catalyst may be a metal complex having the structure of the following formula (I)

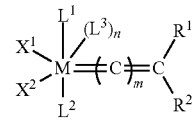

in which the various substituents are as follows:

M is ruthenium, molybdenum, osmium, chromium, rhenium, and/or tungsten.

$L^1$, $L^2$ and $L^3$ are neutral electron donor ligands;

n is 0 or 1, such that $L^3$ may or may not be present;

m is 0, 1, or 2;

$X^1$ and $X^2$ are anionic ligands; and $R^1$ and $R^2$ are independently selected from hydrogen, hydrocarbyl, substituted hydrocarbyl, heteroatom-containing hydrocarbyl, substituted heteroatom-containing hydrocarbyl, and functional groups, wherein any two or more of $X^1$, $X^2$, $L^1$, $L^2$, $L^3$, $R^1$, and $R^2$ can be taken together to form a cyclic group, and further wherein any one or more of $X^1$, $X^2$, $L^1$, $L^2$, $L^3$, $R^1$, and $R^2$ may be attached to a support.

The catalysts may contain Ru, W and/or Mo, with Ru being especially advantageous.

Numerous embodiments of the catalysts useful in the reactions of the disclosure are described in more detail infra. For the sake of convenience, the catalysts are described in groups, but it should be emphasized that these groups are not meant to be limiting in any way. That is, any of the catalysts useful in the disclosure may fit the description of more than one of the groups described herein.

A first group of catalysts, which may be referred to as $1^{st}$ Generation Grubbs-type catalysts, have the structure of formula (I). For the first group of catalysts, M and m are as described above, and n, $X^1$, $X^2$, $L^1$, $L^2$, $L^3$, $R^1$, and $R^2$ are described as follows.

For the first group of catalysts, n may be 0, and $L^1$ and $L^2$ may independently be phosphine, sulfonated phosphine, phosphite, phosphinite, phosphonite, arsine, stibine, ether, amine, amide, imine, sulfoxide, carboxyl, nitrosyl, pyridine, substituted pyridine, imidazole, substituted imidazole, pyrazine, and/or thioether. Exemplary ligands include trisubstituted phosphines.

$X^1$ and $X^2$ may be anionic ligands, and may be the same or different, or may be linked together to form a cyclic group which may be a five- to eight-membered ring. $X^1$ and $X^2$ may each be independently hydrogen, halide, or one of the following groups: $C_1$-$C_{20}$ alkyl, $C_5$-$C_{24}$ aryl, $C_1$-$C_{20}$ alkoxy, $C_5$-$C_{24}$ aryloxy, $C_2$-$C_{20}$ alkoxycarbonyl, $C_6$-$C_{24}$ aryloxycarbonyl, $C_2$-$C_{24}$ acyl, $C_2$-$C_{24}$ acyloxy, $C_1$-$C_{20}$ alkylsulfonato, $C_5$-$C_{24}$ arylsulfonato, $C_1$-$C_{20}$ alkylsulfanyl, $C_5$-$C_{24}$ arylsulfanyl, $C_1$-$C_{20}$ alkylsulfinyl, or $C_5$-$C_{24}$ arylsulfinyl. $X^1$ and $X^2$ may be substituted with one or more moieties selected from $C_1$-$C_{12}$ alkyl, $C_1$-$C_{12}$ alkoxy, $C_5$-$C_{24}$ aryl, and halide, which may, in turn, with the exception of halide, be further substituted with one or more groups selected from halide, $C_1$-$C_6$ alkyl, $C_1$-$C_6$ alkoxy, and phenyl. $X^1$ and $X^2$ may be halide, benzoate, $C_2$-$C_6$ acyl, $C_2$-$C_6$ alkoxycarbonyl, $C_1$-$C_6$ alkyl, phenoxy, $C_1$-$C_6$ alkoxy, $C_1$-$C_6$ alkylsulfanyl, aryl, or $C_1$-$C_6$ alkylsulfonyl. $X^1$ and $X^2$ may each be halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, or trifluoromethane-sulfonate. $X^1$ and $X^2$ may each be chloride.

$R^1$ and $R^2$ may independently be selected from hydrogen, hydrocarbyl (e.g., $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), substituted hydrocarbyl (e.g., substituted $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), heteroatom-containing hydrocarbyl (e.g., heteroatom-containing $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), and substituted heteroatom-containing hydrocarbyl (e.g., substituted heteroatom-containing $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, $C_6$-$C_{24}$ aralkyl, etc.), and functional groups. $R^1$ and $R^2$ may also be linked to form a cyclic group, which may be aliphatic or aromatic, and may contain substituents and/or heteroatoms. Generally, such a cyclic group may contain 4 to about 12, or 5, 6, 7, or 8 ring atoms.

$R^1$ may be hydrogen and $R^2$ may be selected from $C_1$-$C_{20}$ alkyl, $C_2$-$C_{20}$ alkenyl, $C_5$-$C_{24}$ aryl, $C_1$-$C_6$ alkyl, $C_2$-$C_6$ alkenyl, or $C_5$-$C_{14}$ aryl. $R^2$ may be phenyl, vinyl, methyl, isopropyl, or t-butyl, optionally substituted with one or more moieties selected from $C_1$-$C_6$ alkyl, $C_1$-$C_6$ alkoxy, phenyl, or a functional group. $R^2$ may be phenyl or vinyl substituted with one or more moieties selected from methyl, ethyl, chloro, bromo, iodo, fluoro, nitro, dimethylamino, methyl, methoxy, and phenyl. $R^2$ may be phenyl or —C=C(CH$_3$)$_2$.

Any two or more (typically two, three, or four) of $X^1$, $X^2$, $L^1$, $L^2$, $L^3$, $R^1$, and $R^2$ can be taken together to form a cyclic group, as disclosed, for example, in U.S. Pat. No. 5,312,940. When any of $X^1$, $X^2$, $L^1$, $L^2$, $L^3$, $R^1$, and $R^2$ are linked to form cyclic groups, those cyclic groups may contain 4 to about 12, or 4, 5, 6, 7 or 8 atoms, or may comprise two or three of such rings, which may be either fused or linked. The cyclic groups may be aliphatic or aromatic, and may be heteroatom-containing and/or substituted. The cyclic group may form a bidentate ligand or a tridentate ligand. Examples of bidentate ligands may include bisphosphines, dialkoxides, alkyldiketonates, and aryldiketonates.

A second group of catalysts, which may be referred to as 2$^{nd}$ Generation Grubbs-type catalysts, have the structure of formula (I), wherein $L^1$ is a carbene ligand having the structure of formula (II)

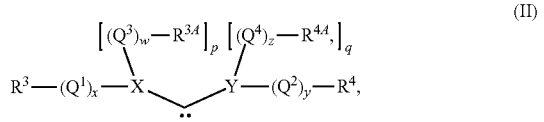

(II)

such that the complex may have the structure of formula (III)

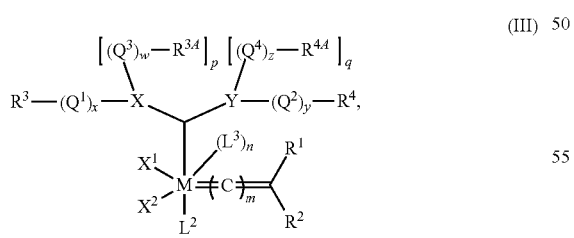

(III)

wherein M, m, n, $X^1$, $X^2$, $L^2$, $L^3$, $R^1$, and $R^2$ are as defined for the first group of catalysts, and the remaining substituents are as follows.

X and Y may be heteroatoms typically selected from N, O, S, and P. Since O and S are divalent, p is zero when X is O or S, and q is zero when Y is O or S. When X is N or P, then p is 1, and when Y is N or P, then q is 1. Both X and Y may be N.

$Q^1$, $Q^2$, $Q^3$, and $Q^4$ may be linkers, e.g., hydrocarbylene (including substituted hydrocarbylene, heteroatom-containing hydrocarbylene, and substituted heteroatom-containing hydrocarbylene, such as substituted and/or heteroatom-containing alkylene) or —(CO)—, and w, x, y, and z are independently zero or 1, meaning that each linker is optional. w, x, y, and z may all be zero. Two or more substituents on adjacent atoms within $Q^1$, $Q^2$, $Q^3$, and $Q^4$ may be linked to form an additional cyclic group.

$R^3$, $R^{3A}$, $R^4$, and $R^{4A}$ may be selected from hydrogen, hydrocarbyl, substituted hydrocarbyl, heteroatom-containing hydrocarbyl, and substituted heteroatom-containing hydrocarbyl.

In addition, any two or more of $X^1$, $X^2$, $L^1$, $L^2$, $L^3$, $R^1$, $R^2$, $R^3$, $R^{3A}$, $R^4$, and $R^{4A}$ can be taken together to form a cyclic group, and any one or more of $X^1$, $X^2$, $L^1$, $L^2$, $L^3$, $R^1$, $R^2$, $R^3$, $R^{3A}$, $R^4$, and $R^{4A}$ may be attached to a support.

$R^{3A}$ and $R^{4A}$ may be linked to form a cyclic group so that the carbene ligand is an heterocyclic carbine, for example, an N-heterocyclic carbene, such as the N-heterocyclic carbene having the structure of formula (IV):

(IV)

where $R^3$ and $R^4$ are defined above at least one of $R^3$ and $R^4$, and advantageously both $R^3$ and $R^4$, may be alicyclic or aromatic of one to about five rings, and optionally containing one or more heteroatoms and/or substituents. Q may be a linker, typically a hydrocarbylene linker, including substituted hydrocarbylene, heteroatom-containing hydrocarbylene, and substituted heteroatom-containing hydrocarbylene linkers, wherein two or more substituents on adjacent atoms within Q may also be linked to form an additional cyclic structure, which may be similarly substituted to provide a fused polycyclic structure of two to about five cyclic groups. Q may comprise a two-atom linkage or a three-atom linkage.

Examples of N-heterocyclic carbene ligands suitable as $L^1$ may include the following:

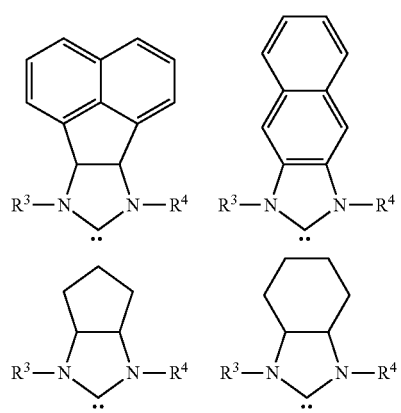

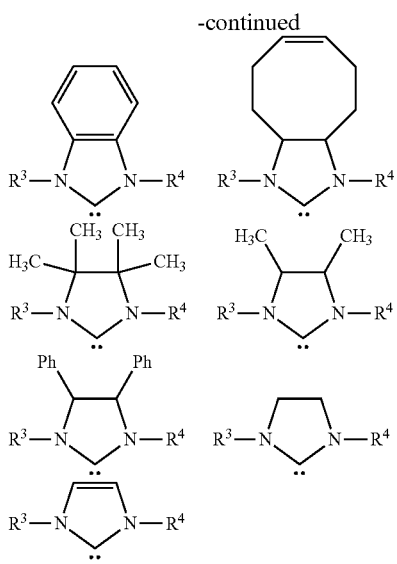

When M is ruthenium, the complex may have the structure of formula (V).

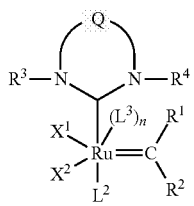

Q may be a two-atom linkage having the structure —$CR^{11}R^{12}$—$CR^{13}R^{14}$— or —$CR^{11}$=$CR^{13}$—, wherein $R^{11}$, $R^{12}$, $R^{13}$, and $R^{14}$ are independently selected from hydrogen, hydrocarbyl, substituted hydrocarbyl, heteroatom-containing hydrocarbyl, substituted heteroatom-containing hydrocarbyl, and functional groups. Examples of functional groups may include carboxyl, $C_1$-$C_{20}$ alkoxy, $C_5$-$C_{24}$ aryloxy, $C_2$-$C_{20}$ alkoxycarbonyl, $C_5$-$C_{24}$ alkoxycarbonyl, $C_2$-$C_{24}$ acyloxy, $C_1$-$C_{20}$ alkylthio, $C_5$-$C_{24}$ arylthio, $C_1$-$C_{20}$ alkylsulfonyl, and $C_1$-$C_{20}$ alkylsulfinyl, optionally substituted with one or more moieties selected from $C_1$-$C_{12}$ alkyl, $C_1$-$C_{12}$ alkoxy, $C_5$-$C_{14}$ aryl, hydroxyl, sulfhydryl, formyl, and halide. $R^{11}$, $R^{12}$, $R^{13}$, and $R^{14}$ may be independently selected from hydrogen, $C_1$-$C_{12}$ alkyl, substituted $C_1$-$C_{12}$ alkyl, $C_1$-$C_{12}$ heteroalkyl, substituted $C_1$-$C_{12}$ heteroalkyl, phenyl, and substituted phenyl. Any two of $R^{11}$, $R^{12}$, $R^{13}$, and $R^{14}$ may be linked together to form a substituted or unsubstituted, saturated or unsaturated ring structure, e.g., a $C_4$-$C_{12}$ alicyclic group or a $C_5$ or $C_6$ aryl group, which may itself be substituted, e.g., with linked or fused alicyclic or aromatic groups, or with other substituents.

When $R^3$ and $R^4$ are aromatic, they may be composed of one or two aromatic rings, which may or may not be substituted, e.g., $R^3$ and $R^4$ may be phenyl, substituted phenyl, biphenyl, substituted biphenyl, or the like. $R^3$ and $R^4$ may be the same and each may be unsubstituted phenyl or phenyl substituted with up to three substituents selected from $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, $C_6$-$C_{24}$ aralkyl, $C_6$-$C_{24}$ alkaryl, or halide. Any substituents present may be hydrogen, $C_1$-$C_{12}$ alkyl, $C_1$-$C_{12}$ alkoxy, $C_5$-$C_{14}$ aryl, substituted $C_5$-$C_{14}$ aryl, or halide. As an example, $R^3$ and $R^4$ may be mesityl.

In a third group of catalysts having the structure of formula (I), M, m, n, $X^1$, $X^2$, $R^1$, and $R^2$ are as defined for the first group of catalysts, $L^1$ may be a strongly coordinating neutral electron donor ligand such as any of those described for the first and second groups of catalysts, and $L^2$ and $L^3$ may be weakly coordinating neutral electron donor ligands in the form of optionally substituted heterocyclic groups. n is zero or 1, such that $L^3$ may or may not be present. In the third group of catalysts, $L^2$ and $L^3$ may be optionally substituted five- or six-membered monocyclic groups containing 1 to about 4, or 1 to about 3, or 1 to 2 heteroatoms, or are optionally substituted bicyclic or polycyclic structures composed of 2 to about 5 such five- or six-membered monocyclic groups. If the heterocyclic group is substituted, it should not be substituted on a coordinating heteroatom, and any one cyclic moiety within a heterocyclic group may not be substituted with more than 3 substituents.

For the third group of catalysts, examples of $L^2$ and $L^3$ may include, heterocycles containing nitrogen, sulfur, oxygen, or a mixture thereof.

Examples of nitrogen-containing heterocycles appropriate for $L^2$ and $L^3$ may include pyridine, bipyridine, pyridazine, pyrimidine, bipyridamine, pyrazine, 1,3,5-triazine, 1,2,4-triazine, 1,2,3-triazine, pyrrole, 2H-pyrrole, 3H-pyrrole, pyrazole, 2H-imidazole, 1,2,3-triazole, 1,2,4-triazole, indole, 3H-indole, 1H-isoindole, cyclopenta(b)pyridine, indazole, quinoline, bisquinoline, isoquinoline, bisisoquinoline, cinnoline, quinazoline, naphthyridine, piperidine, piperazine, pyrrolidine, pyrazolidine, quinuclidine, imidazolidine, picolylimine, purine, benzimidazole, bisimidazole, phenazine, acridine, and carbazole.

Examples of sulfur-containing heterocycles appropriate for $L^2$ and $L^3$ may include thiophene, 1,2-dithiole, 1,3-dithiole, thiepin, benzo(b)thiophene, benzo(c)thiophene, thionaphthene, dibenzothiophene, 2H-thiopyran, 4H-thiopyran, and thioanthrene.

Examples of oxygen-containing heterocycles appropriate for $L^2$ and $L^3$ may include 2H-pyran, 4H-pyran, 2-pyrone, 4-pyrone, 1,2-dioxin, 1,3-dioxin, oxepin, furan, 2H-1-benzopyran, coumarin, coumarone, chromene, chroman-4-one, isochromen-1-one, isochromen-3-one, xanthene, tetrahydrofuran, 1,4-dioxan, and dibenzofuran.

Examples of mixed heterocycles appropriate for $L^2$ and $L^3$ may include isoxazole, oxazole, thiazole, isothiazole, 1,2,3-oxadiazole, 1,2,4-oxadiazole, 1,3,4-oxadiazole, 1,2,3,4-oxatriazole, 1,2,3,5-oxatriazole, 3H-1,2,3-dioxazole, 3H-1,2-oxathiole, 1,3-oxathiole, 4H-1,2-oxazine, 2H-1,3-oxazine, 1,4-oxazine, 1,2,5-oxathiazine, o-isooxazine, phenoxazine, phenothiazine, pyrano[3,4-b]pyrrole, indoxazine, benzoxazole, anthranil, and morpholine.

The $L^2$ and $L^3$ ligands may be aromatic nitrogen-containing and oxygen-containing heterocycles. The $L^2$ and $L^3$ ligands may be monocyclic N-heteroaryl ligands that may be optionally substituted with 1 to 3, or 1 or 2, substituents. Specific examples of $L^2$ and $L^3$ ligands may include pyridine and substituted pyridines, such as 3-bromopyridine, 4-bromopyridine, 3,5-dibromopyridine, 2,4,6-tribromopyridine, 2,6-dibromopyridine, 3-chloropyridine, 4-chloropyridine, 3,5-dichloropyridine, 2,4,6-trichloropyridine, 2,6-dichloropyridine, 4-iodopyridine, 3,5-diiodopyridine, 3,5-dibromo-4-methylpyridine, 3,5-dichloro-4-methylpyridine, 3,5-dimethyl-4-bromopyridine, 3,5-dimethylpyridine, 4-methylpyridine, 3,5-diisopropylpyridine, 2,4,6-trimethylpyridine, 2,4,6-triisopropylpyridine, 4-(tert-butyl)pyridine, 4-phenylpyridine, 3,5-diphenylpyridine, 3,5-dichloro-4-phenylpyridine, and the like.

Any substituents present on $L^2$ and/or $L^3$ may be selected from halo, $C_1$-$C_{20}$ alkyl, substituted $C_1$-$C_{20}$ alkyl, $C_1$-$C_{20}$ heteroalkyl, substituted $C_1$-$C_{20}$ heteroalkyl, $C_5$-$C_{24}$ aryl, substituted $C_5$-$C_{24}$ aryl, $C_5$-$C_{24}$ heteroaryl, substituted $C_5$-$C_{24}$ heteroaryl, $C_6$-$C_{24}$ alkaryl, substituted $C_6$-$C_{24}$ alkaryl, $C_6$-$C_{24}$ heteroalkaryl, substituted $C_6$-$C_{24}$ heteroalkaryl, $C_6$-$C_{24}$ aralkyl, substituted $C_6$-$C_{24}$ aralkyl, C6-$C_{24}$ heteroaralkyl, substituted $C_6$-$C_{24}$ heteroaralkyl, and functional groups, with suitable functional groups including, without limitation, $C_1$-$C_{20}$ alkoxy, $C_5$-$C_{24}$ aryloxy, $C_2$-$C_{20}$ alkylcarbonyl, $C_6$-$C_{24}$ arylcarbonyl, $C_2$-$C_{20}$ alkylcarbonyloxy, $C_6$-$C_{24}$ arylcarbonyloxy, $C_2$-$C_{20}$ alkoxycarbonyl, $C_6$-$C_{24}$ aryloxycarbonyl, halocarbonyl, $C_2$-$C_{20}$ alkylcarbonato, $C_6$-$C_{24}$ arylcarbonato, carboxy, carboxylato, carbamoyl, mono-($C_1$-$C_{20}$ alkyl)-substituted carbamoyl, di-($C_1$-$C_{20}$ alkyl)-substituted carbamoyl, di-N—($C_1$-$C_{20}$ alkyl), N—($C_5$-$C_{24}$ aryl)-substituted carbamoyl, mono-($C_5$-$C_{24}$ aryl)-substituted carbamoyl, di-($C_6$-$C_{24}$ aryl)-substituted carbamoyl, thiocarbamoyl, mono-($C_1$-$C_{20}$ alkyl)-substituted thiocarbamoyl, di-($C_1$-$C_{20}$ alkyl)-substituted thiocarbamoyl, di-N—($C_1$-$C_{20}$ alkyl)-N—($C_6$-$C_{24}$ aryl)-substituted thiocarbamoyl, mono-($C_6$-$C_{24}$ aryl)-substituted thiocarbamoyl, di-($C_6$-$C_{24}$ aryl)-substituted thiocarbamoyl, carbamido, formyl, thioformyl, amino, mono-($C_1$-$C_{20}$ alkyl)-substituted amino, di-($C_1$-$C_{20}$ alkyl)-substituted amino, mono-($C_5$-$C_{24}$ aryl)-substituted amino, di-($C_5$-$C_{24}$ aryl)-substituted amino, di-N—($C_1$-$C_{20}$ alkyl),N—($C_5$-$C_{24}$ aryl)-substituted amino, $C_2$-$C_{20}$ alkylamido, $C_6$-$C_{24}$ arylamido, imino, $C_1$-$C_{20}$ alkylimino, $C_5$-$C_{24}$ arylimino, nitro, and nitroso. In addition, two adjacent substituents may be taken together to form a ring, generally a five- or six-membered alicyclic or aryl ring, optionally containing 1 to about 3 heteroatoms and 1 to about 3 substituents.

The substituents on $L^2$ and $L^3$ may include halo, $C_1$-$C_{12}$ alkyl, substituted $C_1$-$C_{12}$ alkyl, $C_1$-$C_{12}$ heteroalkyl, substituted $C_1$-$C_{12}$ heteroalkyl, $C_5$-$C_{14}$ aryl, substituted $C_5$-$C_{14}$ aryl, $C_5$-$C_{14}$ heteroaryl, substituted $C_5$-$C_{14}$ heteroaryl, $C_6$-$C_{16}$ alkaryl, substituted $C_6$-$C_{16}$ alkaryl, $C_6$-$C_{16}$ heteroalkaryl, substituted $C_6$-$C_{16}$ heteroalkaryl, $C_6$-$C_{16}$ aralkyl, substituted $C_6$-$C_{16}$ aralkyl, $C_6$-$C_{16}$ heteroaralkyl, substituted $C_6$-$C_{16}$ heteroalkaryl, $C_1$-$C_{12}$ alkoxy, $C_5$-$C_{14}$ aryloxy, $C_2$-$C_{12}$ alkylcarbonyl, $C_6$-$C_{14}$ arylcarbonyl, $C_2$-$C_{12}$ alkylcarbonyloxy, $C_6$-$C_{14}$ arylcarbonyloxy, $C_2$-$C_{12}$ alkoxycarbonyl, $C_6$-$C_{14}$ aryloxycarbonyl, halocarbonyl, formyl, amino, mono-($C_1$-$C_{12}$ alkyl)-substituted amino, di-($C_1$-$C_{12}$ alkyl)-substituted amino, mono-($C_5$-$C_{14}$ aryl)-substituted amino, di-($C_5$-$C_{14}$ aryl)-substituted amino, and nitro.

The substituents may be halo, $C_1$-$C_6$ alkyl, $C_1$-$C_6$ haloalkyl, $C_1$-$C_6$ alkoxy, phenyl, substituted phenyl, formyl, N,N-di$C_1$-$C_6$ alkyl)amino, nitro, or nitrogen heterocycles as described above (including, for example, pyrrolidine, piperidine, piperazine, pyrazine, pyrimidine, pyridine, pyridazine, etc.).

$L^2$ and $L^3$ may also be taken together to form a bidentate or multidentate ligand containing two or more, generally two, coordinating heteroatoms such as N, O, S, or P. These may include diimine ligands of the Brookhart type. A representative bidentate ligand has the structure of formula (VI)

wherein $R^{15}$, $R^{16}$, $R^{17}$, and $R^{18}$ may be hydrocarbyl (e.g., $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, or $C_6$-$C_{24}$ aralkyl), substituted hydrocarbyl (e.g., substituted $C_1$-$C_{20}$ alkyl, $C_2$-$C_{20}$ alkenyl, $C_2$-$C_{20}$ alkynyl, $C_5$-$C_{24}$ aryl, $C_6$-$C_{24}$ alkaryl, or $C_6$-$C_{24}$ aralkyl), heteroatom-containing hydrocarbyl (e.g., $C_1$-$C_{20}$ heteroalkyl, $C_5$-$C_{24}$ heteroaryl, heteroatom-containing $C_6$-$C_{24}$ aralkyl, or heteroatom-containing $C_6$-$C_{24}$ alkaryl), or substituted heteroatom-containing hydrocarbyl (e.g., substituted $C_1$-$C_{20}$ heteroalkyl, $C_5$-$C_{24}$ heteroaryl, heteroatom-containing $C_6$-$C_{24}$ aralkyl, or heteroatom-containing $C_6$-$C_{24}$ alkaryl), or (1) $R^{15}$ and $R^{16}$, (2) $R^{17}$ and $R^{18}$, (3) $R^{16}$ and $R^{17}$, or (4) both $R^{15}$ and $R^{16}$, and $R^{17}$ and $R^{18}$, may be taken together to form a ring, i.e., an N-heterocycle. Preferred cyclic groups in such a case are five- and six-membered rings, typically aromatic rings.

In a fourth group of catalysts that have the structure of formula (I), two of the substituents may be taken together to form a bidentate ligand or a tridentate ligand. Examples of bidentate ligands may include bisphosphines, dialkoxides, alkyldiketonates, and aryldiketonates. These may include —P(Ph)$_2$CH$_2$CH$_2$P(Ph)$_2$-, —As(Ph)$_2$CH$_2$CH$_2$As(Ph$_2$)—, —P(Ph)$_2$CH$_2$CH$_2$C(CF$_3$)$_2$O—, binaphtholate dianions, pinacolate dianions, —P(CH$_3$)$_2$(CH$_2$)$_2$P(CH$_3$)$_2$—, and —OC(CH$_3$)$_2$(CH$_3$)$_2$CO—. Preferred bidentate ligands are —P(Ph)$_2$CH$_2$CH$_2$P(Ph)$_2$- and —P(CH$_3$)$_2$(CH$_2$)$_2$P(CH$_3$)$_2$—. Tridentate ligands include, but are not limited to, (CH$_3$)$_2$NCH$_2$CH$_2$P(Ph)CH$_2$CH$_2$N(CH$_3$)$_2$. Other tridentate ligands may be those in which any three of $X^1$, $X^2$, $L^1$, $L^2$, $L^3$, $R^1$, and $R^2$ (e.g., $X^1$, $L^1$, and $L^2$) are taken together to be cyclopentadienyl, indenyl, or fluorenyl, each optionally substituted with $C_2$-$C_{20}$ alkenyl, $C_2$-$C_{20}$ alkynyl, $C_1$-$C_{20}$ alkyl, $C_5$-$C_{20}$ aryl, $C_1$-$C_{20}$ alkoxy, $C_2$-$C_{20}$ alkenyloxy, $C_2$-$C_{20}$ alkynyloxy, $C_5$-$C_{20}$ aryloxy, $C_2$-$C_{20}$ alkoxycarbonyl, $C_1$-$C_{20}$ alkylthio, $C_1$-$C_{20}$ alkylsulfonyl, or $C_1$-$C_{20}$ alkylsulfinyl, each of which may be further substituted with $C_1$-$C_6$ alkyl, halide, $C_1$-$C_6$ alkoxy or with a phenyl group optionally substituted with halide, $C_1$-$C_6$ alkyl, or $C_1$-$C_6$ alkoxy. In compounds of this type, X, $L^1$, and $L^2$ may be taken together to be cyclopentadienyl or indenyl, each optionally substituted with vinyl, $C_1$-$C_{10}$ alkyl, $C_5$-$C_{20}$ aryl, $C_1$-$C_{10}$ carboxylate, $C_2$-$C_{10}$ alkoxycarbonyl, $C_1$-$C_{10}$ alkoxy, or $C_5$-$C_{20}$ aryloxy, each optionally substituted with $C_1$-$C_6$ alkyl, halide, $C_1$-$C_6$ alkoxy or with a phenyl group optionally substituted with halide, $C_1$-$C_6$ alkyl or $C_1$-$C_6$ alkoxy. X, $L^1$ and $L^2$ may be taken together to be cyclopentadienyl, optionally substituted with vinyl, hydrogen, methyl, or phenyl. Tetradentate ligands may include O$_2$C(CH$_2$)$_2$P(Ph)(CH$_2$)$_2$P(Ph)(CH$_2$)$_2$CO$_2$, phthalocyanines, and porphyrins.

Complexes wherein $L^2$ and $R^2$ are linked are examples of the fourth group of catalysts. These may be called "Grubbs-Hoveyda" catalysts. Examples of Grubbs-Hoveyda-type catalysts may include the following:

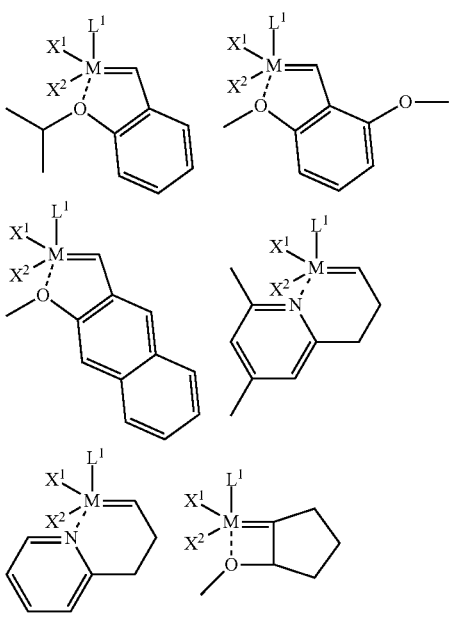

wherein $L^1$, $X^1$, $X^2$, and M are as described for any of the other groups of catalysts.

In addition to the catalysts that have the structure of formula (I), as described above, other transition metal carbene complexes may include;

neutral ruthenium or osmium metal carbene complexes containing metal centers that are formally in the +2 oxidation state, have an electron count of 16, are penta-coordinated, and are of the general formula (VII);

neutral ruthenium or osmium metal carbene complexes containing metal centers that are formally in the +2 oxidation state, have an electron count of 18, are hexa-coordinated, and are of the general formula (VIII);

cationic ruthenium or osmium metal carbene complexes containing metal centers that are formally in the +2 oxidation state, have an electron count of 14, are tetra-coordinated, and are of the general formula (IX); and cationic ruthenium or osmium metal carbene complexes containing metal centers that are formally in the +2 oxidation state, have an electron count of 14, are tetra-coordinated, and are of the general formula (X)

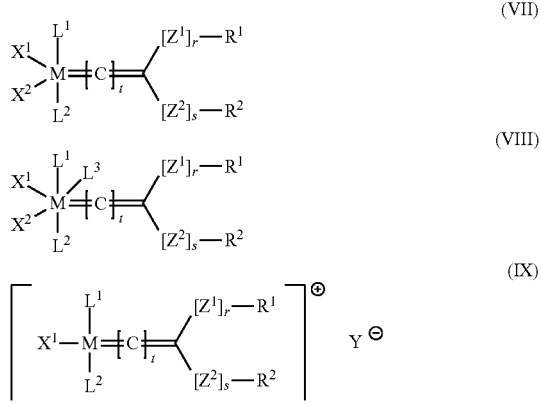

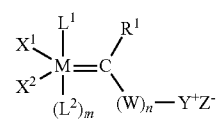

wherein: $X^1$, $X^2$, $L^1$, $L^2$, n, $L^3$, $R^1$, and $R^2$ may be as defined for any of the previously defined four groups of catalysts; r and s are independently zero or 1; t may be an integer in the range of zero to 5;

Y may be any non-coordinating anion (e.g., a halide ion, $BF_4^-$, etc.); $Z^1$ and $Z^2$ may be independently selected from —O—, —S—, —$NR^2$—, —$PR^2$—, —P(=O)$R^2$—, —P(O$R^2$)—, —P(=O)(O$R^2$)—, —C(=O)—, —C(=O)O—, —OC(=O)—, —OC(=O)O—, —S(=O)—, and —S(=O)$_2$—; $Z^3$ may be any cationic moiety such as —P($R^2$)$_3^+$ or —N($R^2$)$_3$+; and any two or more of $X^1$, $X^2$, $L^1$, $L^2$, $L^3$, n, $Z^1$, $Z^2$, $Z^3$, $R^1$, and $R^2$ may be taken together to form a cyclic group, e.g., a multidentate ligand, and wherein any one or more of $X^1$, $X^2$, $L^1$, $L^2$, n, $L^3$, $Z^1$, $Z^2$, $Z^3$, $R^1$, and $R^2$ may be attached to a support.

Other suitable complexes include Group 8 transition metal carbenes bearing a cationic substituent, such as are disclosed in U.S. Pat. No. 7,365,140 (Piers et al.) having the general structure (XI):

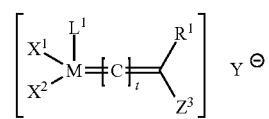

wherein:
M is a Group 8 transition metal;
$L^1$ and $L^2$ are neutral electron donor ligands;
$X^1$ and $X^2$ are anionic ligands;
$R^1$ is hydrogen, $C_1$-$C_{12}$ hydrocarbyl, or substituted $C_1$-$C_{12}$ hydrocarbyl;
W is an optionally substituted and/or heteroatom-containing $C_1$-$C_{20}$ hydrocarbylene linkage;
Y is a positively charged Group 15 or Group 16 element substituted with hydrogen, $C_1$-$C_{12}$ hydrocarbyl, substituted $C_1$-$C_{12}$ hydrocarbyl; heteroatom-containing $C_1$-$C_{12}$ hydrocarbyl, or substituted heteroatom-containing hydrocarbyl;
$Z^-$ is a negatively charged counterion;
m is zero or 1; and
n is zero or 1;
wherein any two or more of $L^1$, $L^2$, $X^1$, $X^2$, $R^1$, W, and Y can be taken together to form a cyclic group.

Each of M, $L^1$, $L^2$, $X^1$, and $X^2$ in structure (XI) may be as previously defined herein.

W may be an optionally substituted and/or heteroatom-containing $C_1$-$C_{20}$ hydrocarbylene linkage, typically an optionally substituted $C_1$-$C_{12}$ alkylene linkage, e.g., —(CH$_2$)$_i$— where i is an integer in the range of 1 to 12 inclusive and any of the hydrogen atoms may be replaced with a non-hydrogen substituent as described earlier herein with regard to the definition of the term "substituted." The subscript n may be zero or 1, meaning that W may or may not be present. In an embodiment, n is zero.

Y may be a positively charged Group 15 or Group 16 element substituted with hydrogen, $C_1$-$C_{12}$ hydrocarbyl, substituted $C_1$-$C_{12}$ hydrocarbyl, heteroatom-containing $C_1$-$C_{12}$ hydrocarbyl, or substituted heteroatom-containing hydrocarbyl. Y may be a $C_1$-$C_{12}$ hydrocarbyl-substituted, positively charged Group 15 or Group 16 element. Representative Y groups may include $P(R^2)_3$, $P(R^2)_3$, $As(R^2)_3$, $S(R^2)_2$, $O(R^2)_2$, where the $R^2$ may be independently selected from $C_1$-$C_{12}$ hydrocarbyl. Within these, the Y groups may be phosphines of the structure $P(R^2)_3$ wherein the $R^2$ may be independently selected from $C_1$-$C_{12}$ alkyl and aryl, and thus include, for example, methyl, ethyl, n-propyl, isopropyl, n-butyl, isobutyl, t-butyl, cyclopentyl, cyclohexyl, and phenyl. Y may also be a heterocyclic group containing the positively charged Group 15 or Group 16 element. For instance, when the Group 15 or Group 16 element is nitrogen, Y may be an optionally substituted pyridinyl, pyrazinyl, or imidazolyl group.

$Z^-$ may be a negatively charged counterion associated with the cationic complex, and may be virtually any anion, so long as the anion is inert with respect to the components of the complex and the reactants and reagents used in the metathesis reaction. The $Z^-$ moieties may be weakly coordinating anions, such as, for instance, $[B(C_6F_5)_4]^-$, $[BF_4]^-$, $[B(C_6H_6)_4]^-$, $[CF_3S(O)_3]^-$, $[PF_6]^-$, $[SbF_6]^-$, $[AlCl_4]^-$, $[FSO_3]^-$, $[CB_{11}H_6Cl_6]^-$, $[CB_{11}H_6Br_6]^-$, and $[SO_3F:SbF_5]^-$. Anions suitable as Z may be of the formula $B(R^{15})_4$ where $R^{15}$ is fluoro, aryl, or perfluorinated aryl, typically fluoro or perfluorinated aryl. Anions suitable as Z may be $BF_4$ or $B(C_6F_5)^-$.

Any two or more of $X^1$, $X^2$, $L^1$, $L^2$, $R^1$, W, and Y may be taken together to form a cyclic group, as disclosed, for example, in U.S. Pat. No. 5,312,940. When any of $X^1$, $X^2$, $L^1$, $L^2$, $R^1$, W, and Y are linked to form cyclic groups, those cyclic groups may be five- or six-membered rings, or may comprise two or three five- or six-membered rings, which may be either fused or linked. The cyclic groups may be aliphatic or aromatic, and may be heteroatom-containing and/or substituted.

One group of exemplary catalysts encompassed by the structure of formula (XI) are those wherein m and n are zero, such that the complex has the structure of formula (XII)

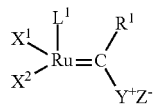

(XII)

The $X^1$, $X^2$, and $L^1$ ligands are as described earlier with respect to complexes of formula (XI), as are $Y^+$ and $Z^-$. M may be Ru or Os and $R^1$ may be hydrogen or $C_1$-$C_{12}$ alkyl. M may be Ru, and $R^1$ may be hydrogen.

In formula (XII)-type catalysts, $L^1$ may be a heteroatom-containing carbene ligand having the structure of formula (XIII)

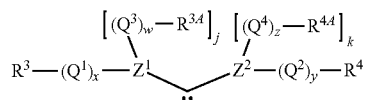

(XIII)

such that complex (XII) has the structure of formula (XIV)

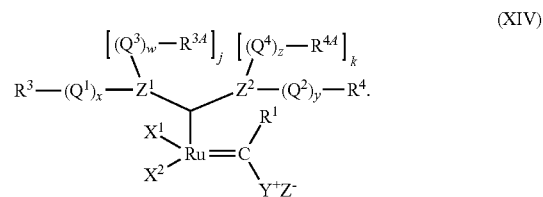

(XIV)

wherein $X^1$, $X^2$, $R^1$, $R^2$, Y, and Z are as defined previously, and the remaining substituents are as follows:

$Z^1$ and $Z^2$ may be heteroatoms typically selected from N, O, S, and P. Since O and S are divalent, j may be zero when $Z^1$ is O or S, and k may be zero when $Z^2$ is O or S. However, when $Z^1$ is N or P, then j may be 1, and when $Z^2$ is N or P, then k may be 1. Both $Z^1$ and $Z^2$ may be N.

$Q^1$, $Q^2$, $Q^3$, and $Q^4$ are linkers, e.g., $C_1$-$C_{12}$ hydrocarbylene, substituted $C_1$-$C_{12}$ hydrocarbylene, heteroatom-containing $C_1$-$C_{12}$ hydrocarbylene, substituted heteroatom-containing $C_1$-$C_{12}$ hydrocarbylene, or —(CO)—, and w, x, y, and z may be independently zero or 1, meaning that each linker may be optional. w, x, y, and z may all be zero.

$R^3$, $R^{3A}$, $R^4$, and $R^{4A}$ may be selected from hydrogen, $C_1$-$C_{20}$ hydrocarbyl, substituted $C_1$-$C_{20}$ hydrocarbyl, heteroatom-containing $C_1$-$C_{20}$ hydrocarbyl, and substituted heteroatom-containing $C_1$-$C_{20}$ hydrocarbyl.

w, x, y, and z may be zero, $Z^1$ and $Z^1$ may be N, and $R^{3A}$ and $R^{4A}$ may be linked to form —Q—, such that the complex has the structure of formula (XV)

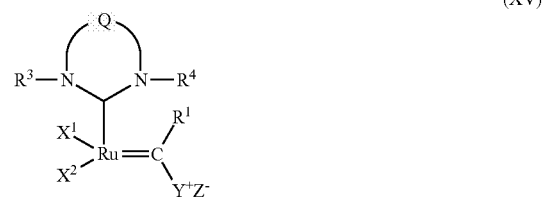

(XV)

wherein $R^3$ and $R^4$ are defined above. At least one of $R^3$ and $R^4$, and optionally both $R^3$ and $R^4$, may be alicyclic or aromatic of one to about five rings, and optionally containing one or more heteroatoms and/or substituents. Q may be a linker, typically a hydrocarbylene linker, including $C_1$-$C_{12}$ hydrocarbylene, substituted $C_1$-$C_{12}$ hydrocarbylene, heteroatom-containing $C_1$-$C_{12}$ hydrocarbylene, or substituted heteroatom-containing $C_1$-$C_{12}$ hydrocarbylene linker, wherein two or more substituents on adjacent atoms within Q may be linked to form an additional cyclic structure, which may be similarly substituted to provide a fused polycyclic structure of two to about five cyclic groups. Q may be a two-atom linkage or a three-atom linkage, e.g., —CH$_2$—CH$_2$—, —CH(Ph)-CH(Ph)- where Ph is phenyl; =CR—N=, giving rise to an unsubstituted (when R=H) or substituted (R=other than H) triazolyl group; or —CH$_2$—SiR$_2$—CH$_2$— (where R is H, alkyl, alkoxy, etc.).

Q may be a two-atom linkage having the structure —CR$^8$R$^9$—CR$^{10}$R$^{11}$— or —CR$^8$=CR$^{10}$—, wherein R$^8$, R$^9$, R$^{10}$, and R$^{11}$ may be independently selected from hydrogen, $C_1$-$C_{12}$ hydrocarbyl, substituted $C_1$-$C_{12}$ hydrocarbyl, heteroatom-containing $C_1$-$C_{12}$ hydrocarbyl, substituted heteroatom-containing $C_1$-$C_{12}$ hydrocarbyl, and functional groups. Examples of the functional groups may include carboxyl, $C_1$-$C_{20}$ alkoxy, $C_5$-$C_{20}$ aryloxy, $C_2$-$C_{20}$ alkoxycarbonyl, $C_2$-$C_{20}$ alkoxycarbonyl, $C_2$-$C_{20}$ acyloxy, $C_1$-$C_{20}$ alkylthio, $C_5$-$C_{20}$ arylthio, $C_1$-$C_{20}$ alkylsulfonyl, and $C_1$-$C_{20}$ alkylsulfinyl, optionally substituted with one or more moieties selected from $C_1$-$C_{10}$ alkyl, $C_1$-$C_{10}$ alkoxy, $C_5$-$C_{20}$ aryl, hydroxyl, sulfhydryl, formyl, and halide. Alternatively, any two of $R^8$, $R^9$, $R^{10}$, and $R^{11}$ may be linked together to form a substituted or unsubstituted, saturated or unsaturated ring structure, e.g., a $C_4$-$C_{12}$ alicyclic group or a $C_5$ or $C_6$ aryl group, which may itself be substituted, e.g., with linked or fused alicyclic or aromatic groups, or with other substituents.

Further details concerning such formula (XI) complexes, as well as associated preparation methods, may be obtained from U.S. Pat. No. 7,365,140.

Suitable solid supports for any of the catalysts described herein may be made of synthetic, semi-synthetic, or naturally occurring materials, which may be organic or inorganic, e.g., polymeric, ceramic, or metallic. Attachment to the support may be covalent, and the covalent linkage may be direct or indirect, if indirect, typically through a functional group on a support surface.

Examples of the catalysts that may be used may include the following, some of which for convenience are identified throughout this disclosure by reference to their molecular weight:

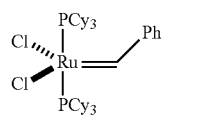
12

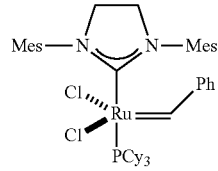
14

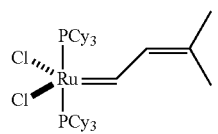
16

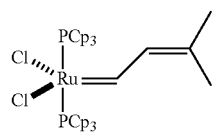
18

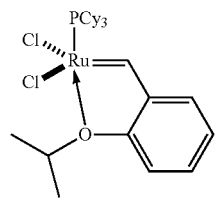
20

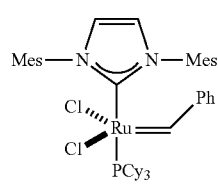
22

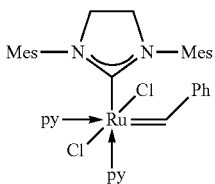
24

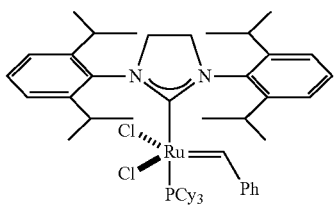
26

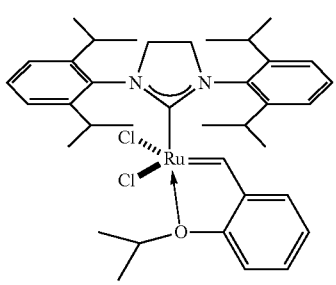
28

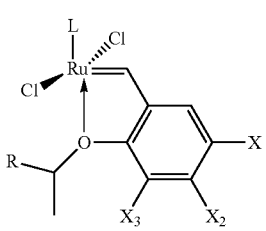
50 where
L = PCy3, siMes, Mes, Phobane
X = H, NO2, SO2N(CH3)2
X2 = H, N+(C2H5)2CH3
X3 = H, Phenyl
R = H, alkyl, aryl, CO2Me

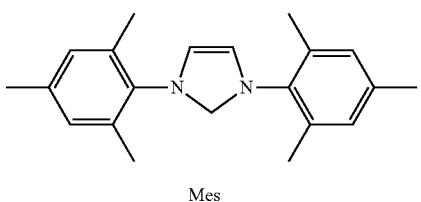
Mes

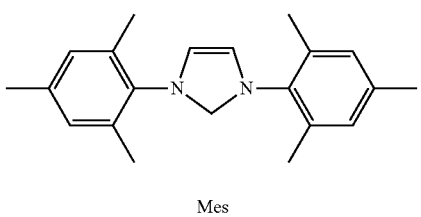
Mes

-continued
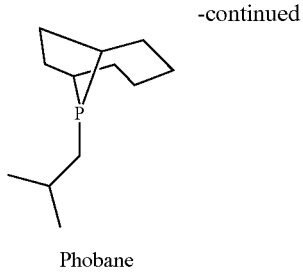
Phobane
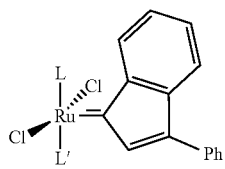
where
L = PCy₃, siMes, Mes, Phobane
L' = PCy₃, Phobane
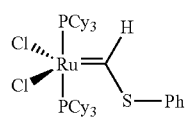
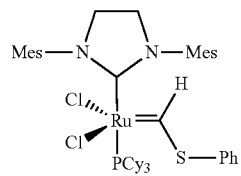
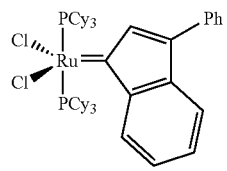
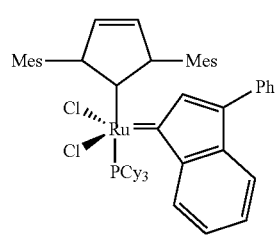
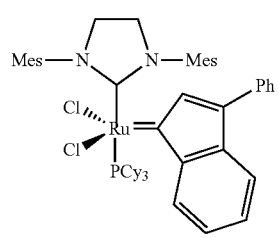
-continued
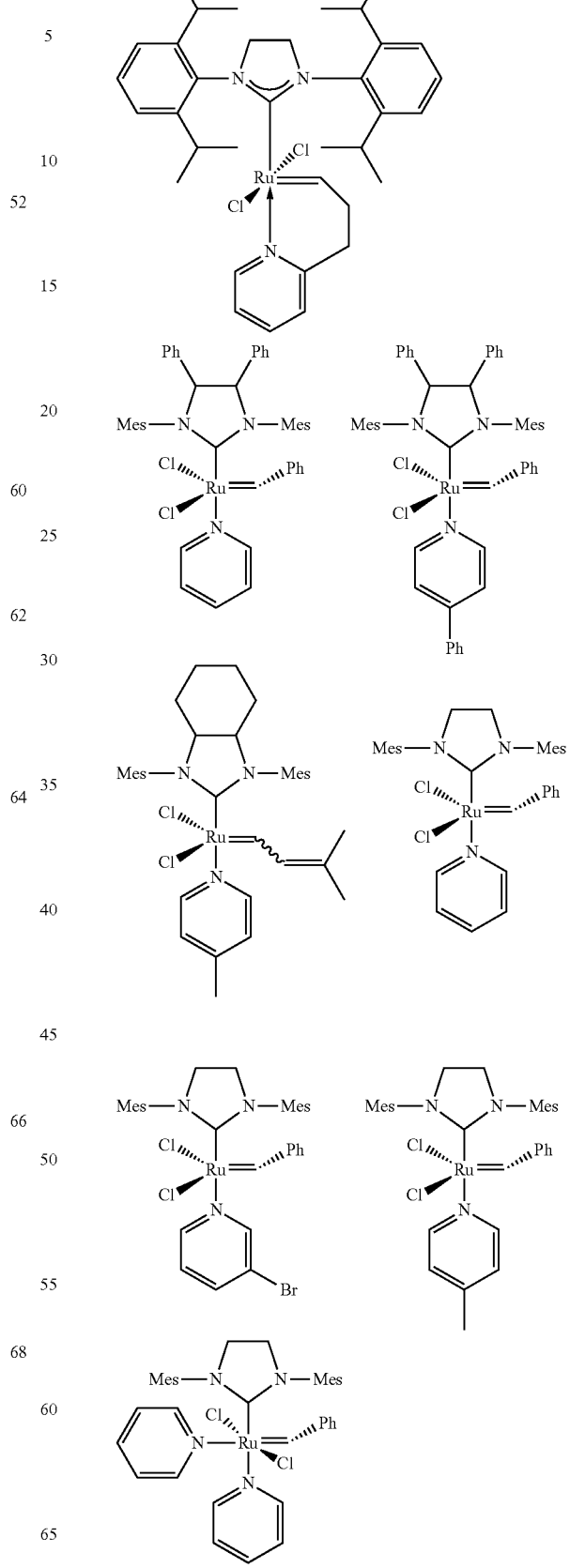

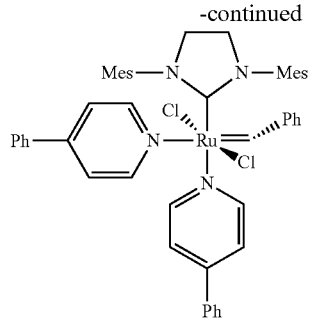
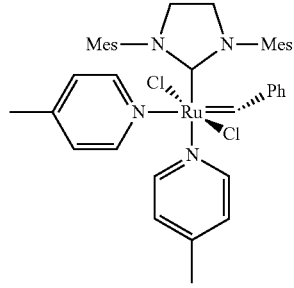
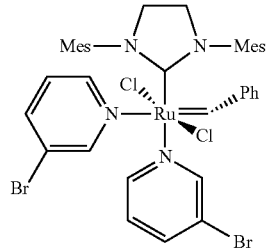
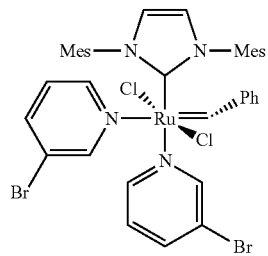
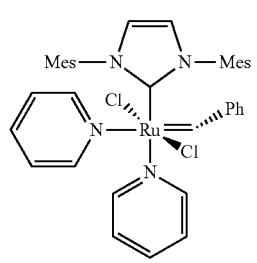
C827
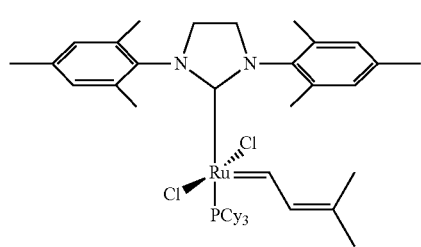
C859
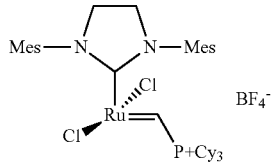
C841-n
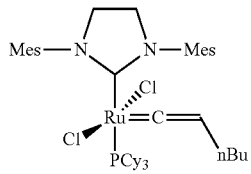
C916
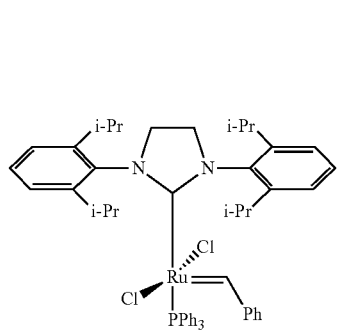
C965-p
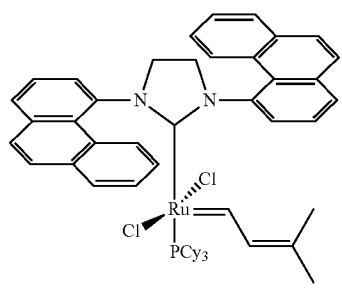
C727
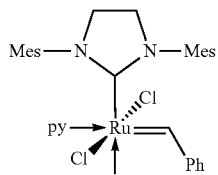
C577
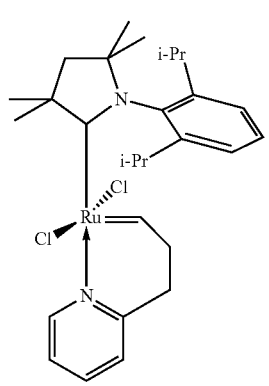

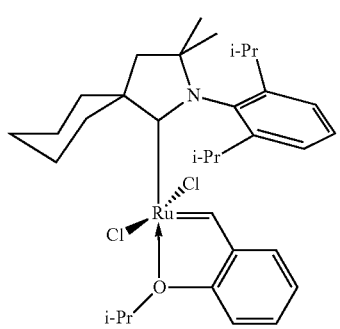
C646
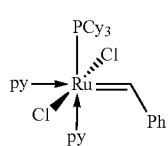
C701
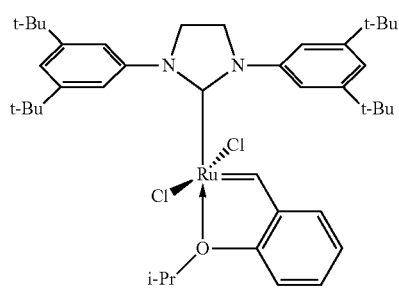
C767-m
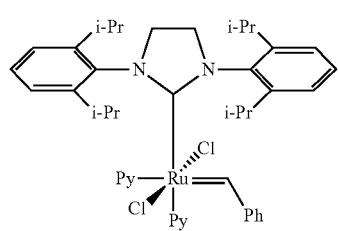
C811
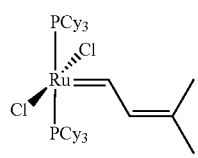
C801
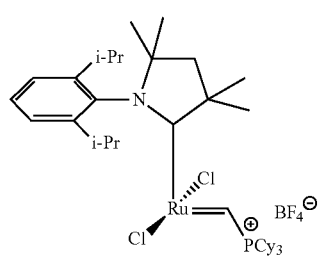
C838
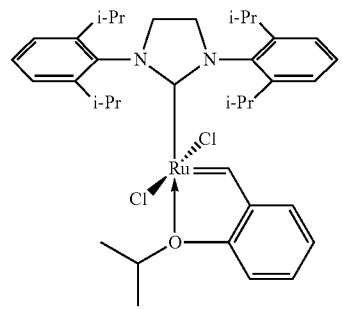
C712
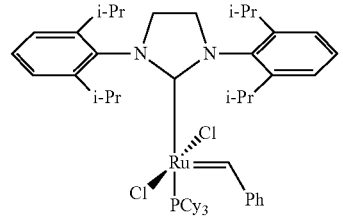
C933
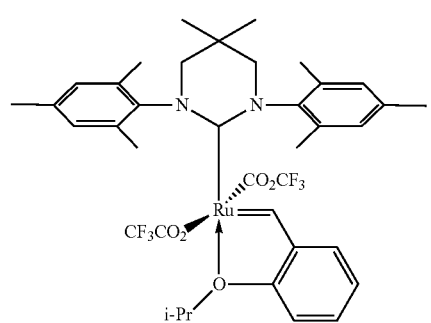
C824
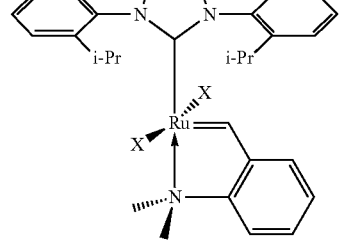
C697 (X = Cl)
C785 (X = Br)
C879 (X = I)
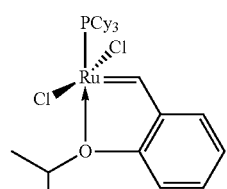
C601
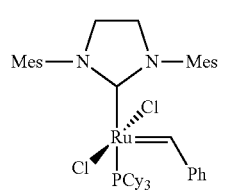
C848

-continued
C831
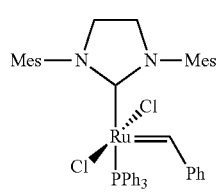
C627
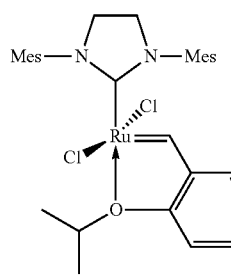
C672
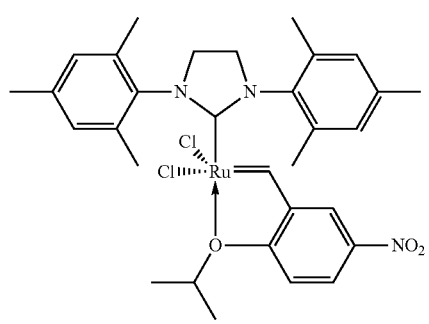
C657
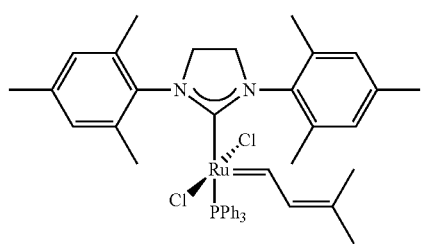
C734
-continued
C767
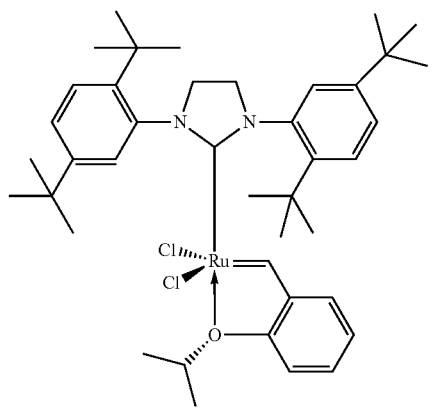
C809
C849
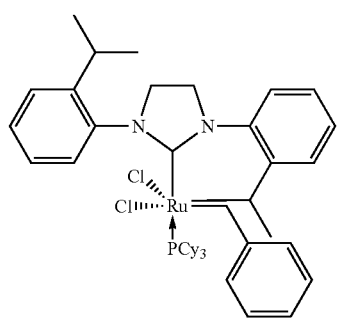
C923
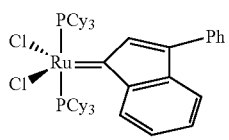
C-524
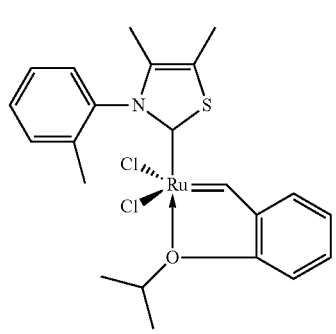

C-552
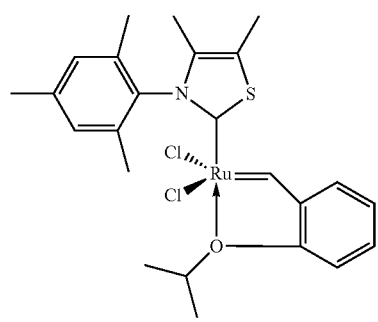
C-566
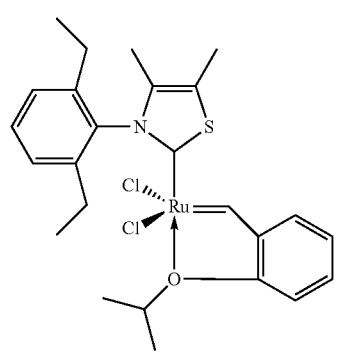
DPA1-278
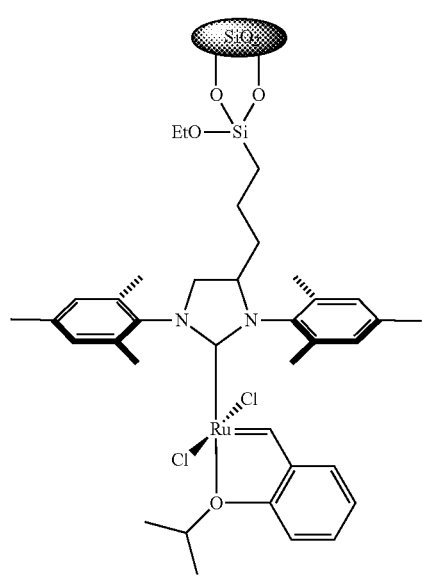
C-598
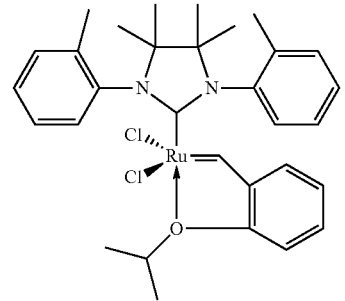
C-626
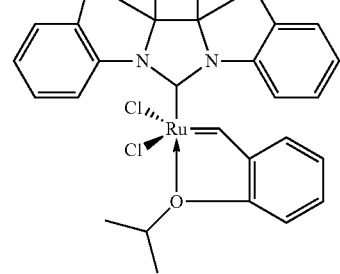
C949
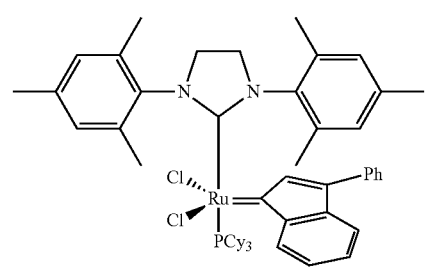
C823
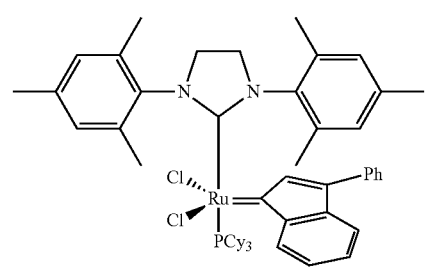
C606
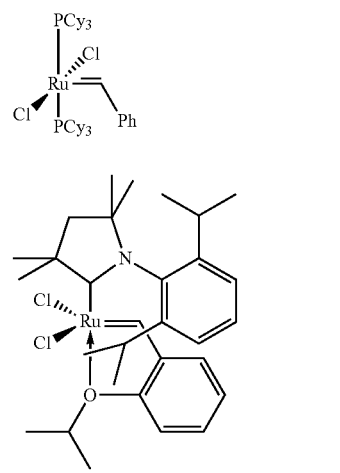
C629
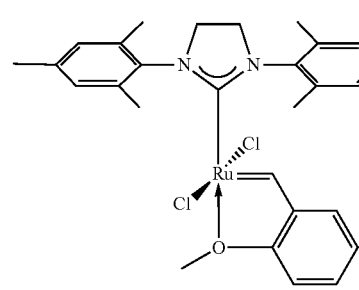

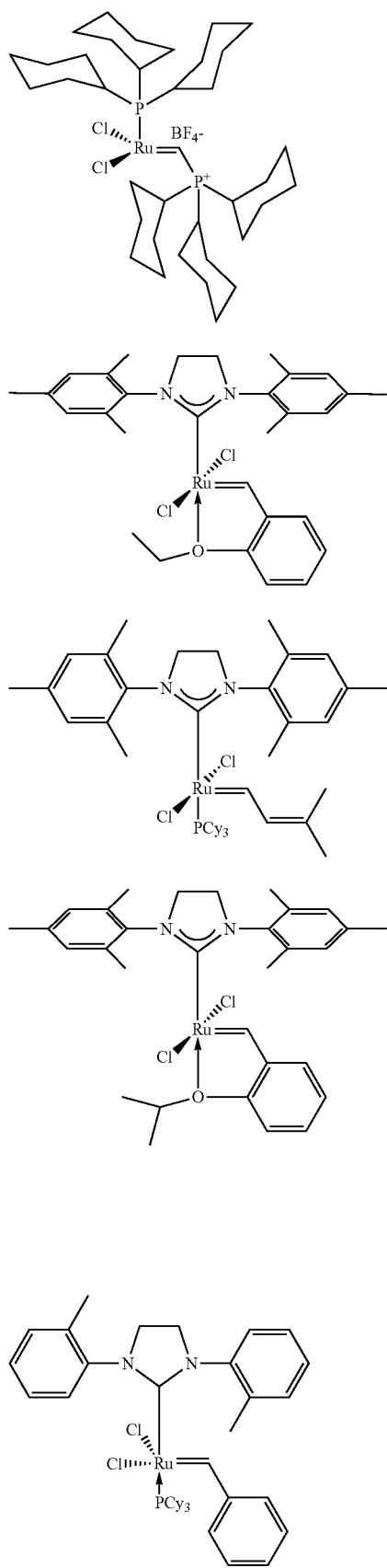
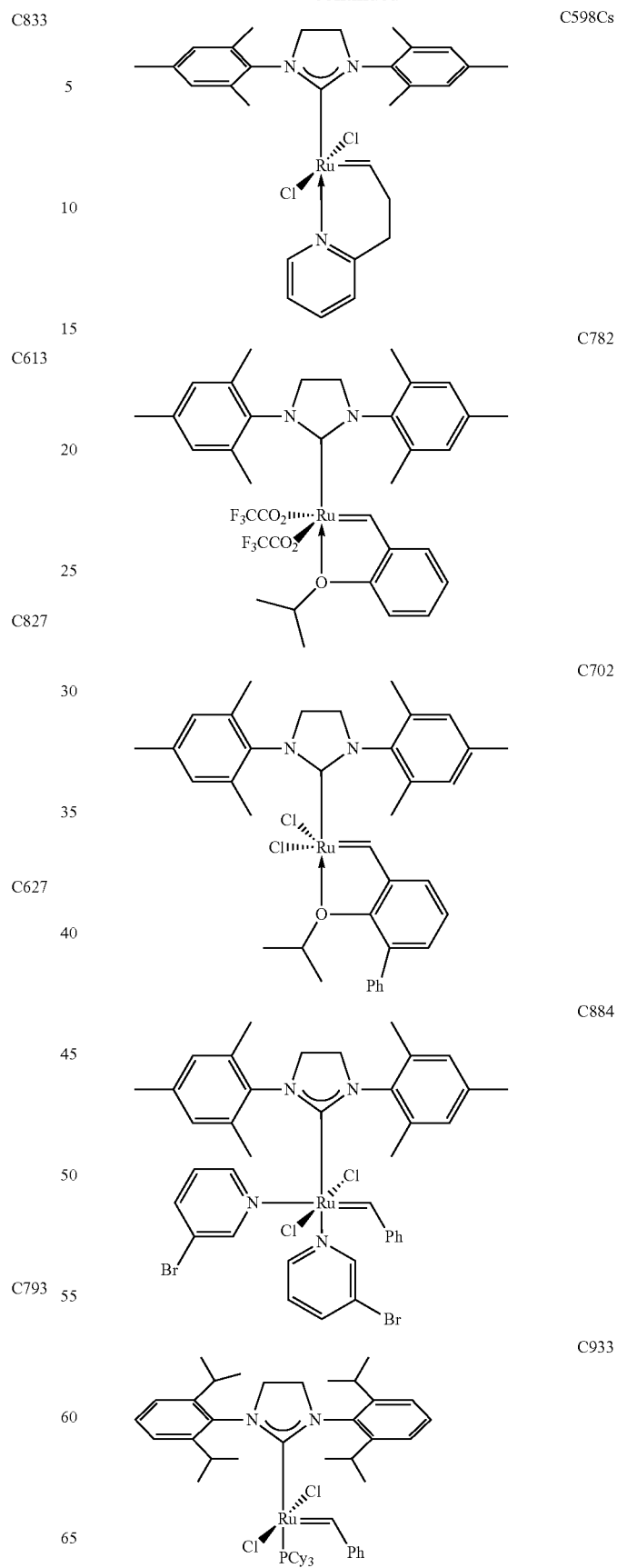

-continued

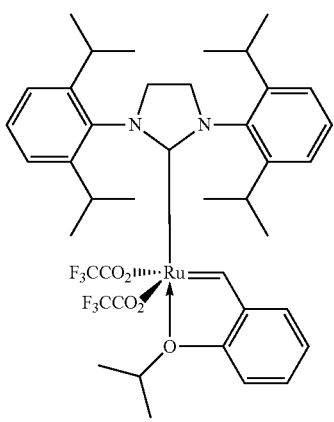

C866

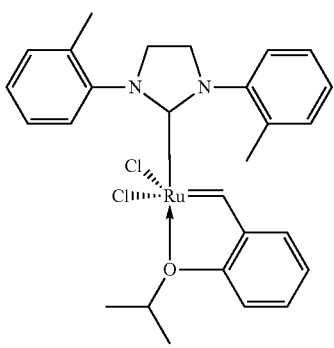

C571

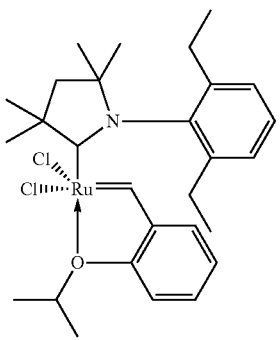

C578

In the foregoing molecular structures and formulae, Ph represents phenyl, Cy represents cyclohexane, Me represents methyl, nBu represents n-butyl, i-Pr represents isopropyl, py represents pyridine (coordinated through the N atom), and Mes represents mesityl (i.e., 2,4,6-trimethylphenyl).

Further examples of catalysts that may be used may include the following: ruthenium (II) dichloro (3-methyl-1, 2-butenylidene) bis(tricyclopentylphosphine) (C716); ruthenium (II) dichloro (3-methyl-1,2-butenylidene) bis(tricyclohexylphosphine) (C801); ruthenium (II) dichloro (phenylmethylene) bis(tricyclohexylphosphine) (C823); ruthenium (II) [1,3-bis-(2,4,6-trimethylphenyl)-2-imidazolidinylidene) dichloro (phenylmethylene) (triphenylphosphine) (C830), and ruthenium (II) dichloro (vinyl phenylmethylene) bis(tricyclohexylphosphine) (C835); ruthenium (II) dichloro (tricyclohexylphosphine) (o-isopropoxyphenylmethylene) (C601), and ruthenium (11) (1, 3-bis-(2, 4, 6-trimethylphenyl)-2-imidazolidinylidene) dichloro (phenylmethylene) (bis 3-bromopyridine (C884)).

Exemplary ruthenium-based metathesis catalysts may include those represented by structures 12 (commonly known as Grubbs's catalyst), 14 and 16. Structures 18, 20, 22, 24, 26, 28, 60, 62, 64, 66, and 68 represent additional ruthenium-based metathesis catalysts. Catalysts C627, C682, C697, C712, and C827 represent still additional ruthenium-based catalysts. General structures 50 and 52 represent additional ruthenium-based metathesis catalysts of the type reported in *Chemical & Engineering News*; Feb. 12, 2007, at pages 37-47. In the structures, Ph is phenyl, Mes is mesityl, py is pyridine, Cp is cyclopentyl, and Cy is cyclohexyl.

Techniques for using the metathesis catalysts are known in the art (see, for example, U.S. Pat. Nos. 7,102,047; 6,794,534; 6,696,597; 6,414,097; 6,306,988; 5,922,863; 5,750,815; and metathesis catalysts with ligands in U.S. Patent Publication No. 2007/0004917 A1). A number of the metathesis catalysts as shown are manufactured by Materia, Inc. (Pasadena, Calif.).

Additional exemplary metathesis catalysts may include metal carbene complexes selected from molybdenum, osmium, chromium, rhenium, and tungsten. The term "complex" refers to a metal atom, such as a transition metal atom, with at least one ligand or complexing agent coordinated or bound thereto. Such a ligand may be a Lewis base in metal carbene complexes useful for alkyne or alkene-metathesis. Typical examples of such ligands include phosphines, halides and stabilized carbenes. Some metathesis catalysts may employ plural metals or metal co-catalysts (e.g., a catalyst comprising a tungsten halide, a tetraalkyl tin compound, and an organoaluminum compound).

An immobilized catalyst can be used for the metathesis process. An immobilized catalyst may be a system comprising a catalyst and a support, the catalyst associated with the support. Exemplary associations between the catalyst and the support may occur by way of chemical bonds or weak interactions (e.g. hydrogen bonds, donor acceptor interactions) between the catalyst, or any portions thereof, and the support or any portions thereof. Support may be any material suitable to support the catalyst. Typically, immobilized catalysts may be solid phase catalysts that act on liquid or gas phase reactants and products. Exemplary supports may include polymers, silica or alumina. Such an immobilized catalyst may be used in a flow process. An immobilized catalyst may simplify purification of products and recovery of the catalyst so that recycling the catalyst may be more convenient.

Polymerizaiton of the Functionalized Monomers

One or more of the functionalized monomers may be polymerized to form a functionalized polymer (or oligomer) or copolymerized with one or more comonomers to form a functionalized copolymer (or co-oligomer). The term "polymer" is used herein to refer to polymers and copolymers, as well as oligomers and co-oligomers. The term "polymerize" is used herein to include polymerization reactions, co-polymerization reactions, oligomerization reactions and co-oligomerization reactions. The functionalized monomers and functionalized polymers may have utility in many applications including lubricants, functional fluids, fuels, molded or extruded articles, pharmaceuticals, cosmetics, personal care products, adhesives, coatings, pharmaceuticals, cosmetics, personal care products, industrial cleaners, institutional cleaners, foods, beverages, oil field chemicals, agricultural chemicals, and the like. The functionalized monomers and polymers may be used as base oils for lubricants and functional fluids, and/or as functional additives for lubricants, functional fluids and fuels. The functionalized polymers may be referred to as polymeric resins.

The comonomer may comprise an olefin, acrylic acid, acrylic acid ester, methacrylic acid, methacrylic acid ester, unsaturated nitrile, vinyl ester, vinyl ether, halogenated monomer, unsaturated polycarboxylic acid or derivative thereof, polyhydric alcohol, polyamine, polyalkylene polyamine, isocyanate, diisocyanate, alkenyl-substituted aromatic compound (e.g., styrene), akenyl-substituted heterocyclic compound, organosilane, or a mixture of two or more thereof.

The olefin comonomer may contain from 2 to about 30 carbon atoms, or from 2 to about 24 carbon atoms, or from about 6 to about 24 carbon atoms. The olefin comonomer may comprise an alpha olefin, an internal olefin, or a mixture thereof. The internal olefin may be symmetric or asymmetric. The olefin may be linear or branched. The olefin may be a monoene, diene, triene, tetraene, or mixture of two or more thereof. The monoenes may comprise one or more of ethene, 1-propene, 1-butene, 2-butene, isobutene, 1-pentene, 2-pentene, 3-pentene, cyclopentene, 1-hexene, 2-hexene, 3-hexene, cyclohexene, 1-heptene, 2-heptene, 3-heptene, 1-octene, 2-octene, 3-octene, 1-nonene, 2-nonene, 3-nonene, 4-nonene, 1-decene, 1-undecene, 1-dodecene, 1-tridecene, 1-tetradecene, 1-pentadecene, 1-hexadecene, 1-octadecene, 1-eicosene, 2-methyl-1-butene, 2-methyl-2-butene, 3-methyl-1-butene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, 2,2-dimethyl-3-pentene, styrene, vinyl cyclohexane, or a mixture of two or more thereof. The dienes, trienes and tetraenes may comprise butadiene, isoprene, hexadiene, decadiene, octatriene, ocimene, farnesene, or a mixture of two or more thereof.

The alphaolefin may comprise ethene, 1-propene, 1-butene, 1-pentene, 1-hexene, 1-octene, 1-nonene, 1-decene, 1-undecene, 1-dodecene, 1-tridecene, 1-tetradecene, 1-pentadecene, 1-hexadecene, 1-octadecene, 1-eicosene, or a mixture of two or more thereof.

The olefin comonomer may be a conjugated diene. The conjugated diene may include one or more dienes containing from 4 to about 12 carbon atoms, or from about 4 to about 8 carbon atoms. Examples may include 1,3-butadiene, isoprene, 1,3-pentadiene, 1,3-hexadiene, 2-ethylbutadiene, 2-propylbutadiene, 2-propyl butadiene, 2-butylbutadiene, 2-octylbutadiene, 4-methylpentadiene, 2,3-dimethylbutadiene, 2-phenyl butadiene, 1-chlorobutadiene, 2-methoxybutadiene, or a mixture of two or more thereof.

The acrylic acids, acrylic acid esters, methacrylic acids and methacrylic acid esters (which collectively may be referred to as (meth) acrylic acids and/or esters) may be represented by the following formula:

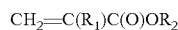

CH$_2$=C(R$_1$)C(O)OR$_2$ wherein R$_1$ is hydrogen or a methyl group, and R$_2$ is hydrogen or a hydrocarbyl group containing from 1 to about 30 carbon atoms, or from 1 to about 20, or from 1 to about 10 carbon atoms, and optionally, one or more sulfur, nitrogen, phosphorus, silicon, halogen and/or oxygen atoms. Examples may include methyl (meth)acrylate, ethyl (meth)acrylate, propyl (meth)acrylate, butyl (meth)acrylate, amyl (meth)acrylate, hexyl (meth)acrylate, 2-hydroxyethyl (meth)acrylate, 2-hydroxypropyl (meth)acrylate, 4-hydroxybutyl (meth)acrylate, N,N-dimethylaminoethyl (meth)acrylate, N,N-diethylaminoethyl (meth)acrylate, 2-sulfoethyl (meth)acrylate, trifluoroethyl (meth)acrylate, glycidyl (meth)acrylate, benzyl (meth)acrylate, 2-chloroethyl (meth)acrylate, 2-ethylhexyl (meth)acrylate, phenyl (meth)acrylate, acrylamide, and mixtures of two or more thereof.

The unsaturated nitriles may comprise acrylonitrile or C$_1$-C$_4$ alkyl derivatives thereof. These may include acrylonitrile, methacrylonitrile, and the like.

The alkenyl-substituted aromatic compounds may comprise an alkenyl group attached to an aromatic group. The alkenyl group may contain from 2 to about 30 carbon atoms. The alkenyl group may include a carbon-carbon double bond in alpha-position to the aromatic group. The alkenyl group may be a vinyl group. The aromatic group may be mononuclear, such as phenyl, or polynuclear. The polynuclear compounds or groups may be of the fused type wherein an aromatic nucleus is fused at two points to another nucleus such as found in anthranyl. The polynuclear group may be of the linked type wherein at least two nuclei (either mononuclear or polynuclear) are linked through bridging linkages to each other. The bridging linkages may include carbon-to-carbon single bonds, ether linkages, keto linkages, sulfide linkages, polysulfide linkages of 2 to about 6 sulfur atoms, sulfinyl linkages, sulfonyl linkages, alkylene linkages, alkylidene linkages, alkylene ether linkages, alkylene keto linkages, alkylene sulfur linkages, alkylene polysulfide linkages, amino linkages, polyamino linkages, mixtures of such divalent bridging linkages, and the like. Examples may include styrene; ortho, meta, or para-methylstyrene; ortho-, meta- or para-ethylstyrene; o-methyl-p-isopropylstyrene; p-chlorostyrene; p-bromostyrene; ortho-, meta- or para-methoxystyrene; vinylnaphthalene; and mixtures of two or more thereof.

The vinyl ester monomers may be derived from carboxylic acids containing 1 to about 30, or 1 to about 20, or 1 to about 10 carbon atoms. These may include vinyl acetate, vinyl propionate, vinyl hexanoate, vinyl 2-ethylhexanoate, vinyl octanoate, vinyl laurate, and mixtures of two or more thereof. The vinyl ethers may include methyl-, ethyl-, and/or butyl vinyl ethers.

The halogenated monomers, that is, fluorine, chlorine, bromine, and/or iodine-containing monomers, may contain from 2 to about 30 carbon atoms and at least one halogen atom. These may include vinyl halides. Examples of these monomers may include vinyl fluoride, vinyl chloride, vinyl bromide, vinylidene fluoride, vinylidene chloride, halogenated (meth)acrylic acid, allyl chloride and mixtures of two or more thereof.

The unsaturated polycarboxylic acids and derivatives thereof may include unsaturated polycarboxylic acids and their corresponding anhydrides. These may include those which have at least one ethylenic linkage in an alpha, beta-position with respect to at least one carboxyl group. Exemplary acids and anhydrides may include maleic acid, maleic anhydride, fumaric acid, itaconic acid, itaconic anhydride, citraconic acid, citraconic anhydride, mesaconic acid, mesaconic anhydride, glutaconic acid, glutaconic anhydride, chloromaleic acid, aconitic acid, mixtures of two or more thereof, and the like.

The polyhydric alcohols may contain from 2 to about 10 carbon atoms, and from 2 to about 6 hydroxyl groups. Examples may include ethylene glycol, glycerol, trimethylolpropane, 1,2-propanediol, 1,3-propanediol, 1,2-butanediol, 1,3-butanediol, 2,3-butanediol, 2-ethyl-1,3-propanediol, 2-ethyl-2-butyl-1,3-propanediol, neopentyl glycol, 2,2,4-trimethyl-1,3-pentanediol, pentaerythritol, sorbitol, mixtures of two or more thereof, and the like.

The polyamines and polyalkylene polyamines may be represented by the formula

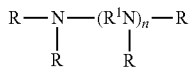

wherein each R is independently hydrogen, a hydrocarbyl group or a hydroxy-substituted hydrocarbyl group containing up to about 30 carbon atoms, or up to about 10 carbon atoms, with the proviso that at least two of the R groups are hydrogen, n is a number in the range from 1 to about 10, or from about 2 to about 8, and $R^1$ is an alkyene group containing 1 to about 18 carbon atoms, or 1 to about 10 carbon atoms, or from about 2 to about 6 carbon atoms. Examples of these polyamines may include methylene polyamine, ethylene polyamine, propylene polyamine, butylenes polyamine, pentylene polyamine, hexylene polyamine, heptylene polyamine, ethylene diamine, triethylene tetramine, tris(2-aminoethyl)amine, propylene diamine, trimethylene diamine, hexamethylene diamine, decamethylene diamine, octamethylene diamine, di(heptamethylene) triamine, tripropylene tetramine, tetraethylene pentamine, trimethylene diamine, pentaethylene hexamine, di(trimethylene) triamine, 2-heptyl-3-(2-aminopropyl)imidazoline, 1,3-bis(2-amino-ethyl)piperazine, 1,4-bis(2-aminoethyl) piperazine, 2-methyl-1-(2-aminobutyl)piperazine, or a mixture of two or more thereof.

The isocyanate monomers may include one or more isocyanate groups (—N=C=O). These may include monoisocyanates and diisocyanates. Examples may include methyl isocyanate, methylene diphenyl diisocyanate, toluene diisocyanate, isophorone diisocyanate, and mixtures of two or more thereof.

The alkenyl-substituted heterocyclic monomers may include heterocyclic compounds wherein the hetero atom is N, O or S. The alkenyl group may contain from 2 to about 30 carbon atoms. The alkenyl group may be a vinyl group. The heterocyclic group may be a 5 or 6 member ring. Examples may include vinyl pyridine, N-vinyl pyrolidone, mixtures thereof, and the like.

The organosilanes may include gamma-aminopropyltrialkoxysilanes, gamma-isocyanatopropyltriethoxysilane, vinyl-trialkoxysilanes, glycidoxypropyltrialkoxysilanes, ureidopropyltrialkoxysilanes, and mixtures of two or more thereof.

The olefin comonomer may comprise 1-decene, and the functionalized monomer may comprise an ester of 8-nonenoic acid, an ester of 9-decenoic acid, an ester of 10-undeceneoic acid, an ester of 9-dodecenoic acid, a mono- or di-ester of 9-octadecenedioic acid, or a mixture of two or more thereof. The esters may be methyl esters.

The olefin comonomer may comprise 1-octene, 1-decene, 1-dodecene, or a mixture of two or more thereof, and the functionalized monomer may comprise methyl 9-decenoate.

The olefin comonomer may comprise 1-octene, 1-decene, dodecene, or a mixture of two or more thereof, and the functionalized monomer may comprise a pentaerythritol tetra-ester of 9-decenoic acid.

Transesterification of an ester (e.g., methyl ester) of 8-decenoic acid, 9-decenoic acid, 10-undecenoic acid, 9-dodecenoic acid, 9-octadecenoic acid, or a mixture of two or more thereof, with pentaerythritol may provide for the making of a tetraester, thereby enabling formation of star or network-type copolymers. The tetraesters may be used as comonomers with olefins to provide for viscosity index (VI) improvers. The tetraesters may be post-treated with polyamines, polyhydric alcohols, and/or alkali or alkaline-earth metal bases to provide materials with dispersant, detergent and/or fuel economy properties.

The functionalized polymer may be derived from one or more unsaturated fatty esters, and subsequent to polymerization the polymer may be transesterified with one or more of the above-indicated alcohols or polyols. For example, a functionalized polymer derived from methyl 8-nonenoate, methyl 9-decenoate, methyl 10-undecenoate, methyl 9-dodecenoate, methyl 9-octadecenoate, or a mixture of two or more thereof, may be transesterified with an alcohol and/or a polyol. The alcohol may contain 2 to about 20 carbon atoms, or from 2 to about 12 carbon atoms, or from 2 to about 8 carbon atoms, or from 2 to about 4 carbon atoms, and may include ethanol, propanol, butanol, mixtures of two or more thereof, and the like. The polyol may contain from 2 to about 10 carbon atoms, and from 2 to about 6 hydroxyl groups. Examples may include ethylene glycol, glycerol, trimethylolpropane, 1,2-propanediol, 1,3-propanediol, 1,2-butanediol, 1,3-butanediol, 2,3-butanediol, 2-ethyl-1,3-propanediol, 2-ethyl-2-butyl-1,3-propanediol, neopentyl glycol, 2,2,4-trimethyl-1,3-pentanediol, pentaerythritol, sorbitol, mixtures of two or more thereof, and the like.

The functionalized polymer may comprise a homopolymer or oligomer wherein a single functionalized monomer is polymerized. The functionalized polymer may comprise a copolymer or co-oligomer when two or more functionalized monomers are copolymerized.

The functionalized polymer may comprise a copolymer or co-oligomer derived from one or more of the functionalized monomers and one or more comonomers wherein from about 1 to about 99 mole percent, or from about 5 to about 95 mole percent, or from about 5 to about 50 mole percent, or from about 5 to about 30 mole percent, of the repeating units are derived from the one or more functionalized monomers.

The functionalized polymer may comprise a copolymer or co-oligomer containing structural repeating units derived from an ester selected from methyl 8-nonenoate, methyl 9-decenoate, methyl 10-undecenoate, methyl 9-octadecenoate, or a mixture of two or more thereof; and structural repeating units derived from an alpha olefin selected from 1-octene, 1-decene, 1-dodecene, or a mixture of two or more thereof. The molar ratio of ester to alpha olefin may range from about 10:1 to about 1:10, or from about 5:1 to about 1:5, or from about 2:1 to about 1:2, or about 1:1. The functionalized polymer may be hydrogenated. The functionalized polymer may be used as a base oil for a lubricant or functional fluid. This base oil may be referred to as a functional base oil. The polymerization reaction is illustrated below.

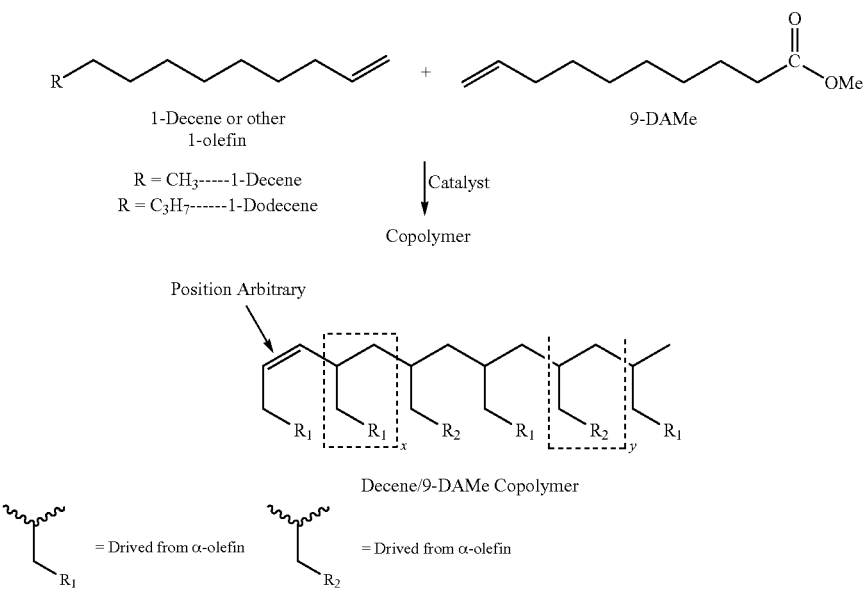

The functionalized polymer may be reacted with one or more enophilic reagents to form one or more enophilic reagent modified functionalized polymers. These may be referred to as polyfunctionalized polymers. This is described below.

The functionalized polymer may have any desired molecular weight, for example, a number average molecular weight in the range from about 100 to about 50,000 or more, or from about 300 to about 50,000, or from about 300 to about 20,000, or from about 300 to about 10,000, or from about 300 to about 5,000, or from about 500 to about 3000, as determined by gel permeation chromatography (GPC), NMR spectroscopy, vapor phase osometry (VPO), wet analytical techniques such as acid number, base number, saponification number or oxirane number, and the like. The polymer may comprise a homopolymer, copolymer, oligomer or a co-oligomer.

The functionalized polymer may be formed using conventional polymerization techniques. The polymerization process may comprise a batch process, a continuous process, or a staged process. Polymerization may be effected either via the one or more carbon-carbon double bonds, the functional groups and/or the additional functionality provided by the enophilic reagent. Polymerization may be effected through a condensation reaction between one or more of the functionalized monomers, polyfunctionalized monomers, and/or comonomers. The polymerization may involve employing one or more cationic, free radical, anionic, Ziegler-Natta, organometallic, metallocene, or ring-opening metathesis polymerization (ROMP) catalysts. Free radical initiators may include azo compounds, peroxides, light (photolysis), and combinations thereof. The azo compounds may include azobisisobutyronitrile (AIBN), 1, 1'-azobis (cyclohexanecarbonitrile), and the like, and combinations thereof. The peroxide compounds may include benzoyl peroxide, methyl ethyl ketone peroxide, tert-butyl peroxide, di-tert-butylperoxide, t-butyl peroxy benzoate, di-t-amyl peroxide, lauroyl peroxide, dicumyl peroxide, tert-butyl perpivalate, di-tert-amyl peroxide, dicetyl peroxydicarbonate, tert-butyl peracetate, 2,2-bis(tert-butylperoxy)butane, 2,5-bis(tert-butylperoxy)-2,5-dimethyl-3-hexyne, 2,5-bis (tert-butylperoxy)-2,5-dimethylhexane, 2,5-dimethyl-2,5-di (t-butyl peroxy) hexane, and the like, and combinations thereof. The free radical initiator may comprise di-t-butyl peroxide. The anionic catalyst may include butyl lithium.

Optionally, it may be desirable to control the molecular weight and molecular architecture prior to or during polymerization by the addition of a chain transfer agent. Suitable chain transfer agents may include dodecanethiol, t-nonylthiol, tetramethylsilane, cyclopropane, sulfur hexafluoride, methane, t-butanol, ethane, ethylene oxide, 2,2-dimethylpropane, benzene, carbon tetrachloride, and bromotrichloromethane.

Polymerization may be achieved under cationic conditions and, in such embodiments, the acid catalyst may comprise a Lewis Acid, a Brønsted acid, or a combination thereof. The Lewis acids may include $BF_3$, $AlCl_3$, zeolite, and the like, and complexes thereof, and combinations thereof. The Brønsted acids may include HF, HCl, $H_2SO_4$, phosphoric acid, acid clay, Amberlyst 15 (a product of Rohm and Haas identified as a sulfonic acid, macroreticular polymeric resin based on crosslinked styrene divinylbenzene copolymers), trifluoromethanesulfonic acid ($CF_3SO_3H$), fluorosulfonic acid ($FSO_3H$), and the like, and combinations thereof.

Polymerization may be achieved using an olefin polymerization catalyst (e.g., $BF_3$) and a promoter (e.g., an alcohol) or a dual promoter (e.g., an alcohol and an ester) as described U.S. Pat. Nos. 7,592,497 B2 and 7,544,850 B2.

The catalysts described herein may be supported on a support. For example, the catalysts may be deposited on, contacted with, vaporized with, bonded to, incorporated within, adsorbed or absorbed in, or on, one or more supports or carriers. The catalysts described herein may be used individually or as mixtures. The polymerizations using multiple catalysts may be conducted by addition of the catalysts simultaneously or in a sequence.

The functionalized polymer may comprise a mixture of different size polymers. Although the degree of polymerization (DP) of a polymer in accordance with the present teachings is not restricted, it is to be understood that polymerization may result in mixtures of polymers having different DP values. The DP of the functionalized polymers may range from about 2 to about 350. It is to be understood that some polymers in the mixture may correspond to homopolymers of the functionalized monomers as well as to copolymers. The functionalized polymer, which may be a homopolymer, copolymer, oligomer or co-oligomer, may have any desired molecular weight depending on its intended use, for example, a number average molecular weight in the range from about 100 to about 50,000 or more, or from about 300 to about 50,000, or in the range from about 300 to about 25,000, or in the range from about 300 to about 10,000 or in the range from about 500 and about 3000, as determined by gel permeation chromatography (GPC), spectroscopy, vapor phase osometry (VPO), wet analytical techniques such as acid number, base number, saponification number or oxirane number, and the like.

In an embodiment, the functionalized polymer may be represented by the following structure:

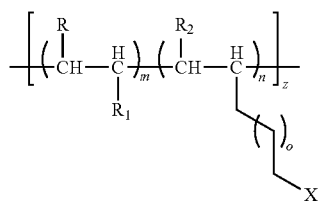

wherein: R, $R_1$, and $R_2$ may be independently hydrogen, a $C_1$-$C_{22}$ alkyl, or —$CH_2(CH_2)_oCH_2X$. When $R_1$ and $R_2$ are alkyl groups, the total number of carbon atoms in these groups may be in the range from about 4 to about 35 carbon atoms. X may be —OH, —$NH_2$, alkylamino, dialkylamino, or —$CO_2R_3$, wherein $R_3$ may be hydrogen or a $C_1$-$C_{10}$ alkyl group derived from a monohydric alcohol, polyhydric alcohol, amine, and/or polyalkylene polyamine. m may be an integer from 0 to about 400. n may be an integer from 1 to about 300. m+n may be in the range from 1 to about 320. o may be an integer from 1 to about 16. z may be an integer from 1 to about 350.

The functionalized polymer may be combined with other polymers by methods known to those skilled in the art. These may include polyurethanes, polyacrylates, polyesters, silicones, and the like.

Adjuvants useful in the preparation of the functionalized polymer and/or in its subsequent use may be added during or subsequent to the polymerization reaction. These may include surfactants, defoamers, leveling agents, antioxidants, thixotropic additives, plasticizers, preservatives, mixtures of two or more thereof, and the like.

Example 1

The following example discloses the oligomerization of 1-decene with methyl 9-decenoate (which may be referred to as 9-DAME or 9-DAMe) in the presence of di-t-amyl peroxide. The reaction proceeds according to the following equation using the reagents shown in the table below.

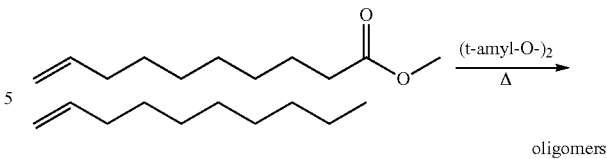

|  | 1-decene | 9-DAME | di-t-amyl peroxide |
|---|---|---|---|
| FW | 140.27 | 184.28 | 174.28 |
| equivalents | 10.00 | 1.00* |  |
| mol | 0.8046 | 0.0805 | 0.1408** |
| g | 112.86 | 14.83 | 24.54 |
| d (g/ml) | 0.74 | 0.90 | 0.82 |
| ml | 152.3 | 16.5 | 30.00 |

*Note: 9-DAME is 9.09 mol % of the total monomer mixture.
**1.75X the "original" peroxide loading The following process steps are followed:

A 250 ml 3-necked round-bottomed flask, equipped with a magnetic stirrer, inert gas inlet/outlet, rubber septum, thermocouple controlled heating mantle, and Dean-Stark trap with condenser, is charged with 1-decene and 9-DAME. The monomer mixture is sparged with inert gas for 1 hour to overnight.

After sparging, the monomer mixture is heated to 150° C. After reaching reaction temperature, the first 1/10 volume portion of peroxide is added by syringe. Peroxide is added in 1/10 portions every 30 minutes (4.5 hours total addition time).

After the initiator addition is complete, the reaction mixture is stirred at 150° C. for 4 hours (8 half lives for the peroxide initiator), then heating is stopped and the reaction is allowed to cool to ambient temperature.

The completed reaction is stripped by equipping the three-neck round-bottom flask with a short path distillation head and receiving flask. With thermocouple controlled heating, the mixture is heated slowly to 200° C. under vacuum. Stripping to 200-205° C. at <2 torr removes the residual monomer to the target <0.25%. The pot residue is the desired product.

The product is filtered while warm (at about 70 to 100° C.) using a medium coarseness paper filter or a coarse fritted filter.

The Dean-Stark trap is used to remove the low boiling point byproducts generated by decomposition of the initiator (e.g. alcohols, ketones). The reaction can be carried out without the trap; however, vigorous refluxing occurs during the reaction, which can reduce the reaction temperature due to evaporative cooling.

The monomers are sparged before heating and the reaction is carried out under a blanket of inert gas.

The baseline, "original" level of peroxide is ~8.3 mol % of the total reaction mixture (mol peroxide/(mol peroxide+decene+9DAME)=0.0833).

Reaction of the Functionalized Monomers and/or Polymers with Enophilic Reagents to Form Enophilic Reagent Modified Functionalized Monomers and/or Polymers The functionalized monomer and/or polymer may be reacted with an enophilic reagent to form an enophilic reagent modified functionalized monomer and/or functionalized polymer. This may provide the functionalized monomers and polymers with additional levels of functionality. These monomers and polymers may be referred to as polyfunctionalized monomers and polymers. The enophilic reagent may comprise an enophilic acid, anhydride and/or ester reagent (e.g., maleic anhydride), an oxidizing agent, an aromatic compound, a sulfurizing agent, hydroxylating agent, halogenating agent, or a mixture of two or more thereof. The enophilic reagent may be reactive towards one or more of the carbon-carbon double bonds in the functionalized monomer or polymer.

The enophilic reagent modified functionalized monomer may be polymerized to form an enophilic reagent modified functionalized polymer (or oligomer), or copolymerized with a comonomer to form an enophilic reagent modified functionalized copolymer (or co-oligomer). The comonomer may comprise an olefin, acrylic acid, acrylic acid ester, methacrylic acid, methacrylic acid ester, unsaturated polycarboxylic acid or derivative thereof, polyhydric alcohol, polyamine, polyalkylene polyamine, isocyanate, diisocyanate, unsaturated nitrile, vinyl ester, vinyl ether, halogenated monomer, alkenyl-substituted aromatic compound (e.g., styrene), akenyl-substituted heterocyclic compound, organosilane, or a mixture of two or more thereof. The comonomer may comprise an olefin containing from 2 to about 30, or from about 6 to about 24, carbon atoms per molecule. These are discussed above.

The polymerization procedure may be the same as discussed above. The polymerization procedure may comprise an acid- or base-catalyzed condensation type polymerization. The polyfunctionalized monomers and/or polymer (which may comprise a copolymer, an oligomer or co-oligomer) may have any desired molecular weight depending upon its intended use, for example, a number average molecular weight in the range from about 100 to about 50,000 or higher, or from about 300 to about 50,000, or from about 150 to about 20,000, or from about 200 to about 10,000, or from about 300 to about 5,000, or from about 500 to about 3000, as determined by gel permeation chromatography (GPC), NMR spectroscopy, vapor phase osmometry (VPO), wet analytical techniques such as acid number, base number, saponification number or oxirane number, and the like.

The ratio of the reactants in the reaction between the functionalized monomer or polymer and the enophilic reagent may be measured by the ratio of the reaction equivalents of the monomer or polymer in the reaction to the reaction equivalents of the enophilic reagent in the reaction. The number of equivalents of the functionalized monomer or polymer may be based on the number of carbon-carbon double bonds in the monomer or polymer. Thus, for example, one mole of a functionalized monomer having two carbon-carbon double bonds in its hydrocarbyl group would have an equivalent weight equal to one-half a mole of the monomer, if the reaction of both double bonds is intended. However, if the reaction of one double bond is intended, then the equivalent weight of such a compound will be the same as its molecular weight. The number average molecular weight of an equivalent of a functionalized polymer having an overall number average molecular weight of 1000 and five carbon-carbon double bonds in its molecular structure would be 200, 400, 600, 800, and 1000; depending upon the number of double bonds taking part in the reaction.

Enophilic Acid-Functionalized Derivative

The functionalized monomer or functionalized polymer of the invention may be reacted with an enophilic acid, anhydride and/or ester reagent to form an enophilic acid functionalized derivative. This derivative may be referred to as a enophilic acid modified functionalized monomer or polymer. When the enophilic acid reagent is maleic anhydride, the derivative may be referred to as a maleinated derivative.

The enophilic acid, anhydride and/or ester reagent may comprise one or more unsaturated carboxylic acids and/or derivatives thereof. The derivative may comprise one or more anhydrides or esters, or one or more amides, aldehydes, acyl halides, and the like. The carboxylic acid or derivative may comprise one or more monobasic and/or polybasic unsaturated carboxylic acids or derivatives thereof. The monobasic carboxylic acids may comprise one or more compounds represented by the formula

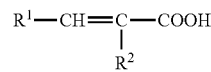

wherein $R^1$ and $R^2$ are independently hydrogen or hydrocarbyl groups. $R^1$ and $R^2$ independently may be hydrocarbyl groups containing 1 to about 20 carbon atoms, or from 1 to about 12 carbon atoms, or from 1 to about 4 carbon atoms.

The polybasic carboxylic acid reagents may comprise one or more alpha, beta unsaturated dicarboxylic acids or derivatives thereof. These may include those wherein a carbon-carbon double bond is in an alpha, beta-position to at least one of the carboxy functions (e.g., itaconic acid, or derivative thereof) or in an alpha, beta-position to both of the carboxy functions (e.g., maleic acid, anhydride or derivative thereof). The carboxy functions of these compounds may be separated by up to about 4 carbon atoms, or about 2 carbon atoms.

Examples of the enophilic acid, anhydride or esters, reagents may include one or more of acrylic acid, methacrylic acid, cinnamic acid, crotonic acid, 3-phenyl propenoic acid, decenoic acid, maleic acid, fumaric acid, mesconic acid, itaconic acid, citraconic acid, and/or anhydrides of any of the foregoing acids including maleic anhydride, and/or esters of any of the foregoing acids and/or anhydrides, and/or mixtures of two or more thereof. The esters may be derived from any of the foregoing acids and/or anhydrides and one or more alcohols and/or one or more polyols. The alcohols may contain from 1 to about 18 carbon atoms, or from 1 to about 8 carbon atoms. The alcohols may include methanol, ethanol, propanol, butanol, pentanol, hexanol, heptanol, octanol, decanol, dodecanol, tetradecanol, hexadecanol, octadecanol, isopropanol, isobutanol, sec-butanol, tert-butanol, isopentanol, amyl alcohol, isoamyl alcohol, neopentyl alcohol, tert-pentanol, cyclopentanol, cyclohexanol, 2-ethyl-hexanol, allyl alcohol, crotyl alcohol, methylvinyl carbinol, benzyl alcohol, alpha-phenylethyl alcohol, beta-phenylethyl alcohol, diphenylcarbinol, triphenylcarbinol, cinnamyl alcohol, mixtures of two or more thereof, and the like. The polyols may contain from 2 to about 10 carbon atoms, and from 2 to about 6 hydroxyl groups. The polyols may include ethylene glycol, glycerol, trimethylolpropane, 1,2-propanediol, 1,3-propanediol, 1,2-butanediol, 1,3-butanediol, 2,3-butanediol, 2-ethyl-1,3-propanediol, 2-ethyl-2-butyl-1,3-propanediol, neopentyl glycol, 2,2,4-trimethyl-1,3-pentanediol, pentaerythritol, sorbitol, mixtures of two or more thereof, and the like.

The ratio of equivalents of the functionalized monomer or functionalized polymer to equivalents the enophilic acid, anhydride and/or ester reagent may be from about 1 to about 4, or from about 1 to about 2. The weight of an equivalent of an enophilic acid, anhydride and/or ester reagent is dependent on the number of carbon-carbon double bonds and/or reactive functional groups in its molecular structure. For example, one mole of an enophilic acid reagent having one carbon-carbon double bond in its molecular structure (e.g., maleic anhydride) would have an equivalent weight equal to its molecular weight, if the reaction was with an olefin, commonly referred to as ene reaction. However, if maleic anhydride were used in an esterification reaction, its equivalent weight would be one-half of its molecular weights. If the ene product, which would have a single carbon-carbon double bond, underwent another ene reaction, its equivalent weight would be the same as its molecular weight.

The reaction between the functionalized monomer or functionalized polymer and the enophilic acid, anhydride and/or ester reagent may be a thermal reaction conducted without a catalyst, or it may be a catalytic reaction. The catalyst may comprise a dialkylperoxide, or a Lewis acid such as $AlCl_3$. The reaction temperature (with or without a catalyst) may be in the range from about 100° C. to about 300° C., or from about 150° C. to about 250° C.

The amount of catalyst added to the reaction may be from about 5 percent by weight to about 15 percent by weight of the functionalized monomer or functionalized polymer, or from about 5 percent by weight to about 10 percent by weight.

The reaction may be conducted in an inert atmosphere, for example, a nitrogen atmosphere. The time of reaction may range from about 1 to about 24 hours, or from about 6 to about 12 hours.

Following the reaction, the product mixture may be subjected to isolation of the crude material. The crude material may be subjected to a vacuum to separate undesired volatile materials from the product.

The malienated derivative may comprise the product made by the reaction of maleic anhydride with one or more internal olefinic esters. The ester may comprise an alkene chain of from about 4 to about 30 carbon atoms, or from about 6 to about 24 carbon atoms, or from about 8 to about 18 carbon atoms, or about 12 carbon atoms, and 1, 2 or 3 internal carbon-carbon double bonds. The ester may comprise an alkene chain of about 12 carbon atoms with an internal carbon-carbon double bond. The molar ratio of the maleic anhydride to the ester may range from about 1:1 to about 2:1. This derivative may be further reacted with one or more alcohols to provide one or more functional products (e.g., polyester) which may be useful as functional base oils for lubricants and functional fluids. The functional base oil may provide the lubricant or functional fluid with enhanced dispensency characteristics.

The malienated derivative may comprise the product made by the reaction of methyl 9-decenoate with maleic anhydride. The molar ratio of the maleic anhydride to methyl 9-decenoate may range from about 1:1 to about 2:1. This derivative may be further reacted with one or more alcohols to provide polyesters which may be useful as functional base oils for lubricants and functional fluids. This is discussed below.

Example 2

The following example discloses a process for the maleinization of methyl 9-decenoate (9-DAME). 9-DAME is reacted with maleic anhydride in an ene reaction to introduce one to two succinic groups per ester. Maleic anhydride is known to participate in ene reactions; this is due to the combined electron-withdrawing power of the two carbonyl groups adjacent to the double bond. The mechanism is believed to involve an allylic shift of one double bond by transferring the allylic hydrogen to the enophile and generating a new bond. The reaction may be promoted by heat and/or Lewis acids. In this reaction no catalyst is used.

2532.9 g (13.74 mol) 9-DAME and 1684.8 g (17.18 mol, 1.25 eq) of maleic anhydride are added into a 5 L three neck flask equipped with a large egg-shaped magnetic stirbar. The flask is then set into a heating mantel (two piece soft heating mantel with zipper). Two condensers are attached, one for incoming nitrogen gas and the other one for the outgoing gas flow. The condensers are air cooled to prevent maleic anhydride to sublime into the gasline. The third neck is used for the thermocouple to control the temperature. After the maleic anhydride is molten the stirrer is set to 750 rpm (two layers combine into one clear phase) and the temperature is stepwise increased to 200° C. The color changes during the reaction starting from colorless to yellow, orange and then to dark red with increasing viscosity. The reaction is kept at 200° C. for 6 hours. After the reaction mixture cools down to room temperature, a shortpath distillation bridge with ice cooled receiving flask is attached and high vacuum is applied starting at ambient temperature and stepwise increasing the temperature up to 200° C. to adjust the distillate flow. Unreacted maleic anhydride distills first. Later at higher temperature it is a mixture of maleic anhydride and unreacted 9-DAME. The distillation is carried out until the distillate flow diminishes. The product is a viscous clear oil with a honey like appearance. Small volumes show a golden color. Larger samples are more red. The yield is 3520 g (83.5%, reactor charge 4217.7 g) after stripping. The acid value (AV) is determined for two samples using a Metrohm 848 Titrino Plus following USP 31: Sample 1 (0.367 g): AV 407.1 mg KOH/g; and Sample 2 (0.265 g): AV 407.2 mg KOH/g. Dynamic viscosties are measured at 40° C. and 100° C. using a RVDV3 Ultra with the results being: $\eta=300$ cP (40° C.); and $\eta=22.5$ cP (100° C.).

Example 3

The following example discloses a process for the maleinization of 9-octadecenoic acid dimethyl ester (ODDA FAME). After filtration over silica gel 1277.7 g (3.75 mol) of ODDA FAME are reacted with 441.5 g (4.50 mol, 1.2 eq) of maleic anhydride. After a reaction time of 6 hours at 200° C. the product is stripped in high vacuum to remove unreacted maleic anhydride. The product is a viscos, brown oil, which is transparent in smaller volumes. NMR shows no residual free maleic anhydride in the stripped product. The AV for the product is 233.8. The conversion is 91.4%. The KV (cSt) at 100° C. is 17.32. The product may be represented by the following formula:

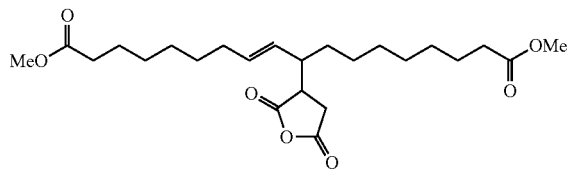 [SMILES: COC(=O)CCCCCC/C=C/C(CCCCCCCC(=O)OC)C1CC(=O)OC1=O]

Oxidized Derivative

The functionalized monomer or functionalized polymer of the invention may be reacted with one or more oxidizing agents. This may result in the formation of one or more oxidized derivatives which may be in the form of one or more epoxides. These may be referred to as polyfunctionalized monomers or polymers The oxidizing agent may comprise any compound that provides oxygen atoms for reaction with one or more of the carbon-carbon double bonds of the functionalized monomer or functionalized polymer. The oxidizing agent may comprise any compound containing an oxygen-oxygen single bond, or a peroxide group or peroxide ion. Examples include hydrogen peroxide, organic peroxides such as peroxy acids (e.g., peroxy carboxylic acid) and organic hydroperoxides (e.g., cumene hydroperoxide), and inorganic peroxides such as peroxide salts (e.g., alkali metal or alkaline earth metal peroxides) and acid peroxides (e.g., peroxymonosulfuric acid, peroxydisulfuric acid, and the like).

The ratio of equivalents of the functionalized monomer or functionalized polymer to equivalents of the oxidizing agent may be from about 3 to about 1, or from about 2 to about 1. The weight of an equivalent of an oxidizing agent is dependent on the number of oxygen atoms in the oxidizing agent that are reactive with the carbon-carbon double bonds in the functionalized monomer or polymer. For example, one mole of an oxidizing agent having one oxygen atom available for reaction with the carbon-carbon double bonds in the functionalized monomer or polymer would have an equivalent weight equal to a fraction of the molecular weight of the oxidizing agent, depending upon the number of carbon-carbon double bonds in the molecule being oxidized.

The reaction between the functionalized monomer or functionalized polymer and the oxidizing agent may be carried out in the presence of a catalyst. The catalyst may comprise Amberlyst (polymer based catalyst available from Rohm & Haas), Amberlite (ion exchange resin available from Rohm & Haas), formic acid, acetic acid and/or sulfuric acid.

The reaction of the functionalized monomer or functionalized polymer with the oxidizing agent may be enhanced by heating the reaction mixture (with or without a catalyst) to a temperature in the range from about 30° C. to about 180° C., or from about 50° C. to about 70° C.

The amount of catalyst added to the reaction may be from about 5 percent by weight to about 25 percent by weight of the functionalized monomer or functionalized polymer in the reaction mixture, or from about 5 percent by weight to about 20 percent by weight.

The reaction may be conducted in an inert atmosphere, for example, a nitrogen atmosphere, in a solvent or neat (without solvent). The time of reaction may range from about 6 to about 24 hours, or from about 8 to about 12 hours.

Following the reaction, the product mixture may be subjected to isolation of the crude material. The crude material may be subjected to a vacuum to separate undesired volatile materials from the product.

Alkylated Aromatic Compound

The functionalized monomer or functionalized polymer of the invention may be reacted with one or more aromatic compounds to form an alkylated aromatic compound. These may be referred to as alkylation reactions wherein the functionalized monomer or polymer may be attached to the aromatic compound via one or more of the carbon-carbon double bonds in the functionalized monomer or polymer. The product may be referred to as a polyfunctionalized monomer or polymer.

The aromatic compound may comprise any aromatic compound capable of reacting with the functionalized monomer or polymer of the invention. The aromatic compound may comprise an aromatic, aliphatic-substituted aromatic, or aromatic-substituted aliphatic compound. The aromatic compound may comprise a substituted aromatic compound, that is, an aromatic compound containing one or more non-hydrocarbon groups such as hydroxyl, halo, nitro, amino, cyano, alkoxy, acyl, epoxy, acryloxy, mercapto, mixtures of two or more thereof, and the like. The aromatic compound may comprise a hetero substituted aromatic compound, that is, an aromatic compound containing one or more atoms other than carbon in a chain or ring otherwise comprising carbon atoms; examples of such hetero atoms including nitrogen, oxygen and sulfur.

The aromatic compound may comprise one or more of benzene, naphthalene, naphthacene, alkylated derivatives thereof, and the like. The aromatic compound may contain from 6 to about 40 carbon atoms, or from 6 to about 30 carbon atoms, or from 6 to about 20 carbon atoms, or from 6 to about carbon atoms, or from 6 to about 12 carbon atoms. Examples may include benzene, toluene, ethylbenzene, styrene, alpha-methyl styrene, propylbenzene, xylene, mesitylene, methylethylbenzene, naphthalene, anthracene, phenanthrene, methynaphthalene, dimethylnaphthalene, tetralin, mixtures of two or more thereof, and the like. The aromatic compound may comprise phenol and/or its derivatives, dihydroxybenzene, naphthol and/or dihydroxynaphthalene. The aromatic compound may comprise an aromatic amine and/or a pyridine. The aromatic compound may comprise aniline, diphenylamine, toluidine, phenylenediamine, diphenylamine, alkyldiphenylamine, and/or phenothiazine. The aromatic compound may comprise an alkylbenzene with a multi-substituted benzene ring, examples including o-, m- and p-xylene, toluene, tolyl aldehyde, toluidine, o-, m- and p-cresol, phenyl aldehyde, mixtures of two or more thereof, and the like.

The ratio of equivalents of the functionalized monomer or polymer to equivalents of the aromatic compound may be from about 4:1 to about 1:1, or from about 2:1 to about 1:1. The weight of an equivalent of an aromatic compound would be equal to the molecular weight of the aromatic compound, if only a single carbon-carbon double bond were to take part in the reaction. Otherwise, it would be a fraction of 1 (i.e., less than 1).

The reaction between the functionalized monomer or polymer and the aromatic compound may be carried out in the presence of a catalyst. The catalyst may comprise a Lewis acid, Bronsted acid, acid clay and/or zeolite.

The reaction of the functionalized monomer or polymer with the aromatic compound may be enhanced by heating the reaction mixture (with or without a catalyst) to a temperature in the range from about 50° C. to about 300° C., or from about 100° C. to about 200° C.

The amount of catalyst added to the reaction may be from about 1 percent by weight to about 100 percent by weight of the functionalized monomer or polymer in the reaction mixture, or from about 30 percent by weight to about 50 percent by weight.

The reaction may be conducted in an inert atmosphere, for example, a nitrogen atmosphere. The time of reaction may range from about 2 to about 24 hours, or from about 6 to about 12 hours.

Following the reaction, the product mixture may be subjected to isolation of the crude material. The crude material may be subjected to a vacuum to separate undesired volatile materials from the product.

Sulfurized Derivative

The functionalized monomer or polymer of the invention may be reacted with one or more sulfurizing agents to form a sulfurized derivative. The sulfurized derivative may be referred to as a polyfunctionalized monomer or polymer.

The sulfurizing agent may comprise elemental sulfur and/or any suitable sulfur source. The sulfur source may comprise a variety of materials capable of supplying sulfur to the reaction. Examples of useful sulfur sources may include sulfur halides, combinations of sulfur or sulfur oxides with hydrogen sulfide, and various sulfurized organic compounds as described below. The sulfur halides may include sulfur monochloride, sulfur dichloride, mixtures thereof, and the like. Combinations of sulfur and sulfur oxides (such as sulfur dioxide), with hydrogen sulfide may be used.

The sulfurizing agent may comprise one or more of the sulfur-coupled compounds. These may include one or more sulfur-coupled organic compounds, for example, disulfides (RSSR), trisulfides ($RS_3R$), polysulfides ($RS_xR$, where x is from 4 to 7), mixtures of two or more thereof, and the like.

The sulfurizing agent may comprise one or more phosphorus sulfides. Examples may include $P_2S_5$, $P_4S_{10}$, $P_4S_7$, $P_4S_3$ and $P_2S_3$, mixtures of two or more thereof, and the like.

The sulfurizing agent may comprise one or more aromatic and/or alkyl sulfides such as dibenzyl sulfide, dixylyl sulfide, dicetyl sulfide, diparaffin wax sulfide and/or polysulfide, cracked wax oleum sulfides, mixtures of two or more thereof, and the like. The aromatic and alkyl sulfides may be prepared by the condensation of a chlorinated hydrocarbon with an inorganic sulfide whereby the chlorine atom from each of two molecules may be displaced, and the free valence from each molecule may be joined to a divalent sulfur atom. The reaction may be conducted in the presence of elemental sulfur.

Dialkenyl sulfides that may be used may be prepared by reacting an olefinic hydrocarbon containing from about 3 to about 12 carbon atoms with elemental sulfur in the presence of zinc or a similar metal generally in the form of an acid salt. Examples of sulfides of this type may include 6,6'-dithiobis(5-methyl-4-nonene), 2-butenyl monosulfide and disulfide, and 2-methyl-2-butenyl monosulfide and disulfide.

Sulfurized olefins which may be used as the sulfurizing agent may include sulfurized olefins prepared by the reaction of an olefin of about 3 to about 6 carbon atoms, or a lower molecular weight polyolefin derived therefrom, with a sulfur-containing compound such as sulfur, sulfur monochloride, sulfur dichloride, hydrogen sulfide, mixtures of two or more thereof, and the like.

The sulfurizing agent may comprise one or more sulfurized oils which may be derived from one or more natural or synthetic oils including mineral oils, lard oil, carboxylic acid esters derived from aliphatic alcohols and fatty acids or aliphatic carboxylic acids (e.g., myristyl oleate and oleyl oleate), sperm whale oil and synthetic sperm whale oil substitutes, and synthetic unsaturated esters or glycerides. Sulfurized mineral oils may be obtained by heating a suitable mineral oil with from about 1 to about 5% by weight of sulfur at a temperature in the range from about 175° C. to about 260° C. The mineral oils sulfurized in this manner may be distillate or residual oils obtained from paraffinic, naphthenic or mixed base crudes. Sulfurized fatty oils such as a sulfurized lard oil may be obtained by heating lard oil with about 10 to 15% of sulfur at a temperature of about 150° C. for a time sufficient to obtain a homogeneous product.

The sulfurized fatty acid esters may be prepared by reacting sulfur, sulfur monochloride, and/or sulfur dichloride with an unsaturated fatty ester at elevated temperatures. Typical esters may include $C_1$-$C_{20}$ alkyl esters of $C_8$-$C_{24}$ unsaturated fatty acids such as palmitoleic, oleic, ricinoleic, petroselic, vaccenic, linoleic, linolenic, oleostearic, licanic, etc. Sulfurized fatty acid esters prepared from mixed unsaturated fatty acid esters such as those that may be obtained from animal fats and vegetable oils such as tall oil, linseed oil, olive oil, castor oil, peanut oil, rapeseed oil, fish oil, sperm oil, etc. also may be used. Specific examples of the fatty esters which may be sulfurized may include methyl oleate, ethyl oleate, lauryl oleate, cetyl oleate, cetyl linoleate, lauryl ricinoleate, oleyl linoleate, oleyl stearate, alkyl glycerides, mixtures of two or more thereof, and the like.

Another class of organic sulfur-containing compounds which may be used as the sulfurizing agent may include sulfurized aliphatic esters of olefinic mono- or dicarboxylic acids. For example, aliphatic alcohols of from 1 to about 30 carbon atoms may be used to esterify monocarboxylic acids such as acrylic acid, methacrylic acid, 2,4-pentadienic acid, fumaric acid, maleic acid, muconic acid, etc. Sulfurization of these esters may be conducted with elemental sulfur, sulfur monochloride and/or sulfur dichloride.

Another class of sulfurized organic compounds which may be used as the sulfurizing agent may include diester-sulfides represented by the formula

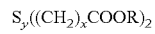

$$S_y((CH_2)_xCOOR)_2$$

wherein x is a number in the range of about 2 to about 5; y is a number in the range of 1 to about 6, or 1 to about 3; and R is an alkyl group having from about 4 to about 20 carbon atoms. The R group may be a straight chain or branched chain group. Typical diesters may include the butyl, amyl, hexyl, heptyl, octyl, nonyl, decyl, tridecyl, myristyl, pentadecyl, cetyl, heptadecyl, stearyl, lauryl, and eicosyl diesters of thiodialkanoic acids such as propionic, butanoic, pentanoic and hexanoic acids. The diester sulfides may include dilauryl 3,3'-thiodipropionate.

The sulfurizing agent may comprise one or more sulfurized olefins. These may include the organic polysulfides which may be prepared by the sulfochlorination of olefins containing four or more carbon atoms and further treatment with inorganic higher polysulfides according to U.S. Pat. No. 2,708,199.

The sulfurized olefins may be produced by (1) reacting sulfur monochloride with a stoichiometric excess of a low carbon atom olefin, (2) treating the resulting product with an alkali metal sulfide in the presence of free sulfur in a mole ratio of no less than 2:1 in an alcohol-water solvent, and (3) reacting that product with an inorganic base. This procedure is described in U.S. Pat. No. 3,471,404. The olefin reactant may contain from about 2 to about 5 carbon atoms. Examples may include ethylene, propylene, butylene, isobutylene, amylene, and mixtures of two or more thereof. In the first step, sulfur monochloride may be reacted with from one to two moles of the olefin per mole of the sulfur monochloride. The reaction may be conducted by mixing the reactants at a temperature of from about 20° C. to 80° C. In the second step, the product of the first step may be reacted with an alkali metal, preferably sodium sulfide, and sulfur. The mixture may comprise up to about 2.2 moles of the metal sulfide per gram atom of sulfur, and the mole ratio of alkali metal sulfide to the product of the first step may be about 0.8 to about 1.2 moles of metal sulfide per mole of step (1) product. The second step may be conducted in the presence of an alcohol or an alcohol-water solvent under reflux conditions. The third step of the process may comprise the reaction between the phosphosulfurized olefin which may contain from about 1 to about 3% of chlorine with an inorganic base in a water solution. Alkali metal hydroxide such as sodium hydroxide may be used. The reaction may be continued until the chlorine content is reduced to below about 0.5%. This reaction may be conducted under reflux conditions for a period of from about 1 to about 24 hours.

The sulfurizing agent may be prepared by the reaction, under superatmospheric pressure, of olefinic compounds with a mixture of sulfur and hydrogen sulfide in the presence of a catalyst, followed by removal of low boiling materials.

This procedure is described in U.S. Pat. No. 4,191,659. An optional final step described in this patent is the removal of active sulfur by, for example, treatment with an alkali metal sulfide. The olefinic compounds which may be sulfurized by this method may contain at least one carbon-carbon double bond. These compounds may be represented by the formula

wherein each of $R^1$, $R^2$, $R^3$ and $R^4$ is hydrogen or a hydrocarbyl group. Any two of $R^1$, $R^2$, $R^3$ and $R^4$ may together form an alkylene or substituted alkylene group; i.e., the olefinic compound may be alicyclic.

The ratio of equivalents of the functionalized monomer or polymer to equivalents of the sulfurizing agent may be from about 1 to about 10, or from about 1 to about 6. The weight of an equivalent of a sulfurizing agent is dependent on the number of sulfur atoms in the sulfurizing agent that are reactive with the carbon-carbon double bonds in the functionalized monomer or polymer. For example, one mole of a sulfurizing agent having one sulfur atom available for reaction with the carbon-carbon double bonds in the functionalized monomer or polymer would have an equivalent weight equal to the molecular weight of the sulfurizing agent.

The reaction between the functionalized monomer or polymer and the sulfurizing agent may be carried out in the presence of a catalyst. The catalyst may comprise tertiary phosphine, iodine, $BF_3$, metal dithiocarbamate, and the like.

The reaction of the functionalized monomer or polymer with the sulfurizing agent may be enhanced by heating the reaction mixture (with or without a catalyst) to a temperature in the range from about 130° C. to about 200° C., or from about 150° C. to about 180° C.

The amount of catalyst added to the reaction may be from about 1 percent by weight to about 20 percent by weight of the functionalized monomer or polymer, or from about 5 percent by weight to about 10 percent by weight.

The reaction may be conducted in an inert atmosphere, for example, a nitrogen atmosphere. The time of reaction may range from about 2 to about 8 hours, or from about 4 to about 6 hours.

Following the reaction, the product mixture may be subjected to isolation of the crude material. The crude material may be subjected to a vacuum to separate undesired volatile materials from the product.

Hydroxylated Derivative

The functionalized monomer or polymer of the invention may be reacted with one or more hydroxylating agents to form a hydroxylated derivative. The hydroxylated derivative may be referred to as a polyfunctionalized monomer or polymer.

The hydroxylation agent may comprise any compound that introduces a hydroxyl into the monomer or polymer. The hydroxylating agent may comprise water, hydrogen peroxide, or a mixture thereof.

The ratio of equivalents of the functionalized monomer or polymer to equivalents of the hydroxylating agent may be from about 1 to about 8, or from about 1 to about 4. The weight of an equivalent of an hydroxylating agent is dependent on the number of hydroxyl groups in the hydroxylating agent that are reactive with the carbon-carbon double bonds in the functionalized monomer or polymer. For example, one mole of an hydroxylating agent having one hydroxyl group available for reaction with each carbon-carbon double bond in the functionalized monomer or polymer would have an equivalent weight equal to the molecular weight of the hydroxylating agent.

The reaction between the functionalized monomer or polymer and the hydroxylating agent may be carried out in the presence of a catalyst. The catalyst may comprise oxygen, or a strong mineral acid such as hydrochloric acid, sulfuric acid, hydroiodic acid, or a mixture of two or more thereof.

The reaction of the functionalized monomer or polymer with the hydroxylating agent may be enhanced by heating the reaction mixture (with or without a catalyst) to a temperature in the range from about 20° C. to about 100° C., or from about 25° C. to about 60° C.

The amount of catalyst added to the reaction may be from about 1 percent by weight to about 20 percent by weight of the functionalized monomer or polymer in the reaction mixture, or from about 5 percent by weight to about 10 percent by weight. The time of reaction may range from about 2 to about 12 hours, or from about 3 to about 5 hours.

Following the reaction, the product mixture may be subjected to isolation of the crude material. The crude material may be subjected to a vacuum to separate undesired volatile materials from the product.

Halogenated Derivative

The functionalized monomer or polymer of the invention may be reacted with one or more halogenating agents to form a halogenated derivative. The halogenated derivative may be referred to as a polyfunctionalized monomer or polymer.

The halogenating agent may comprise any compound that provides for the addition of a halogen atom (e.g., F, Cl, Br, I, or a mixture of two or more thereof) to the monomer or polymer. The halogenating agent may comprise fluorine, chlorine, bromine, iodine, hydrogen chloride, hydrogen bromide, hydrogen fluoride, iodine monochloride, antimony pentafluoride, molybdenum pentachloride, nitrogen fluoride oxide, antimony pentachloride, tungsten hexafluoride, tellurium hexafluoride, sulfur tetrafluoride, sulfur monochloride, silicon tetrafluoride, phosphorus pentafluoride, or a mixture of two or more thereof.

The ratio of equivalents of the functionalized monomer or polymer to equivalents of the halogenating agent may be from about 1 to about 8, or from about 1 to about 4. The weight of an equivalent of a halogenating agent is dependent on the number of halogen atoms in the halogenating agent that are reactive with each carbon-carbon double bond in the functionalized monomer or polymer. For example, one mole of a halogenating agent having one halogen atom available for reaction with the carbon-carbon double bonds in the functionalized monomer or polymer would have an equivalent weight equal to the molecular weight of the halogenating agent.

The reaction between the functionalized monomer or polymer and the halogenating agent may be carried out in the presence of a catalyst. The catalyst may comprise light, oxygen, one or more peroxides, one or more metal halides, or a mixture of two or more thereof.

The reaction of the functionalized monomer or polymer with the halogenating agent may be enhanced by heating the reaction mixture (with or without a catalyst) to a temperature in the range from about 20° C. to about 100° C., or from about 40° C. to about 60° C.

The amount of catalyst added to the reaction may be from about 2 percent by weight to about 10 percent by weight of the functionalized monomer or polymer in the reaction mixture, or from about 3 percent by weight to about 5 percent by weight. The time of reaction may range from about 1 to about 12 hours, or from about 2 to about 6 hours.

Following the reaction, the product mixture may be subject to isolation of the crude material. The crude material may be subjected to a vacuum to separate undesired volatile materials from the product.

Derivatized Functionalized Compounds

The functionalized or polyfunctionalized monomers and/or polymers, or enophilic reagent modified functionalized monomers and/or polymers, of the invention may be further derivatized by reaction with one or more oxygen-containing reagents (e.g., alcohols, polyols, etc.), one or more nitrogen-containing reagents (e.g., ammonia, amines, polyamines, aminoalcohols, amine terminated polyoxyalkylenes, etc.), metals, metal compounds, or a mixture of two or more thereof, to form one or more derivatized functionalized compounds. These compounds may comprise esters, di-esters, tri-esters, amides, di-amides, triamides, imides, amide esters, amine salts, ammonium salts, ester salts, metal salts, mixtures of two or more thereof, and the like.

The polyfunctionalized monomers and/or polymers may comprise malienated functionalized monomers and/or polymers, including malienated methyl 8-nonenoate, malienated methyl 9-decenoate, malienated methyl 10-undecenoate, malienated methyl 9-dodecenoate, malienated dimethyl esters of 9-octadecenoic acid, mixtures of two or more thereof, and the like.

The metal may be an alkali metal (e.g., a Group IA metal such as Li, Na, K, Rb, and Cs); alkaline earth metal (e.g., Group IIA metals such as Be, Mg, Ca, Sr, and Ba); Group IIIA metal (e.g., B, Al, Ga, In, and Tl); Group IVA metal (e.g., Sn and Pb), Group VA metal (e.g., Sb and Bi); transition metal (e.g., Sc, Ti, V, Cr, Mn, Fe, Co, Ni, Cu, Zn, Zr, Mo, Ru, Rh, Pd, Ag and Cd), lanthanide or actinides, or a mixture of two or more thereof. The metal may comprise an alkali metal, alkaline earth metal, titanium, zirconium, molybdenum, iron, copper, aluminum, zinc, or a mixture of two or more thereof.

The nitrogen-containing reagent may comprise ammonia and/or a compound containing one or more primary and/or secondary amino groups. These may be referred to as amines. The amine may be a monoamine or a polyamine. The amine may be a mono-substituted amine having one non-hydrogen substituted group (such as an alkyl, aryl group, alkyl-amino group, or aryl-amino group), a di-substituted amine having two non-hydrogen substituted groups, an amino-alcohol, an amine terminated poly (oxyalkylene) or a combination of two or more thereof.

The mono-substituted and di-substituted amines may include methylamine, dimethylamine, ethylamine, diethylamine, propylamine, dipropylamine, butylamine, dibutylamine, pentylamine, dipentylamine, hexylamine, dihexylamine, heptylamine, diheptylamine, octylamine, dioctylamine, or a mixture thereof. In other non-limiting embodiments, the amine is an amino-alcohol such as: methanolamine, dimethanolamine, ethanolamine, diethanolamine, propanolamine, dipropanolamine, butanolamine, dibutanolamine, pentanolamine, dipentanolamine, hexanolamine, dihexanolamine, heptanolamine, diheptanolamine, octanolamine, dioctanolamine, aniline, or a mixture of two or more thereof.

The amine may be a diamine. Examples may include ethylenediamine (1,2-ethanediamine), 1,3-propanediamine, 1,4-butanediamine (putrescine), 1,5-pentanediamine, 1,6-hexanediamine, 1,7-heptanediamine, 1,8-octanediamine, 1,3-bis(aminomethyl)cyclohexane, meta-xylenediamine, 1,8-naphthalenediamine, p-phenylenediamine, N-(2-aminoethyl)-1,3-propanediamine, or a mixture of two or more thereof.

The amine may be a triamine, a tetramine, or a mixture thereof. Examples of these may include diethylenetriamine, dipropylenetriamine, dibutylenetriamine, dipentylenetriamine, dihexylenetriamine, diheptylenetriamine, dioctylenetriamine, spermidine, melamine, triethylenetetramine, tripropylenetetramine, tributylenetetramine, tripentylenetetramine, trihexylenetetramine, triheptylenetetramine, trioctylenetetramine, hexamine, or a mixture of two or more thereof. The amine may be an imidazole, such as aminopropylimidazole, or an oxazolidine.

The amine may comprise ethanolamine, diethanolamine, diethylamine, ethylenediamine, hexamethyleneamine, or a mixture of two or more thereof. The amine may be ethylenediamine. The amine may be diethanolamine.

The amine may comprise an amino-alcohol. Examples may include methanolamine, dimethanolamine, ethanolamine, diethanolamine, propanolamine, dipropanolamine, butanolamine, dibutanolamine, pentanolamine, dipentanolamine, hexanolamine, dihexanolamine, heptanolamine, diheptanolamine, octanolamine, dioctanolamine, aniline, or a mixture of two or more thereof.

The amine may comprise a polyamine or polyalkylene polyamine represented by the formula

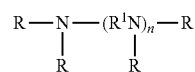

wherein each R is independently hydrogen, a hydrocarbyl group or a hydroxy-substituted hydrocarbyl group containing up to about 30 carbon atoms, or up to about 10 carbon atoms, with the proviso that at least one R is hydrogen, n is a number in the range from 1 to about 10, or from about 2 to about 8, and $R^1$ is an alkyene group containing 1 to about 18 carbon atoms, or 1 to about 10 carbon atoms, or from about 2 to about 6 carbon atoms. Examples of these polyamines may include methylene polyamine, ethylene polyamine, propylene polyamine, butylenes polyamine, pentylene polyamine, hexylene polyamine, heptylene polyamine, ethylene diamine, triethylene tetramine, tris(2-aminoethyl)amine, propylene diamine, trimethylene diamine, hexamethylene diamine, decamethylene diamine, octamethylene diamine, di(heptamethylene) triamine, tripropylene tetramine, tetraethylene pentamine, trimethylene diamine, pentaethylene hexamine, di(trimethylene) triamine, 2-heptyl-3-(2-aminopropyl)imidazoline, 1,3-bis(2-amino-ethyl)piperazine, 1,4-bis(2-aminoethyl)piperazine, 2-methyl-1-(2-aminobutyl)piperazine, or a mixture of two or more thereof.

The amine may comprise one or more amine terminated poly (oxyalkylenes). These may include one or more alpha omega diaminopoly (oxyalkylenes). The amine terminated, or alpha omega diamino terminated, poly(oxyalkylenes) may include amine terminated poly (oxyethylenes), amine terminated poly (oxypropylenes), amine terminated poly (oxyethylene) poly (oxypropylenes), amine terminated poly (oxypropylene) poly (oxyethylene) poly(oxyprolyene)s, mixtures of two or moe thereof, and the like. The amine terminated polyoxyalkylenes may comprise urea condensates of such alpha omega diamino poly(oxyethylene)s, alpha omega diamino poly(oxypropylene) poly(oxyethylene) poly(oxypropylene)s, or alpha omega diamino propylene oxide capped poly(oxypropylene) poly(oxyethylene) poly(oxypropylene)s, or alpha omega diamino propylene oxide capped poly(oxyethylene)s. The amine terminated polyoxyalkylene may be a polyamine (e.g., triamino, tetramino, etc.) polyoxyalkylene. In the compounds that contain both poly(oxyethylene) and poly(oxypropylene) groups, the poly(oxyethylene) groups may dominate if water solubility is desired. The terminal amines may be primary amines, e.g., —NH$_2$, or secondary amines, e.g. —NHR* wherein R* is a hydrocarbyl group of from 1 to about 18 carbon atoms, or from 1 to about 4 carbon atoms. R* may be an alkyl or an alkenyl group. These compounds may have number average molecular weights of at least about 1000, or in the range of about 1000 to about 30,000, or in the range of about 2000 to about 10,000, or in the range of about 3500 to about 6500. Mixtures of two or more of these compounds may be used.

The equivalent ratio of C=O in the functionalized or polyfunctionalized monomer or polymer to N in the nitrogen-containing reagent may be from about 1 to about 10, or from about 1 to about 5.

The reaction between the functionalized or polyfunctionalized monomer or polymer and the nitrogen-containing reagent may be carried out in the presence of a catalyst. The catalyst may be a basic catalyst. The catalyst may comprise one or more of sodium carbonate, lithium carbonate, sodium methanolate, potassium hydroxide, sodium hydride, potassium butoxide, potassium carbonate, or a mixture thereof. The catalyst may be added to the reaction mixture in dry form or in the form of a solution. The reaction may be enhanced by heating the reaction mixture (with or without a catalyst) to at least about 80° C., or at least about 100° C., or at least about 120° C., or at least about 140° C., or at least about 160° C.

The amount of catalyst added to the reaction may be in the range from about 0.01 percent by weight to about 5 percent by weight of the functionalized or polyfunctionalized monomer or polymer, in the reaction mixture, or from about 0.01 percent by weight to about 1 percent by weight, or from about 0.2 percent by weight to about 0.7 percent by weight.

The reaction may be conducted in an inert atmosphere, for example, a nitrogen atmosphere. The time of reaction may range from about 1 to about 24 hours, or from about 1 to about 12 hours, or from about 1 to about 6 hours, or from about 1 to about 4 hours.

The product may comprise one or more amides, di-amides, tri-amides, amide esters, imides, amine salts, ammonium salts, mixtures of two or more thereof, and the like.

The oxygen-containing reagent may comprise one or more alcohols and/or one or more polyols. The alcohols may contain from 1 to about 18 carbon atoms, or from 1 to about 8 carbon atoms. These may include methanol, ethanol, propanol, butanol, pentanol, hexanol, heptanol, octanol, decanol, dodecanol, tetradecanol, hexadecanol, octadecanol, isopropanol, isobutanol, sec-butanol, tert-butanol, isopentanol, amyl alcohol, isoamyl alcohol, neopentyl alcohol, 2-ethyl-1-hexanol, tert-pentanol, cyclopentanol, cyclohexanol, allyl alcohol, crotyl alcohol, methylvinyl carbinol, benzyl alcohol, alpha-phenylethyl alcohol, beta-phenylethyl alcohol, diphenylcarbinol, triphenylcarbinol, cinnamyl alcohol, mixtures of two or more thereof, and the like.

The polyols may contain from 2 to about 10 carbon atoms, and from 2 to about 6 hydroxyl groups. Examples may include ethylene glycol, glycerol, trimethylolpropane, 1,2-propanediol, 1,3-propanediol, 1,2-butanediol, 1,3-butanediol, 2,3-butanediol, 2-ethyl-1,3-propanediol, 2-ethyl-2-butyl-1,3-propanediol, neopentyl glycol, 2,2,4-trimethyl-1,3-pentanediol, pentaerythritol, sorbitol, mixtures of two or more thereof, and the like.

The equivalent ratio of C=O in the functionalized or polyfunctionalized monomer or polymer to —OH in the oxygen-containing reagent may be from about 1 to about 6, or from about 1 to about 3, or from about 1 to about 2, or about 1.

The reaction between the functionalized or polyfunctionalized monomer or polymer and the oxygen-containing reagent may be carried out in the presence of a catalyst. The catalyst may be a Lewis acid, a Bronsted acid and/or a sulfonic acid. The reaction may be enhanced by heating the reaction mixture (with or without a catalyst) to a temperature in the range from about 100° C. to about 250° C., or from about 150° C. to about 200° C.

The amount of catalyst added to the reaction may be from about 0.01 percent by weight to about 5 percent by weight of the functionalized or polyfunctionalized monomer or polymer in the reaction mixture, or from about 0.5 percent by weight to about 2 percent by weight.

The reaction may be conducted in an inert atmosphere, for example, a nitrogen atmosphere. The time of reaction may range from about 3 to about 24 hours, or from about 8 to about 12 hours.

The product may comprise one or more mono-, di- and/or tri-esters. The product may comprise one or more polyesters which may be useful as base oils for lubricants and functional fluids. These base oils may provide the lubricant or functional fluid with enhanced disperency properties, and as such may be referred to as functional base oils.

The following drawings are provided to disclose useful esterification reactions for malienated methyl 9-decenoate (9-DAMe, which may also be referred to as 9-DAME). In the drawings, the following abbreviations are used: 9-DAMe for methyl 9-decenoate; 9-DDAMe for methyl 9-dodecenoate; 10-UDAMe for methyl 10-undecenoate; FAMe for fatty acid methyl ester; and 9-ODDA Me$_2$ for di-methyl ester 9-octadecenoic acid.

Monohydric Alcohol Esters of Maleinated 9-DAMe
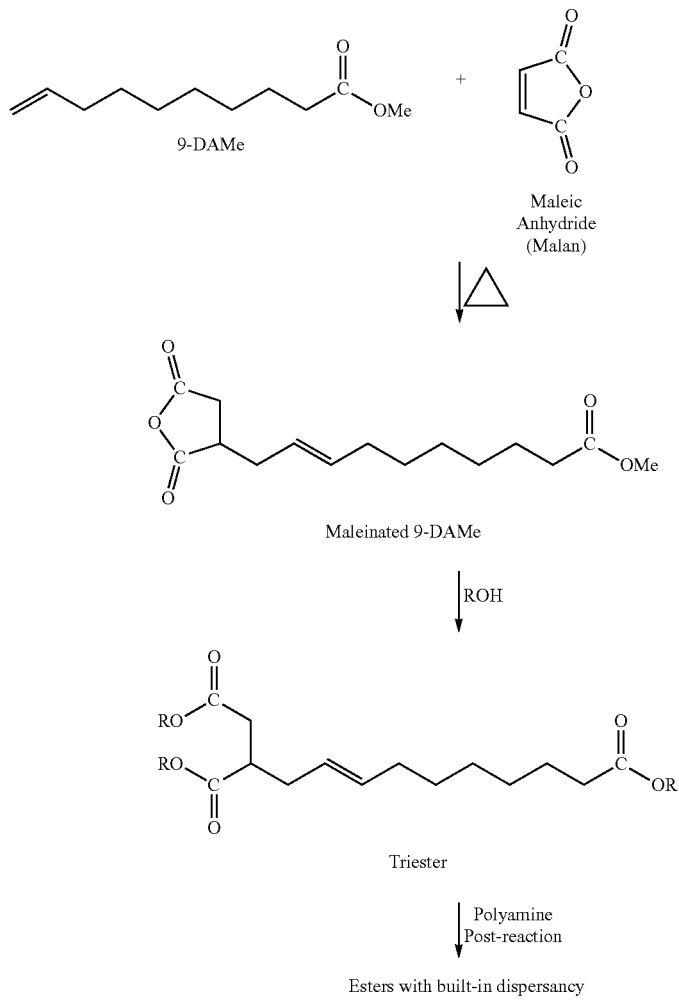
Maleinated 9-DAMe
Triester
Esters with built-in dispersancy
Similar Esters from 9-DDAMe, 10-UDAMe, FAMe, and 9-ODDAMe$_2$ are Possible
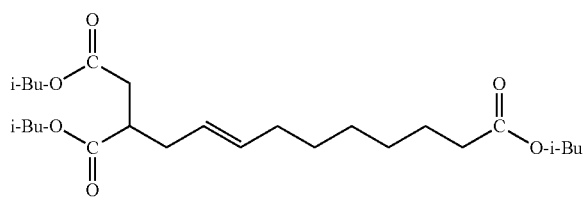
Isobutyl Triester of Maleinated 9-DAMe
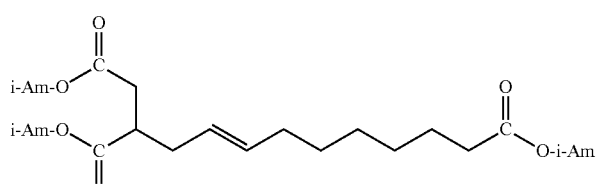
Isoamyl Triester of Maleinated 9-DAMe -continued
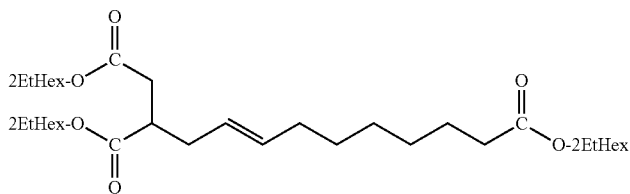
2-Ethylhexyl Triester Maleinated 9-DAMe
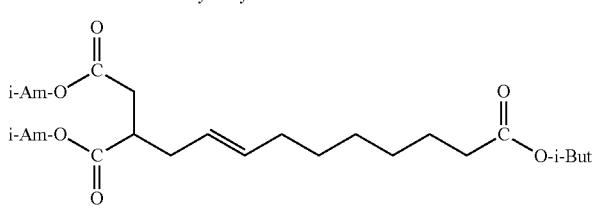
Mixed Alcohol Triester of Maleinated 9-DAMe
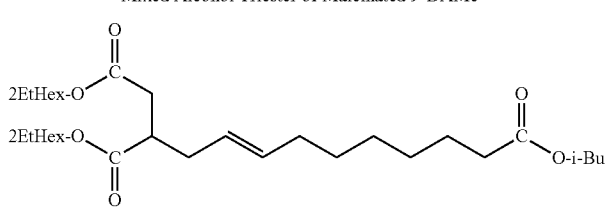
Mixed Alcohol Triester of Maleinated 9-DAMe
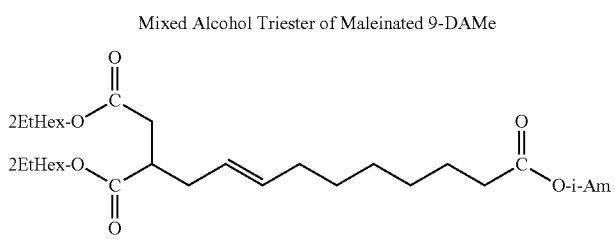
Mixed Alcohol Triester of Maleinated 9-DAMe
Monohydric Alcohol Esters of Maleinated 9-DAMe
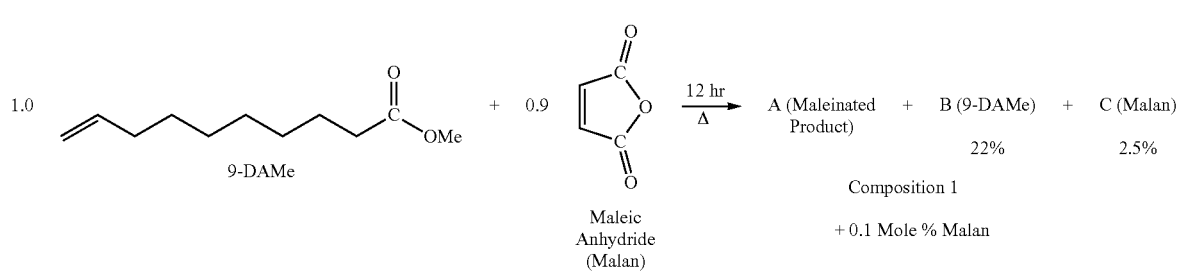
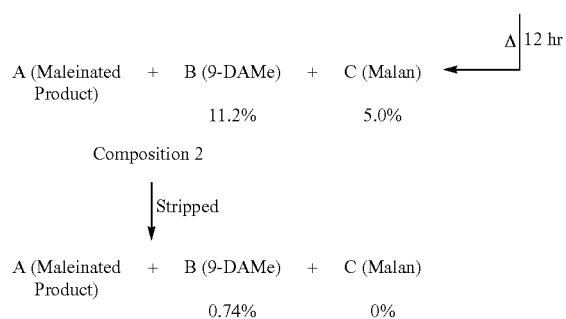

Composition + 3 ROH ⟶ 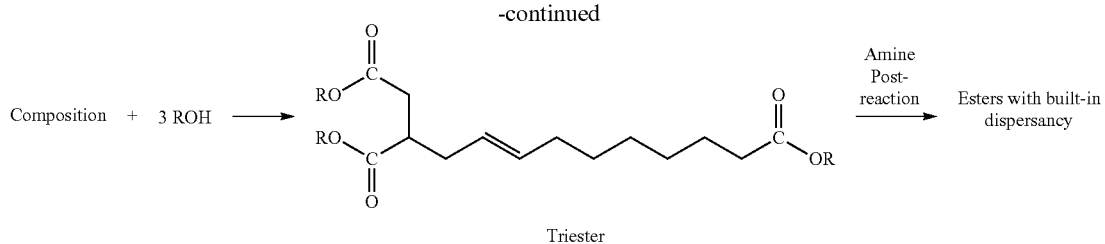 —Amine Post-reaction→ Esters with built-in dispersancy Triester ROH = i-BuOH, i-AmOH, 2-EtHexanol
Similar Esters from 9-DDAMe, 10-UDAMe, FAMe, and 9-ODDAMe$_2$ are Possible The following equations illustrate the preparation of polyhydric alcohol (i.e., polyol) esters of malienated methyl 9-decenoate (9-DAMe).

Polyhydric Alcohol Esters of Maleinated 9-DAMe

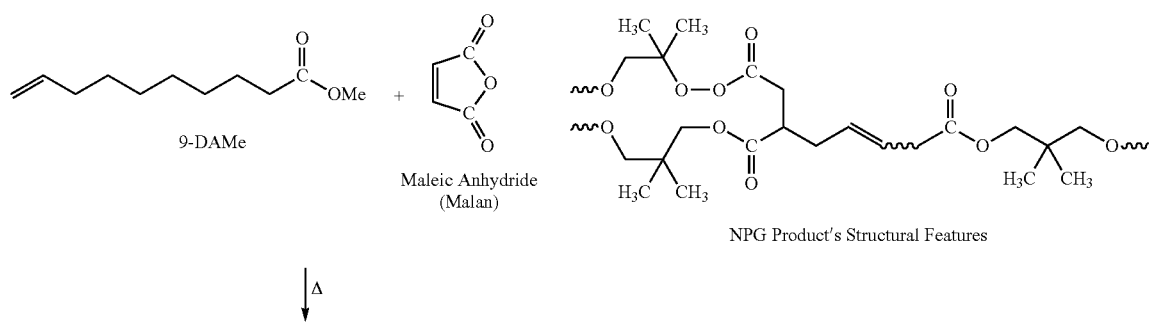

| Δ

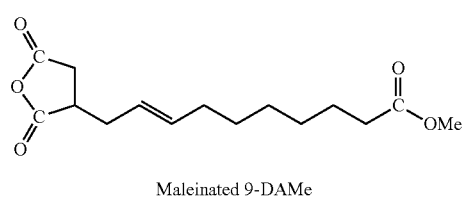

Maleinated 9-DAMe

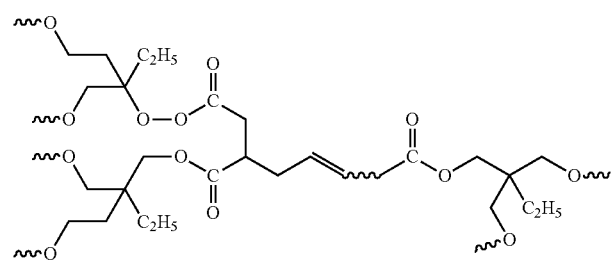

THMP Product's Structural Features

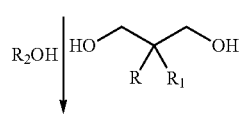

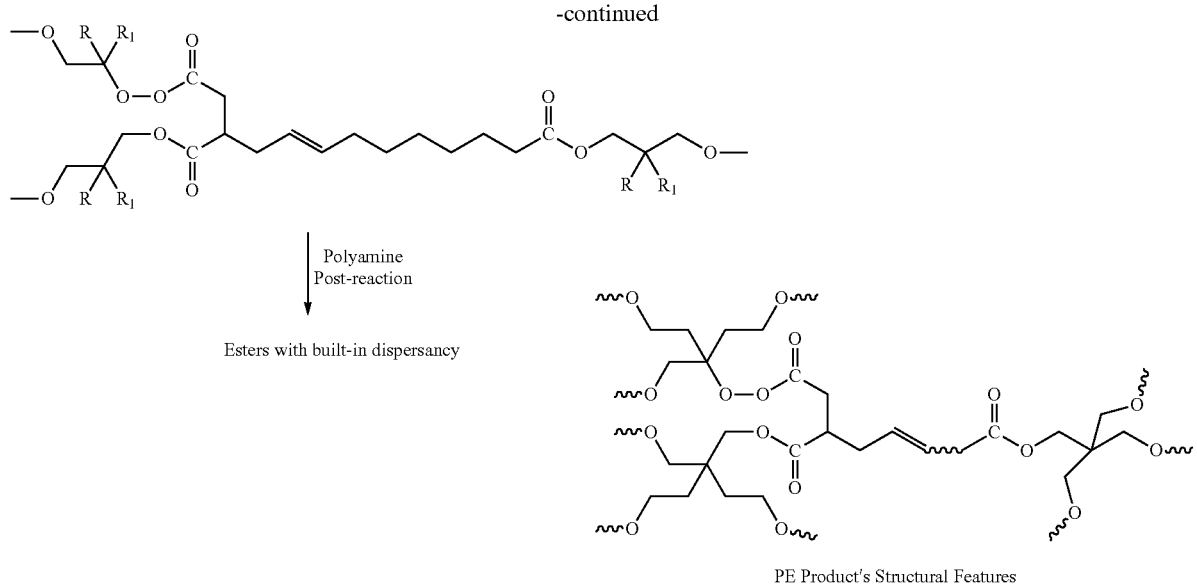

R, $R_1$ = H, $CH_3$, $C_2H_5$, $CH_2OH$; $R_2$ = i-But, i-Am, 2-EtHex
Products may contain both monohydric and polyhydric alcol-derived moieties.
Similar condensation polymers are possible from 9-ODDAMe, 10-UDAMe, and 9-ODDAMe$_2$ PE Product's Structural Features

Example 4A

A lubricant composition is prepared that contains a maleinated 9-DAME reacted with iso-amyl alcohol, which is then blended with a polyalphaolefin (PAO) 4 cSt, and additized with 0.5 w % of hindered aryl amine and 0.5 w % of a polyisobutenyl succinic anhydride (PIBSA) based dispersant with a 25 total base number (TBN). The preparation of the ester is shown above.

Example 4B

Maleinized methyl 9-decenoate (MA9-DAMe) is reacted with several monofunctional alcohols in different ratios to produce half- and fully converted esters. Methanesulfonic acid (MSA) is used as catalyst. The reactions are carried out solvent-free under nitrogen. All alcohol ratios are calculated based on the acid value (AV) of the maleinized starting material. Reaction of the succinic anhydride of MA9-DAMe with half an equivalent of alcohol gives half esters, no water as byproduct is generated. Alcohol ratios higher than 50% of the AV of the maleinized 9-DAMe generate water from the condensation reaction. The reaction mixtures are heated for several hours. Reaction temperature is limited by the boiling point of the alcohol. Water is allowed to evaporate during heating. After the reaction the products are stripped in vacuum to remove additional water, residual free alcohols, and other volatiles.

| Alcohol | Acid Value | Conversion | Kinematic Visclsity | Pour Point (ASTM D97) |
|---|---|---|---|---|
| Isoamyl alcohol 1.2 eq | 2 | 93 | 6.0 cSt/100° C. | −35° C. |

Neat Synthetic Lubricant
KV100=6 mm$^2$/s
CCS (−30° C.)=5000 mPa·s

Blended lubricant with 79 w % derivative, 20% w 4 cSt PAO, 0.5 w % hinder aryl amine, 0.5 w % PIBSA based succinimide dispersant. This blend has improved KV and CCS for use as a PCMO high fuel economy oil.

KV100=4.336 mm$^2$/s
CCS (−30° C.)=1520 mPa·s

Example 4C

Maleinized methyl 9-decenoate (MA9-DAMe) is reacted with several monofunctional alcohols in different ratios to produce half- and fully converted esters. Methanesulfonic acid (MSA) is used as catalyst. The reactions are carried out solvent-free under nitrogen. All alcohol ratios are calculated based on the acid value (AV) of the maleinized starting material. Reaction of the succinic anhydride of MA9-DAMe with half an equivalent of alcohol gives half esters, no water as byproduct is generated. Alcohol ratios higher than 50% of the AV of the maleinized 9-DAMe generate water from the condensation reaction. The reaction mixtures are heated for several hours. Reaction temperature is limited by the boiling point of the alcohol. Water is allowed to evaporate during heating. After the reaction the products are stripped in vacuum to remove additional water, residual free alcohols, and other volatiles.

a) Isobutyl Alcohol

Isobutyl alcohol is reacted in 4 different ratios with maleinized 9-DAMe.

The low boiling point (bp 107.9° C.) of isobutyl alcohol makes it difficult to target exact conversions between half- and fully converted esters. Water cannot be removed by distillation during the reaction. To achieve high conversion an excess of isobutyl alcohol is used in one of the samples; see the table below. The equations below show the synthesis of the isobutyl half- and full-esters of maleinized 9-DAMe.

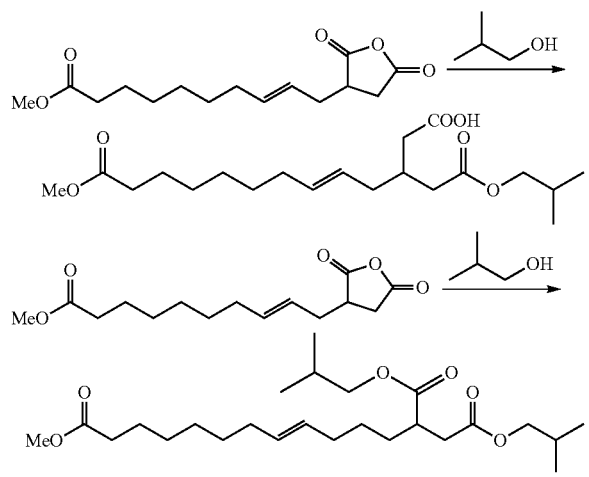

b) 2-Ethyl-1-hexanol

2-Ethyl-1-hexanol has a boiling point of 183-185° C. Esters in different ratios are synthesized. The data in the table below show an AV for the equal ratio sample. An AV of around 10-15 units is generated from the residual acid catalyst, which is not removed. Using a small excess (0.1-0.2 eq) of 2-ethyl-1-hexanol gives a more complete ester formation. The following equations show the synthesis of the 2-ethyl-1-hexanol half- and full-esters of maleinized 9-DAMe.

c) Isoamyl Alcohol

Due to the lower boiling point of isoamyl alcohol (bp 131° C.), an excess of alcohol is used to drive the ester formation closer to completion. The following equations show the synthesis of the isoamyl half- and full-esters of maleinized 9-DAMe.

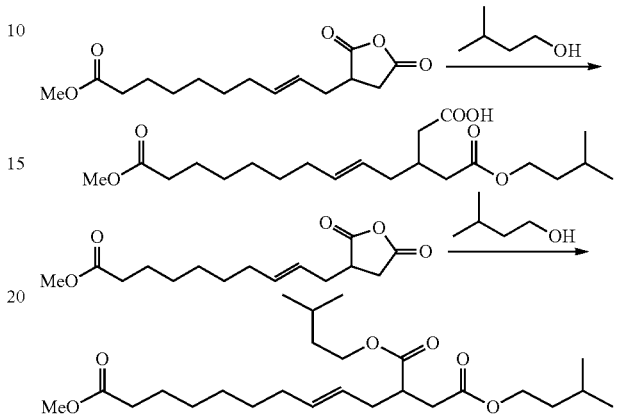

d) Neopentyl Alcohol

Esterification with neopentyl alcohol to obtain a full ester is carried out. The synthesis of the neopentyl alcohol ester of maleinized 9-DAMe is shown below.

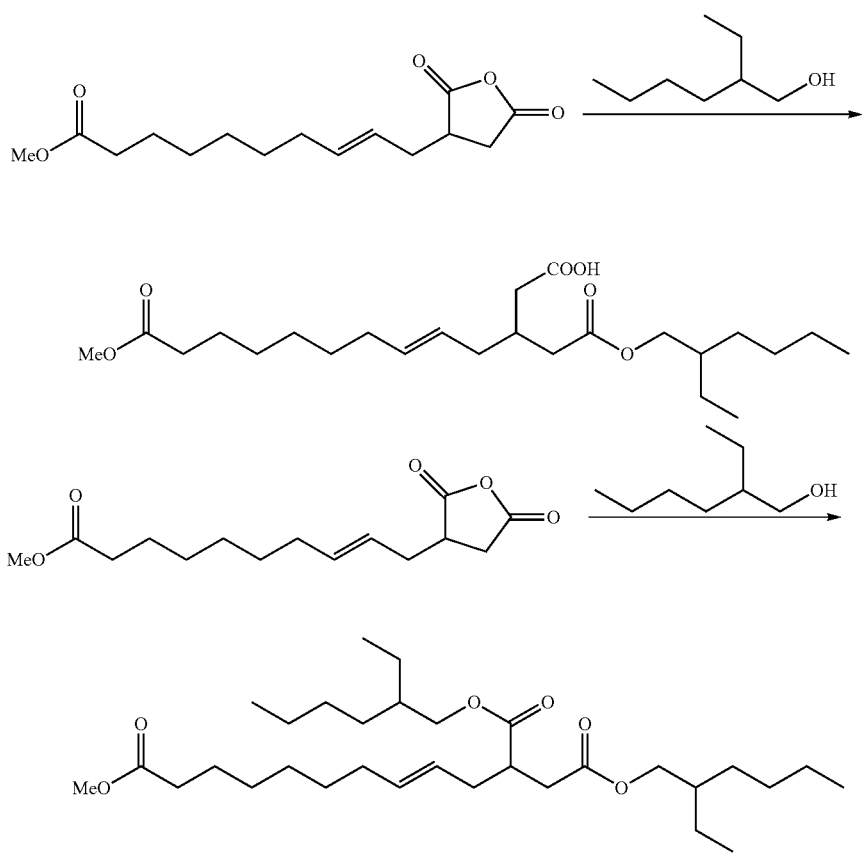

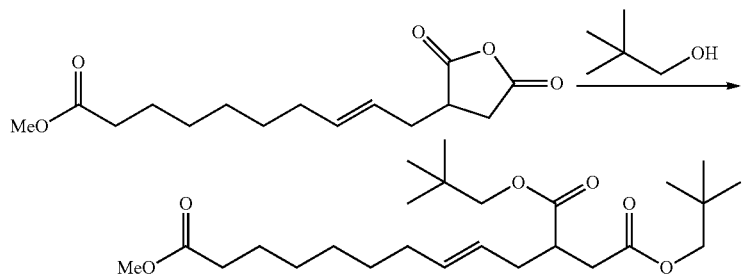

The following table provides data for esters synthesized from maleinized 9-DAMe:

| Sample ID | Alcohol | AV | Ester*) in % | η (40° C.), cP | η (100° C.), cP | KV**) (100° C.), cSt | PP (° C.) |
|---|---|---|---|---|---|---|---|
| 1 | Isobutanol, 1.0 eq | 88.2 | 82 | 125 | 15 | 12.42 | |
| 2 | Isobutanol, 0.5 eq | 77.8 | 60 | 435 | 30 | 24.41 | |
| 3 | Isobutanol, 0.75 eq | 124.4 | 73 | 175 | 15 | 14.97 | |
| 4 | Isobutanol, 2 eq | 30.8 | 96 | 55 | 10 | 8.11 | 28 |
| 5 | 2-Ethyl-1-hexanol, 0.5 eq | 162.1 | 64 | 430 | 30 | 26.19 | |
| 6 | 2-Ethyl-1-hexanol, 1.0 eq | 57.3 | 90 | 120 | 15 | 13.83 | 25 |
| 7 | Isoamyl alcohol, 1.0 eq | 76.8 | 85 | | | 10.86 | 35 |
| 8 | Isoamyl alcohol, 0.5 eq | 184.0 | 58 | | | 23.11 | |
| 9 | Isoamyl alcohol, 1.2 eq | 43.6 | 93 | | 10 | 7.90 | |
| 10 | 2-Ethyl-1-hexanol, 1.2 eq | 21.7 | 98 | | | | |

*)estimated ester conversion, 1-[(AV(product)-15(MSA))/AV(MA9-DAMe)], slight error due to change in Mw;
**)Viscosity Standard S200 @100° C. KV = 22.13 cSt, ρ = 0.7914 g/mL, η = 17.51 cP, test value KV = 24.88 cSt).

The full esters have a lower viscosity than the half ester of the same alcohol. The starting material (i.e., 9-DAMe) has a golden-red color. During the esterification the red disappears. The full esters are very clear golden oils. The half esters show a color between the starting material and the full esters. The redness decreases with the ester content of the oils. Pour points are determined for some of the higher converted esters, which shows a lower viscosity at room temperature. Values between −25 and −35° C. are found. Free carboxylic groups increase the viscosity of the oils. The hydrolyzed product of MA9-DAMe, the diacid, has a high viscosity at room temperature.

Dispersants

The dispersant composition may be derived from a nitrogen-containing reagent and/or an oxygen-containing reagent, a functionalized monomer and/or polymer, and an enophilic reagent, wherein the enophilic reagent comprises an enophilic acid, anhydride and/or ester reagent (e.g., maleic anhydride). In an embodiment, the enophilic acid, anhydride and/or ester reagent may be reacted with the functionalized monomer and/or polymer to form an enophilic reagent modified functionalized monomer or polymer, which may then be reacted with the nitrogen-containing reagent and/or oxygen containing reagent to form the dispersant. In an embodiment, the enophilic acid, anhydride and/or ester reagent may be reacted with the nitrogen-containing reagent and/or oxygen containing reagent to form an enophilic reagent modified nitrogen-containing reagent and/or oxygen-containing reagent, which may then be reacted with the functionalized monomer and/or polymer to form the dispersant. The functionalized monomer or polymer, or enophilic reagent modified functionalized monomer or polymer, optionally in combination with an alkenylsuccinic acid and/or anhydride (e.g., polyisobutenylsuccinic anhydride), may be reacted with the nitrogen-containing reagent and/or an oxygen-containing reagent to form the dispersant. The dispersant may be used in a lubricant, functional fluid or fuel composition.

The dispersant may comprise the reaction product of a nitrogen-containing reagent or an oxygen-containing reagent, with: (i) the reaction product of an enophilic acid reagent with a functionalized monomer comprising a hydrocarbyl group with one or more carbon-carbon double bonds and one or more functional groups attached to the hydrocarbyl group, the hydrocarbyl group containing at least about 5 carbon atoms, or from about 5 to about 30 carbon atoms, or from about 6 to about 30 carbon atoms, or from about 8 to about 30 carbon atoms, or from about 10 to about 30 carbon atoms, or from about 12 to about 30 carbon atoms, or from about 14 to about 30 carbon atoms, or from about 16 to about 30 carbon atoms, or from about 5 to about 18 carbon atoms, or from about 5 to about 18 carbon atoms, or about 18 carbon atoms, or from about 8 to about 12 carbon atoms, or about 10 carbon atoms, the functional group comprising a carboxylic acid or anhydride; (ii) a polymer (or oligomer) derived from one or more of the functionalized monomers (i); (iii) a copolymer (or co-oligomer) derived from one or more of the functionalized monomers (i) and one or more olefin comonomers; (iv) the reaction product of an enophilic acid, anhydride and/or ester reagent with the polymer (ii) or copolymer (iii); or (v) a mixture of two or more of (i), (ii), (iii) and (iv). The reaction product (iv) may comprise a polyfunctionalized monomer or polymer. The olefin comonomer may contain from 2 to about 30 carbon atoms, or from about 6 to about 24 carbon atoms.

The enophilic acid, anhydride or ester reagent may comprise any of those discussed above, including maleic anhydride. The nitrogen-containing reagents and oxygen containing reagents may be any of those discussed above. The dispersant may comprise one or more amides, diamides, triamides, imides, esters, di-esters, tri-esters, amide esters, amine salts, ammonium salts, mixtures of two or more thereof, and the like. These may be prepared using the procedures described above.

The functionalized or polyfunctionalized polymer may comprise a homopolymer (or homo-oligomer) derived from the functionalized monomer, or a copolymer (or co-oligomer) derived from one or more of the functionalized monomers and/or one or more olefin comonomers. The polymer may contain at least about 30 mole percent of repeating units derived from one or more of the functionalized monomers, or at least about 50 mole percent, or at least about 70 mole percent, or from about 30 to about 100 mole percent, or from about 50 to about 100 percent, or from about 70 to about 100 mole percent. The olefin comonomer may contain from 2 to about 30 carbon atoms, or from about 6 to about 24 carbon atoms. The polymer may have any desired molecular weight depending on its end use, for example, a number average molecular weight in the range from about 100 to about 10,000, or from about 300 to about 10,000, or from about 500 to about 1000, or from about 700 to about 50,000, or from about 1000 to about 5000, or from about 1000 to about 3000, as determined by GPC. The polymer may be prepared using the procedures described above. The polymer may be partially or fully hydrogenated.

The functionalized monomer (i), polymer (ii), copolymer (iii) and/or reaction product (iv) may optionally be mixed with an alkenylsuccinic acid or anhydride, such as polyisobutenylsuccinic anhydride, and then reacted with the nitrogen-containing reagent and/or oxygen-containing reagent. The alkenylsuccinic anhydride may have a number average molecular weight in the range from about 750 to about 3000. The ratio of equivalents of the functionalized monomer (i), polymer (ii), copolymer (iii), and/or reaction product (iv) to equivalents of the alkenylsuccinic acid or anhydride (e.g., polyisobutenylsuccinic anhydride) may be in the range from about 1 to about 4, or from about 1 to about 2. The weight of an equivalent of the monomer (i), polymer (ii), copolymer (iii) or reaction product (iv) as well as the alkenylsuccinic acid or anhydride is dependent on the number of carbonyl groups to be reacted with the amine or an alcohol reagent. For example, if one mole of a functionalized monomer (i) has two carbonyl groups in its molecular structure and one of the carbonyl groups is reacted with an amine to form a cyclic imide, the functionalized monomer (i) would have an equivalent weight equal to its molecular weight. Conversely, if both carbonyl groups were to be reacted with the amine to form a diamide or a monohydric alcohol to form a diester, the equivalent weight of the functionalized monomer (i) would be one-half of its molecular weight.

Alternatively, the alkenyl succinic acid and/or anhydride may be separately reacted with the nitrogen-containing reagent to form a succinimide (e.g., polyisobutenyl succinimide) and/or an oxygen containing reagent to form a succinic acid ester, and then mixed with the above-indicated dispersant. The alkenylsuccinic acid and/or anhydride may have a number average molecular weight in the range from about 750 to about 3000.

The dispersants may be post-treated or post-reacted by conventional methods using any of a variety of agents. Among these may be boron compounds (such as boric acid), urea, thiourea, dimercaptothiadiazoles, carbon disulfide, aldehydes, ketones, carboxylic acids such as terephthalic acid, hydrocarbon-substituted succinic anhydrides, maleic anhydride, nitriles, epoxides, phosphorus compounds, and the like.

Detergents

The detergent composition may comprise a neutral or overbased detergent derived from a metal or metal compound, and one or more of the above-discussed functionalized monomers and/or polymers, and an enophilic reagent, wherein the enophilic reagent comprises an enophilic acid, anhydride and/or ester reagent (e.g., maleic anhydride). In an embodiment, the enophilic acid, anhydride and/or ester reagent may be reacted with the functionalized monomer and/or polymer to form an enophilic reagent modified functionalized monomer and/or polymer, which may then be reacted with the metal or metal compound to form the detergent. In an embodiment, the enophilic reagent may be reacted with the metal or metal compound to form an enophilic reagent modified metal or metal compound, which may then be reacted with the functionalized monomer and/or polymer to form the detergent. The functionalized polymer may be derived from the functionalized monomer and a comonomer. The comonomer may comprise an olefin containing from 2 to about 30 carbon atoms, or from about 6 to about 24 carbon atoms.

The detergent may comprise a neutral or overbased material derived from a metal or metal compound, and: (i) the reaction product of an enophilic acid reagent with a functionalized monomer comprising a hydrocarbyl group with one or more carbon-carbon double bonds and one or more functional groups attached to the hydrocarbyl group, the hydrocarbyl group containing at least about 5 carbon atoms, or from about 5 to about 30 carbon atoms, or from about 6 to about 30 carbon atoms, or from about 8 to about 30 carbon atoms, or from about to about 30 carbon atoms, or from about 12 to about 30 carbon atoms, or from about 14 to about 30 carbon atoms, or from about 16 to about 30 carbon atoms, or from about 5 to about 18 carbon atoms, or from about 12 to about 18 carbon atoms, or about 18 carbon atoms, or from about 8 to about 12 carbon atoms, or about 10 carbon atoms, the functional group comprising a carboxylic acid group or an anhydride thereof; (ii) a polymer (or oligomer) derived from one or more of the functionalized monomers (i); (iii) a copolymer (or co-oligomer) derived from one or more of the functionalized monomers (i) and one or more olefin comonomers; (iv) the reaction product of an enophilic acid, anhydride or ester reagent with the polymer (ii) and/or copolymer (iii) to form a polyfunctionalized polymer or copolymer; or (v) a mixture of two or more of (i), (ii), (iii) and (iv). The olefin comonomer may contain from 2 to about 30 carbon atoms, or from about 6 to about 24 carbon atoms. The functionalized or polyfunctionalized polymer (or oligomer, copolymer or co-oligomer) may contain at least about 30 mole percent of repeating units derived from the functionalized or polyfunctionalized monomer, or at least about 50 mole percent, or at least about 70 mole percent, or from about 30 to about 100 mole percent, or from about 50 to about 100 percent, or from about 70 to about 100 mole percent. The enophilic acid, anhydride or ester reagent may comprise any of those discussed above, including maleic anhydride. The monomer (i), polymer (ii), copolymer (iii) and/or reaction product (iv), may be mixed with an alkarylsulfonic acid (e.g., alkylbenzenesulfonic acid) prior to or during the reaction to form the overbased material. The functionalized or polyfunctionalized monomer or polymer may have any desired molecular weight, for example, a number average molecular weight in the range from about 100 to about 50,000 or higher, or from about 300 to about 50,000, or from about 150 to about 20,000, or from about 200 to about 10,000, or from about 300 to about 5000, as determined by gel permeation chromatography (GPC), NMR spectroscopy, vapor phase osometry (VPO), wet analytical techniques such as acid number, base number, saponification number of oxirane number, and the like. The monomer or polymer may be prepared using the procedures described above.

The term "overbased" is a term of art which is generic to well known classes of metal salts or complexes. These products or materials have also been referred to as "basic", "superbased", "hyperbased", "complexes", "metal complexes", "high-metal containing salts", and the like. Overbased products or materials may be regarded as metal salts or complexes characterized by a metal content in excess of that which would be present according to the stoichiometry of the metal and the particular acidic organic compound, e.g., a carboxylic acid, reacted with the metal. Thus, if a monocarboxylic acid,

RCOOH is neutralized with a basic metal compound, e.g., calcium hydroxide, the "neutral" or "normal" metal salt produced will contain one equivalent of calcium for each equivalent of acid, i.e.,

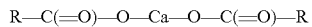

R—C(=O)—O—Ca—O—C(=O)—R

However, various processes may be used to produce an inert organic liquid solution of a product containing more than the stoichiometric amount of metal. This solution may be referred to as overbased product or material. Following these procedures, the carboxylic acid may be reacted with a metal base. The resulting product may contain an amount of metal in excess of that necessary to neutralize the acid. For example, 4 times as much metal as present in the neutral salt, or a metal excess of 3 equivalents, may be used. The actual stoichiometric excess of metal may vary considerably, for example, from about 0.1 equivalent to about 40 or more equivalents depending on the reactions, the process conditions, and the like. An equivalent of a metal is dependent upon its valence, and the nature/structure of the functional group in the substrate. Thus, for a reaction with a substrate, such as a monocarboxylic acid, one mole of a monovalent metal such as sodium provides one equivalent of the metal, whereas 0.5 moles of a divalent metal such as calcium are required to provide one equivalent of such metal. The number of equivalents of a metal base in a detergent can be measured using standard techniques (e.g., titration using bromophenol blue as the indicator to measure total base number, TBN).

The term "metal ratio" is used herein to designate the ratio of the total chemical equivalents of the metal in the overbased material (e.g., a metal carboxylate) to the chemical equivalents of the metal in the product which would be expected to result from the reaction between the organic material to be overbased (e.g., carboxylic acid) and the metal-containing reactant (e.g., calcium hydroxide, barium oxide, etc.) according to the known chemical reactivity and stoichiometry of the two reactants. Thus, in the normal or neutral calcium carboxylate discussed above, the metal ratio is one, and in the overbased carboxylate, the metal ratio is 4, or more. If there is present in the material to be overbased more than one compound capable of reacting with the metal, the "metal ratio" of the product will depend upon whether the number of equivalents of metal in the overbased product is compared to the number of equivalents expected to be present for a given single component or a combination of all such components.

The neutral or overbased product or material useful as a detergent may be neutral or may be overbased with a metal ratio in excess of 1 and generally up to about 40 or more. The metal ratio may be in the range from an excess of 1 up to about 35, or from an excess of 1 up to about 30. The metal ratio may range from about 1.1 or about 1.5 to about 40; or from about 1.1 or about 1.5 to about 35; or from about 1.1 or about 1.5 to about 30; or from about 1.1 or about 1.5 to about 25. The metal ratio may range from about 1.5 to about 30 or 40, or from about 5 to about 30 or 40, or from about 10 to about 30 or 40, or from about 15 to about or 40. The metal ratio may range from about 20 to about 30.

The overbased product or material may be prepared using the functionalized monomer (i), polymer (ii), copolymer (iii) and/or reaction product (iv) of the invention, alone or in combination with an alkarylsulfonic acid. The monomer (i), polymer (ii), copolymer (iii), and/or reaction product (iv) and, optionally, the alkarylsulfonic acid, may be referred to herein as (1) the organic material to be overbased. The overbased product or material may be prepared by the reaction of a mixture of (1) the organic material to be overbased, (2) a reaction medium comprising an inert, organic solvent/diluent for the organic material to be overbased, a stoichiometric excess of (3) at least one metal base, and (4) a promoter, with (5) an acidic material. The overbased product or material may be borated by reacting the overbased product or material with a boron containing compound.

The alkarylsulfonic acids may include alkylbenzenesulfonic acids wherein the alkyl group contains at least about 8 carbon atoms, or from about 8 to about carbon atoms. The ratio of equivalents of the functionalized monomer (i), polymer (ii), copolymer (iii) and/or reaction product (iv) to the alkarylsulfonic acid may be from about 1 to about 5, or from about 1 to about 2. The weight of an equivalent of an alkarylsulfonic acid agent is dependent on the number of sulfonic acid groups in the alkarylsulfonic acid that are reactive with the metal base (3). For example, one mole of an alkarylsulfonic acid having one sulfonic acid available for reaction with the metal base would have an equivalent weight equal to the molecular weight of the alkarylsulfonic acid.

The organic material to be overbased (1) may be soluble in the reaction medium (2). When the reaction medium (2) is a petroleum fraction (e.g., mineral oil), the organic material to be overbased may be oil-soluble. However, if another reaction medium is employed (e.g., aromatic hydrocarbons, aliphatic hydrocarbons, kerosene, etc.) the organic material to be overbased (1) may not necessarily be soluble in mineral oil as long as it is soluble in the given reaction medium. When referring to the solubility of the (1) organic material to be overbased in (2) the reaction medium, it is to be understood that the organic material to be overbased may be soluble in the reaction medium to the extent of at least one gram of the material to be overbased per liter of reaction medium at 20° C.

The reaction medium (2) may be a substantially inert, organic solvent/diluent for the (1) organic material to be overbased. Examples of the reaction medium (2) may include alkanes and haloalkanes of about 5 to about 18 carbons, polyhalo- and perhalo-alkanes of up to about 6 carbons, cycloalkanes of about 5 or more carbons, the corresponding alkyl- and/or halo-substituted cycloalkanes, aryl hydrocarbons, alkylaryl hydrocarbons, haloaryl hydrocarbons, ethers such as dialkyl ethers, alkyl aryl ethers, cycloalkyl ethers, cycloalkylalkyl ethers, alkanols, alkylene glycols, polyalkylene glycols, alkyl ethers of alkylene glycols and polyalkylene glycols, dibasic alkanoic acid diesters, silicate esters, and mixtures of these. Examples may include petroleum ether, Stoddard Solvent, pentane, hexane, octane, isooctane, undecane, tetradecane, cyclopentane, cyclohexane, isopropylcyclohexane, 1,4-dimethylcyclohexane, cyclooctane, benzene, toluene, xylene, ethyl benzene, tert-butyl-benzene, halobenzenes such as mono- and polychlorobenzenes including chlorobenzene per se and 3,4-dichlorotoluene, mineral oils, n-propylether, isopropylether, isobutylether, n-amylether, methyl-n-amylether, cyclohexylether, ethoxycyclohexane, methoxybenzene, isopropoxybenzene, p-methoxytoluene, methanol, ethanol, propanol, isopropanol, hexanol, n-octyl alcohol, n-decyl alcohol, alkylene glycols such as ethylene glycol and propylene glycol, diethyl ketone, dipropyl ketone, methylbutyl ketone, acetophenone, 1,2-difluorotetrachloroethane, dichlorofluoromethane, 1,2-dibromotetrafluoroethane, trichlorofluoromethane, 1-chloropentane, 1,3-dichlorohexane, formamide, dimethylformamide, acetamide, dimethylacetamide, diethylacetamide, propionamide, diisoctyl azelate, polyethylene glycols, polypropylene glycols, hexa-2-ethylbutoxy disiloxane, etc.

Also useful as the reaction medium (2) may be low molecular weight liquid polymers, generally classified as oligomers, which may include dimers, trimers, tetramers, pentamers, etc. Illustrative of this class of materials may be such liquids as propylene tetramers, isobutylene dimers, and the like.

The metal base (3) used in preparing the neutral or overbased products or materials may comprise one or more alkali metals, alkaline-earth metals, titanium, zirconium, molybdenum, iron, copper, zinc, aluminum, mixture of two or more thereof, or basically reacting compounds thereof. Lithium, sodium, potassium, magnesium, calcium, strontium, barium, zinc, or a mixture of two or more thereof, may be useful.

The basically reacting compound may comprise any compound of any of the foregoing metals or mixtures of metals that is more basic than the corresponding metal salt of the acidic material (5) used in preparing the overbased product or material. These compounds may include hydroxides, alkoxides, nitrites, carboxylates, phosphites, sulfites, hydrogen sulfites, carbonates, hydrogen carbonates, borates, hydroxides, oxides, alkoxides, amides, etc. The nitrites, carboxylates, phosphites, alkoxides, carbonates, borates, hydroxides and oxides may be useful. The hydroxides, oxides, alkoxides and carbonates may be useful.

The promoters (4), that is, the materials which facilitate the incorporation of an excess metal into the overbased product or material may include those materials that are less acidic than the acidic material (5) used in making the overbased products. These may include alcoholic and phenolic promoters. The alcohol promoters may include alkanols of one to about 12 carbon atoms. Phenolic promoters may include a variety of hydroxy-substituted benzenes and naphthalenes. The phenolic promoters may include alkylated phenols such as heptylphenol, octylphenol, nonylphenol, dodecyl phenol, propylene tetramer phenol, and mixtures of two or more thereof.

The promoters (4) may include water, ammonium hydroxide, nitromethane, organic acids of up to about 8 carbon atoms, metal complexing agents such as the salicylaldoximes (e.g., alkyl ($C_1$-$C_{20}$) salicylaldoxime), and alkali metal hydroxides such as lithium hydroxide, sodium hydroxide and potassium hydroxide, and mono- and polyhydric alcohols of up to about 30 carbon atoms, or up to about 20 carbon atoms, or up to about 10 carbon atoms. Examples may include methanol, ethanol, isopropanol, amyl alcohol, cyclohexanol, octanol, dodecanol, decanol, behenyl alcohol, ethylene glycol, diethylene glycol, triethylene glycol, monomethylether of ethylene glycol, trimethylene glycol, hexamethylene glycol, glycerol, pentaerythritol, benzyl alcohol, phenylethyl alcohol, sorbitol, nitropropanol, chloroethanol, aminoethanol, cinnamyl alcohol, allyl alcohol, and the like.

The acidic material (5) may comprise one or more of carbamic acid, acetic acid, formic acid, boric acid, trinitromethane, $SO_2$, $CO_2$, sources of said acids, and mixtures thereof. $CO_2$ and $SO_2$, and sources thereof, are preferred. Sources of $CO_2$ may include ammonium carbonate and ethylene carbonate. Sources of $SO_2$ may include sulfurous acid, thiosulfuric acid, dithionous acid, and/or their salts.

The overbased products or materials may be prepared by reacting a mixture of the organic material to be overbased, the reaction medium, the metal base, and the promoter, with the acidic material. A chemical reaction may then ensue. The temperature at which the acidic material reacts with the remainder of the reaction mass may depend upon the promoter that is used. With a phenolic promoter, the temperature may range from about 60° C. to about 300° C., or from about 100° C. to about 200° C. When an alcohol or mercaptan is used as the promoter, the temperature may not exceed the reflux temperature of the reaction mixture. The exact nature of the resulting overbased product or material may not be known. However, it may be described for purposes of the present specification as a single phase homogeneous mixture of the reaction medium and either a metal complex formed from the metal base, the acidic material, and the organic material to be overbased and/or an amorphous metal salt formed from the reaction of the acidic material with the metal base and the organic material to be overbased.

The overbased product or material may comprise a boron-containing overbased product or material. These borated overbased products or materials may be prepared by reacting at least one overbased product with at least one boron compound. The boron compound may comprise one or more of boron oxide, boron oxide hydrate, boron trioxide, boron trifluoride, boron tribromide, boron trichloride, boron acids such as boronic acid (i.e., alkyl-B(OH)2 or aryl-B(OH)$_2$), boric acid (i.e., $H_3BO_3$), tetraboric acid (i.e., $H_2B_4O_7$), metaboric acid (i.e., $HBO_2$), boron anhydrides, and various esters of such boron acids. The boronic acids may include methyl boronic acid, phenyl-boronic acid, cyclohexyl boronic acid, p-heptylphenyl boronic acid, dodecyl boronic acid, or a mixture of two or more thereof. The boron acid esters may include mono-, di-, and.or tri-organic esters of boric acid with alcohols or phenols such as, e.g., methanol, ethanol, isopropanol, cyclohexanol, cyclopentanol, 1-octanol, 2-octanol, dodecanol, behenyl alcohol, oleyl alcohol, stearyl alcohol, benzyl alcohol, 2-butyl cyclohexanol, ethylene glycol, propylene glycol, trimethylene glycol, 1,3-butanediol, 2,4-hexanediol, 1,2-cyclohexanediol, 1,3-octanediol, glycerol, pentaerythritol diethylene glycol, or a mixture of two or more thereof.

The reaction of the overbased product with the boron compound can be effected using standard mixing techniques. The ratio of equivalents of the boron compound to equivalents of the overbased product may range up to about 40:1 or higher, or in the range of about 0.05:1 to about 30:1, or in the range of about 0.2:1 to about 20:1. Equivalent ratios of about 0.5:1 to about 5:1, or about 0.5:1 to about 2:1, or about 1:1 may be used. An equivalent of a boron compound may be based upon the number of moles of boron in the compound. Thus, boric acid has an equivalent weight equal to its molecular weight, while tetraboric acid has an equivalent weight equal to one-fourth of its molecular weight. An equivalent weight of an overbased product or material is based upon the number of equivalents of metal in the overbased product available to react with the boron. Thus, an overbased product having one equivalent of metal available to react with the boron has an equivalent weight equal to its actual weight. An overbased product having two equivalents of metal available to react with the boron has an equivalent weight equal to one-half its actual weight. The temperature can range from about room temperature up to the decomposition temperature of the reactants or desired products having the lowest such temperature, and may be in the range of about 20° C. to about 200° C., or about 20° C. to about 150° C., or about 50° C. to about 150° C., or about 80° C. to about 120° C. The reaction time may be the time required to form the desired concentration of metal borate (e.g., sodium borate) in the boron-containing overbased product. The reaction time may be from about 0.5 to about 50 hours, or from about 1 to about 25 hours, or about 1 to about 15 hours, or about 4 to about 12 hours.

The Lubricant and Functional Fluid Compositions

The lubricant and/or functional fluid compositions of the invention may comprise one or more base oils comprising one or more of the above-identified functionalized or polyfunctionalized monomers or polymers. These base oils may be referred to as functional base oils. These base oils may be blended with one or more conventional base oils. The dispersants and/or detergents described above, which may be derived from one or more of the above-identified functionalized or polyfunctional monomers or polymers, may be used in these lubricants and/or functional fluids.

The lubricant compositions may be effective as engine oil or crankcase lubricating oils for spark-ignited and compression-ignited internal combustion engines, including automobile and truck engines, two-stroke cycle engines, aviation piston engines, marine and diesel engines, stationary gas engines, and the like. The functional fluids may comprise a driveline fluid such as an automatic transmission fluid, manual transmission fluid, transaxle lubricant, fluid for continuously variable transmissions, dual clutch automatic transmission fluid, farm tractor fluid, fluids for hybrid vehicle transmission, or gear oil. The functional fluid may comprise a metal-working lubricant, hydraulic fluid, or other lubricating oil or grease composition.

In an embodiment, the base oil may comprise one or more of the above-identified functionalized or polyfunctionalized monomers or polymers. When the above-identified functionalized or polyfunctionalized polymer is a copolymer, the copolymer may be derived from one or more of the above-discussed functionalized or polyfunctionalized monomers and one or more olefin comonomers. The copolymer may contain from about 5 to about 30 mole percent, or from about 10 to about 25 mole percent, repeating units derived from the functionalized or polyfunctionalized monomer. The polymer may be partially or fully hydrogenated. The polymer may have a number average molecular weight in the range from about 100 to about 50,000, or from about 300 to about 20,000, or from about 200 to about 10,000, or from about 300 to about 5000, or from about 500 to about 3000.

The base oil may comprise a functionalized polymer in the form of a functionalized copolymer (or co-oligomer) containing structural repeating units derived from a functionalized or polyfunctionalized monomer and structural repeating unts derived from an alpha olefin. This base oil may be referred to as a functional base oil. This base oil may be referred to as a functionalized polyalphaolefin. This base oil may be used in lubricants or functional fuels employed as engine oils and/or drive line fuels. The functionalized or polyfunctionalized monomers may comprise esters of unsaturated carboxylic acids of about 4 to about 30 carbon atoms, or from about 5 to about 18 carbon atoms. The unsaturated carboxylic acids may be fatty acids. The fatty acids may comprise 9-decenoic acid (9DA), 10-undecenoic acid (10UDA), 9-dodecenoic acid (9DDA), 9-octadecenoic acid (9ODDA), mixtures of two or more thereof, and the like. The esters may comprise methyl-, di-methyl, ethyl-, n-propyl-, isopropyl-, n-butyl-, sec-butyl-, tert-butyl- and/or pentaerythritol esters of 9DA, 10UDA, 9DDA, 9ODDA, mixtures of two or more thereof, and the like. Examples of the 9DA esters, 10UDA esters, 9DDA esters, and 9ODDA esters may include methyl 9-decenoate ("9-DAME"), methyl 10-undecenoate ("10-UDAME"), methyl 9-dodecenoate ("9-DDAME") and methyl 9-octadecenoate ("9-ODDAME"), respectively. The alpha olefin may have from 2 to about 30 carbon atoms, or from 2 to about 24 carbon atoms, or from about 4 to about 24 carbon atoms, or from about 6 to about 24 carbon atoms. The alpha olefin may be linear or branched. The alpha olefin may comprise one or more of ethene, 1-propene, 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-octadecene, 1-eicosene, or a mixture of two or more thereof. The molar ratio of functionalized or polyfunctionalized monomer to the alpha olefin may range from about 100:1 to about 1:100, or from about 50:1 to about 1:50, or from about 10:1 to about 1:10, or from about 5:1 to about 1:5, or from about 2:1 to about 1:2, or from about 1.5:1 to about 1:1.5, or about 1:1. The functional base oil may comprise a copolymer (or co-oligomer) comprising structural units derived from methyl 9-decenoate and 1-decene. The molar ratio of methyl 9-decenoate to 1-decene may be in the range from about 10:1 to about 1:1.

The base oil may comprise a polyester derived from a malienated fatty ester and one or more alcohols and/or aminoalcohols. This base oil may be referred to as a functional base oil. This base oil may be used in the fill-for-life lubricants or functional fluids. The maleinated fatty ester may be derived from an ester of an unsaturated carboxylic acid and maleic anhydride. The unsaturated carboxylic acid may have from about 4 to about 30 carbon atoms, or from about 5 to about 18 carbon atoms. The unsaturated carboxylic acids may be fatty acids. The fatty acids may comprise 9-decenoic acid (9DA), 10-undecenoic acid (10UDA), 9-dodecenoic acid (9DDA), 9-octadecenoic acid (9ODDA), mixtures of two or more thereof, and the like. The esters may comprise methyl-, ethyl-, n-propyl-, isopropyl-, n-butyl-, sec-butyl-, tert-butyl- and/or pentaerythritol esters of 9DA, 10UDA, 9DDA, 9ODDA, mixtures of two or more thereof, and the like. Examples of the 9DA esters, 10UDA esters, 9DDA esters, and 9ODDA esters may include methyl 9-decenoate ("9-DAME"), methyl 10-undecenoate ("10-UDAME"), methyl 9-dodecenoate ("9-DDAME") and methyl 9-octadecenoate ("9-ODDAME"), respectively. The alcohols may comprise one or more of the alcohols or amino-alcohols discussed above. These may include isobutyl alcohol, iso-amyl alcohol, 2-ethylhexyl alcohol, neopentyl alcohol, mixtures of two or more thereof, and the like. The polyester functional base oil may comprise a monohydric or polyhydric alcohol ester of maleinated methyl 9-decenoate. These polyester base oils may be biodegradable and may be used as high performance lubricant base oils.

The functional base oil may comprise a mixture of one or more of the above-identified functionalized copolymer base oils, and one or more of the above-identified polyester based oils. The weight ratio of functionalized copolymer base oil to polyester base oil may be in the range from about 10:1 to about 1:10, or from about 5:1 to about 1:5, or from about 2:1 to about 1:2, or about 1:1.

The functional base oil may have any desired molecular weight, for example, a number average molecular weight in the range from 100 to about 20,000, or from about 250 to about 20,000, or from about 500 to about 20,000, or from about 700 to about 10,000, or from about 1000 to about 5000, or from about 1000 to about 3000, as determined by GPC.

The functional base oil may have a kinetic viscosity (ASTM D-445) in the range from about 2 to about 1000 cSt at 100° C., or from about 2 to about 500, or from about 2 to about 100, or from about 4 to about 10 cSt. The base oil may have a viscosity up to about 35 cSt at 100° C., or in the range from about 3 to about 35 cSt, or in the range from about 5 to about 35 cSt at 100° C.

The functional base oil may have a viscosity index (ASTM D2270) in the range from about 120 to about 250, or from about 130 to about 150.

The functional base oil may have a pour point (ASTM D97) in the range from about –20 to about –70° C., or from about –30 to about –45° C., or about –40° C.

The functional base oil may have an aniline point (ASTM D611) in the range from about 25 to about 120° C., or from about 50 to about 100° C.

The functional base oil may have oxidation induction time (ASTM D6186) at 210° C. in the range from about 1 to about 10 minutes, or from about 1 to about 3 minutes, or from about 5 to about 10 minutes.

The functional base oil may have an oxidation onset temperature (ASTM E2009) in the range from about 170° C. to about 220° C., or from about 190° C. to about 210 C.

The cold crank simulator viscosity test values (ASTM D5293) for the functional base oil may be in the range from about 13000 to about 9500 cP, or from about 7000 to about 9500 cP, at a temperature of –15° C.; or in the range from about 7000 to about 6600 cP, or from about 1000 to about 6200 cP, at a temperature of –35° C.

The evaporation loss (ASTM D5293) for the functional base oils may be in the range from about 5 to about 15%, or from about 4 to about 7%.

The functional base oils may exhibit enhanced values for high temperature shear stability, fuel economy, deposit control, oxidative stability, thermal stability, and the like.

The functional base oil may be used alone as the base oil or may be blended with an American Petroleum Institute (API) Group II, III, IV or V base oil, a natural oil, an estolide fluid, or a mixture of two or more thereof. Examples of the natural oil may include soybean oil, rapeseed oil, and the like. The blended base oil may contain from about 1% to about 75%, or from about 5% to about 60% by weight of the functionalized copolymer and/or polyester.

The API Group I-V base oils have the following characteristics:

| Base Oil Category | Sulfur (%) | | Saturates (%) | Viscosity Index |
|---|---|---|---|---|
| Group I | >0.03 | and/or | <90 | 80 to 120 |
| Group II | ≤0.03 | and | ≥90 | 80 to 120 |
| Group III | ≤0.03 | and | ≥90 | ≥120 |
| Group IV | All polyalphaolefins (PAO) | | | |
| Group V | All others not included in Groups I, II, III, or IV | | | |

The Group I-III Base Oils are Mineral Oils.

The base oil may be present in the lubricant or functional fluid composition at a concentration of greater than about 60% by weight based on the overall weight of the lubricant or functional fluid composition, or greater than about 65% by weight, or greater than about 70% by weight, or greater than about 75% by weight.

The lubricant or functional fluid may further comprise one or more of the above-identified dispersants and/or detergents. The dispersant may be present in the lubricant or functional fluid composition at a concentration in the range from about 0.01 to about 20% by weight, or from about 0.1 to about 15% by weight based on the weight of the lubricant or functional fluid. The detergent may be present in the lubricant or functional fluid composition at a concentration in the range from about 0.01% by weight to about 50% by weight, or from about 1% by weight to about 30% by weight based on the weight of the lubricant or functional fluid composition. The detergent may be present in an amount suitable to provide a TBN (total base number) in the range from about 2 to about 100 to the lubricant composition, or from about 3 to about 50. TBN is the amount of acid (perchloric or hydrochloric) needed to neutralize all or part of a material's basicity, expressed as milligrams of KOH per gram of sample.

The lubricant or functional fluid composition may further comprise one or more additional functional additives, including, for example, one or more supplemental detergents and/or dispersants, as well as corrosion- and oxidation-inhibiting agents, pour point depressing agents, extreme pressure (EP) agents, antiwear agents, viscosity index (VI) improvers, friction modifiers (e.g., fatty friction modifiers), hindered amine, phenolic and/or sulfurized inhibitors, anti-oxidants, metal cutting additives (e.g., sulfur chloride), antimicrobial additives, color stabilizers, viscosity modifiers (e.g., ethylene propylene diene (EPDM) viscosity modifiers), demulsifiers, seal swelling agents, anti-foam agents, mixtures of two or more thereof, and the like.

The supplemental detergent may include one or more overbased materials prepared by reacting an acidic material (typically an inorganic acid or lower carboxylic acid, such as carbon dioxide) with a mixture comprising an acidic organic compound, a reaction medium comprising at least one inert, organic solvent (mineral oil, naphtha, toluene, xylene, etc.) for said acidic organic material, a stoichiometric excess of a metal base, and a promoter such as a calcium chloride, acetic acid, phenol or alcohol. The acidic organic material may have a sufficient number of carbon atoms to provide a degree of solubility in oil. The metal may be zinc, sodium, calcium, barium, magnesium, or a mixture of two or more thereof. The metal ratio may be from an excess of 1 to about 40, or in the range from about 1.1 to about 40. These detergents may include overbased sulfonates, overbased phenates, mixtures thereof, and the like.

The supplemental dispersants that may be used may include any dispersant known in the art which may be suitable for the lubricant or functional fluid compositions of this invention. These may include:

(1) Reaction products of carboxylic acids (or derivatives thereof), with nitrogen containing compounds such as amines, hydroxy amines, organic hydroxy compounds such as phenols and alcohols, and/or basic inorganic materials. These may be referred to as carboxylic dispersants. These may include succinimide dispersants, such as polyisobutenylsuccinimide.

(2) Reaction products of relatively high molecular weight aliphatic or alicyclic halides with amines, for example, polyalkylene polyamines. These may be referred to as "amine dispersants."

(3) Reaction products of alkylphenols with aldehydes (e.g., formaldehyde) and amines (e.g., polyalkylene polyamines), which may be referred to as "Mannich dispersants."

(4) Products obtained by post-treating the carboxylic, amine or Mannich dispersants with such reagents as urea, thiourea, carbon disulfide, aldehydes, ketones, carboxylic acids, hydrocarbon-substituted succinic anhydrides, nitriles, epoxides, boron compounds, phosphorus compounds or the like.

(5) Interpolymers of oil-solubilizing monomers such as decyl methacrylate, vinyl decyl ether and high molecular weight olefins with monomers containing polar substituents, e.g., aminoalkyl acrylates or acrylamides and poly-(oxyethylene)-substituted acrylates. These may be referred to as "polymeric dispersants."

Extreme pressure (EP) agents and corrosion and oxidation-inhibiting agents which may be included in the lubricants and/or functional fluids of the invention, may include chlorinated aliphatic hydrocarbons such as chlorinated wax; organic sulfides and polysulfides such as benzyl disulfide, bis(chlorobenzyl)disulfide, dibutyl tetrasulfide, sulfurized methyl ester of oleic acid, sulfurized alkylphenol, sulfurized dipentene, and sulfurized terpene; phosphosulfurized hydrocarbons such as the reaction product of a phosphorus sulfide with turpentine or methyl oleate, phosphorus esters including principally dihydrocarbyl and trihydrocarbyl phosphites such as dibutyl phosphite, diheptyl phosphite, dicyclohexyl phosphite, pentylphenyl phosphite, dipentylphenyl phosphite, tridecyl phosphite, distearyl phosphite, dimethyl naphthyl phosphite, oleyl 4-pentylphenyl phosphite, polypropylene (molecular weight 500)-substituted phenyl phosphite, diisobutyl-substituted phenyl phosphite; metal thiocarbamates, such as zinc dioctyldithiocarbamate, and barium heptylphenyl dithiocarbamate; Group II metal phosphorodithioates such as zinc dicyclohexylphosphorodithioate, zinc dioctyl phosphorodithioate, barium di(heptylphenyl)phosphorodithioate, cadmium dinonyl phosphorodithioate, and the zinc salt of a phosphorodithioic acid produced by the reaction of phosphorus pentasulfide with an equimolar mixture of isopropyl alcohol and n-hexyl alcohol.

Many of the above-mentioned extreme pressure agents and corrosion-oxidation inhibitors may also serve as antiwear agents. Zinc dialkyl phosphorodithioates are examples of such multifunctional additives.

Pour point depressants may be used to improve low temperature properties of the oil-based compositions. Examples of useful pour point depressants may include polymethacrylates; polyacrylates; polyacrylamides; condensation products of haloparaffin waxes and aromatic compounds; vinyl carboxylate polymers; and terpolymers of dialkyl fumarates, vinyl esters of fatty acids, alkyl vinyl ethers, or mixtures of two or more thereof.

The viscosity modifiers may include one or more polyacrylates, polymethacrylates, polyolefins, and/or styrene-maleic ester copolymers.

Anti-foam agents may be used to reduce or prevent the formation of stable foam. The anti-foam agents may include silicones, organic polymers, and the like.

The lubricant or functional fluid may include one or more thickeners to provide the lubricant or functional fluid with a grease-like consistency. The thickener may comprise lithium hydroxide, lithium hydroxide monohydrate, or a mixture thereof. The thickener may comprise 9-decenoic acid diol.

The functional additives may be added directly to the lubricant or functional fluid composition. Alternatively, the additives may be diluted with a substantially inert, normally liquid organic diluent such as mineral oil, naphtha, benzene, toluene or xylene, to form an additive concentrate, which may then be added to the lubricant and/or functional fluid. These concentrates may contain from about 0.1 to about 99%, or from about 10% to about 90% by weight, of one or more of the additives. The remainder of the concentrate may comprise the substantially inert normally liquid diluent.

This invention relates to a lubricant or functional fluid composition, comprising: an alcohol ester derived from the reaction of a malienated methyl 9-decenoate with iso-amyl alcohol; a polyalphaolefin; a hindered aryl amine; and a polyisobutenyl succinic anhydride based dispersant.

The Fuel Composition

The fuel composition may contain a major proportion of a normally liquid fuel. The normally liquid fuel may comprise motor gasoline or a middle distillate fuel. The middle distillate fuel may comprise diesel fuel, fuel oil, kerosene, jet fuel, heating oil, naphtha, or a mixture of two or more thereof. The fuel composition may also comprise one or more non-hydrocarbonaceous materials such as alcohols, ethers, organo-nitro compounds and the like (e.g., methanol, ethanol, diethyl ether, methyl ethyl ether, nitromethane). Normally liquid fuels which are mixtures of one or more hydrocarbonaceous fuels and one or more non-hydrocarbonaceous materials may be used. Examples of such mixtures may include combinations of gasoline and ethanol, or combinations of diesel fuel and ether. Gasoline may comprise a mixture of hydrocarbons having an ASTM distillation range from about 60° C. at the 10% distillation point to about 205° C. at the 90% distillation point.

The normally liquid fuel may comprise a natural oil, including vegetable oil, animal fat or oil, or a mixture thereof. These may be referred to as biofuels or biodiesel fuels. The normally liquid fuel may comprise a hydrocarbon oil (e.g., a petroleum or crude oil distillate). The fuel may comprise a mixture of a hydrocarbon oil and a natural oil.

The normally liquid fuel may comprise a synthetic fuel. The synthetic fuel may be derived from coal, natural gas, oil shale, biomass, or a mixture of two or more thereof. The synthetic fuel may be derived from a Fischer-Tropsch process.

The fuel composition may contain a property improving amount of one or more of the above-described dispersants. This amount may be from about 10 to about 1000 parts by weight, or from about 100 to about 500 parts by weight, of the dispersant per million parts of the normally liquid fuel.

The fuel composition may contain other additives well known to those of skill in the art. These may include deposit preventers or modifiers such as triaryl phosphates, dyes, cetane improvers, antioxidants such as 2,6-di-tertiary-butyl-4-methyl-phenol, rust inhibitors such as alkenylsuccinic acids and anhydrides, bacteriostatic agents, gum inhibitors, metal deactivators, demulsifiers, upper cylinder lubricants, anti-icing agents, mixtures of two or more thereof, and the like.

The fuel composition may further comprise a cold flow improver; additive for increasing horsepower; additive for improving fuel economy; additive for lubricating and reducing wear of engine components; additive for cleaning and preventing deposit buildup; additive for reducing smoke and particulate emissions; additive for removing water; additive for reducing rust and corrosion; additive for upgrading and stabilizing the fuel; additive for improving storage and combustion capabilities; antioxidant; antistatic agent; corrosion inhibitor; fuel system icing inhibitor; cold flow improver; biocide; metal deactivator; additive for reducing fuel line and filter clogging; additive for improving fuel atomization; additive for reducing deposits on burner nozzles; additive for enhancing flame stabilization; additive for improving combustion; additive for reducing soot formation; additive for neutralizing vanadium and sodium; additive for improving heat transfer; additive for reducing the formation of sulfur trioxide; additive for reducing stack temperatures; additive for reducing carbon monoxide, oxygen and/or unburnt hydrocarbon in stack gases; additive for reducing fuel consumption; polar compound for dispersing paraffins; oil-soluble amphiphile; pour point depressant; dewaxing additive; sludge inhibitor; dehazer; additive for reducing cloud point; or a mixtures of two or more thereof.

Functional Compositions

The functionalized or polyfunctionalized monomer or polymer may be useful in polymer compositions or plastic formulations for making extruded or molded articles, or for use in adhesives, coating compositions, including protective and/or decorative coatings (e.g., paint), or for use in pharmacetucials, cosmetics, personal care products, industrial cleaners, institutional cleaners, foods, beverages, oil filed chemicals, agricultural chemicals, and the like. The monomer or polymer may be partially or fully hydrogenated, depending on its intended use.

The functional composition may further comprise one or more solvents (e.g., water or organic), thixotropic additives, pseudoplastic additives, rheology modifiers, anti-settling agents, leveling agents, defoamers, pigments, dyes, plasticizers, viscosity stabilizers, biocides, viricides, fungicides, crosslinkers, humectants, surfactants, detergents, soaps, fragrances, sweeteners, alcohol, food, food additives, mixtures of two or more thereof, and the like.

The thixotropic additive may comprise fumed silica and/or clay, and the like. The leveling agent may comprise polysiloxane, dimethylpolysiloxane, polyether modified dimethylpolysiloxane, polyester modified dimethylpolysiloxane, polymethylalkysiloxane, aralkyl modified polymethylalkylsiloxane, alcohol alkoxylates, polyacrylates, polymeric fluorosurfactants, fluoro modified polyacrylates, or a mixture of two or more thereof.

The plasticizer may comprise ethylene glycol, polyethylene glycol, propylene glycol, polypropylene glycol, butane diol, polybutylene glycol, glycerine, or a mixture of two or more thereof.

The viscosity stabilizer may comprise a mono or multifunctional hydroxyl compound. These may include methanol, ethanol, propanol, butanol, ethylene glycol, polyethylene glycol, propylene glycol, polyethylene glycol, propylene glycol, polypropylene glycol, butane diol, polybutylene glycol, glycerine, or a mixture of two or more thereof.

The biocide, viricide or fungicide may comprise sodium hypochlorite, potassium hypochlorite, quaternary ammonium chloride, and the like.

The humectant may comprise polyacrylic acid, polyacrylic acid salt, an acrylic acid copolymer, a polyacrylic acid salt copolymer, or a mixture of two or more thereof.

The surfactant may comprise one or more ionic and/or nonionic compounds. The ionic compounds may be cationic or amphoteric compounds. The surfactants that may be used may include alkanolamines, alkylarylsulfonates, amine oxides, poly(oxyalkylene) compounds, including block copolymers comprising alkylene oxide repeat units, carboxylated alcohol ethoxylates, ethoxylated alcohols, ethoxylated alkyl phenols, ethoxylated amines and amides, ethoxylated fatty acids, ethoxylated fatty esters and oils, fatty esters, fatty acid amides, glycerol esters, glycol esters, sorbitan esters, imidazoline derivatives, lecithin and derivatives, lignin and derivatives, monoglycerides and derivatives, olefin sulfonates, phosphate esters and derivatives, propoxylated and ethoxylated fatty acids or alcohols or alkyl phenols, sorbitan derivatives, sucrose esters and derivatives, sulfates or alcohols or ethoxylated alcohols or fatty esters, sulfonates of dodecyl and tridecyl benzenes or condensed naphthalenes or petroleum, sulfosuccinates and derivatives, and tridecyl and dodecyl benzene sulfonic acids. The surfactant may comprise sodium lauryl sulfonate, cetyltrimethyl ammonium bromide, and the like.

The concentration of each of the foregoing additives in the functional composition may be up to about 25% by weight, or up to about 10% by weight, or up to about 5% by weight.

The functional composition, which may be in the form of a polymer composition, may be provided in a solid form, e.g., powder, pellets, and the like, or in a liquid form, optionally, with a solvent or vehicle. The solvent or vehicle may comprise an aqueous based solvent or vehicle or an organic solvent or vehicle. The organic solvent or vehicle may comprise one or more alcohols, for example, methanol, ethanol, propanol, butanol, one or more ketones, for example, acetone, one or more acetates, for example, methyl acetate, or a mixture of two or more thereof.

EXAMPLES

The following additional examples illustrate features in accordance with the present invention, and are provided solely by way of illustration. They are not intended to limit the scope of the appended claims.

Example 5—Methyl 9-Decenoate Homopolymer Using t-Bu$_2$O$_2$

Methyl 9-decenoate (50 g, 0.271 mole) and di-t-butyl peroxide (4 g, 0.0271 mole) are charged into a reaction flask that is equipped with a thermometer, nitrogen inlet, magnetic stirrer, and reflux condenser. The resulting reaction mixture is heated to 130° C. An exotherm occurs and the temperature of the reaction mixture increases to 160° C. The exotherm subsides over time and the reaction temperature is dropped to 130° C. Heating is continued at 120-130° C. for 6.5 hrs. An additional amount of di-t-butyl peroxide (4 g, 0.0271 mole) is added and the reaction mixture is heated for an additional time of 5 hrs. The reaction mixture is then stripped to 150° C. using vacuum of 2 torr (0.27 kilopascal).

Residue left after stripping, which is in the form of a viscous fluid, is the desired product. The amount of desired product is 40 g (80% yield).

Example 6—9-Decenoic Acid Homopolymer Using t-Bu$_2$O$_2$

9-Decenoic acid (100 g, 0.59 mole) and di-t-butyl peroxide (8.6 g, 0.06 mole) are charged into a 2-necked 250-mL flask that is equipped with a magnetic stirrer, Dean-Stark trap, nitrogen inlet, thermometer, and reflux condenser. The reaction mixture is heated to 130° C. An exotherm occurs and the temperature of the reaction mixture increases to 157° C. The exotherm subsides over time and the reaction temperature drops to 130° C. Heating is continued at 120-130° C. for 6.5 hrs. The reaction mixture is then stripped at 150-180° C. using a vacuum of 2 torr (0.27 kilopascal). Residue left after stripping, which is in the form of a viscous fluid, is the desired product. The amount of desired product is 55 g (55% yield). The product has an acid number of 314 mg KOH/g.

Example 7—Homopolymerization of Pentaerythritol Ester of 9-Decenoic Acid by the Use of t-Bu$_2$O$_2$ Pentaerythritol ester of 9-decenoic acid (30 g, 0.04 mole) is charged into a 3-necked 100-mL flask that is equipped with a magnetic stirrer, nitrogen inlet, thermometer, and a reflux condenser. The ester is heated to 150° C. and di-t-butyl peroxide (0.64 g, 0.0046 mole) is added in two portions, 30 minutes apart. The reaction mixture is heated at 150° C. for 1 hr. The viscosity of the reaction mixture increases and polymer is formed.

Example 8—Copolymerization of 1-Decene and Pentaerythritol Ester of 9-Decenoic Acid by the Use of t-Bu$_2$O$_2$ 1-Decene (200 g, 1.43 moles) and pentaerythritol ester of 9-decenoic acid (40 g, 0.053 mole) are charged into a 3-necked 500-mL flask that is equipped with a magnetic stirrer, nitrogen inlet, thermometer, and reflux condenser. Di-t-butyl peroxide (20.8 g, 0.142 mole) is added in five portions that are 30 minutes apart. The reaction mixture is heated at 130° C. for 10 hr. Distillation is then carried out to remove unreacted decene (122 g), leaving behind 130 g of a copolymer in the form of a clear viscous fluid.

Example 9—Copolymerization of 1-Decene and Methyl 9-Decenoate by the Use of t-Bu$_2$O$_2$ 1-Decene (250 g, 1.786 mole), and methyl 9-decenoate (33 g, 0.179 mole) are charged into a 3-necked 500-mL flask that is equipped with a magnetic stirrer, nitrogen inlet, thermometer, Dean-Stark trap, and reflux condenser. The reaction mixture is brought to 150° C. and di-t-butyl peroxide (32.5 g, 0.223 mole) is added in ten portions 30 minutes apart. The reaction mixture is heated at 150° C. for a total of 10 hr. Distillation is then carried out to remove the starting material and low-boiling components, leaving behind 198 g of a clear viscous product (70% conversion).

Example 10—Copolymerization of 1-Decene and 9-Decenoic Acid by the Use of t-Bu$_2$O$_2$ 1-Decene (200 g, 1.43 moles), and 9-decenoic acid (27 g, 0.159 mole) are charged into a 3-necked 500-mL flask that is equipped with a magnetic stirrer, nitrogen inlet, thermometer, and reflux condenser. The reaction mixture is brought to 150° C. and di-t-butyl peroxide (23.2 g, 0.159 mole) is added in six portions that are 30 minutes apart. The reaction mixture is heated at 140° C. for 3 hr. Distillation is then carried out to remove the starting material and the low-boiling components, leaving behind a clear viscous product that has an acid number of 60.

Example 11—Dispersants Derived from 1-Decene/9-Decenoic Acid Polymer

1-Decene (200 g, 1.43 moles), and 9-decenoic acid (27 g, 0.159 mole) are charged into a 3-necked 500-mL flask that is equipped with a magnetic stirrer, nitrogen inlet, thermometer, and reflux condenser. The reaction mixture is brought to 170° C. and di-t-amyl peroxide (27.5 g, 0.159 mole) is added in six portions that are 30 minutes apart. The reaction mixture is heated at 150° C. for a total of 6.5 hr. Distillation is carried out to remove the starting material and the low-boiling components, leaving behind a clear viscous product that has an acid number of 56.

A first dispersant is made by reacting 50 g of the 1-decene/9-decenoic acid polymer with diethylenetriamine at 150° C. The carboxylic acid to nitrogen ratio is 2:3. The reaction mixture is held at this temperature until the acid number of the mixture is 10. A small amount of toluene is used in the reaction to remove water of reaction. Toluene is removed at the end of reaction.

A second dispersant is made by reacting 50 g of the 1-decene/9-decenoic acid polymer with pentaerythritol at 150° C. The carboxylic acid to hydroxyl ratio is 4:1. The reaction is continued until an acid number of 10 is achieved. A small amount of toluene is used in the reaction to remove water of reaction. Toluene is removed at the end of reaction.

Both the first and second dispersants have good American Petroleum Institute (API) Group I oil and Group II oil miscibility at 20 percent and 50 percent by weight.

Example 12—Polymerization of Methyl 9-Decenoate by the Use of an Acid Catalyst (Montmorillonite K10)

Methyl 9-decenoate (250 g) and Montmorillonite K10 (50 g) are placed in a glass liner. The glass liner is inserted in a Parr reaction vessel. The vessel is sealed, purged with N$_2$ for 15 minutes, and an initial N$_2$ pressure of 8 psi (55.2 kilopascals) is applied. The mixture is heated to 200° C. with 600 rpm stirring. The reaction mixture reaches the desired temperature in 30 minutes. The reaction mixture is stirred at this temperature for 8 hours. The final pressure is 135 psi (930.8 kilopascals). The reaction mixture is hot-filtered to remove the catalyst. The filtrate is subjected to vacuum distillation at 190° C. and 20 mmHg (2.67 kilopascals). The distillation residue (130 g) is the desired product. The average molecular weight is about 500.

Example 13—Polymerization of 1-Decene-Methyl 9-Decenoate Mixture by the Use of an Acid Catalyst (Montmorillonite K10)

1-Decene (140 g, 1 mole), methyl 9-decenoate (184 g, 1 mole), and Montmorillonite K10 (50 g) are placed in a glass liner which is inserted in a Parr reaction vessel. The vessel is sealed, purged with N$_2$ for 15 minutes, and an initial N$_2$ pressure of 8 psi (55.2 kilopascals) is applied. The mixture is heated at 250° C. with 600 rpm stirring for 11 hours. The final pressure is 135 psi (930.8 kilopascals). The reaction mixture is hot-filtered to remove the catalyst. The filtrate is subjected to vacuum distillation at 190° C. and 20 mmHg (2.67 kilopascals). TLC and GC/MS indicate the presence of copolymer.

Example 14—Copolymerization of 1-Hexene and Methyl 9-Decenoate by the use of t-Bu$_2$O$_2$ 1-Hexene (150 g, 1.786 mole), and methyl 9-decenoate (33 g, 0.179 mole) are charged into a 3-necked 500-mL flask that is equipped with a magnetic stirrer, nitrogen inlet, thermometer, Dean-Stark trap, and reflux condenser. The reaction mixture is brought to 150° C. and di-t-butyl peroxide (32.5 g, 0.223 mole) is added in ten portions 30 minutes apart. The reaction mixture is heated at 150° C. for 10 hours. Distillation is then carried out to remove the starting material and low-boiling components, leaving behind the desired product.

Example 15—Copolymerization of 1-Hexadecene and Methyl 9-Decenoate by the Use of t-Bu$_2$O$_2$ 1-Hexadecene (400 g, 1.786 mole), and methyl 9-decenoate (33 g, 0.179 mole) are charged into a 3-necked 1 L-flask that is equipped with a magnetic stirrer, nitrogen inlet, thermometer, Dean-Stark trap, and reflux condenser. The reaction mixture is brought to 150° C. and di-t-butyl peroxide (32.5 g, 0.223 mole) is added in ten portions 30 minutes apart. The reaction mixture is heated at 150° C. for 10 hours. Distillation is carried out to remove the starting material and low-boiling components, leaving behind the desired product.

Example 16—Copolymerization of 12-Tetraeicosene and Methyl 9-Decenoate by the use of t-Bu$_2$O$_2$ 12-Tetraeicosene (600 g, 1.786 mole), and methyl 9-decenoate (33 g, 0.179 mole) are charged into a 3-necked 1 L-flask that is equipped with a magnetic stirrer, nitrogen inlet, thermometer, Dean-Stark trap, and reflux condenser. The reaction mixture is brought to 150° C. and di-t-butyl peroxide (32.5 g, 0.223 mole) is added in ten portions 30 minutes apart. The reaction mixture is heated at 150° C. for 10 hours. Distillation is carried out to remove the starting material and low-boiling components, leaving behind the desired product.

Example 17—Copolymerization of 1-Decene and Methyl 5-Hexenoate by the use of t-Bu$_2$O$_2$ 1-Decene (250 g, 1.786 mole), and methyl 9-hexenoate (23 g, 0.179 mole) are charged into a 3-necked 500-mL flask that is equipped with a magnetic stirrer, nitrogen inlet, thermometer, Dean-Stark trap, and reflux condenser. The reaction mixture is brought to 130° C. and di-t-butyl peroxide (32.5 g, 0.223 mole) is added in ten portions 30 minutes apart. The reaction mixture is heated at 130° C. for 10 hours. Distillation is carried out to remove the starting material and low-boiling components, leaving behind the desired product.

Example 18—Copolymerization of 1-Decene and Methyl 9-Octadecenoate by the Use of t-Bu$_2$O$_2$ 1-Decene (250 g, 1.786 mole), and methyl 9-octadecenoate (53 g, 0.179 mole) are charged into a 3-necked 500-mL flask that is equipped with a magnetic stirrer, nitrogen inlet, thermometer, Dean-Stark trap, and reflux condenser. The reaction mixture is brought to 130° C. and di-t-butyl peroxide (32.5 g, 0.223 mole) is added in ten portions 30 minutes apart. The reaction mixture is heated at 130° C. for 10 hours. Distillation is carried out to remove the starting material and low-boiling components, leaving behind the desired product.

Example 19—Copolymerization of 1-Hexadecene and Methyl 9-Octadecenoate by the use of t-Bu$_2$O$_2$ 1-Hexadecene (400 g, 1.786 mole), and methyl 9-octadecenoate (53 g, 0.179 mole) are charged into a 3-necked 1 L-flask that is equipped with a magnetic stirrer, nitrogen inlet, thermometer, Dean-Stark trap, and reflux condenser. The reaction mixture is brought to 150° C. and di-t-butyl peroxide (32.5 g, 0.223 mole) is added in ten portions 30 minutes apart. The reaction mixture is heated at 150° C. for 10 hours. Distillation is carried out to remove the starting material and low-boiling components, leaving behind the desired product.

Example 20—Copolymerization of Dodecene and Methyl 9-Octadecenedioate by the Use of t-Bu$_2$O$_2$ 1-Dodecene (300 g, 1.786 mole), and methyl 9-octadecenedioate (63.6 g, 0.179 mole) are charged into a 3-necked 500-mL flask that is equipped with a magnetic stirrer, nitrogen inlet, thermometer, Dean-Stark trap, and reflux condenser. The reaction mixture is brought to 130° C. and di-t-butyl peroxide (32.5 g, 0.223 mole) is added in ten portions 30 minutes apart. The reaction mixture is heated at 130° C. for 10 hours. After this time, distillation is carried out to remove the starting material and low-boiling components, leaving behind the desired product.

Example 21—Methyl 9-Decenoate Homopolymer Using t-Bu$_2$O$_2$

Methyl 9-decenoate (35 g, 0.271 mole) and di-t-butyl peroxide (4 g, 0.0271 mole) are charged into a reaction flask that is equipped with a thermometer, nitrogen inlet, magnetic stirrer, and reflux condenser. Reaction mixture is heated to 130° C. An exotherm occurs and the temperature of the reaction mixture rises to 160° C. The exotherm subsides over time and the reaction temperature drops to 130° C. Heating is continued at 120-130° C. for 6.5 hrs. An additional amount of di-t-butyl peroxide (4 g, 0.0271 mole) is added and the reaction mixture is heated for an additional time of 5 hrs. The reaction mixture is then stripped to 150° C. using vacuum of 2 torr (0.27 kilopascal) to yield product in the form of a viscous fluid.

Example 22—5-Hexenoic Acid Homopolymer Using t-Bu$_2$O$_2$

5-Hexenoic acid (67 g, 0.59 mole) and di-t-butyl peroxide (8.6 g, 0.06 mole) are charged into a 2-necked 250-mL flask that is equipped with a magnetic stirrer, Dean-Stark trap, nitrogen inlet, thermometer, and reflux condenser. The reaction mixture is heated to 130° C. An exotherm occurs and the temperature of the reaction mixture rises to 150° C. The exotherm subsides over time and the reaction temperature drops to 130° C. Heating is continued at 120-130° C. for 6.5 hrs. The reaction mixture is then stripped at 150-180° C. using vacuum of 2 torr (0.27 kilopascals). Residue left after stripping, which is in the form of a viscous fluid, is the desired product.

Example 23—Methyl Octadecenoate Homopolymer Using t-Bu$_2$O$_2$

Methyl octadecenoate (81 g) and di-t-butyl peroxide (4 g) are charged into a reaction flask that is equipped with a thermometer, nitrogen inlet, magnetic stirrer, and reflux condenser. The reaction mixture is heated to 130° C. An exotherm occurs and the temperature of the reaction mixture rises to 160° C. The exotherm subsides over time and the reaction temperature drops to 130° C. Heating is continued at 120-130° C. for 6.5 hrs. An additional amount of di-t-butyl peroxide (4 g, 0.0271 mole) is added and the reaction mixture is heated for an additional time of 5 hrs. The reaction mixture is then stripped to 150° C. using a vacuum of 2 torr (0.27 kilopascals) to yield the desired product which is in the form of a viscous fluid.

Example 24—Octadecenoic Acid Homopolymer Using t-Bu$_2$O$_2$

Octadecenoic acid (79 g) and di-t-butyl peroxide (8.6 g) are charged into a 2-necked 250-mL flask that is equipped with a magnetic stirrer, Dean-Stark trap, nitrogen inlet, thermometer, and reflux condenser. The reaction mixture is heated to 130° C. An exotherm occurs and the temperature of the reaction mixture rises to 150° C. The exotherm subsides over time and the reaction temperature drops to 130° C. Heating is continued at 120-130° C. for 6.5 hrs. The reaction mixture is then stripped at 150-180° C. using vacuum of 2 torr (0.27 kilopascals). Residue left after stripping, which is in the form of a viscous fluid, is the desired product.

Example 25—Dispersant Preparation from 1-Decene/9-Decenoic Acid Polymer Composition A 1-liter round-bottomed flask is charged with 400 g of a solution of 75% polymer composition, prepared from a free radical polymerization of 1-decene:9-decenoic acid (75:25) mole percent mixture, in xylenes. The contents of the flask are then heated with stirring to 175° C. Aminopropylimidazole (38 g) is added dropwise via a pressure equalizing dropping funnel over a period of 30 minutes. The reaction mixture is then maintained at 175° C. with stirring and water removal for 3 hours. Solvent and low-boiling volatiles are removed via distillation, leaving behind an amber viscous product that is filtered through a 12 mm Celite pad.

Example 26—Imide Dispersant Preparation from Methyl 9-Decenoate Homopolymer

A mixture of 500 g of homopolymer and 30 g of maleic anhydride is heated to 110° C. This mixture is heated to 200° C. and is held there for 6 hr. The reaction mixture is then stripped of starting materials, leaving behind succinated homopolymer. To this material is added 113 g of mineral oil, and 10 g of a commercial mixture of ethylene polyamines having from about 3 to about 10 nitrogen atoms per molecule. The reaction mixture is heated to 150° C. for 2 hr and is stripped by blowing with nitrogen. The reaction mixture is filtered to yield the filtrate as an oil solution of the desired product.

Example 27—Dispersant Preparation from Methyl 9-Decenoate Homopolymer

A mixture of 500 g of methyl 9-decenoate homopolymer and 30 g of maleic anhydride is heated to 110° C. This mixture is heated to 200° C. and is held there for 6 hr. After this time the reaction is stripped of starting materials, leaving behind succinated homopolymer. To this material is added 30 g of pentaerythritol and the reaction mixture is heated to 210° C. and held at this temperature for 3 hr. The reaction mixture is cooled to 190° C. and 8 g of a commercial mixture of ethylene polyamines having an average of about 3 to about 10 nitrogen atoms per molecule is added. The reaction mixture is stripped by heating at 205° C. with nitrogen blowing for 3 hours, then filtered to yield the filtrate as an oil solution of the desired product.

Example 28—Detergent Preparation from 1-Decene/9-Decenoic Acid Polymer Composition A mixture of 200 g of mineral oil, 30 g polyisobutenylsuccinic acid anhydride, 50 g of a mixture of 61% by weight isobutanol and 39% by weight amyl alcohol, and Mississippi Lime (86% available Ca) are charged to a stainless steel reactor having a stirrer, condenser, and an oil system to a jacket around the reactor for both heating and cooling. With stirrer agitation of the mixture and a nitrogen gas purge above the reaction mixture, 200 g of 1-decene/1-decenoic acid polymer composition, prepared from free radical polymerization of 1-decene:9-decenoic acid (75:25) mole percent mixture. The mixture is then heated to 90° C. to complete the acid and acid anhydride neutralization. 25 g methanol and 140 g of the above-mentioned Mississippi Lime are added after cooling the batch to 40° C. The material in the reaction vessel is carbonated at 50-60° C. by passing carbon dioxide into the reaction mixture until the reaction mixture has a base number of approximately zero. After carbonation, the material is flash dried to remove the alcohol promoters and water by raising the temperature to 150° C. and purging with nitrogen gas. The material is then cooled, solvent clarified by adding approximately 150 parts hexane, and vacuum stripped of volatiles to 150° C. and 70 mm absolute Hg. The product is filtered and diluent oil is added to adjust calcium content to 14.2 percent by weight calcium.

Example 29—Detergent Preparation from Methyl 9-Decenoate Homopolymer and Alkyl Benzenesulfonic Acid Mixture To a solution of 100 g of an alkylbenzenesulfonic acid, 100 g of methyl 9-decenoate homopolymer, 10 g of polyisobutenylsuccinic anhydride, and 50 g mineral oil is added 100 g of calcium hydroxide, and 50 g of a mixture of 61 percent by weight isobutanol and 39 percent by weight amyl alcohol. The temperature of the mixture increases to 89° C. over 10 minutes due to an exotherm. During this period, the mixture is blown with carbon dioxide at 4 cubic feet/hr (cfh) (113.3 liters per hour). Carbonation is continued for about 30 minutes as the temperature gradually decreases to 74° C. The alcohols and other volatile materials are stripped from the carbonated mixture by blowing nitrogen through it at 2 cfh (56.6 liters per hour) while the temperature is slowly increased to 150° C. over 90 minutes. After stripping is completed, the remaining mixture is held at 155-165° C. for about 30 minutes and filtered to yield an oil solution of the desired basic detergent.

The following table shows data for homopolymers and various polymer compositions prepared using functionalized monomers in accordance with the present teachings.

| Monomer/s | Catalyst/Reaction Temperature | Yield % | Viscosity Measurement (100° C.) |
|---|---|---|---|
| Methyl 9-Decenoate | 10 m % Di-t-butyl peroxide catalyst/130° C., 6.5 hrs.; then add another 10 m % initiator and heat at 130° C. for 5 hrs. | 80 | 31.8 cPs; 37 cSt |
| 9-Decenoic Acid | 10 m % Di-t-butyl peroxide catalyst 130° C., 6.5 hrs., | 55 | Too viscous to measure |
| 1-Decene/Methyl 9-Decenoate (9/1)m | 10 m % Di-t-butyl peroxide catalyst; starts out at 150° C., then 135-140° C., 6.5 hrs. | 66 | 12 cPs; 14 cSt |
| 1-Decene/Methyl 9-Decenoate (9/1)m | 10 m % Di-t-butyl peroxide catalyst Starts out at 150 C., then 135-140° C., 10 hrs. | 64 | 12.8 cSt |
| 1-Decene/Methyl 9-Decenoate (9/1)m | 10 m % di-t-butyl peroxide catalyst 150° C. for 10 hrs. | 71 | 14 cSt |
| 1-Decene/Methyl 9-Decenoate (9/1)m | 10 m % di-t-butyl peroxide catalyst 135-140° C., 6.5 hrs. | 56 | 15.6 cPs |
| 1-Decene/9-Decenoic Acid (9/1)m | 10 m % di-t-amyl peroxide catalyst, 140-150° C., 6 hrs. | 63 | 24 cPs |
| 1-Decene/9-Decenoic Acid (75/25)m | 30 m % di-t-butyl peroxide catalyst, 135-140° C., 6.5 hrs. | 70 | 121 cPs |
| Pentaerythritol Ester of 9-Decenoic Acid | 10 m % di-t-butyl peroxide catalyst 150° C., 1 hr. | Unk. | Polymer |
| Pentaerythritol Ester of 9-Decenoic Acid | 10 m % di-t-butyl peroxide catalyst 130° C., 8 hrs. | Unk. | Very Viscous Fluid; 477 cPs |
| 1-Decene/Pentaerythritol Ester of 9-Decenoic Acid (80:20)wt | 10 m % di-t-butyl peroxide catalyst 130° C., 10 hrs. | 65 | 50 cPs |
| 1-Decene/9-Decenoic Acid (75:25))m | 30 m % di-t-butyl peroxide catalyst DTBP, 135-140° C., 6.5 hrs. | 75.5 | 49.5 cPs |

Example 30

To a solution of maleinated methyl 9-decenoate (50.0 g, 0.535 mol), 3-methyl-1-butanol (47.2 g, 0.535 mol), and Exxal 10 (84.7 g, 0.535 mol) in toluene (80 mL) p-toluenesulfonic acid (3.1 g, 0.016 mol) is added. The reaction is heated to reflux (120° C.) and azeotropic removal of water and methanol is performed using a Dean-Stark apparatus. After 5 h, the reaction is cooled to room temperature and diluted with ethyl acetate (100 mL), washed with aqueous potassium hydroxide (0.07 M, 250 mL), followed by water (2×250 mL). The organic phase is collected, dried over MgSO$_4$, filtered, and concentrated to a crude oil residue. Volatiles are removed by vacuum distillation (2 Torr, 140° C., 1.5 h) to yield the desired product as a yellow oil (88.5 g). Product has kinematic viscosity of 5.8 cSt at 100° C. GC/MS (m/z) 496, 549.

Example 31

Maleinated methyl 9-decenoate (200 g, NNA=422 mg KOH/g) and Exxal 8 (branched primary alcohol supplied by ExxonMobil) (100 g, 0.77 mol) are charged into a reaction flask that is equipped with a thermocouple, nitrogen inlet, magnetic stirrer, and short-path distillation bridge. The mixture is heated to 80° C. and methanesulfonic acid (0.3 mol %, 70% aqueous solution) is added. The resulting reaction mixture is heated to 100° C. The generated water is removed during distillation to drive the reaction to high conversion. The progress of the reaction is monitored by acid value analysis. Once the distillation rate slows down the reaction temperature is increased. Heating is continued at 130-150° C. until water formation diminishes and the acid value reaches around 20. The reaction mixture is allowed to cool to 80° C. and vacuum (2 torr) is applied to remove residual water and drive the reaction to an acid value of <5. The temperature is increased stepwise to 160° C. to remove excess alcohol and other volatiles. The remaining ester product is filtered over a bed of silica (1 inch, fritted funnel) by applying vacuum. The filtration yields a golden to amber oil. The amount of desired product is 270 g (93% yield). Kinematic viscosity at 40° C.=51.28 cSt, at 100° C.=8.32, VI=136, and pour point=−39° C.

Example 32—Copolymerization of 1-Dodecene and Methyl 9-Decenoate by the Use of Di-t-Butyl Peroxide 1-Dodecene (128.27 g, 0.7261 mole), and methyl 9-decenoate (14.04 g, 0.0762 mole) are charged into a 3-necked 250-mL flask that is equipped with a magnetic stirrer, nitrogen inlet, thermometer, Dean-Stark trap, and reflux condenser. The reaction mixture is brought to 160° C. and di-t-butyl peroxide (11.14 g, 0.0762 mole) is added in ten portions 30 minutes apart. The reaction mixture is heated at 160° C. for a total of 8.5 hr. Vacuum distillation to 200° C. is then carried out to remove the unreacted starting material and low-boiling components, leaving behind 105.71 g of a clear viscous product (74% conversion). The kinematic viscosity at 100° C. is 22.09 cSt.

Example 33—Copolymerization of 1-Dodecene and Methyl 9-Decenoate by the Use of Di-t-Butyl Peroxide with Dodecanethiol Chain Transfer Agent 1-Dodecene (128.27 g, 0.7261 mole), methyl 9-decenoate (14.04 g, 0.0762 mole), and dodecane thiol (0.5090 g, 0.0025 mole) are charged into a 3-necked 250-mL flask that is equipped with a magnetic stirrer, nitrogen inlet, thermometer, Dean-Stark trap, and reflux condenser. The reaction mixture is brought to 160° C. and di-t-butyl peroxide (11.14 g, 0.0762 mole) is added in ten portions 30 minutes apart. The reaction mixture is heated at 160° C. for a total of 8.5 hr. Vacuum distillation to 200° C. is then carried out to remove the unreacted starting material and low-boiling components, leaving behind 92.36 g of a clear viscous product (65% conversion). The kinematic viscosity at 100° C. is 15.69 cSt. Sulfur in the product is 847 ppm.

Example 34—Copolymerization of 1-Dodecene and Methyl 9-Decenoate by the Use of Di-t-Butyl Peroxide with t-Nonyl Thiol Chain Transfer Agent 1-Dodecene (128.27 g, 0.7261 mole), methyl 9-decenoate (14.04 g, 0.0762 mole), and t-nonyl thiol (0.4032 g, 0.0025 mole) are charged into a 3-necked 250-mL flask that is equipped with a magnetic stirrer, nitrogen inlet, thermometer, Dean-Stark trap, and reflux condenser. The reaction mixture is brought to 160° C. and di-t-butyl peroxide (11.14 g, 0.0762 mole) is added in ten portions 30 minutes apart. The reaction mixture is heated at 160° C. for a total of 8.5 hr. Vacuum distillation to 200° C. is then carried out to remove the unreacted starting material and low-boiling components, leaving behind 73.54 g of a clear viscous product (50% conversion). The kinematic viscosity at 100° C. is 11.92 cSt. Sulfur in the product is 927 ppm.

Example 35—Copolymerization of 1-Dodecene and Methyl 9-Decenoate by the Use of Di-t-Butyl Peroxide with Bromotrichloromethane Chain Transfer Agent 1-Dodecene (128.27 g, 0.7261 mole), methyl 9-decenoate (14.04 g, 0.0762 mole), and bromotrichloromethane (0.4986 g, 0.0025 mole) are charged into a 3-necked 250-mL flask that is equipped with a magnetic stirrer, nitrogen inlet, thermometer, Dean-Stark trap, and reflux condenser. The reaction mixture is brought to 150° C. and di-t-butyl peroxide (11.14 g, 0.0762 mole) is added in ten portions 30 minutes apart. The reaction mixture is heated at 150° C. for a total of 8.5 hr. Vacuum distillation to 200° C. is then carried out to remove the unreacted starting material and low-boiling components, leaving behind 72.11 g of a clear yellow viscous product (51% conversion). The kinematic viscosity at 100° C. is 11.31 cSt. Chlorine in the product is 2500 ppm Example 36—Copolymerization of 1-Dodecene and Methyl 9-Decenoate by the Use of 2,5-Dimethyl-2,5-Di(t-Butylperoxy)Hexane 1-Dodecene (133.13 g, 0.7909 mole), methyl 9-decenoate (14.57 g, 0.0791 mole), are charged into a 3-necked 250-mL flask that is equipped with a magnetic stirrer, nitrogen inlet, thermometer, Dean-Stark trap, and reflux condenser. The reaction mixture is brought to 150° C. and 2,5-dimethyl-2, 5-di(t-butylperoxy)hexane (10.52 g, 0.0362 mole) is added in ten portions 30 minutes apart. The reaction mixture is heated at 150° C. for a total of 8.5 hr. Vacuum distillation to 200° C. is then carried out to remove the unreacted starting material and low-boiling components, leaving behind 94.79 g of a clear viscous product (64% conversion). The kinematic viscosity at 100° C. is 17.73 cSt.

Example 37—Copolymerization of 1-Dodecene and Methyl 9-Decenoate by the Use of Di-t-Amyl Peroxide 1-Dodecene (132.05 g, 0.7845 mole), methyl 9-decenoate (14.46 g, 0.0785 mole), are charged into a 3-necked 250-mL flask that is equipped with a magnetic stirrer, nitrogen inlet, thermometer, Dean-Stark trap, and reflux condenser. The reaction mixture is brought to 150° C. and di-t-amyl peroxide (13.09 g, 0.0751 mole) is added in ten portions 30 minutes apart. The reaction mixture is heated at 150° C. for a total of 8.5 hr. Vacuum distillation to 200° C. is then carried out to remove the unreacted starting material and low-boiling components, leaving behind 114.72 g of a clear viscous product (78% conversion). The kinematic viscosity at 100° C. is 15.81 cSt.

Example 38—Copolymerization of 1-Dodecene and Methyl 9-Decenoate by the Use of t-Butyl Peroxybenzoate 1-Dodecene (137.72 g, 0.8182 mole), methyl 9-decenoate (15.08 g, 0.0818 mole), are charged into a 3-necked 250-mL flask that is equipped with a magnetic stirrer, nitrogen inlet, thermometer, Dean-Stark trap, and reflux condenser. The reaction mixture is brought to 150° C. and t-butyl peroxybenzoate (15.32 g, 0.0788 mole) is added in ten portions 30 minutes apart. The reaction mixture is heated at 150° C. for a total of 8.5 hr. Vacuum distillation to 200° C. is then carried out to remove the unreacted starting material and low-boiling components, leaving behind 97.83 g of a clear viscous product (64% conversion). The kinematic viscosity at 100° C. is 19.52 cSt.

Example 39

The following table shows the viscosity index for a series of polymers with varying dodecene/9DAME ratios.

| Polymer | Dodecene/ Methyl 9-decenoate | Kinematic Viscosity at 100° C. (cSt) | Kinematic Viscosity at 40° C. (cSt) | Viscosity Index VI |
| --- | --- | --- | --- | --- |
| 1 | 95/5 | 22.30 | 157.70 | 169 |
| 2 | 75/25 | 20.77 | 146.90 | 165 |
| 3 | 50/50 | 20.34 | 141.46 | 167 |
| 4 | 25/75 | 21.49 | 159.49 | 160 |
| 5 | 0/100 | 23.17 | 177.85 | 158 |

Example 40

Scheme 1. $BF_3$-mediated co-oligomerization of methyl 9-decenoate and 1-dodecene

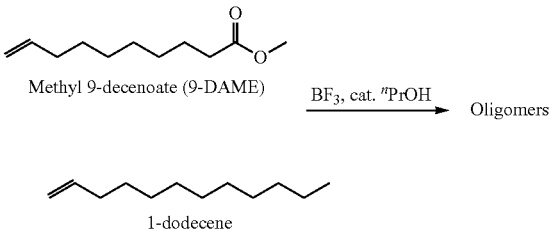

| Reagent | Mass | Moles | Equivalents |
| --- | --- | --- | --- |
| 1-Dodecene | 100.0 g | 594 mmol | 1.00 equiv |
| 9-DAME | 11.0 g | 60 mmol | 0.10 equiv |
| $^n$Propanol | 1.1 g (1.4 mL) | 18 mmol | 1.0 wt % |
| $BF_3$ | 34.5 g | 508 mmol | 0.85 equiv |

The reaction is conducted in a 500-mL borosilicate glass bubbler with a single gas inlet and outlet. The reactor is equipped with a magnetic stirrer. A thermometer is placed inside the reaction vessel for temperature monitoring and a water bath is provided for external cooling of the reactor. The reactor outlet port is connected to a scrubber (tap water) for the neutralization of the gaseous $BF_3$. Between the reactor and $BF_3$ lecture bottle, and scrubber and reactor, are situated dry traps to prevent migration of material between apparatus due to potential pressure changes. A borosilicate glass three-way valve is used to separating $N_2$ and $BF_3$ inlet lines. The lecture bottle is fitted with a 3000-psig connection-rated control valve for flow control. Tygon tubing is used for delivery of material between unit operations; Teflon tape secures all tube-glassware junctions. 1-Dodecene, methyl 9-decenoate (9-DAME) and n-Propanol (1.1 g, 1.0 wt % versus olefins) are charged to the reactor. The reactor contents are sparged with $N_2$ for 30 min, with mild agitation. $N_2$ sparge is discontinued, but inert atmosphere maintained. $BF_3$ is bubbled into the olefin-alcohol mixture for 2 h, at a rate to maintain the temperature below 30° C. Maximum observed exotherm is 29° C. The mass of $BF_3$ delivered is determined by mass difference at the lecture bottle before and after the reaction. To terminate the reaction, $BF_3$ (g) feed is discontinued then $N_2$ sparging is carried out for 30 min. Aqueous $NH_4OH$ (8.27 M) is introduced into the reaction to quench residual $BF_3$ and $BF_3$.nPrOH complex; $BF_3.NH_3$ complex precipitates as a white solid. 20 g $MgSO_4$ is added, the mixture stirred for 15 min then solids are removed by filtration through a glass frit. The organics obtained are submitted to vacuum distillation for the removal of residual monomer (170° C., 2 mmHg).

Results:
Mass In=100.0 g dodecene+11.0 g 9-DAME+1.1 g nPrOH+ 34.5 g $BF_3$=165.6 g
Mass Out=117 g reactor+27 g scrubber=144 g
% Mass Recovery=98%
98.5 g crude (1100-15-1) is submitted to vacuum distillation (170° C., 2 mmHg).
Bulk of distillate (38.6 g, 1100-15-3) is collected at 53-55° C., 2 torr). 59 g stripped material recovered as a pale yellow oil. 60% conversion.
Kinematic Viscosity (100° C.): 4.9 cSt
Kinematic Viscosity (40° C.): 21.5 cSt
VI: 160
IR: 1746 $cm^{-1}$ (ester resonance)

Example 41—Preparation of a Methyl 9-Decenoate Homo-oligomer Using $BF_3$

Scheme 1. $BF_3$-mediated homo-oligomerization of methyl 9-decenoate.

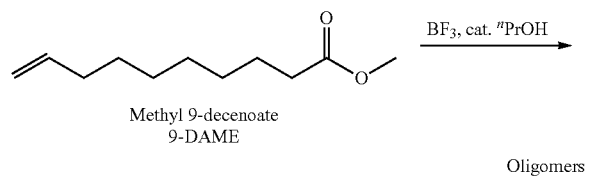

Methyl 9-decenoate
9-DAME

Oligomers

| Reagent | Mass | Moles | Equivalents |
|---------|------|-------|-------------|
| 9-DAME | 100.0 g | 542 mmol | 1.00 equiv |
| "Propanol | 1.0 g (1.3 mL) | 17 mmol | 1.0 wt % |
| $BF_3$ | 49.4 g | 729 mmol | 1.34 equiv |

Procedure:
The reaction is conducted in a 500-mL borosilicate glass bubbler with a single gas inlet and outlet. The reactor is equipped with a magnetic stirrer. A thermometer is placed inside the reaction vessel for temperature monitoring and a water bath is provided for external cooling of the reactor. The reactor outlet port is connected to a scrubber (water, 250 mL) for the neutralization of the gaseous $BF_3$. Between the reactor and $BF_3$ lecture bottle, and scrubber and reactor, are situated dry traps to prevent migration of material between apparatus due to potential pressure changes. A borosilicate glass three-way valve is used to separate $N_2$ and $BF_3$ inlet lines. The lecture bottle is fitted with a 3000-psig connection-rated control valve for flow control. Tygon tubing is used for delivery of material between unit operations; Teflon tape secured all tube-glassware junctions. Methyl 9-decenoate (9-DAME) and n-Propanol (1.0 wt % versus olefins) are charged to the reactor. The reactor contents are sparged with $N_2$ for 30 min, with mild agitation. $N_2$ sparge is discontinued, but inert atmosphere maintained. $BF_3$ is bubbled into the olefin-alcohol mixture. To terminate the reaction, $BF_3$ (g) feed is discontinued then $N_2$ sparging is carried out for 60 min. The mass of $BF_3$ delivered is determined by mass difference at the lecture bottle before the reaction and after the $N_2$ sparge. Pre- and post-reaction scrubber masses are obtained for mass balance purposes. To quench residual $BF_3$, $BF_3$.9-DAME and $BF_3$.nPrOH complexes, aqueous ammonia (8.27 M) is introduced into the reaction. The resulting emulsion is extracted with 50% EtOAc in hexanes, dried ($MgSO_4$) and submitted to vacuum distillation for the removal of residual monomer (175° C., 2 mmHg, 90 min).

Results:
Mass In=100.0 g 9-DAME+1.0 g nPrOH+49.4 g $BF_3$=150.4 g
Mass Out=138.4 g reactor+9.7 g scrubber=148.1 g
% Mass Balance=98%
66.1 g crude (1100-24-1) is submitted to vacuum distillation (175° C., 2 mmHg).
Bulk of distillate (17.3 g, 1100-24-3) is collected at 78-84° C. (2 torr). 48.8 g of residual material (1100-24-2) is recovered. Conversion=73.5%. Yield=49%.
GC-MS of 1100-24-3: 9-DAME isomers (5 peaks of MW=184, retention times from 4.81-5.25 min).
Kinematic Viscosity (100° C.): 6.7 cSt
Kinematic Viscosity (40° C.): 33.2 cSt
VI: 164
Pour point: <-45° C.
Aniline point: Miscible at ambient temperature.
Noack volatility: 8.75% (Hategan on Mar. 1, 2012)

Example 42—Preparation of a 9-DAME/1-Dodecene Oligomer (1:4) Using $BF_3$ (No Solvent)

Scheme 1. $BF_3$-mediated co-oligomerization of methyl 9-decenoate and 1-dodecene

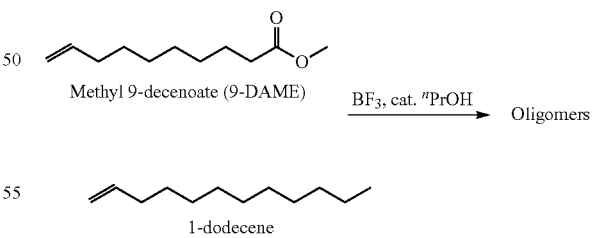

Methyl 9-decenoate (9-DAME)

Oligomers 1-dodecene

| Reagent | Mass | Moles | Equivalents |
|---------|------|-------|-------------|
| 1-Dodecene | 300.0 g | 1782 mmol | 1.00 |
| 9-DAME | 67.7 g | 356 mmol | 0.20 |
| "Propanol | 3.65 g | 61 mmol | 1.0 wt % |
| $BF_3$ | 38.8 g | mmol | Equiv |

Procedure:

The reaction is conducted in a 4-neck 1-L resin kettle equipped with a single gas inlet and outlet tube and a thermocouple. Unused ports are closed with glass stoppers. A perfluoropolymer O-ring is used at head and kettle juncture. The reactor is equipped with a magnetic stirrer and a 15-20° C. water bath is provided for external cooling of the reactor. The reactor outlet is connected to a scrubber (water, 200 mL) for the neutralization of the gaseous $BF_3$. Between the reactor and $BF_3$ lecture bottle, and scrubber and reactor, are situated 1 L dry traps to prevent migration of material between apparatus due to potential pressure changes. A borosilicate three-way valve is used to separate $BF_3$ and $N_2$ inlets. The lecture bottle is fitted with a 3000-psig connection-rated control valve for flow control. Tygon tubing is used for delivery of material between unit operations; Teflon tape secured all tube-glassware junctions. 1-dodecene, methyl 9-decenoate (9-DAME) and n-Propanol (1.0 wt % versus olefins) were charged to the reactor. The reactor contents were sparged with $N_2$ for 30 min, with stirring. $N_2$ sparge is discontinued, but inert atmosphere maintained. $BF_3$ is bubbled into the olefin-alcohol mixture. To terminate the reaction, $BF_3$ (g) feed is discontinued then $N_2$ sparging is carried out for 60 min. The mass of $BF_3$ delivered is determined by mass difference at the lecture bottle before the reaction and after the $N_2$ sparge. Pre- and post-reaction scrubber masses are obtained for mass balance purposes. To quench residual $BF_3$, $BF_3$·9-DAME and $BF_3$·nPrOH complexes, aqueous ammonia (8.27 M) is introduced into the reaction; an exothermic reaction is cooled on a room temperature water bath. The resulting emulsion is treated with 40 g $MgSO_4$, stirred for 30 min then filtered through a glass sintered funnel. The crude material is submitted to vacuum distillation for the removal of residual monomer (175° C., 2 mmHg, 90 min).

Results:

299.5 g crude is submitted to vacuum distillation (175° C., 2 mmHg). Bulk of distillate (109.8 g, 1100-28-3) is collected at 78-84° C. (2 torr). 184.9 g of residual material (1100-28-2) is recovered.

Conversion=62%. Isolated yield=50%.

Kinematic Viscosity (100° C.): 4.30 cSt; Kinematic Viscosity (40° C.): 18.58 cSt; VI: 143

Pour point: −36° C.

Aniline point: 68° C.

Noack volatility: 15.2%

Example 43—Post-Oligomerization Recovery of $BF_3$ as a Mixed Alcohol (MeOH, nPrOH) Complex Via Vacuum Distillation Schemed 1. $BF_3$-n-propanol complex-mediated oligomerization of methyl 9-decenoate (9-DAME).

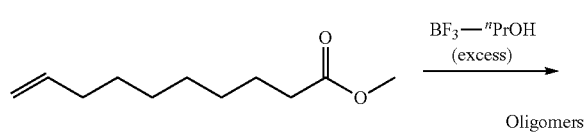

| Reagent | Mass | Moles | Equivalents |
| --- | --- | --- | --- |
| 9-DAME | 18.4 g | 100 mmol | 1.0 |
| $BF_3$·nPrOH complex | 14.0 g | 110 mmol | 1.1 |

Purpose: To determine if $BF_3$-nPrOH complex can be separated from an oligomerization reaction via distillation under reduced pressure.

Procedure:

The reaction is conducted in a 3-neck 50-mL round bottom flask equipped with gas inlet and outlet tubes and digital thermocouple. The reactor is equipped with a magnetic stirrer, and a 3° C. water bath is provided for external cooling. The reactor outlet is connected to a scrubber (water, 679 g) for the neutralization of any liberated gaseous $BF_3$. Between the reactor and $BF_3$ lecture bottle, and scrubber and reactor, are situated 250 mL dry traps. These are used to prevent migration of material between apparatus due to potential pressure changes. A borosilicate glass three-way valve is used to separate $BF_3$ and $N_2$ inlet lines. The lecture bottle is fitted with a 3000-psig connection-rated control valve for flow control. Tygon tubing is used for delivery of material between unit operations; Teflon tape secures all tube-glassware junctions. $BF_3$-nPrOH complex (1100-33) is charged to the reactor. The reactor contents are purged with $N_2$ for 30 min, with stirring. 9-DAME is then introduced to the reactor, dropwise via syringe. An exothermic reaction is observed; the rate of ester addition is controlled such that the reaction temperature does not exceed 10° C. After 2 at 2° C. then 1 h at ambient temperature, $N_2$ sweep is discontinued and a short path distillation head placed on the reactor. (The reaction is still proceeding at this time, but prematurely processed for time constraints.) Vacuum distillation of the orange reaction solution followed (to 175° C./3 torr).

Results:

Two species are collected in the distillation receiver, forming two liquid phases. The top phase is colorless and clear and the bottom (15.3 g), clear and orange-red. The residue in the distillation pot (5.8 g) is light orange and clear (dark amber, mid-distillation).

The two distillates are separated, with trace bottom material contaminating the top phase. $BF_3$ content is determined qualitatively in the distillation residue (oligomer) and top phase. Aqueous ammonia is titrated into each sample; no precipitate ($BF_3$·$NH_3$) forms in the distillation residue. 1.8 g 29% aq. ammonia (14 mmol) is added to the top layer distillate to achieve a colorless supernatant liquid and precipitate $BF_3$·$NH_3$.

The mass balance of materials in/out suggests that the bottom distillate layer contains the bulk of $BF_3$ (~96 mmol) from the reaction pot. The efficacy of the recovered catalyst complex is investigated.

Mass In=18.4 g 9-DAME+13.8 g $BF_3$·nPrOH=32.2 g

Mass Out=5.8 g 1100-34-2+11.4 g 1100-34-3-top+13.0 g 1100-34-3-bot=30.2 g

% Mass Balance=94%

Isolated yield (oligomer)=31%.

Recovered BF3.ROH=94%

Example 44

A solution of 9-decenoic acid methyl ester (65.6 g, 0.356 mol), 1-dodecene (60.0 g, 0.357 mol), and 1-butanol (1.20 g, 16.2 mmol) in 30.0 mL of 1,2-dichloroethane is placed in a water bath and is sparged with nitrogen for 25 min. Boron trifluoride (59.6 g, 0.879 mol) is sparged into the stirred solution over a period of 3.5 hours. During the course of the reaction, the temperature increases from 20 to 58° C. over a period of 15 minutes, then slowly returned to 22° C. over a period of three hours. After sparging with boron trifluoride is complete, the reaction mixture is sparged with nitrogen for 45 minutes. The reaction is quenched by slow addition of 35 mL of concentrated (28-30%) aqueous over 15 min. The organic layer is collected, dried with $MgSO_4$, filtered, and concentrated via rotary evaporation. The filtrate is distilled (2 Torr, 175° C., 1.5 h) to give 66.7 g (53% yield) of a pale yellow oil. Kinematic Viscosity (100° C.)=4.23 cSt., Kinematic Viscosity (40° C.)=20.72 cSt., VI=108, Acid value=0.89, Noack (TGA)=20.1%. The product is soluble as a 60:40 blend in PAO4.

Example 45

A solution of 9-decenoic acid methyl ester (32.9 g, 0.178 mol), 1-dodecene (150.0 g, 0.891 mol), and 1-propanol (1.82 g, 30.3 mmol) in 30.0 mL of 1,2-dichloroethane is placed in a water bath and is sparged with nitrogen for 20 min. Boron trifluoride (24.0 g, 0.354 mol) is sparged into the stirred solution over a period of 3.0 hours. During the course of the reaction, the temperature increases from 18 to 40° C. over a period of 35 minutes, then slowly returned to 23° C. over a period of 2.5 hours. After sparging with boron trifluoride is complete, the reaction vessel is sealed, and the mixture is stirred for an additional 1 hour before being sparged with nitrogen for 45 minutes. The reaction is quenched by slow addition of 20 mL of concentrated (28-30%) aqueous over 15 min. The organic layer is collected, dried with $MgSO_4$, filtered, and concentrated via rotary evaporation. The filtrate is distilled (2 Torr, 175° C., 1.5 h) to give 124.4 g (68% yield) of a pale yellow oil. Kinematic Viscosity (100° C.)=4.16 cSt., Kinematic Viscosity (40° C.)=18.07 cSt., VI=137, Noack (TGA)=18.6%, aniline point=70° C.

Example 46

To a suspension of aluminum chloride (8.33 g, 62.5 mmol) in 40 mL of heptane at 20° C. is added a solution of 9-decenoic acid methyl ester (9.21 g, 50 mmol) and 1-decene (70.1 g, 500 mmol) at a rate that maintained the internal temperature at 25±1° C. over 1.5 h. Upon complete addition, the reaction mixture is stirred for 2 h at 20-25° C. Water (15 mL, 0.83 mol) is added slowly to the reaction mixture in portions over 30 min, maintaining the temperature between 20-25° C. The mixture is stirred for 0.5 h and then allowed to stand for 1 h. The organic layer is decanted and the remaining residue is rinsed three times with 15 mL each heptane. The combined organic layers are stirred with NaHCO3 (50 g, 0.6 mol) for 30 min. The mixture is filtered and the filtrate is concentrated on a rotovap. The resulting oil is distilled under vacuum (2 Torr, 175° C., 1 h) to give 66 g (83% yield) of a pale yellow oil. Kinematic Viscosity (100° C.) 69.5 cSt. IR ($cm^{-1}$) 1746.

Example 47

To a suspension of aluminum chloride (8.33 g, 62.5 mmol) in 40 mL of heptane at 80° C. is added a solution of 9-decenoic acid methyl ester (9.21 g, 50 mmol) and 1-decene (70.1 g, 500 mmol) at a rate that maintains the internal temperature at 85-90° C. over 0.5 h. Upon complete addition, the reaction mixture is stirred for 2 h at 85° C. Water (15 mL, 0.83 mol) is added slowly to the reaction mixture in portions over 30 min, maintaining the temperature between 25-30° C. The mixture is stirred for 0.5 h and then allowed to stand for 1 h. The organic layer is decanted and the remaining residue is rinsed three times with 15 mL each heptane. The combined organic layers were stirred with NaHCO3 (50 g, 0.6 mol) for 30 min. The mixture is filtered and the filtrate is concentrated on a rotovap. The resulting oil is distilled under vacuum (2 Torr, 175° C., 1 h) to give 64 g (81% yield) of a pale yellow oil. Kinematic Viscosity (100° C.) 25 cSt.

Example 48

To a suspension of aluminum chloride (8.33 g, 62.5 mmol) in 40 mL of octane at 110° C. is added a solution of 9-decenoic acid methyl ester (9.21 g, 50 mmol) and 1-decene (70.1 g, 500 mmol) at a rate that maintains the internal temperature at 115-120° C. over 0.5 h. Upon complete addition, the reaction mixture is stirred for 2 h at 115° C. Water (15 mL, 0.83 mol) is added slowly to the reaction mixture in portions over 30 min, maintaining the temperature between 25-30° C. The mixture is stirred for 0.5 h and then allowed to stand for 1 h. The organic layer is decanted and the remaining residue is rinsed three times with 15 mL each heptane. The combined organic layers were stirred with NaHCO3 (50 g, 0.6 mol) for 30 min. The mixture is filtered and the filtrate is concentrated on a rotovap. The resulting oil is distilled under vacuum (2 Torr, 175° C., 1 h) to give 61 g (77% yield) of a pale yellow oil. Kinematic Viscosity (100° C.) 18.8 cSt.

Example 49

A solution of 9-decenoic acid methyl ester (200 g, 1.09 mol), 1-dodecene (200 g, 1.19 mol), and 1-butanol (4.0 g, 0.054 mol) is cooled to 10° C. and sparged with nitrogen for 15 min. Boron trifluoride is sparged into the stirred solution while the temperature is maintained near 30° C. The temperature spiked briefly to 45° C. when the solution becomes supersaturated with boron trifluoride. After 4 h sparging with boron trifluoride the reaction mixture is sparged with nitrogen for 1.5 h. The amount of boron trifluoride contained in the reaction mixture is 77.7 g (1.15 mol). The reaction mixture is cooled to 10° C. and treated with 98 mL (1.37 mol) of concentrated (28-30%) aqueous ammonia portion-wise over about 15 min. The mixture is stirred for 15 min, treated with 50 g of MgSO4, and filtered. The filtrate is distilled (2 Torr, 190° C., 0.5 h) to give 258 g (65% yield) of a pale yellow oil. Kinematic Viscosity (100° C.)=4.7 cSt.

The properties for various functional base oils of the invention are shown in the tables below.

| Product | Viscosity D445 100 C. (cSt) | CCS D5293 −15 C. (cp) | CCS D5293 −20 C. (cp) | CCS D5293 −25 C. (cp) | CCS D5293 −30 C. (cp) | CCS D5293 −35 C. (cp) | PDSC Oxidation D6186 200 C. OIT (min.) | PDSC Oxidation E2009 OOT (° C.) | Noack Volatility D5800 (wt %) | Apparent Viscosity @ 150 C. D4683 (cP) | Iodine value |
|---|---|---|---|---|---|---|---|---|---|---|---|
| API Group III Oil | 6.2 | 946 | 1572 | 2667 | 4855 | 8796 | | | | 2.18 | |
| API Group II Oil | 10.2 | 3548 | 6384 | 12609 | 29361 | 80028 | | 197 | | 3.23 | |
| PAO10 (Polyalphaolefin) | 10 | 1965 | 3195 | 5296 | 9324 | | | | | | |
| Esterx NP451 (Synthetic Ester) | 5 | | | | 2363 | | | | | | |
| 1-Dodecene/Methyl 9-decenoate(10:1)m | 22.3 | 6072 | 9914 | 17037 | 9522 | | 2.6 | 193 | 2.4 | | 8 |
| 1-Dodecene/Methyl 9-decenoate (10:1)m | 22.4 | | | | | 51971 | | | | | |
| 1-dodecene/9-DAME (10:1)m t-butyl cat 8.3% | 24.6 | | | 14971 | | | | | | | |
| 1-dodecene/9-DAME (3:1)m t-butyl cat 8.5% | 23.4 | 5260 | 8558 | 14521 | | | | | | | |
| 1-Dodecene/Methyl 9-decenoate (1:1)m | NA | 11901 | 20732 | 36436 | | | | | | | |
| 1-Decene/1-Dodecene(1:1)m/ Methyl 9-decenoate (10:1)m | 20.4 | | | | 23891 | | | | | | |
| 1-Decene/1-Dodecene/ Methyl 9-decenoate (10:1:1)m t-butyl cat 8.3% | 21.8 | 5136 | 8296 | 13960 | | | | | | | |
| 1-Decene/Methyl 9-decenoate (10:1)m | 13.0 | 2496 | 3972 | 6516 | 11351 | 22211 | 2.4 | 194 | 3.6 | 4.23 | 30 |
| 1-Decene/Methyl 9-decenoate (10:1)m | 17.7 | 4617 | | 13078 | | 46467 | | | | | 18 |
| 1-Decene/Methyl 9-decenoate (10:1)m | 17.8 | 4350 | 7065 | 12006 | | | | | | | |
| 1-Decene/Methyl 9-decenoate (3:1)m t-butyl cat 8.5% | 16.0 | | | | | 50868 | 2.0 | 173 | 3.0 | | |
| 1-Decene/Methyl 9-decenoate (1:1)m | 28.8 | 10871 | 19037 | 33812 | | | | | | | |
| 1-Octene/Methyl 9-decenoate (10:1)m | | | | 35725 | 13623 | | | | | | |
| 1-Decene/Methyl 9-decenoate/Dimethylamide | | | | | | | | | | | |
| 1-Dodecene/Methyl 9-decenoate (10:1) BF₃ catalyst | 4.8 | | | | 1050 | | 1 | 189 | | | |
| Maleinated methyl 9-decenoate - 3,5,5 tri-methylhexanol ester | 10.5 | | | | 9700 | | 0.1 | 187 | | | |
| Maleinated methyl 9-decenoate - iso-amyl alcohol ester | 6.0 | | | | 4963 | | 0.2 | 190 | | | |
| Maleinated methyl 9-decenoate - 2-ethyl-hexanol ester | 7.1 | | | | 10420 | | 0.5 | 0.191 | | | |

-continued

| Product | Viscosity D445 100 C. (cSt) | CCS D5293 −15 C. (cp) | CCS D5293 −20 C. (cp) | CCS D5293 −25 C. (cp) | CCS D5293 −30 C. (cp) | CCS D5293 −35 C. (cp) | PDSC Oxidation D6186 200 C. OIT (min.) | PDSC Oxidation E2009 OOT (° C.) | Noack Volatility D5800 (wt %) | Apparent Viscosity @ 150 C. D4683 (cP) | Iodine value |
|---|---|---|---|---|---|---|---|---|---|---|---|
| Maleinated Methyl 9-decenoate- Exxal 8 ester | 8.3 | | | | 41721 | | | | | | |
| API Group III Oil | 6.2 | 946 | 1572 | 2667 | 4855 | 8796 | | | | | |
| API Group II Oil | 10.2 | 3548 | 6384 | 12609 | 29361 | 80028 | | 197 | | 2.18 | |
| PAO10 (Polyalphaolefin) | 10 | 1965 | 3195 | 5296 | 9324 | | | | | 3.23 | |
| Esterx NP451 (Synthetic Ester) | 5 | | | | 2363 | | | | | | |
| 1-Dodecene/Methyl 9-decenoate(10:1)m | 22.3 | 6072 | 9914 | 17037 | 9522 | | 2.6 | 193 | 2.4 | | 8 |
| 1-Dodecene/Methyl 9-decenoate (10:1)m | 22.4 | | | | | 51971 | | | | | |
| 1-dodecene/9-DAME (10:1)m t-butyl cat 8.3% | 24.6 | | | 14971 | | | | | | | |
| 1-dodecene/9-DAME (3:1)m t-butyl cat 8.5% | 23.4 | 5260 | 8558 | 14521 | | | | | | | |
| 1-Dodecene/Methyl 9-decenoate (1:1)m | NA | 11901 | 20732 | 36436 | | | | | | | |
| 1-Decene/1-Dodecene(1:1)m/ Methyl 9-decenoate (10:1)m | 20.4 | | | | 23891 | | | | | | |
| 1-Decene/1-Dodecene/ Methyl 9-decenoate (10:1:1)m t-butyl cat 8.3% | 21.8 | 5136 | 8296 | 13960 | | | | | | | |
| 1-Decene/Methyl 9-decenoate (10:1)m | 13.0 | 2496 | 3972 | 6516 | 11351 | 22211 | 2.4 | 194 | 3.6 | 4.23 | 30 |
| 1-Decene/Methyl 9-decenoate (10:1)m | 17.7 | 4617 | | 13078 | | 46467 | | | | | 18 |
| 1-Decene/Methyl 9-decenoate (3:1)m t-butyl cat 8.5% | 17.8 | 4350 | 7065 | 12006 | | | | | | | |
| 1-Decene/Methyl 9-decenoate (1:1)m | 16.0 | | | | | 50868 | 2.0 | 173 | 3.0 | | |
| 1-Octene/Methyl 9-decenoate (10:1)m | 28.8 | 10871 | 19037 | 33812 | | | | | | | |
| 1-Decene/Methyl 9-decenoate/Dimethylamide | | | | 35725 | 13623 | | | | | | |
| 1-Dodecene/Methyl 9-decenoate (10:1) BF3 catalyst | 4.8 | | | | 1050 | | 1 | 189 | | | |
| Maleinated methyl 9-decenoate - 3,5,5 tri-methylhexanol ester | 10.5 | | | | 9700 | | 0.1 | 187 | | | |
| Maleinated methyl 9-decenoate - iso-amyl alcohol ester | 6.0 | | | | 4963 | | 0.2 | 190 | | | |
| Maleinated methyl 9-decenoate - 2-ethyl- | 7.1 | | | | 10420 | | 0.5 | 0.191 | | | |

| Product | Viscosity D445 100 C. (cSt) | CCS D5293 −15 C. (cp) | CCS D5293 −20 C. (cp) | CCS D5293 −25 C. (cp) | CCS D5293 −30 C. (cp) | CCS D5293 −35 C. (cp) | PDSC Oxidation D6186 200 C. OIT (min.) | PDSC Oxidation E2009 OOT (° C.) | Noack Volatility D5800 (wt %) | Apparent Viscosity @ 150 C. D4683 (cP) | Iodine value |
|---|---|---|---|---|---|---|---|---|---|---|---|
| hexanol ester Maleinated Methyl 9-decenoate - Exxal 8 ester | 8.3 | | | | 41721 | | | | | | |

While the invention has been explained in relation to various embodiments, it is to be understood that various modifications thereof will become apparent to those skilled in the art upon reading the specification. Therefore, it is to be understood that the invention disclosed herein includes any such modifications that may fall within the scope of the appended claims.

The invention claimed is:

1. A method of making sulfurized derivatives of metathesis-derived compounds, the method comprising:
providing a functionalized monomer, wherein the functionalized monomer is a compound having an unsaturated hydrocarbyl group having 8 to 12 carbon atoms with a functional group attached thereto, wherein said functional group is a carboxylic acid group of an ester thereof, and wherein the unsaturated hydrocarbyl group has a carbon-carbon double bond in the terminal position; and
reacting the functionalized monomer with a sulfurizing agent to form a sulfurized derivative.

2. The method of claim 1, wherein the unsaturated hydrocarbyl group is linear.

3. The method claim 1, wherein the unsaturated hydrocarbyl group has 1 or 2 carbon-carbon double bonds.

4. The method of claim 2, wherein the unsaturated hydrocarbyl group has 1 or 2 carbon-carbon double bonds.

5. The method of claim 1, wherein the hydrocarbyl group is a 1-decenyl group.

6. The method of claim 1, wherein the functional group is a monoglyceride ester of a carboxylic acid, a diglyceride ester of a carboxylic acid, or a triglyceride ester of a carboxylic acid.

7. The method of claim 5, wherein the functional group is a monoglyceride ester of a carboxylic acid, a diglyceride ester of a carboxylic acid, or a triglyceride ester of a carboxylic acid.

8. The method of claim 1, wherein the functional group is a triglyceride ester of a carboxylic acid.

9. The method of claim 5, wherein the functional group is a triglyceride ester of a carboxylic acid.

10. The method of claim 1, wherein the functional group is a methyl ester of a carboxylic acid, a ethyl ester of a carboxylic acid, or a propyl ester of a carboxylic acid, or a butyl ester of a carboxylic acid.

11. The method of claim 5, wherein the functional group is a methyl ester of a carboxylic acid, a ethyl ester of a carboxylic acid, or a propyl ester of a carboxylic acid, or a butyl ester of a carboxylic acid.

12. The method of claim 1, wherein the functional group is a methyl ester of a carboxylic acid.

13. The method of claim 5, wherein the functional group is a methyl ester of a carboxylic acid.

14. The method of claim 12, wherein the functionalized monomer is selected from the group consisting of: methyl 8-nonenoate, methyl 9-decenoate, methyl 10-undecenoate, and methyl 9-dodecenoate.

15. The method of claim 14, wherein the functionalized monomer is methyl 9-decenoate.

16. The method of claim 14, wherein the functionalized monomer is methyl 10-undecenoate.

17. The method of claim 14, wherein the functionalized monomer is methyl 9-dodecenoate.

18. The method of claim 1, wherein the functionalized monomer is derived from a process that comprises the reaction of a vegetable oil with a short-chain olefin, wherein the short-chain olefin is selected from the group consisting of: ethylene, 1-propene, 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-octadecene, 1-eicosene, and mixtures of two or more thereof.

19. The method of claim 18, wherein the vegetable oil is selected from the group consisting of: soybean oil, rapeseed oil, corn oil, sesame oil, cottonseed oil, sunflower seed oil, canola oil, safflower oil, palm oil, palm kernel oil, linseed oil, castor oil, olive oil, peanut oil, coriander oil, almond oil, and wheat germ oil.

* * * * *